US011471477B2

(12) United States Patent
Clarke et al.

(10) Patent No.: US 11,471,477 B2
(45) Date of Patent: Oct. 18, 2022

(54) METHODS FOR TREATING TRIPLE-NEGATIVE BREAST CANCER

(71) Applicants: Chan Zuckerberg Biohub, Inc., San Francisco, CA (US); The Board of Trustees of the Leland Stanford Junior University, Stanford, CA (US)

(72) Inventors: Michael F. Clarke, San Francisco, CA (US); Robert W. Hsieh, San Francisco, CA (US)

(73) Assignees: Chan Zuckerberg Biohub, Inc., San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/648,088

(22) PCT Filed: Sep. 18, 2018

(86) PCT No.: PCT/US2018/051489

§ 371 (c)(1),
(2) Date: Mar. 17, 2020

(87) PCT Pub. No.: WO2019/055977

PCT Pub. Date: Mar. 21, 2019

(65) Prior Publication Data

US 2021/0121495 A1 Apr. 29, 2021

Related U.S. Application Data

(60) Provisional application No. 62/560,140, filed on Sep. 18, 2017.

(51) Int. Cl.

| | |
|---|---|
| ***C07H 21/02*** | (2006.01) |
| ***C07H 21/04*** | (2006.01) |
| ***A61K 31/713*** | (2006.01) |
| ***A61P 35/00*** | (2006.01) |
| ***A61K 45/06*** | (2006.01) |
| ***C12N 15/113*** | (2010.01) |
| *G01N 33/574* | (2006.01) |

(52) U.S. Cl.

CPC ............ *A61K 31/713* (2013.01); *A61K 45/06* (2013.01); *A61P 35/00* (2018.01); *C12N 15/113* (2013.01); *C12N 2310/14* (2013.01); *C12N 2310/531* (2013.01); *C12N 2320/30* (2013.01); *G01N 33/57415* (2013.01); *G01N 2800/52* (2013.01)

(58) Field of Classification Search

CPC .............. C12N 15/113; C12N 2310/14; C12N 2310/531

See application file for complete search history.

(56) References Cited

U.S. PATENT DOCUMENTS 8,598,344 B2 * 12/2013 Porter ..................... A61P 43/00 544/293
2012/0071477 A1 3/2012 Porter et al.
2017/0115308 A1 4/2017 Roninson

FOREIGN PATENT DOCUMENTS

WO 2013/040153 A1 3/2013
WO 2013/116786 A1 8/2013
WO WO 2013/116786 A1 * 8/2013 ........... C12N 15/113
WO 2014071143 5/2014

OTHER PUBLICATIONS

Elbashir et al. (The EMBO Journal, vol. 20, No. 23, pp. 6877-6888, 2001).*
Serrao et al. (2016, Cdk8 and Cdk19 as Novel Regulators of BMP4 Induced EMT in Cancer, Master's thesis, 1-87).*
Gomez-Miragaya et al. (Stem Cell Reports, 8, 1392-1407, 2017).*
EP18856034.6 , "Extended European Search Report", dated May 19, 2021, 7 pages.
Kren et al., "Preclinical Evaluation of Cyclin Dependent Kinase 11 and Casein Kinase 2 Survival Kinases as RNA Interference Targets for Triple Negative Breast Cancer Therapy", Breast Cancer Research, vol. 17, No. 1, 2015, pp. 1465-5411.
Porter et al., "Targeting tumor microenvironment with selective small-molecule inhibitors of CDK8/19", Abstracts: AACR Special Conference on Cellular Heterogeneity in the Tumor Microenvironment, Feb. 26, 2014, American Association for Cancer Research, Philadelphia, PA.
Porter et al., "Targeting the seed and the soil of cancers with selective small-molecule inhibitors of CDK8/19: Chemopotentiating, chemopreventive, anti-invasive and anti-metastatic activities", Abstract: Proceedings of the 105th Annual Meeting of the American Association for Cancer Research; Apr. 5, 2014, American Association for Cancer Research, Philadelphia, PA.
International Application No. PCT/US2018/051489, Publication No. WO/2019/055977, Internation Search Report and Written Opinion, dated Mar. 21, 2019, 11 Pages.

(Continued)

*Primary Examiner* — Amy H Bowman
(74) *Attorney, Agent, or Firm* — Kilpatrick Townsend & Stockton LLP

(57) ABSTRACT

The invention is directed to methods of treating TNBC in a patient by administering to the patient an agent that inhibits the expression or activity of cyclin-dependent kinase 19 (CDK19). In some embodiments, the agent may be a small molecule inhibitor, a polynucleotide (e.g., shRNA. siRNA), or a protein (e.g., an antibody). In some embodiments, the agent does not inhibit the activity or expression of CDK8.

17 Claims, 65 Drawing Sheets

Specification includes a Sequence Listing.

(56) References Cited

OTHER PUBLICATIONS

Mallinger et al., "Discovery of Potent, Selective, and Orally Bioavailable Small-Molecule Modulators of the Mediator Complex-Associated Kinases CDK8 and CDK19," DOI: 10.1021/acs.jmedchem.5b01685, J. Med. Chem., 2016, 59, 1078-1101.

Czodrowski P et al.; "Structure-Based Optimization of Potent, Selective, and Orally Bioavailable CDK8 Inhibitors Discovered by High-Throughput Screening," J. Med. Chem., 2016, 59, 20, 9337-9349, https://doi.org/10.1021/acs.jmedchem.6b00597.

McDermott et al., "Inhibition of CDK8 mediator kinase suppresses estrogen dependent transcription and the growth of estrogen receptor positive breast cancer," Oncotarget, 2017;8(8):12558-12575.

Hsieh et al., "CDK19 is a Regulator of Triple-Negative Breast Cancer Growth," bioRxiv 317776; doi: https://doi.org/10.1101/317776, 65 pages. May 10, 2018.

* cited by examiner

FIG. 2C

| | PDX-T1 | | | PDX-T2 | | | PDX-T5 | | | PDX-T4 | | | PDX-T6 | | | PDX-T7 | | |
|---|---|---|---|---|---|---|---|---|---|---|---|---|---|---|---|---|---|---|
| Cells injected | 100 | 500 | 2500 | 100 | 500 | 2500 | 100 | 500 | 2500 | 100 | 500 | 2000 | 100 | 500 | 2500 | 100 | 500 | 2500 |
| EPCAM$^{positive}$ CD10$^{-/low}$ | 1/2 | 4/4 | 4/4 | 2/8 | 8/8 | 10/12 | 0/4 | 0/4 | 4/4 | - | - | 4/4 | - | 3/8 | 4/8 | - | 3/4 | 3/4 |
| EPCAM$^{positive}$ CD10$^{positive}$ | 0/4 | 0/8 | 1/8 | 0/8 | 0/8 | 2/12 | 0/8 | 0/8 | 0/8 | - | - | 0/4 | - | 0/4 | 0/4 | - | 0/4 | 0/4 |
| EPCAM- CD10 | 0/2 | 0/4 | 0/4 | 0/4 | 0/4 | 0/4 | 0/4 | 0/4 | 0/4 | - | - | - | - | - | - | - | - | - |

inducCDK19KD-PDX-T1 Organoids

CCT251921

FIG. 5D

| | | | |
|---|---|---|---|
| ARD1A/NAA10 | EIF2S2 | PSMA2 | RPL13A |
| ASCC3L1 | HGF | PSMA6 | RPL14 |
| C15ORF15 | HNRNPC | PSMB3 | RPL4 |
| CDC2/CDK1 | KARS | PSMB6 | RPL6 |
| CDC2L1/CDK11B | KLRK1 | PSMC3 | RRM1 |
| CDC2L6/CDK19 | KPNB1 | PSMD1 | RRM2 |
| CSE1L | NEDD8 | PSMD13 | SEC22B |
| DTYMK | POLA | PSMD3 | SH3GLB2 |
| DUT | POLR2A | RBX1 | TUBA1A |
| EEF2 | POLR2F | RPA1 | TUBA1C |
| EFTUD2 | PSMA1 | RPA2 | WBSCR17 |
| EIF1AX | | RPA3 | |

FIG. 8C

| | 50 cells | 250 cells | 1250 cells |
|---|---|---|---|
| + Dox | 0/5 | 0/5 | 0/5 |

| | 50 cells | 250 cells | 1250 cells |
|---|---|---|---|
| No Dox | 1/5 | 2/5 | 5/5 |

FIG. 9

```
                 10         20         30         40         50
                 ---------+---------+---------+---------+---------+
CDK19   1  MDYDFKAKLAAERERVEDLFEYEGCKVGRGTYGHVYKAKRKDGKDEKEYA   50
CDK8    1  MDYDFKVKLSSERERVEDLFEYEGCKVGRGTYGHVYKAKRKDGKDDKDYA   50
                 60         70         80         90        100
                 ---------+---------+---------+---------+---------+
CDK19  51  LKQIEGTGISMSACREIALLRELKHPNVIALQKVFLSHSDRKVWLLFDYA  100
CDK8   51  LKQIEGTGISMSACREIALLRELKHPNVISLQKVFLSHADRKVWLLFDYA  100
                110        120        130        140        150
                 ---------+---------+---------+---------+---------+
CDK19 101  EHDLWHIIKFHRASKANKKPMQLPRSMVKSLLYQILDGIHYLHANWVLHR  150
CDK8  101  EHDLWHIIKFHRASKANKKPVQLPRGMVKSLLYQILDGIHYLHANWVLHR  150
                160        170        180        190        200
                 ---------+---------+---------+---------+---------+
CDK19 151  DLKPANILVMGEGPERGRVKIADMGFARLFNSPLKPLADLDPVVVTFWYR  200
CDK8  151  DLKPANILVMGEGPERGRVKIADMGFARLFNSPLKPLADLDPVVVTFWYR  200
                210        220        230        240        250
                 ---------+---------+---------+---------+---------+
CDK19 201  APELLLGARHYTKAIDIWAIGCIFAELLTSEPIFHCRQEDIKTSNPFHHD  250
CDK8  201  APELLLGARHYTKAIDIWAIGCIFAELLTSEPIFHCRQEDIKTSNPYHHD  250
                260        270        280        290        300
                 ---------+---------+---------+---------+---------+
CDK19 251  QLDRIFSVMGFPADKDWEDIRKMPEYPTLQKDFRRTTYANSSLIKYMEKH  300
CDK8  251  QLDRIFNVMGFPADKDWEDIKKMPEHSTLMKDFRRNTYTNCSLIKYMEKH  300
                310        320        330        340        350
                 ---------+---------+---------+---------+---------+
CDK19 301  KVKPDSKVFLLLQKLLTMDPTKRITSEQALQDPYFQEDPLPTLDVFAGCQ  350
CDK8  301  KVKPDSKAFHLLQKLLTMDPIKRITSEQAMQDPYFLEDPLPTSDVFAGCQ  350
                360        370        380        390        400
                 ---------+---------+---------+---------+---------+
CDK19 351  IPYPKREFLNEDDPEEKGDKNQQQQQNQHQQPTAPPQQAAAPPQAPPPQQ  400
CDK8  351  IPYPKREFLTEEEPDDKGDKKNQQQQ-----------------------Q  377
                410        420        430        440        450
                 ---------+---------+---------+---------+---------+
CDK19 401  NSTQTNGTAGGAGAGVGGTGAGLQHSQDSSLNQVPPNKKPRLGPSGANSG  450
CDK8  378  GNNHTN-------------GTGHPGNQDSSHTQGPPLKKVRVVPPTTTSG  414
                460        470        480        490        500
                 ---------+---------+---------+---------+---------+
CDK19 451  GPVMPSDYQHSSSRLNYQSSVQGSSQSQSTLGYSSSSQQSSQYHPSHQAH  500
CDK8  415  GLIMTSDYQRSNPHAAYPNPGPSTSQPQSSMGYSATSQQPPQY--SHQTH  462
                 --
CDK19 501  RY                                                  502
CDK8  463  RY                                                  464
```

Upregulated with CDK19 Knockdown

| | NES | FDR q-val |
|---|---|---|
| **OXIDATIVE PHOSPHORYLATION** | 1.663 | 0.019 |
| PANCREAS_BETA_CELLS | 1.529 | 0.086 |
| UV_RSPOLNSE_DN | 1.374 | 0.110 |
| KRAS_SIGNALING_DN | 1.295 | 0.167 |
| *ESTROGEN_RESPONSE_EARLY* ** | 1.278 | 0.153 |
| *EPITHELIAL_MESENCHYMAL_TRANSITION* ** | 1.260 | 0.152 |
| P53_PATHWAY | 1.208 | 0.197 |
| HEME_METABOLISM | 1.181 | 0.210 |

Downregulated with CDK19 Knockdown

| | NES | FDR q-val |
|---|---|---|
| **E2F_TARGETS** * | -3.495 | 0.000 |
| **G2M_CHECKPOINT** * | -3.292 | 0.000 |
| **MYC_TARGETS_V1** * | -2.646 | 0.000 |
| **MTORC1_SIGNALING** * | -2.632 | 0.000 |
| **MITOTIC_SPINDLE** * | -2.331 | 0.000 |
| ANDROGEN_RESPONSE | -2.045 | 0.000 |
| **GLYCOLYSIS** * | -1.977 | 0.000 |
| KRAS_SIGNALING_UP | -1.928 | 0.001 |
| **DNA_REPAIR** * | -1.900 | 0.001 |
| UNFOLDED_PROTEIN_RESPONSE | -1.855 | 0.001 |
| *CHOLESTEROL_HOMEOSTASIS* ** | -1.804 | 0.002 |
| **TNFA_SIGNALING_VIA_NFKB** * | -1.779 | 0.003 |
| REACTIVE_OXIGEN_SPECIES_PATHWAY | -1.686 | 0.005 |
| HYPOXIA | -1.681 | 0.004 |
| **SPERMATOGENESIS** * | -1.676 | 0.004 |
| **APOPTOSIS** * | -1.654 | 0.006 |
| **IL2_STAT 5_SIGNALING** | -1.613 | 0.008 |
| INTERFERON_GAMMA_RESPONSE | -1.609 | 0.008 |
| PEROXISOME | -1.423 | 0.043 |
| *MYC_TARGETS_V2* ** | -1.366 | 0.070 |
| PROTEIN_SECRETION | -1.359 | 0.071 |
| ALLOGRAFT_REJECTION | -1.251 | 0.163 |
| NOTCH_SIGNALING | -1.246 | 0.161 |
| *INTERFERON_ALPHA_RESPONSE* ** | -1.238 | 0.163 |
| TGF_BETA_SIGNALING | -1.225 | 0.173 |
| COMPLEMENT | -1.210 | 0.185 |
| IL6_JAK_STAT3_SIGNALING | -1.180 | 0.219 |
| FATTY_ACID_METABOLISM | -1.180 | 0.212 |
| INFLAMMATORY_RESPONSE | -1.177 | 0.208 |
| UV_RESPONSE_UP | -1.175 | 0.204 |
| **P3K_AKT_MTOR_SIGNALING** * | -1.144 | 0.244 |

Upregulated with CDK8 Knockdown

| | NES | FDR q-val |
|---|---|---|
| **OXIDATIVE PHOSPHORYLATION** * | 2.529 | 0.000 |
| XENOBIOTIC_METABOLISM | 1.937 | 0.000 |
| *MYC_TARGETS_V2* ** | 1.664 | 0.013 |
| FATTY_ACID_METABOLISM | 1.596 | 0.019 |
| ADIPOGENESIS | 1.508 | 0.031 |
| *INTERFERON_ALPHA_RESPONSE* ** | 1.205 | 0.232 |
| *CHOLESTEROL_HOMEOSTASIS* ** | 1.190 | 0.0224 |

Downregulated with CDK8 Knockdown

| | NES | FDR q-val |
|---|---|---|
| **E2F_TARGETS** * | -2.930 | 0.000 |
| **G2M_CHECKPOINT** * | -2.895 | 0.000 |
| **MITOTIC_SPINDLE** * | -2.217 | 0.000 |
| APICAL_SURFACE | 1.720 | 0.005 |
| **PI3K_AKT_MMTOR_SIGNALING** * | 1.667 | 0.007 |
| **DNA_REPAIR** * | 1.641 | 0.008 |
| **MTORC1_SIGNALING** * | 1.597 | 0.012 |
| **SPERMATOGENESIS** * | 1.500 | 0.033 |
| **MYC_TRGETS_V1** * | 1.467 | 0.042 |
| APICAL_JUNCTION | 1.453 | 0.045 |
| INFLAMMATORY_RESPONSE | 1.447 | 0.043 |
| ESTROGEN_RESPONSE_LATE | 1.407 | 0.063 |
| *EPITHDELIAL_MESENCHYMAL_TRANSITION* ** | 1.405 | 0.060 |
| GLYCOLYSIS | 1.382 | 0.071 |
| **APOPTOSIS** * | 1.307 | 0.139 |
| **IL2_STAT5_SIGNALING** * | 1.293 | 0.142 |
| *ESTROGEN_RESPONSE_EARLY* ** | 1.282 | 0.154 |
| **TNFA_SIGNALING_VIA_NFKB** * | 1.233 | 0.222 |

FIG. 10

CDK19KD-EnhancerDOWN leading edge 'core' genes

FIG. 15

| Tumor | Origin | ER/PR/HER2 status | Diagnosis | Treatment Status |
|---|---|---|---|---|
| PDX-T1 (C69) | Breast Primary | -/-/- | IDC | Radiation |
| PDX-T2 (C70) | Breast Primary | -/-/- | IDC | Not treated |
| PDX-T3 (S58T) | Breast Primary | -/-/- | IDC | Not treated |
| PDX-T4 (C87) | Brain metastases | -/-/- | Inflammatory Breast CA | Neo-adjuvant chemotherapy |
| PDX-T5 (C51) | Breast Primary | -/-/+ | Inflammatory Breast CA | Neo-adjuvant chemotherapy |
| PDX-T6 (C64) | Breast Primary | -/-/- | IDC | Neo-adjuvant chemotherapy |
| PDX-T7 (C74) | Breast Primary | +/+/+ | IDC | Unknown |
| PDX-T8 (S11T) | Breast Primary | +/+/- | IDC | Neoadjuvant chemotherapy |

METHODS FOR TREATING TRIPLE-NEGATIVE BREAST CANCER

CROSS-REFERENCE TO RELATED APPLICATIONS

The present patent application is a national phase application of PCT Application No. PCT/US2018/051489, filed Sep. 18, 2018, which claims benefit of U.S. Provisional Patent Application No. 62/560,140, filed Sep. 18, 2017, which is incorporated by reference in its entirety for all purposes.

FEDERALLY SPONSORED RESEARCH AND DEVELOPMENT

This invention was made with Government support under contract W81XWH-11-1-0287 awarded by the Department of Defense; under contract W81XWH-13-1-0281 awarded by the Department of Defense; and under contract CA100225 awarded by the National Institutes of Health. The Government has certain rights in the invention.

REFERENCE TO A SEQUENCE LISTING

The Sequence Listing written in file SequenceListing_1103410.txt created on Sep. 14, 2018, 66 bytes, machine format IBM-PC, MS-Windows operating system, is hereby incorporated by reference in its entirety for all purposes.

FIELD OF THE INVENTION

The invention relates to the field of biomedicine, e.g., oncology.

BACKGROUND

Triple-negative breast cancer (TNBC) is an aggressive breast cancer subtype disproportionately affecting younger women and associated with poor prognoses. See Bauer et al. "Descriptive analysis of estrogen receptor (ER)-negative, progesterone receptor (PR)-negative, and HER2-negative invasive breast cancer, the so-called triple-negative phenotype: a population-based study from the California cancer Registry" Cancer 109, 1721-1728, doi:10.1002/cncr.22618 (2007). Despite affecting 20% of all breast cancer patients, there are currently no clinically approved targeted therapies for these patients. There exists a need in the art for effective methods of treating TNBC.

SUMMARY

The invention is directed to methods of treating TNBC in a patient by administering to the patient an agent that inhibits the expression or activity of cyclin-dependent kinase 19 (CDK19).

In one aspect, the invention features a method of treating a patient diagnosed with triple-negative breast cancer (TNBC) by administering a therapeutically effective dose of an agent that inhibits expression or activity of cyclin-dependent kinase 19 (CDK19) and achieves at least one of a reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, or progression free survival.

In another aspect, the invention features a method of treating a patient diagnosed with triple-negative breast cancer (TNBC), wherein the cancer is characterized by a tumor comprising EpCAM$^{med/high}$/CD10$^{-/low}$ epithelial cells. The method includes administering a therapeutically effective dose of an agent that inhibits cyclin-dependent kinase 19 (CDK19) expression or activity, wherein the treatment reduces the number of EpCAM$^{med/high}$/CD10$^{-/low}$ cells in the tumor, reduces to number of EpCAM$^{med/high}$/CD10$^{-/low}$ cells per unit volume of the tumor, or results in a reduction of the ratio of EpCAM$^{med/high}$/CD10$^{-/low}$ epithelial cells to normal (EpCam$^{Hi}$/CD10$^{-}$) epithelial cells in the tumor.

In yet another aspect, the invention features a method of reducing metastasis of TNBC in a patient by administering a therapeutically effective dose of an agent that inhibits expression or activity of CDK19.

In some embodiments of all aspects of the invention described herein, the patient is treated with a combination therapy comprising (a) an agent that inhibits expression or activity of CDK19 and (b) radiation therapy and/or chemotherapy.

In some embodiments, the method comprises detecting EpCAM$^{med/high}$/CD10$^{-/low}$ cells in a tissue sample from the patient prior to or after initiating therapy.

In some embodiments, the agent administered to the patient in the methods described herein does not significantly inhibit expression or activity of CDK8. In some embodiments, the agent inhibits expression or activity of CDK19 to a greater extent than it inhibits expression or activity of CDK8.

In some embodiments of the methods describe herein, the agent is a nucleic acid. In some embodiments, the agent is a protein. In some embodiments, the agent is a CRISPR/Cas9 system.

In some embodiments of the methods describe herein, the agent is a CDK19 targeting shRNA.

In some embodiments of the methods describe herein, the agent is a CDK19 targeting siRNA.

In some embodiments of the methods describe herein, the agent is a CDK19 targeting shRNA or siRNA complementary or substantially complementary to the 3' UTR of CDK19, but not to the 3'UTR CDK8.

In some embodiments of the methods describe herein, the agent is a CDK19 targeting shRNA or siRNA complementary or substantially complementary to the coding region of CDK19, but not to the coding region of CDK8.

In some embodiments of the methods describe herein, the agent is a CDK19 targeting shRNA or siRNA selected from: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

In some embodiments, the agent binds CDK19 in the cytoplasm of a breast epithelial cell.

In another aspect, the invention also features a method of predicting the likely therapeutic responsiveness of a subject with TNBC to a CDK19 targeting agent. The method includes (a) quantitating EpCAM$^{med/high}$/CD10$^{-/low}$ cells in a tumor sample obtained from the subject; (b) comparing the quantity of EpCAM$^{med/high}$/CD10$^{-/low}$ cells in (a) to a reference value characteristic of tumors responsive to a CDK19 targeting therapy, and treating the patient with the CDK19 targeting agent if the quantity of EpCAM$^{med/high}$/CD10$^{-/low}$ cells is equal to or exceeds the reference value. In some embodiments, the CDK19 targeting agent is an inhibitor of CDK19 expression or activity

BRIEF DESCRIPTION OF THE DRAWINGS

FIG. 1C: MDA-MB468 cells; and FIG. 1D: HS578T cells) assessed 4 days after transduction with control shRNA or CDK19 targeting shRNA (shCDK19-1, shCDK19-2).

FIG. 1H: PDX-T2; FIG. 1I: PDX-T3; and FIG. 1J: PDX-74) grown in NSG mice.

FIG. 2C is a table showing the number of tumors formed and the number of injections performed for six groups of PDX tumor cells. Populations and injections where tumors formed are bolded. PDX tumor cells were isolated by flow cytometry based on the expression of EpCAM and CD10 (as in FIG. 2A, right)

FIG. 5D is a list of 46 candidate genes determined from the in vitro and the in vivo screens after filtering with the criteria shown in FIG. 5C. CDK19 is boxed.

FIG. 8C shows that CDK19 knockdown effectively prevents the growth of xenograft tumors in a limiting dilution assay.

FIG. 9 shows the amino acid sequence alignment showing 84% sequence homology between CDK19 and CDK8. Amino acid positions are shown above the sequence. Alignment is performed using Clustal W method with MegAlign (DNAStar).

FIG. 10 is a table showing hallmark gene sets found enriched by GSEA of the genes upregulated or downregulated by either CDK19 knockdown or CDK8 knockdown.

FIG. 15 is a table showing the pathological features and patient information for the patient derived xenograft tumors used in the experiments.

DETAILED DESCRIPTION OF THE INVENTION

1. Introduction—CDK19 is Required for Triple-Negative Breast Cancer (TNBC) Growth We have discovered that reducing expression or activity of CDK19 in TNBC cell lines or breast cancer patient derived xenografts in mice inhibits growth and metastases of Triple Negative Breast Cancer (TNBC) tumors. See § 4 below (Examples). We have also shown that the biological functions of CDK19 are distinct from those of its paralog, CDK8, and that the CDK19-mediated effect on TNBC tumors is independent of CDK8 activity. These data demonstrate that TNBC can be treated by agents that inhibit CDK19 but do not inhibit CDK8, or agents that preferentially inhibit CDK19 compared to CDK8. The discovery that inhibition of CDK19 is necessary and sufficient for inhibition of TNBC growth and metastases is significant, in part, because of the potential advantages of CDK19 as a therapeutic target. Compared to other ubiquitous transcriptional co-factors, such as CDK8, CDK9, and BRD4, CDK19 has more limited tissue distribution, suggesting reduced toxicity and a broader therapeutic window for CDK19 inhibitors.

Figure 8A:
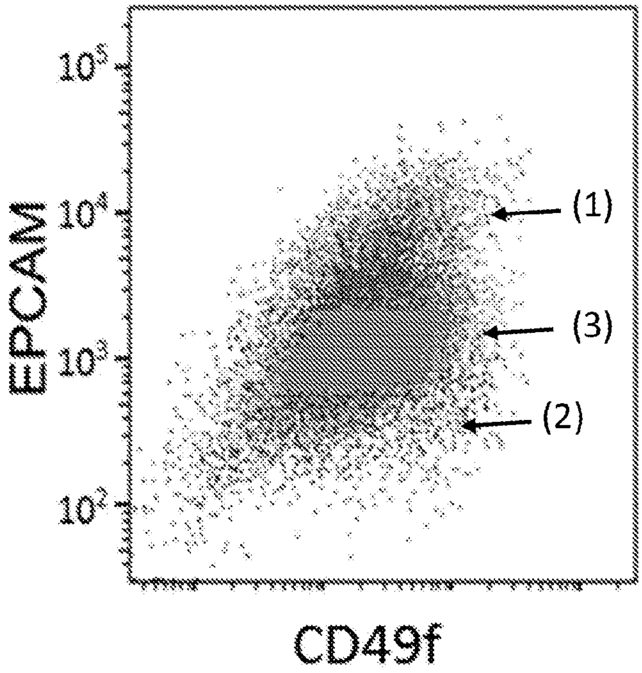
FIG. 8A is a graph showing the flow cytometry analyses of TNBC (PDX-T1) using EpCAM and CD49f and the overlap of the $EpCAM^{med/high}/CD10^{-/low}$ (1), $EPCAM^{low/med}/CD10^{low/+}$ (3) and $EpCAM^{-}/CD10^{-}$ ((2)) sub-populations.

In addition to demonstrating that CDK19 knockdown had tumor growth inhibitory effects, CDK19 expression was also shown to be enriched in tumor initiating cells, e.g., tumorigenic cells having $EpCAM^{med/high}/CD10^{-/low}$ expressions, compared to the less tumorigenic cells, e.g., cells having $EPCAM^{low/high}/CD10^{low/+}$ expressions (see, e.g., Example 4). Further studies also showed that CDK19 knockdown significantly decreased tumor initiating frequencies (FIG. 8D). This discovery indicates that, compared to other agents, targeting CDK19 will result in a more pronounced and significant effect on highly tumorigenic (e.g., tumor initiating) cells. These discoveries also allow development of theranostic methods for identifying certain TNBC patients likely to respond to CDK19 targeted therapy.

2. Definitions

2.1 Triple-Negative Breast Cancer (TNBC)

Triple-negative breast cancer (TNBC) is a breast cancer subtype characterized by lack of expression of estrogen receptor (ER), progesterone receptor (PR), and human epidermal growth factor receptor 2 (Her2). Receptor expression can be measured by immunohistochemical staining or other methods. TNBC is generally a diagnosed by exclusion. Widely used breast cancer therapies that target these receptors are not effective against TNBC, making TNBC treatment particularly challenging.

2.2 Cyclic-Dependent Kinase 19 (CDK19)

Cyclic-Dependent Kinase 19 (CDK19) is described in Broude et al., *Curr. Cancer Drug Targets* 15:739, 2015 and Sato et al., *Molecular Cell* 14:685-691, 2004. CDK19 belongs to a subset of the CDK family that is reportedly more associated with regulation of RNA polymerase II (RNAPII) transcription (see, e.g., Galbraith et al., *Transcription* 1: 4-12, 2010) than cell cycle progression. See UniProt entry NP_055891.1; Genbank entries AY028424 & AL603914. The mRNA sequences for CDK19 are also disclosed herein (e.g., SEQ ID NOs:12-15).

2.3 Cyclic-Dependent Kinase 8 (CDK8)

CDK8 is a paralog of CDK19 with 84% amino acid sequence homology to CDK19. See FIG. 9. CDK8 is described in Broude et al., *Curr. Cancer Drug Targets* 15:739, 2015 and Sato et al., *Molecular Cell* 14:685-691, 2004. See UniProt entry CAA59754.1; Genbank entries X85753 & AL590108. The mRNA sequences for CDK8 are also disclosed herein (e.g., SEQ ID NOs:16-18).

2.4 Agent

As used here, the term "agent" refers to a biological molecule (e.g., nucleic acids, proteins, peptides, antibodies) or small organic molecule (e.g., having a molecular weight less than 1000, usually less than 500) that can reduce or inhibit the expression or activity of CDK19.

2.5 Inhibitors

As used herein, the term "inhibitor" as used in the context of CDK19, refers to a compound, composition or system that reduces the expression or activity of CDK19. An agent may also selectively inhibit CDK19 expression or activity over that of CDK8.

2.6 Knockdown

As used herein, the term "knock down" refers to a reduction in the expression level of the CDK19 gene. Knocking down CDK19 gene expression level may be achieved by reducing the amount of mRNA transcript corresponding to the gene, leading to a reduction in the expression level of CDK19 protein. Knocking down CDK19 gene expression level may also be achieved by reducing the amount of CDK19 protein. An knockdown agent is an example of an inhibitor.

2.7 Knockout

As used herein, the term "knock out" refers to deleting all or a portion of the CDK19 gene in a cell, in a way that interferes with the function of the CDK19 gene. For example, a knock out can be achieved by altering the CDK19 sequence. Those skilled in the art will readily appreciate how to use various genetic approaches, e.g., CRISPR/Cas systems, to knockout the CDK19 gene or a portion thereof. An knockout agent is an example of an inhibitor.

2.8 Reduction Relative to a Reference Level

As used here, the terms "decrease," "reduced," "reduction," and "decreasing" are all used herein to refer to a decrease by at least 10% as compared to a reference level, for example a decrease by at least about 5%, at least about 10%, at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

2.9 Nucleic Acids

As used herein, the terms "polynucleotide," "nucleic acid," and "oligonucleotide" are used interchangeably and refer to a polymeric form of nucleotides of any length, either deoxyribonucleotides or ribonucleotides or analogs thereof. A polynucleotide can comprise modified nucleotides, such as methylated nucleotides and nucleotide analogs, or otherwise be modified by art-known methods to render the polynucleotide resistant to nucleases, improve delivery of the polynucleotide to target cells or tissues, improve stability, reduce degradation, improve tissue distribution or to impart other advantageous properties. For example, the DNA or RNA polynucleotide may include one or more modifications on the oligonucleotide backbone (e.g., a phosphorothioate modification), the sugar (e.g., a locked sugar), or the nucleobase. If present, modifications to the nucleotide structure can be imparted before or after assembly of the oligonucleotide. The sequence of nucleotides can be interrupted by non-nucleotide components. An oligonucleotide can be further modified after polymerization, such as by conjugation with a label component, a targeting component, or other component. Polynucleotides may be double-stranded or single-stranded molecules. Furthermore, in order to improve the oligonucleotide delivery, the DNA or RNA oligonucleotide may be packaged into a lipid molecule (e.g., lipid nanoparticles) or be conjugated to a cell-penetrating peptide.

2.10 Treatment

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, can include treatment resulting in inhibiting the disease, i.e., arresting its development; and relieving the disease, i.e., causing regression of the disease. For example, in the case of cancer, a response to treatment can include a reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs and/or described in Eisenhauer, EA1, et al. "*New response evaluation criteria in solid tumours: revised RECIST guideline* (*version* 1.1)." European journal of cancer 45.2 (2009): 228-247.

2.11 Administration

As used herein, the term "administering" or "administration" includes any route of introducing or delivering an agent that inhibits the expression or activity of CDK19 to the subject diagnosed with TNBC. Administration can be carried out by any route suitable for the delivery of the agent. Thus, delivery routes can include, e.g., intravenous, intramuscular, intraperitoneal, or subcutaneous deliver. In some embodiments, the agent is administered directly to the tumor, e.g., by injection into the tumor.

2.12 Therapeutically Effective Dose

As used here, the term "therapeutically effective amount" refers to an amount, e.g., pharmaceutical dose, effective in inducing a desired biological effect in a subject or patient or in treating a patient having TNBC described herein. The term "therapeutically effective amount" refers to an amount of an active agent being administered that will treat to some extent a disease, disorder, or condition, e.g., TNBC, relieve one or more of the symptoms of the disease being treated, and/or that amount that will prevent, to some extent, one or more of the symptoms of the disease that the subject being treated has or is at risk of developing. For example, for a given parameter (e.g., tumor volume, tumor diameter, metastases, etc.), a therapeutically effective amount will show an increase or decrease of therapeutic effect of at least 5%, 10%, 15%, 20%, 25%, 30%, 40%, 50%, 60%, 70%, 80%, 90%, or 100%, or at least 1-fold, 2-fold, or 3-fold. A therapeutically effective dose is usually delivered over a course of therapy that may extend for a period of days, weeks, or months. A therapeutically effective dose of an agent may be taken alone or in combination with other therapeutic agents. In some cases, a therapeutically effective amount of a CDK19 inhibitor is am amount sufficient to effect a partial response in a patient with TNBC (e.g., a greater than 20% reduction, sometimes a greater than 30% reduction, in the measurable diameter of lesions).

2.13 Patient or Subject

A "patient" or "subject," as used herein, is intended to include either a human or non-human animal, preferably a mammal, e.g., non-human primate. Most preferably, the subject or patient is a human.

2.14 Antisense Strand

A "antisense strand" refers to the strand of a double stranded RNAi agent (siRNA or shRNA) which includes a region that is complementary or substantially complementary to a target sequence (e.g., a human CDK8 or CDK19 mRNA including a 5' UTR, exons of an open reading frame (ORF), or a 3' UTR). Where the region of "complementarity" or "substantially complementary" need not be fully complementary to the target sequence and may have sequence % identity or % similarity of least 70%, 75%, 80%, 85%, 90%, 95%, or 100%.

2.15 Sense Strand

A "sense strand," as used herein, refers to the strand of a RNAi agent (siRNA or shRNA) that includes a region that is complementary or substantially complementary to a region of the antisense strand.

3. Methods of Treatment

In one approach the invention provides a method of treating a patient diagnosed with triple-negative breast cancer (TNBC), comprising administering a therapeutically effective dose of an agent that inhibits expression or activity of cyclin-dependent kinase 19 (CDK19). In some embodiments, the treatment results in an at least 10% reduction in tumor volume within 6 month of initiating therapy.

In one approach the invention provides a method of treating a patient diagnosed with triple-negative breast cancer (TNBC), wherein the cancer is characterized by a tumor comprising $EpCAM^{med/high}/CD10^{-/low}$ epithelial cells, the method comprising administering a therapeutically effective dose of an agent that inhibits cyclin-dependent kinase 19 (CDK19) expression or activity, wherein the treatment results in a reduction of the ratio of cells having a medium to high expression level of EpCAM and a low expression level of CD10 to normal cells in the tumor. In some embodiments, the method includes the step of detecting $EpCAM^{med/high}/CD10^{-/low}$ epithelial cells in a tissue sample from the patient prior to or after initiating therapy.

To determine the phenotype of a tumor or to assess treatment prognosis, a biopsy may be obtained from the patient diagnosed with TNBC. A biopsy may be a needle biopsy, or may be a liquid biopsy be obtained from blood vessels and/or lymph nodes that supply the breast, e.g., internal mammary arteries, lateral thoracic arteries, thoracoacromial arteries, axillary lymph nodes.

As described in § 4, below, CD10 and EpCAM biomarkers identify three distinct sub-populations of Tumor Initiating Cells (TICs) in TNBC. $EpCAM^{med/high}/CD10^{-/low}$, $EPCAM^{low/med}/CD10^{low/+}$, and $EpCAM^{-}/CD10$. The phenotype of cancer cells in a TNBC patient can be determined using art-known methods. In one approach a tissue is obtained from the patient and the cell phenotype determined using immunohistochemistry, mass spectrometry analysis, fluorescence activated cell sorting (FACS) or other methods. The cell phenotype can be assigned relative to standard values characteristic of health or cancerous tissue. In one approach the ratio of $EpCAM^{med/high}/CD10^{-/low}$ cells to normal breast epithelial cells is determined prior to initiation of treatment to assess the likely response of the patient to CDK19 targeted therapy. In one approach a change in the ratio of $EpCAM^{med/high}/CD10^{-/low}$ cells to normal cells, or a change in the quantity of $EpCAM^{med/high}/CD10^{-/low}$ cells per volume tissue is detected after initiation of treatment.

In one approach the invention provides a method for reducing metastasis of TNBC in a patient, the method comprising administering a therapeutically effective dose of an agent that inhibits expression or activity of CDK19

In some embodiments, methods of the invention may be used to treat inflammatory TNBCs or TNBCs that are chemo-resistant. In other embodiments, the methods of the invention may be used to slow down or prevent the metastasis of TNBCs. In further embodiments, the methods described herein that target the CDK19 gene or its corresponding protein may further modulate clinically relevant TNBC pathways regulated by CDK19, such as P53 signaling, KRAS signaling, androgen response, NOTCH signaling, TGF BETA signaling, and IL6-JAK-STAT3 signaling (FIG. 3B), and make them more therapeutically susceptible to cancer treatments.

3.1 Therapeutic Agents (Inhibitors)

3.1.1. Polynucleotides

As demonstrated in the examples, the CDK19 gene is essential for the growth of TNBC. Methods of treating TNBC in a subject as described herein may be accomplished by administering a polynucleotide (e.g., oligonucleotide) to the subject to decrease or inhibit the expression of the CDK19 gene. In some embodiments, the polynucleotide may be, for example, a DNA oligonucleotide or an RNA oligonucleotide. In other embodiments, the oligonucleotide may be used in a CRISPR/Cas system. An oligonucleotide that inhibits or decreases the expression of the CDK19 gene may knock out or knock down the CDK19 gene (e.g., the CDK19 gene in a TNBC cell) in the subject.

In some embodiments, the oligonucleotide may be an shRNA or an miRNA. In some embodiments, the oligonucleotide may mediate an RNase H-dependent cleavage of the mRNA transcript of the CDK19 gene. In other embodiments, the oligonucleotide may be used in a CRISPR/Cas system.

In some embodiments, the mRNA transcript of the CDK19 gene may be targeted for cleavage and degradation. Different portions of the mRNA transcript may be targeted to decrease or inhibit the expression of the CDK19 gene. In some embodiments, a DNA oligonucleotide may be used to target the mRNA transcript and form a DNA:RNA duplex with the mRNA transcript. The duplex may then be recognized and the mRNA cleaved by specific proteins in the cell. In other embodiments, an RNA oligonucleotide may be used to target the mRNA transcript of the CDK19 gene.

3.1.1.1. shRNA

A short hairpin RNA or small hairpin RNA (shRNA) is an artificial RNA molecule with a hairpin turn that can be used to silence target gene expression via the small interfering RNA (siRNA) it produced in cells. See, e.g., Fire et. al., *Nature* 391:806-811, 1998; Elbashir et. Al., *Nature* 411:494-498, 2001; Chakraborty et al. *Mol Ther Nucleic Acids* 8:132-143, 2017; Bouard et al., *Br. J. Pharmacol.* 157:153-165, 2009. Expression of shRNA in cells is typically accomplished by delivery of plasmids or through viral or bacterial vectors. Suitable bacterial vectors include but not limited to adeno-associated viruses (AAVs), adenoviruses, and lentiviruses. Once the vector has integrated into the host genome, the shRNA is then transcribed in the nucleus by polymerase II or polymerase Ill depending on the promoter choice. The resulting pre-shRNA is exported from the nucleus and then processed by Dicer and loaded into the RNA-induced silencing complex (RISC). The sense strand is degraded by RISC and the antisense strand directs RISC to an mRNA that has a complementary sequence. A protein called Ago2 in the RISC then cleaves the mRNA, or in some cases, represses translation of the mRNA, thus, leading to its destruction and an eventual reduction in the protein encoded by the mRNA. Thus, the shRNA leads to targeted gene silencing. shRNA is an advantageous mediator of siRNA in that it has relatively low rate of degradation and turnover.

In some embodiments, the methods described herein include treating TNBC in a subject using an shRNA. The methods may include administering to the subject a therapeutically effective amount of a vector, wherein the vector includes a polynucleotide encoding an shRNA capable of hybridizing to a portion of an mRNA transcript of the CDK19 gene. In some embodiments, the vector may also include appropriate expression control elements known in the art, including, e.g., promoters (e.g., tissue specific promoters), enhancers, and transcription terminators. Once the vector is delivered to the TNBC cell, the shRNA may be integrated into the cell's genome and undergo downstream processing by Dicer and RISC (described in detail further herein) to eventually hybridize to the mRNA transcript of the CDK19 gene, leading to mRNA cleavage and degradation. In some embodiments, the shRNA may include a nucleic acid sequence that has at least 85% sequence identity to the sequence of GCGAGAATTGAAGTACCTTAA (SEQ ID NO: 1) or the sequence of ACCAGCAAATATCCTAGTAAT (SEQ ID NO: 2). In particular embodiments, the shRNA may target the amino acids at the N-terminus of an mRNA transcript of the CDK19 gene. In other embodiments, the shRNA may target the amino acids at an internal region of an mRNA transcript of the CDK19 gene.

Figure 1A:
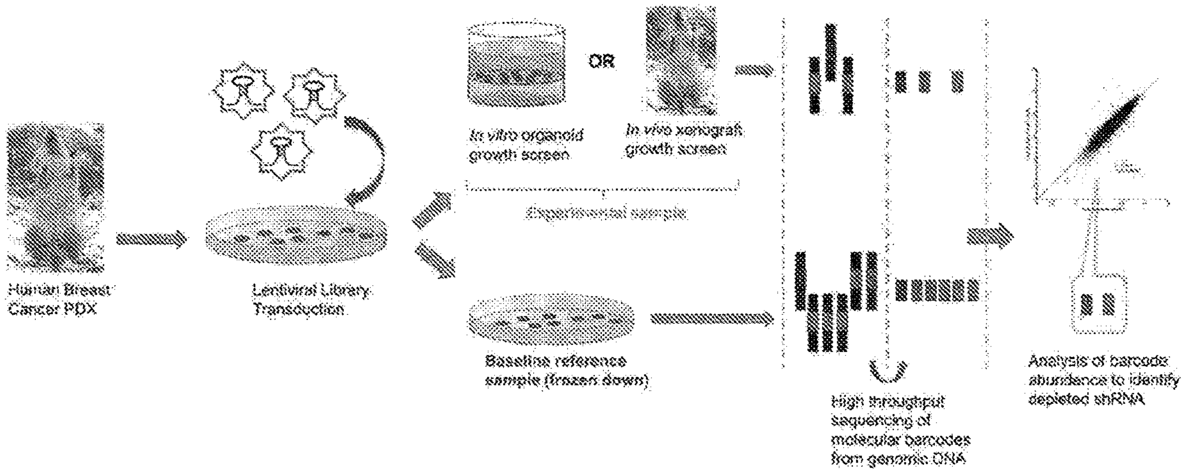
FIG. 1A is a schematic for RNAi dropout viability screens. Two separate screens were performed in a TNBC PDX (PDX-T1). Cells in one experiment were grown in vitro as organoid colonies and in the other in vivo as PDXs in NSG mice.
Figure 1B:
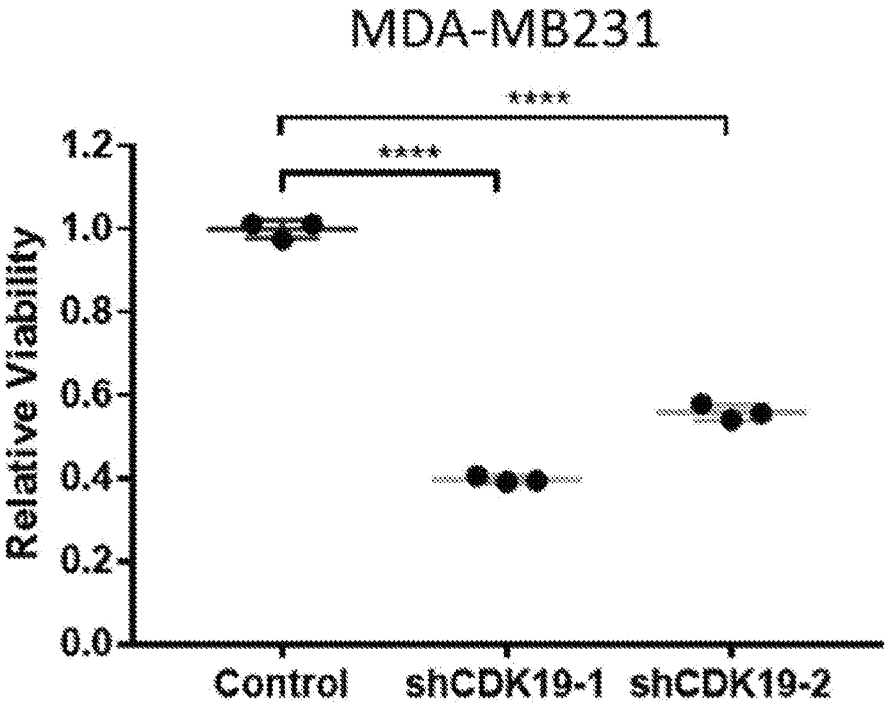
FIGS. 1B-1D are graphs showing that CDK19 knockdown significantly decreased the viability of TNBC cells (FIG. 1B: MDA-MB231 cells.
Figure 1C:
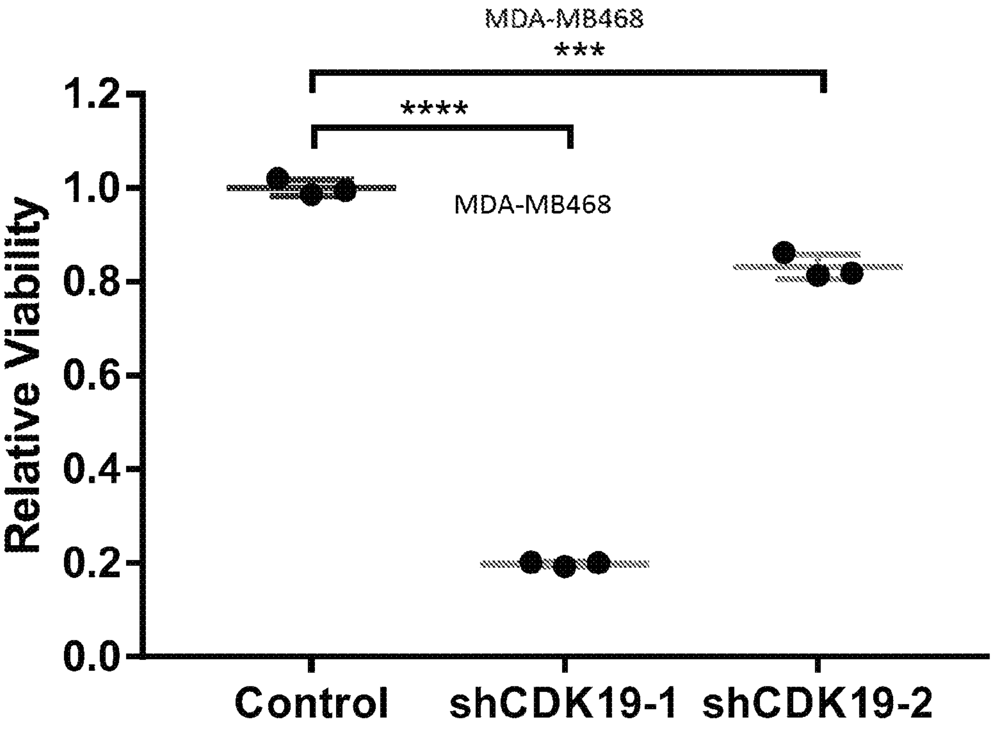
Figure 1D:
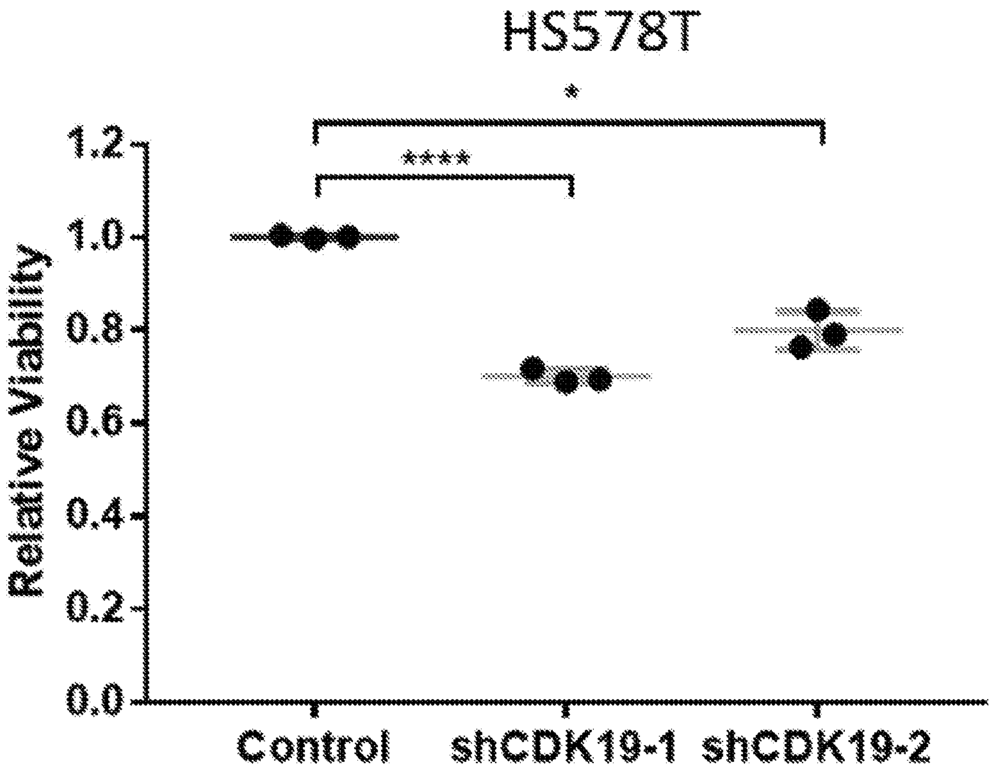

As demonstrated in the Examples, e.g., FIGS. 1G-1J, both shRNAs (GCGAGAATTGAAGTACCTTAA (SEQ ID NO: 1) and ACCAGCAAATATCCTAGTAAT (SEQ ID NO: 2)) targeted against the CDK19 gene were able to knockdown the gene, which led to a significant reduction in the percentage of RFP positive cells in tumors from all three TNBC PDXs. Further, CDK19 knockdown also inhibited the growth of an aggressive PDX obtained from the brain metastasis of a patient with a chemotherapy-resistant inflammatory breast cancer (FIG. 1J), which was known to be aggressive, difficult to treat, and associated with extremely poor prognoses. In addition to inhibiting tumor growth, shRNAs also inhibited the lung metastases of these tumors in mice (FIG. 1L).

In some embodiments, an shRNA targeted against the CDK19 gene may have at least 85% sequence identity (e.g., 87%, 89%, 91%, 93%, 95%, 97%, or 99% sequence identity) to GCGAGAATTGAAGTACCTTAA (SEQ ID NO: 1). In other embodiments, an shRNA targeted against the CDK19 gene may have at least 85% sequence identity (e.g., 87%, 89%, 91%, 93%, 95%, 97%, or 99% sequence identity) to ACCAGCAAATATCCTAGTAAT (SEQ ID NO: 2). In other embodiments, an shRNA targeted against the CDK19 gene may have at least 85% sequence identity (e.g., 87%, 89%, 91%, 93%, 95%, 97%, or 99% sequence identity) to GCTTGTAGAGAGATTGTACTT (SEQ ID NO: 3). In some embodiments, an shRNA targeted against the CDK19 gene may have at least 85% sequence identity (e.g., 87%, 89%, 91%, 93%, 95%, 97%, or 99% sequence identity) to GAGGACTGATAGTTCTTCTTT (SEQ ID NO: 4). In other embodiments, an shRNA targeted against the CDK19 gene may have at least 85% sequence identity (e.g., 87%, 89%, 91%, 93%, 95%, 97%, or 99% sequence identity) to GATATTAGAAAGATGCCAGAA (SEQ ID NO: 5). In other embodiments, an shRNA targeted against the CDK19 gene may have at least 85% sequence identity (e.g., 87%, 89%, 91%, 93%, 95%, 97%, or 99% sequence identity) to GCCAACAGTAGCCTCATAAAG (SEQ ID NO: 6). In other embodiments, an shRNA targeted against the CDK19 gene may have at least 85% sequence identity (e.g., 87%, 89%, 91%, 93%, 95%, 97%, or 99% sequence identity) to CGTTCGTATTTATCTAGTTTC (SEQ ID NO: 7). In other embodiments, an shRNA targeted against the CDK19 gene may have at least 85% sequence identity (e.g., 87%, 89%, 91%, 93%, 95%, 97%, or 99% sequence identity) to GCATGACTTGTGGCATATTAT (SEQ ID NO: 8). In other embodiments, an shRNA targeted against the CDK19 gene may have at least 85% sequence identity (e.g., 87%, 89%, 91%, 93%, 95%, 97%, or 99% sequence identity) to GCTTGTAGAGAGATTGCACTT (SEQ ID NO: 9). In other embodiments, an shRNA targeted against the CDK19 gene may have at least 85% sequence identity (e.g., 87%, 89%, 91%, 93%, 95%, 97%, or 99% sequence identity) to AGGACTGATAGCTCTTCTTTA (SEQ ID NO: 10). In yet other embodiments, an shRNA targeted against the CDK19 gene may have at least 85% sequence identity (e.g., 87%, 89%, 91%, 93%, 95%, 97%, or 99% sequence identity) to GTATGGCTGCTGTTTGATTAT (SEQ ID NO: 11). One of skill in the art has the knowledge and capability to design shRNAs that target different portions of the CDK19 gene (e.g., the 5' UTR region or the 3' UTR region) to achieve the desired reduction in expression of the gene. For example, available tools for designing shRNAs include, e.g., Project Insilico, Genomics and Bioinformatics Group, LMP, CCR, NIH. In some embodiments, an shRNA may be designed to knockout the CDK19 gene.

CDK8 and CDK19 shRNA

There are a number of structural elements that can affect shRNA efficacy. For specific RNAi knockdown of a desired target gene an shRNA can be designed in consideration of its multiple structural elements. Generally, an shRNA should be about 80 nucleotides in length and designed (from 5' to 3') to comprise of the following structural elements to make the hairpin structure of the shRNA: (1) a sense strand (e.g., upper stem); (2) followed by a hairpin loop; (3) an antisense strand (e.g., lower stem or guide strand) that has perfect or near perfect complementary to the target mRNA and is antisense to the target mRNA; (4-5) two cleavage motifs such as, "U" or "UH" at the first position of the guide strand, and "UUC" or "CUUC" at the tail region of the guide strand; and (6) arbitrary spacer nucleotides of about two nucleotides in length between the first nucleotide of guide strand "U" motif and the hairpin loop, and between the last nucleotide of the sense strand and the hairpin loop. The sense strand and antisense strand, making up the stem, may be designed to consist of a range from about 19 to 29 nucleotides in length, which will form the stem. The loop structure may be designed to consist of a range about 2 to 15 nucleotides in length, and preferably free of any internal secondary structure. Some examples of sequences that may be used for making the hairpin loop, include but are not limited to, a nine nucleotide loop comprising the sequence (TTCAAGAGA), and a seven nucleotide loop comprising the sequence (TCAAGAG). Other design strategies can be found in the relevant disclosure of Ros XB-D, Gu S. Guidelines for the optimal design of miRNA-based shRNAs. Methods (San Diego, Calif.) 2016; 103:157-166, which is herein incorporated by reference in its entirety for all purposes. There are also several design programs available such as, The RNAi Consortium software from The Broad Institute, which is made available through Sigma-Aldrich and Thermo-Fisher Scientific.

The specificity of the target sequence should also be considered, as many mRNAs can share similar sequences. Care should be taken in selecting target sequence that has low sequence homology to other genes in the genome to allow for gene-specific knockdown. Where a gene has multiple forms, to achieve complete knockdown of gene expression, shRNA should target sequences shared among all isoforms of the target mRNA.

Figure 17:
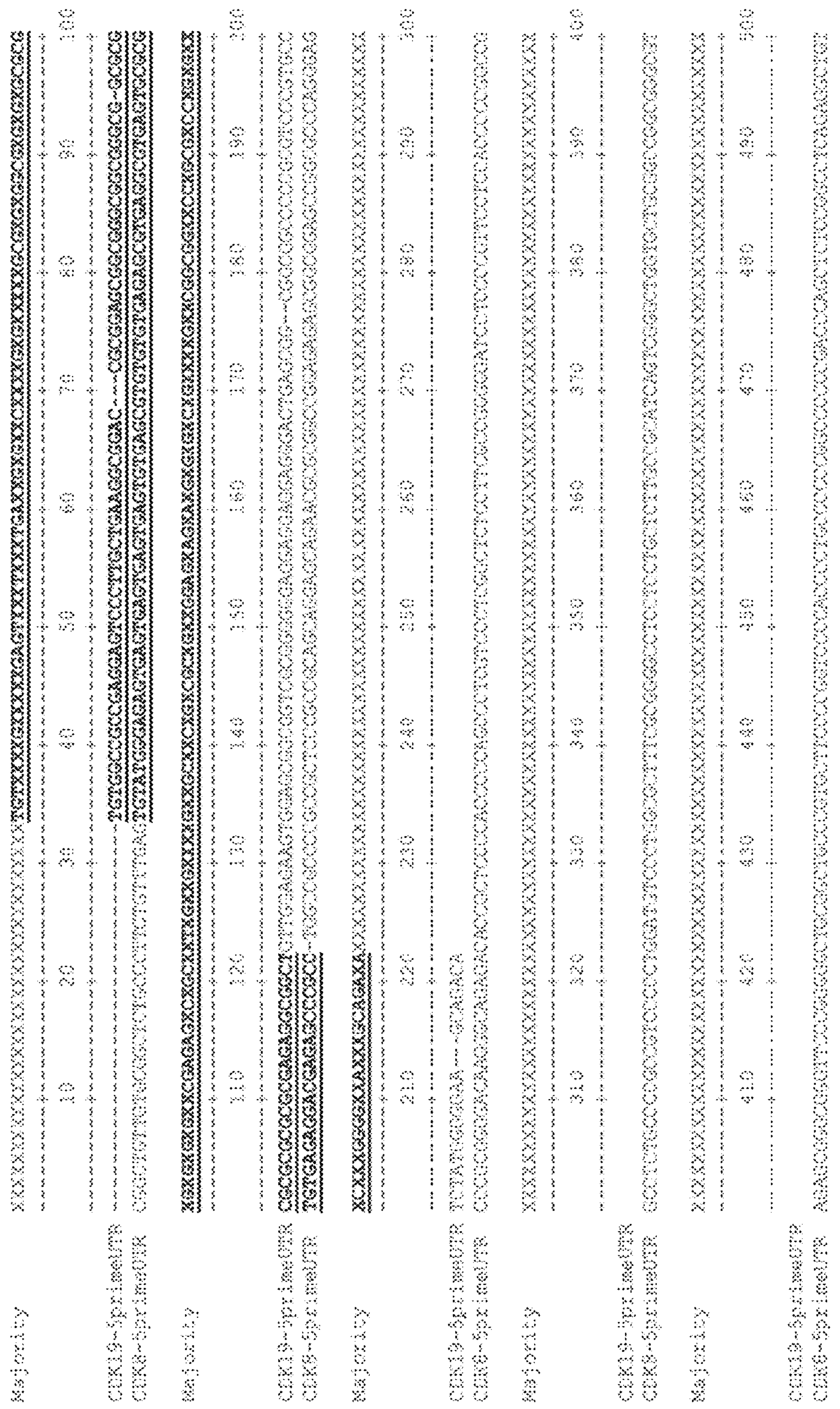
FIG. 17 shows a nucleic acid alignment of the 5' UTR of CDK8 and CDK19. The underlined and bolded text indicates the overlapping regions.

An alignment of CDK19 and CDK8 mRNA sequences can identify not identical or low percent identity or similarity nucleotide sequence regions which can be used to design shRNAs that have a preference to target to CDK19 mRNA but not CDK8, see for example the 3' UTR and 5' UTR alignments in FIG. 16 and FIG. 17.

In some embodiments, shRNA that targets a CDK19 mRNA transcript, and not of CDK8 mRNA transcript can be designed. In one approach the mRNA sequences for human CDK19 and CDK8 from National Center for Biotechnology Information (NCBI, found at Pubmed.gov) and an alignmenti is performed (e.g., with pairwise alignment program such as, LALIGN). A region of about 19 to 29 contiguous nucleotides (e.g., 19-20, 19-21, 19-22, 19-23, 19-24, 19-25, 19-26, 19-27, 19-28, or 19-29) in length is selected based on low sequence identity (e.g., less than 75%, identity, sometimes less than 70% identity, sometimes less than 60% identity. In some embodiments the 19 to 29 nt region has very low (e.g., less than 40%, less than 30% or less than 20% or sequence identity. The contiguous sequence can be in a protein coding region, the 5'-UTR, the 3'-UTR, or span two regions.

In one embodiment, target-specific knockdown of CDK19 can be accomplished by designing an shRNA with a guide strand that is complementary of the 3' UTR region of CDK19 (SEQ ID NO:42) and has low or no homology to the 3'UTR of CDK8 (SEQ ID NO:44). The guide strand may be 19, 20, 21, 22, 23, 24, 25, 26, 27, 28, or 29 nucleotides in length. Some exemplary sequence regions that may be used to design a CDK19 shRNA, include but are not limited to, CTCCAGCTCCCGTTGGGCCAGGCCAGCCC (SEQ ID NO: 20), AGCCCAGAGCACA GGCTCCAGCAATATGT (SEQ ID NO: 21), CTGCATTGAAAAGAAC-CAAAAAAATGCAA (SEQ ID NO: 22), ACTATGATGC-CATTTCTATCTAAAACTCA (SEQ ID NO: 23), TACA-CATGGGAG GAAAACCTTATATACTG (SEQ ID NO: 24), AGCATTGTGCAGGACTGATAGCTCTTCTT (SEQ ID NO: 25), TATTGACTTAAAGAAGATTCTTGT-GAAGT (SEQ ID NO: 26), TTCCCCTATCTCAGCA CCCCTTCCCTGCA (SEQ ID NO: 27), TGTGTTCCAT-TGTGACTTCTCTGATAAAG (SEQ ID NO: 28), CGTCT-GATCTAATCCCAGCACTTCTGTAA (SEQ ID NO: 29), or CCTTCAGCATTTCTTT GAAGGATTCTATC (SEQ ID NO: 30). One of ordinary skill guided by this disclosure understands that other low homology sequence regions in the '3 UTR could also be used. See, for example, FIGS. 16A-D the low homology sequence regions from (1-1186) and (2418-4570). In one embodiment, the shRNA may be designed to be targeted to upstream of CDK19, downstream of CDK19, or in the exons of CDK19. In some cases the expression of the CDK19 shRNA results in knockdown of CDK19 at least about 25%, 50%, 75%, 80%, 85%, 90%, 95%, 96%, 97%, 98%, 99%, or 100%. In another embodiment the expression of the CDK19 shRNA can preferentially knockdown CDK19 compared to CDK8.

To make shRNAs that preferentially target CDK19 one would identify a unique region of CDK19, a region that does not have significant homology to other CDKs (e.g., CDK8) or other mRNAs in the genome. One would use this sequence to make a guide strand that is antisense to this target and comprises 19 to 29 nucleotides in length. To make the expression cassette one would add an appropriate promoter such as a pol II or pol III promotor at the beginning of the cassette, followed by the complementary sense strand (e.g., complementary to the targeting guide strand), which is them followed by the loop structure of about 2 to 15 nucleotides in length. In addition, the two Ago cleavage motifs, "U" or "UH" should be included at the first position of the guide strand, and "UUC" or "CUUC" at the tail region of the guide strand along to 1-2 spacer nucleotides at the end of the loop structure. See, for example US Application No. US2008/0293142 and Ros XB-D, Gu S. Guidelines for the optimal design of miRNA-based shRNAs. Methods (San Diego, Calif.) 2016; 103:157-166, which is herein incorporated by reference in its entirety for all purposes.

In another embodiment, target-specific knockdown of CDK8 can be performed by using an shRNA with a guide strand that comprises a complementary to the 5'UTR of CDK8 (SEQ ID NO: 43) and has low or no homology to the 5' UTR of CDK19 (SEQ ID NO:41). The guide strand may be 19, 20, 21, 22, 23, 24, 25, 26, 27, 28 or 29, nucleotides in length. Some exemplary sequences that may be used to design a CDK8 shRNA include but are not limited to, TGGCCGCCCCGCCGCTCCCGCCGCAGCAG (SEQ ID NO: 31), GAGCAGAACGCGCGGCCGGAGAGAGCGGC (SEQ ID NO: 32), GGAGCCGGCGCCCAGGGAGCCCGCGGGGA (SEQ ID NO: 33), CAAGGGCAGAGACACCGCTCCCCACCCCC (SEQ ID NO: 34), AGCCCTCGTCCCTCGGCTCTCCTTCGCCG (SEQ ID NO: 35), GGGGATCCTCCCCGTTCCTCCACCCCCGG (SEQ ID NO: 36), CCGGCCTCTGCCCCGCCGTCCCCCTGGAT (SEQ ID NO: 37), GTCCCTGGCGCTTTCGCGGGGCCTCCTCC (SEQ ID NO: 38), TGCTCTTGCCGCATCAGTCGGGCTGGTGC (SEQ ID NO: 39), or TGCGGCCGGCGGGCGTAGAGCGGGCGGGT (SEQ ID NO: 40). One of ordinary skill in the art would understand that other low homology sequence regions in the '5 UTR could also be used. See, for example, FIG. 17 the low homology sequence regions from (1-33) or (223-504). In another embodiment the shRNA may be designed to be targeted to upstream of CDK8, downstream of CDK8, or in the exons of CDK8. In some cases, the expression of the CDK8 shRNA can result in a knockdown of CDK8 at least about 25%, 50%, 75%, 80%, 85%, 90%, 95%, 96%, 97%, 98%, 99%, or 100%.

To make shRNAs that preferentially target CDK8 one would identify a unique region of CDK8, a region that does not have significant homology to other CDKs (e.g., CDK19) or other mRNAs in the genome. One would use this sequence to make a guide strand that is antisense to this target and comprises 19 to 29 nucleotides in length. To make the expression cassette one would add an appropriate promoter such as a pol II or pol III promotor at the beginning of the cassette, followed by the complementary sense strand (e.g., complementary to the targeting guide strand), which is them followed by the loop structure of about 2 to 15 nucleotides in length. In addition, the two Ago cleavage motifs, "U" or "UH" should be included at the first position of the guide strand, and "UUC" or "CUUC" at the tail region of the guide strand along to 1-2 spacer nucleotides at the end of the loop structure. See, for example US Application No. US2008/0293142 and Ros XB-D, Gu S. Guidelines for the optimal design of miRNA-based shRNAs. Methods (San Diego, Calif.) 2016; 103:157-166, which is herein incorporated by reference in its entirety for all purposes.

The specificity or knockdown level of an shRNA or siRNA can be confirmed using real-time PCR analysis for mRNA level or ELISA assay for the protein level. Experimental controls may be run in parallel to assess knockdown. Some examples of experimental controls that may be used, include but are not limited to, a mock-infected or mock-transfected sample, an empty vector, an shRNA encoding a scrambled target or seed region, an shRNA targeting another gene entirely such as, housekeeping genes GAPDH or Actin, or a GFP positive control.

To determine if an siRNA or shRNA (e.g., RNAi agent) preferentially targets CDK19 over CDK8 one can transfect or transduce the shRNA or siRNA tagged to marker such as GFP in a cell line or other expression system, select the GFP positive cells (e.g. transformed cells), and determine the level of CDK19 knockdown relative to CDK19 expression in the cell system without transfection or transduction with the RNAi agent. In some embodiments, the expression of RNA is measured. In other embodiments, the expression of the protein is measured. In one example, mRNA may be measured by any PCR-based assay known in the art (e.g., RT-PCR or qRT-PCR or the like). In one example, the protein level may be measured by an immunoassay (e.g., ELISA assay or any antibody-based method known in the art).

In some embodiments, a targeting CDK19 shRNA or siRNA results in CDK19 expression less than about 30% and CDK8 greater than about 70% relative to a system without transfection or transduction. In some other embodiments, a targeting CDK19 shRNA or siRNA results in CDK19 expression at less than about 50% and CDK8 greater than about 95%. In some embodiments, a targeting CDK19 shRNA or siRNA results in CDK19 expression less than about 5% and CDK8 greater than about 80%. In some embodiments, a targeting CDK19 shRNA or siRNA results in CDK19 expression less than about 1% and CDK8 greater than about 60%. In some embodiments, a targeting CDK19 shRNA or siRNA results in CDK19 expression at less than about 0.5% and CDK8 greater than about 90%. In some embodiments, a targeting CDK19 shRNA results in CDK19 expression at about 0% and CDK8 at about 100% relative to a system without transfection or transduction. In some embodiments, the expression of RNA is measured. In other embodiments, the expression of the protein is measured.

CDK8 and CDK19 siRNA

The present disclosure also provides siRNA-based therapeutics for inhibiting expression of CDK8 and CDK19 in a patient with triple-negative breast cancer. The double stranded RNAi therapeutic includes a sense strand complementary to an antisense strand. The sense or antisense strands of the siRNA may be about 14, 15, 16, 17, 18, 19, 20, 21, 22, 23, 24, 25, 26, 27, 28, 29, or 30 nucleotides in length. The antisense strand of the siRNA-based therapeutic includes a region complementary to a part of an mRNA encoding CDK8 or CDK19. Additional methods to make therapeutic siRNA can be found in U.S. Pat. No. 9,399,775, which is incorporated by reference in its entirety for all purposes.

In some cases, the expression of CDK19 siRNA may result in a knockdown of CDK19 at least about 25%, 50%, 75%, 80%, 85%, 90%, 95%, 96%, 97%, 98%, 99%, or 100%. In another embodiment, the expression of CDK19 siRNA may preferentially knockdown CDK19 compared to CDK8. In some cases, the expression of CDK8 siRNA may result in a knockdown of CDK8 at least about 25%, 50%, 75%, 80%, 85%, 90%, 95%, 96%, 97%, 98%, 99%, or 100%.

In a preferred embodiment, CDK19 siRNA may result in a knockdown of CDK19 at least about 25%, 50%, 75%, 80%, 85%, 90%, 95%, 96%, 97%, 98%, 99%, or 100% and CDK8 at least about 10%, 14%, 15%, 16%, 17%, 18%, 19%, 20%, 21%, 22%, 23%, 24%, 25%, 26%, 27%, 28%, 29%, or 30%.

shRNA and siRNA Delivery

Depending on whether transient or stable expression is desired one can select an appropriate delivery vector. Examples of delivery vectors that may be used with the present disclosure are viral vectors, plasmids, exosomes, liposomes, bacterial vectors, or nanoparticles. The present disclosure also provides for delivery by any means known in the art.

For targeted delivery to triple-negative breast cancer cells, one skilled in the art would appreciate that delivery vectors may be genetically modified to target a specific cell type or to tissue type. To make a targeted delivery vector or plasmid one can identify a unique molecule expressed or associated with a triple-negative breast cancer (e.g., receptor, protein, glycoprotein, or combination thereof) and then create a delivery vector or plasmid that harbors or expresses these markers, preferably on the outside of the delivery vector or plasmid (e.g., cytosol facing). In addition, depending on the required therapeutic duration a viral delivery vector can be genetically modified to be continuously replicating, replication-defective, or conditionally replicating as described in, Sliva K, Schnierle B S. Selective gene silencing by viral delivery of short hairpin RNA. *Virology Journal.* 2010.

In one embodiment, the CDK8 or CDK19 shRNA or siRNA can be delivered by an adenovirus vector. Adenoviruses non-enveloped viruses with a nucleocapsid and a linear dsDNA genome. While they are able to replicate in the nucleus of mammalian cells, they do not efficiently integrate into the host's genome and therefore pose only minimal risks of insertional mutagenesis but are inadequate for long-term therapy.

In another embodiment, the CDK8 or CDK19 shRNA or siRNA can be delivered by an adeno-associated viral vector (AAV). AAV is one of the smallest viruses and belongs to the genus Dependovirus. It has a small, single-stranded DNA genome and can accommodate about eight individual shRNA. AAV permits entry retargeting, allowing delivery of the shRNA to specific cell or tissue types. In a further embodiment, the present disclosure provides for a modified AAV that is targeted for delivery to a triple-negative breast cancer cell or tissue type.

In another embodiment, the CDK8 or CDK19 shRNA or siRNA can be delivered by a retrovirus vector. A retrovirus is a single-stranded RNA virus that belongs to the family of Retroviridae and replicate through a double-stranded DNA intermediate. They can integrate into a host's genome thereby allowing long-term expression of a shRNA. The Env protein plays a central role in targeting retrovirus to a target cell. In a further embodiment, the present disclosure provides for a retrovirus vector with a modified env gene or its protein product for delivery to a triple-negative breast cancer cell or tissue type. In a further embodiment, the present disclosure provides for delivery of CDK8 or CDK19 shRNA of siRNA using a retrovirus vector with protease-activated Env proteins.

In another embodiment, the CDK8 or CDK19 shRNA or siRNA can be delivered by a lentivirus vector. Lentivirus is a subclass of retrovirus in the genus Lentivirinae which can accommodate large amounts of DNA. For some applications, it may be preferable to use a lentivirus vector engineered to be "self-inactivating" known as "SIN" vectors. In a further embodiment, the present disclosure provides for delivery of a CDK8 or CDK19 shRNA by a lentivirus vector with a modified env gene or its protein product for delivery to a triple-negative breast cancer cell or tissue type.

In another embodiment, the shRNA or siRNA can be delivered by a nanoparticle. Examples of nanoparticles that can be use with the present disclosure, include but are not limited to, exosomes, liposomes, organic nanoparticles, or inorganic nanoparticles. Other non-limiting examples of nanoparticles include, but are not limited to, e.g., those provided in Hong, Cheol Am, and Yoon Sung Nam. "Functional Nanostructures for Effective Delivery of Small Interfering RNA Therapeutics." *Theranostics* 4.12 (2014): 1211-1232. PMC. Web. 13 Sep. 2018, which is hereby incorporated by reference in its entirety for all purposes. In some embodiments, the delivery of the shRNA or siRNA is mediated by receptor, protein, glycoprotein or combination thereof present or specific to triple-negative breast cancer cells.

In some embodiments, the siRNA CDK19 therapeutic is administered in a solution. The siRNA may be administered in an unbuffered solution. In one embodiment, the siRNA is administered in water. In other embodiments, the siRNA is administered with a buffer solution, such as an acetate buffer, a citrate buffer, a prolamine buffer, a carbonate buffer, or a phosphate buffer or any combination thereof. In some embodiments, the buffer solution is phosphate buffered saline.

3.1.1.2. Rnase H-Mediated mRNA Degradation/Antisense

RNase H-dependent antisense oligonucleotides (ASOs) are single-stranded, chemically modified oligonucleotides that bind to complementary sequences in target mRNAs and reduce gene expression both by RNase H-mediated cleavage of the target RNA and by inhibition of translation by steric blockade of ribosomes.

RNase H is an endonuclease enzyme that catalyzes the cleavage of RNA in an RNA:DNA duplex. The most well studied endogenous function for this enzyme is the removal of Okazaki fragments (small RNAs) used to prime the DNA duplication during cell division. In some embodiments, to target the mRNA transcript of the CDK19 gene for degradation, a nucleic acid (e.g., DNA oligonucleotide) capable of hybridizing to a portion of the mRNA may be administered to the subject. Once inside the cell (e.g., a TNBC cell), the DNA oligonucleotide base pairs with its targeted mRNA transcript. RNase H may bind to the resulting duplex and cleave the mRNA transcript at one or more places. The DNA oligonucleotide may further bind to other mRNA transcripts to target them for RNase H degradation. Thus, the expression of the CDK19 gene may be greatly reduced in a subject with TNBC.

The DNA oligonucleotide capable of hybridizing to an mRNA transcript of a CDK19 gene may contain, e.g., between 10 and 30 nucleotides (e.g., 10, 12, 14, 16, 18, 20, 22, 24, 26, 28, or 30 nucleotides). In some embodiments, the DNA oligonucleotide may have 100% complementarity to the portion of the mRNA transcript it binds. In other embodiments, the DNA oligonucleotide may have less than 100% complementarity (e.g., 95%, 90%, 85%, 80%, 75%, or 70% complementarity) to the portion of the mRNA transcript it binds, but can still form a stable RNA:DNA duplex for the RNase H to cleave the mRNA transcript. The DNA oligonucleotide may bind to the 5' UTR or the 3' UTR of the mRNA transcript of the CDK19 gene.

Further, the DNA oligonucleotide capable of hybridizing to an mRNA transcript of a CDK19 gene may contain modified nucleotides at the 5' end and the 3' end. The modified nucleotides at the termini may function to protect the internal portion of the DNA oligonucleotide from nuclease degradation and to increase the binding affinity for the target mRNA transcript. In some embodiments, the modified nucleotides at the termini may include a modified nucleobase (e.g., 5-methylcytosine) and/or a modified sugar (e.g., a locked sugar). In some embodiments, 3-5 nucleotides at each of the 5' and 3' ends of the DNA oligonucleotide may be modified.

3.1.1.3. miRNA

A microRNA (miRNA) is a small non-coding RNA molecule that functions in RNA silencing and post-transcriptional regulation of gene expression. miRNAs base pair with complementary sequences within the mRNA transcript. As a result, the mRNA transcript may be silenced by one or more of the mechanisms such as cleavage of the mRNA strand, destabilization of the mRNA through shortening of its poly(A) tail, and decrease translation efficiency of the mRNA transcript into proteins by ribosomes. In some embodiments, miRNAs resemble the siRNAs of the shRNA pathway, except that miRNAs derive from regions of RNA transcripts that fold back on themselves to form short hairpins, which are also called pri-miRNA. Once transcribed as pri-miRNA, the hairpins are cleaved out of the primary transcript in the nucleus by an enzyme called Drosha. The hairpins, or pre-miRNA, are then exported from the nucleus into the cytosol. In the cytosol, the loop of the hairpin is cleaved off by an enzyme called Dicer. The resulting product is now a double strand RNA with overhangs at the 3' end, which is then incorporated into RISC. Once in the RISC, the second strand is discarded and the miRNA that is now in the RISC is a mature miRNA, which binds to mRNAs that have complementary sequences.

The difference between miRNAs and siRNAs from the shRNA pathway is that base pairing with miRNAs comes from the 5' end of the miRNA, which is also referred to as the seed sequence. Since the seed sequence is short, each miRNA may target many more mRNA transcript. In some embodiments, an miRNA targeting the CDK19 gene may be used in methods described herein.

3.1.2. Crispr/Cas System

In some embodiments, the knocking out or knocking down of the CDK19 gene is performed using a gene editing system such as the CRISPR/Cas system. See Sanders and Joung, Nature *Biotechnol* 32:347-355, 2014, Huang et al., *J Cell Physiol* 10:1-17, 2017 and Mitsunobu et al., *Trends Biotechnol* 17:30132-30134, 2017. The CRISPR/Cas system includes a Cas protein and at least one or two ribonucleic acids that are capable of directing the Cas protein to and hybridizing to a target motif in the CDK19 sequence. The Cas protein then cleaves the target motif and results in a double-strand break or a single-strand break. Any CRISPR/Cas system that is capable of altering a target polynucleotide sequence in a cell can be used in methods described here. In some embodiments, the CRISPR/Cas system is a CRISPR type I system. In some embodiments, the CRISPR/Cas system is a CRISPR type II system. In some embodiments, the CRISPR/Cas system is a CRISPR type V system.

The Cas protein used in the methods described herein can be a naturally occurring Cas protein or a functional derivative thereof. A "functional derivative" includes, but are not limited to, fragments of a native sequence and derivatives of a native sequence polypeptide and its fragments, provided that they have a biological activity in common with the corresponding native sequence polypeptide. A biological activity contemplated herein is the ability of the functional derivative to hydrolyze a DNA substrate (e.g., a CDK19 gene) into fragments. The term "derivative" encompasses both amino acid sequence variants of polypeptide, covalent modifications, and fusions thereof. Suitable derivatives of a Cas protein or a fragment thereof include but are not limited to mutants, fusions, or covalent modifications of Cas protein.

In some embodiments, the Cas protein used in methods described herein is Cas9 or a functional derivative thereof. In some embodiments, the Cas9 protein is from *Streptococcus pyogenes*. Cas9 contains 2 endonuclease domains, including an RuvC-like domain which cleaves target DNA that is noncomplementary to crRNA, and an HNH nuclease domain which cleaves target DNA complementary to crRNA. The double-stranded endonuclease activity of Cas9 also requires that a short conserved sequence (e.g., 2-5 nucleotides), known as a protospacer-associated motif (PAM), follows immediately after the 3' end of a target motif in the target sequence.

In some embodiments, the Cas protein is introduced into TNBC cells in polypeptide form. In certain embodiments, the Cas protein may be conjugated to a cell-penetrating polypeptide. Non-limiting examples of cell-penetrating peptides include, but are not limited to, e.g., those provided in Milletti et al., *Drug Discov. Today* 17: 850-860, 2012, the relevant disclosure of which is hereby incorporated by reference in its entirety. In other embodiments, a TNBC cell may be genetically engineered to produce the Cas protein.

In some embodiments, the target motif in the CDK19 gene, to which the Cas protein is directed by the guide RNAs, may be between 15 and 25 nucleotides in length (e.g., 15, 16, 17, 18, 19, 20, 21, 22, 23, 24, or 25 nucleotides in length). In some embodiments, the target motif is at least 20 nucleotides in length. In some embodiments, the target motif in the CDK19 gene immediately precedes a short conserved sequence known as a protospacer-associated motif (PAM), recognized by the Cas protein. In some embodiments, the PAM motif is an NGG motif. In some embodiments, the target motif of the CDK19 gene is within the first exon. In some embodiments, the target motifs can be selected to minimize off-target effects of the CRISPR/Cas systems. Those skilled in the art will appreciate that a variety of techniques can be used to select suitable target motifs for minimizing off-target effects (e.g., bioinformatics analyses).

The ribonucleic acids that are capable of directing the Cas protein to and hybridizing to a target motif in the CDK19 gene are referred to as single guide RNA ("sgRNA"). The sgRNAs can be selected depending on the particular CRISPR/Cas system employed, and the sequence of the target polynucleotide, as will be appreciated by those skilled in the art. In some embodiments, the one or two ribonucleic acids can also be selected to minimize hybridization with nucleic acid sequences other than the target polynucleotide sequence. In some embodiments, the one or two ribonucleic acids are designed to hybridize to a target motif immediately adjacent to a deoxyribonucleic acid motif recognized by the Cas protein. Guide RNAs can also be designed using available software, for example, CRISPR Design Tool (Massachusetts Institute of Technology). In some embodiments, the one or more sgRNAs can be transfected into TNBC cells, according to methods known in the art.

The use of antibodies for therapeutic purposes has been used to treat cancer. Passive immunotherapy involves the use of monoclonal antibodies (mAbs) in cancer treatments (see for example, Devita, Hellman, And Rosenberg's *Cancer: Principles & Practice Of Oncology*, Eighth Edition (2008), DeVita, V. et al. Eds., Lippincott Williams & Wilkins, Philadelphia, Pa., pp. 537-547, 2979-2990). These antibodies can have inherent therapeutic biological activity both by direct inhibition of tumor cell growth or survival and by their ability to recruit the natural cell killing activity of the body's immune system. The antibodies can be administered alone or in conjunction with radiation or chemotherapeutic agents. Trastuzumab, approved for treatment of breast cancer is an example of such a therapeutic. Alternatively, antibodies can be used to make antibody-drug conjugates in which the antibody is linked to a drug and directs that agent to the tumor by specifically binding to the tumor. Ado-Trastuzumab emtansine (T-DM1) is an example of an approved antibody-drug conjugate used for the treatment of breast cancer (see, Deng et al., *Curr. Med. Chem.*, Vol. 24(23), 2505-2527 (2017). Another type of immunotherapy is active immunotherapy, or vaccination, with an antigen present on a specific cancer (e.g., TNBC cells) or a DNA construct that directs the expression of the antigen, which then evokes the immune response in the subject, i.e., to induce the subject to actively produce antibodies against their own cancer.

Antibodies have been highly effective in targeting cell surface proteins involved in disease. Though it is generally believed that their large size, complex architecture, and structural reliance on disulfide bonds preclude intracellular application, a number of examples of both in situ-expressed (see, e.g, Miersch and Sidhu, F1000Res doi: 10.12688/f1000research.8915.1, 2016) and exogenously supplied whole antibodies shown to maintain functional intracellular activity exist in the literature (see, e.g., Biocca et al., Expression and targeting of intracellular antibodies in mammalian cells. *EMBOJ.* (1990); 9(1): 101-8 and Steinberger et al., Functional deletion of the CCR5 receptor by intracellular immunization produces cells that are refractory to CCR5-dependent HIV-1 infection and cell fusion. *Proc Natl Acad Sci USA*. (2000); 97(2): 805-10). Attempts to use smaller, less complex binding proteins such as antigen-binding fragments (Fabs) and single-chain variable fragments (scFvs) for intracellular application have similarly shown success in their ability to bind and modulate cytoplasmic protein function (See for example, Marasco et al., Design, intracellular expression, and activity of a human anti-human immunodeficiency virus type 1 gp120 single-chain antibody. *Proc Natl Acad Sci USA*. (1993); 90(16): 7889-93).

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

As used herein, the term "epitope" is meant to include any determinant capable of specific interaction with the provided antibodies. Epitopic determinants usually consist of chemically active surface groupings of molecules such as amino acids or sugar side chains and usually have specific three dimensional structural characteristics, as well as specific charge characteristics. Identification of the epitope that the antibody recognizes is performed as follows. First, various partial structures of the target molecule that the monoclonal antibody recognizes are prepared. The partial structures are prepared by preparing partial peptides of the molecule. Such peptides are prepared by, for example, known oligopeptide synthesis technique or by incorporating DNA encoding the desired partial polypeptide in a suitable expression plasmid. The expression plasmid is delivered to a suitable host, such as *E. coli*, to produce the peptides. For example, a series of polypeptides having appropriately reduced lengths, working from the C- or N-terminus of the target molecule, can be prepared by established genetic engineering techniques. By establishing which fragments react with the antibody, the epitope region is identified. The epitope is more closely identified by synthesizing a variety of smaller peptides or mutants of the peptides using established oligopeptide synthesis techniques. The smaller peptides are used, for example, in a competitive inhibition assay to determine whether a specific peptide interferes with binding of the antibody to the target molecule. If so, the peptide is the epitope to which the antibody binds. Commercially available kits, such as the SPOTs Kit (Genosys Biotechnologies, Inc., The Woodlands, Tex.) and a series of multipin peptide synthesis kits based on the multipin synthesis method (Chiron Corporation, Emeryvile, Calif.) may be used to obtain a large variety of oligopeptides.

The term antibody or fragments thereof can also encompass chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain CDK19 binding activity are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies, A Laboratory Manual. Cold Spring Harbor Publications, New York (1988)). Also included within the meaning of antibody or fragments thereof are conjugates of antibody fragments and antigen binding proteins (single chain antibodies) as described, for example, in U.S. Pat. No. 4,704,692, the contents of which are hereby incorporated by reference in their entirety.

In one embodiment, a therapeutic antibody (or antibody fragment) can be prepared using methods known in the art, having specificity for an antigen present in breast cancer, and in particular TNBC cells, that is absent or present only at low levels in any normal (non-cancerous) tissue. The therapeutic antibody would therefore have biological activity against TNBC cells and be able to recruit the immune system's response to treat the disease. The therapeutic antibody can be administered as a therapeutic alone or in combination with current treatments (such as chemotherapy, radiation, or platinum-based therapies) or used to prepare immunoconjugates linked to toxic agents, such as drugs.

Monoclonal antibodies to CDK19 (e.g., anti-CKD19 antibodies), made by methods known in the art, can be used to identify the presence or absence of cancerous cells in breast tissue, for purposes of diagnosis or treatment. Anti-CKD19 antibodies can also be used to identify the presence or absence of cancerous cells, or the level thereof, which are circulating in the blood after their release from a solid tumor. Such circulating antigen can include an intact CDK19 antigen, or a fragment thereof that retains the ability to be detected according to the methods taught herein. Such detection may be effected for example, by FACS analysis using standard methods commonly used in the art.

In some embodiments, methods of targeting CDK19 can include administering to a subject in need thereof, a therapeutically effective amount of an antibody (e.g., an anti-CKD19 antibody) that is immunoreactive to CDK19 for the treatment of breast cancer, in particular treatment of TNBC. In one embodiment, the antibody having immunoreactivity to CDK19 targets intracellular signaling molecules, such as kinases, as opposed to cell surface molecules, whereby the specificity of the antibody is provided by neutralizing epitope(s) present on CDK19 that are not present on CDK8. In another embodiment, the anti-CDK19 antibody can target the PI3K/mTOR/AKT pathway or ERK5 (see, Ocana and Pandiella, Oncotarget, 8(13), 22218-22234 (2017)). In one embodiment, the anti-CDK19 antibody can target multiple intracellular signaling molecules, for example, the PI3K/mTOR and JAK/STAT pathway. In yet another embodiment, the anti-CDK19 antibody can comprise an engineered protein that binds to a neutralizing epitope present on CDK19 that is not present on CDK8.

In one embodiment, methods of targeting CDK19 can include administering to a subject in need thereof, a therapeutically effective amount of a tumor antigen (TA)-specific monoclonal antibody for the treatment of TNBC. In one embodiment, the TA-specific mAB can be directed to an intracellular antigen associated with TNBC (See for example, Wang et al., *Molecular Oncology*, Vol. 9(10), (2015) 1982-1993 and Just, *FEBS letters,* 2:21 (2014), 350-355).

In one aspect, provided is a method of treating a subject with breast cancer, the method including the step of administering to the subject a pharmaceutically effective amount of a composition comprising a CDK19 targeting agent. The CDK19 targeting agent may be a CDK19 targeted antibody, a CDK19 targeted peptide, a CDK19 targeted small molecule, a CDK19 targeted RNA molecule, or a combination thereof. In some instances, the CDK19 targeted agent may be conjugated to a therapeutic agent. In some instances, the method further includes administering a second form of cancer therapy (e.g., chemotherapy or radiation therapy) to the subject. In one embodiment, the breast cancer is TNBC. In another aspect, provided is a method of inhibiting expression of the CDK19 gene in a breast cancer cell, the method including the steps of contacting a breast cancer cell expressing the CDK19 gene with a synthetic CDK19 targeted RNA molecule.

In another aspect, provided is a method of assessing responsiveness of a subject with cancer to a CDK19 targeted agent including the steps of: (a) measuring in a tumor sample from a subject the amount of CDK19; (b) determining if a subject has a cancer characterized as having a high level of CDK19 expression; and (c) indicating that the subject is more likely to respond to the CDK19 targeted agent if the subject's cancer is characterized as having a high level of CDK19 expression or that the subject is less likely to respond to the CDK19 targeted agent if the subject's cancer is characterized as having a low level of CDK19 expression.

In one aspect, provided is a method of treating a subject with cancer, the method comprising administering to the patient a pharmaceutically effective amount of a composition comprising a CDK19 targeted agent. The CDK19 targeted agent is an agent that specifically binds to CDK19 protein or to CDK19 mRNA. CDK19 targeted agents include antibodies, or fragments thereof, peptides, small molecules, and polynucleotides (such as RNA molecules) that specifically bind to CDK19 protein or to CDK19 mRNA. The composition may further comprise a pharmaceutically acceptable carrier. In some instances, CDK19 targeted agents that bind to the CDK19 protein may directly inhibit CDK19 activity. In other instances, CDK19 targeted agents that bind to CDK19 mRNA may inhibit CDK19 expression and thereby inhibit CDK19 activity.

In one instance, the CDK19 targeted agent may comprise a CDK19 targeted antibody. The CDK19 targeted antibody may be a monoclonal antibody. In some instances, the CDK19 targeted antibody may be a humanized antibody. In another instance, the CDK19 targeted agent may be a CDK19 targeted peptide. In yet another instance, the CDK19 targeted agent may be a CDK19 targeted small molecule. The CDK19 targeted peptides and small molecules may be derived in a variety of manners as discussed further below. In some instances, the peptides are derived from the sequence of a CDK19 targeted antibody.

In some instances, treating a subject with the methods described herein inhibits at least one of: formation of a tumor, the proliferation of tumor cells, the growth of tumor cells, or metastasis of tumor cells in the subject. In another embodiment, treating a subject with the methods described herein may result in reduction of tumor size and, in some instances, elimination of one or more tumors in the subject.

3.1.4. Small Molecule Inhibitors

In one approach, methods for treating TNBC include targeting the CDK19 protein using a small molecule inhibitor of CDK19 activity. Examples of small molecule inhibitors of CDK19 are described in U.S. Pat. No. 9,321,737, US Patent Publication No. US 20170071942, Mallinger et al., *J. Med. Chem.* 59:1078, 2016, and Czodrowski et al., *J. Med. Chem.* 59:9337, 2016. In some embodiments, the small molecule inhibitors bind to the ATP binding site of CDK19 to inhibit its activity.

The small molecule inhibitor of CDK19 may bind to the ATP binding site of CDK19 covalently or non-covalently to inhibit its activity. In other embodiments, the small molecule inhibitor may bind to other parts of CDK19 outside of the ATP binding site. For example, the small molecule inhibitor may form a covalent interaction with an amino acid (e.g., methionine, tyrosine, or serine) outside of the ATP binding site to inhibit CDK19 activity. In addition to occupying the ATP binding to inhibit kinase activity, a small molecule inhibitor may also bind to CDK19 to cause a conformational change in CDK19 that prevents CDK19 from functioning. In some embodiments, the small molecule inhibitor may bind to CDK19 with a higher affinity than to CDK8. As shown in FIG. 9, the vast majority of amino acid differences between CDK19 and CDK8 are in the C-terminal domain. In some embodiments, without being bound by any theory, a small molecule inhibitor may bind to an amino acid or a portion in the C-terminal domain of CDK19, that is different from the corresponding amino acid or portion of CDK8, to achieve selective inhibition of CDK19 over CDK8.

In some embodiments the small molecule inhibitor is other than a compound described in U.S. Pat. No. 9,321,737. In some embodiments the small molecule inhibitor is other than a compound described in US Patent Publication No. US 20170071942. In some embodiments the small molecule inhibitor is other than a compound described in, Mallinger et al., *J. Med. Chem.* 59:1078, 2016. In some embodiments the small molecule inhibitor is other than a compound described in Czodrowski et al., *J. Med. Chem.* 59:9337, 2016. In some embodiments the small molecule inhibitor is other than one or more compounds selected from the group consisting of Cortistatin A, Sorafenib, Linifanib, Ponatinib, Senexin B, CCT251545, and CCT251921

3.1.5. CDK19 Inhibitors that do not Significantly Inhibit Expression or Activity of CDK8 or which Inhibits Expression or Activity of CDK19 to a Greater Extent than it Inhibits Expression or Activity of CDK8

Agents that inhibitors expression or activity of CDK19 but do not inhibit expression or activity of CDK8, or agents that inhibit expression or activity of CDK19 to a greater extent than expression or activity of CDK8 is inhibited can be designed based on differences in sequence and structure of the CDK19 and CDK8 proteins and their corresponding genes and mRNAs. For example, an alignment of CDK19 and CDK8 mRNA sequences can identify non-identical or low identity nucleotide sequences that can be used to design shRNAs or other nucleic acid agents that associate with CDK19 mRNA but not CDK8 sequences. (see, FIGS. 16 and 17). Likewise, aligning CDK19 and CDK8 amino acid sequences can identify divergent regions and antibodies or other binding agents can be produced to specifically bind the CDK19 protein. Likewise, small molecule agents can be identified (by rational drug design or screening) that specifically inhibit CDK19 activity or inhibit CDK19 activity to a greater degree that CDK8 activity.

The term "an agent that inhibits CDK19 activity but does not significantly inhibit activity of CDK8" as used herein; refers to an agent that is capable of specifically binding and inhibiting the activity of CDK19 such that minimal CDK19 activity is detected in vivo or in vitro; while the agent causes no significant decrease in CDK8 activity under the same conditions. For example, an agent that inhibits activity of CDK19 can specifically bind to CDK19 and fully or significantly inhibit CDK19 activity in vivo or in vitro. In some cases, a CDK19 inhibitor can be identified by its ability to preferentially bind to the CDK19 gene or a CDK19 gene product, and fully inhibit expression or activity of CDK19. Inhibition of CDK19 occurs when CDK19 activity, when exposed to an agent, is at least about 70% less, for example, at least about 75%, 80%, 90%, or 95% less than CDK19 activity in the presence of a control or in the absence of the agent. No significant decrease in CDK8 activity occurs when CDK8 activity, upon exposure to the agent, is at least about 90%, for example, at least 95%, 96%, 97%, 98%, 99%, or 100%, in comparison to CDK8 activity in the absence of the agent. As set forth herein, the agent can include small molecules (i.e., a molecule having a formula weight of 1000 Daltons or less), such as small molecule chemical inhibitors or large molecules, such as siRNA, shRNA, antisense oligonucleotides, or proteins.

Determining the effect of the agent on CDK19 and/or CDK8 activity can be measured using one or more methods known in the art, including but not limited to, half maximal inhibitory concentration ($IC_{50}$), dissociation constant ($K_D$), and inhibitor constant ($K_I$). For example, $IC_{50}$ is a measure of the effectiveness of a substance in inhibiting a specific biological or biochemical function. This value indicates the concentration of the substance needed to inhibit a given biological process (or component of the biological process) by half. The $IC_{50}$ values are typically expressed as molar concentration. According to the Food and Drug Administration (FDA), $IC_{50}$ represents the concentration of a drug required for 50% inhibition in vitro. In one embodiment, an agent that inhibits CDK19 activity but does not significantly inhibit activity of CDK8 has an $IC_{50}$ that is at least about 2-fold, 5-fold, 10-fold, 50-fold, 75-fold, or 100-fold, lower than the concentration of the agent required to effect CDK8 activity under the same conditions. In another embodiment, the $IC_{50}$ for the agent to inhibit CDK19 activity is at least about 25%, 50%, 75%, 80%, 85%, 90%, 95%, 96%, 97%, 98%, or 99%, lower than the $IC_{50}$ for the agent to inhibit the activity of CDK8.

In another embodiment, the effect of the agent on CDK19 and CDK8 activity can be determined by calculating the equilibrium dissociation constant ($K_D$) of the agent to each CDK. For example, an agent that inhibits the activity of CDK19 but does not significantly inhibit activity of CDK8 has a $K_D$ that is at least about 2-fold, 5-fold, 10-fold, 50-fold, or 100-fold lower than the $K_D$ of the agent to CDK8 under the same conditions. In one embodiment, the $K_D$ for the agent (to CDK19) is at least about 25%, 50%, 75%, 80%, 85%, 90%, 95%, 96%, 97%, 98%, or 99%, lower than the $K_D$ for the agent (to CDK8). In a preferred embodiment, the KD is lower for the agent to CDK19 as compared to the $K_D$ of the agent to CDK8. Said differently, the equilibrium dissociation constant of the agent (to CDK8) is greater than the equilibrium dissociation constant of the agent (to CDK19). In one embodiment, the agent can include an antibody having a $K_D$ value in the micromolar ($10^{-6}$) to nanomolar ($10^{-7}$ to $10^{-9}$) range. In another embodiment, the agent can include an antibody having a $K_D$ in the nanomolar range ($10^{-9}$) to the picomolar ($10^{-12}$) range. In yet another embodiment, the agent can have a nanomolar (nM) equilibrium dissociation constant to CDK19 and a micromolar (μM) equilibrium dissociation constant to CDK8. US Patent Publication No. US20120071477 describes kinase inhibition assays in which a compound at a single concentration (2,000 nM) to inhibit ATP pocket binding.

In another embodiment, the effect of the agent on CDK19 and CDK8 activity can be determined by calculating the inhibitor constant ($K_I$) of the agent to each CDK. The $K_I$ is an indication of how potent an inhibitor is; it is the concentration required to produce half maximum inhibition. The lower the $K_I$, the greater the binding affinity between the agent and the CDK gene. For example, an agent that inhibits the activity of CDK19 but does not significantly inhibit activity of CDK8 has a $K_I$ that is at least about 2-fold, 5-fold, 10-fold, 50-fold, 75-fold, or 100-fold lower than the $K_I$ of the agent (to CDK8) under the same conditions. In one embodiment, the $K_I$ for the agent to CDK19 is at least about 25%, 50%, 75%, 80%, 85%, 90%, 95%, 96%, 97%, 98%, or 99%, lower than the $K_I$ for the agent to CDK8. In a preferred embodiment, the $K_I$ is lower for the agent to CDK19 as compared to the $K_I$ of the agent to CDK8. Said differently, the inhibitor constant of the agent to CDK8 is greater than the inhibitor constant of the agent to CDK19. For example, an agent that inhibits activity of CDK19 can bind to CDK19 and significantly inhibit CDK19 activity in vivo or in vitro. In some cases, a CDK19 inhibitor can be identified by its ability to preferentially bind to CDK19 and fully inhibit activity of CDK19. Inhibition of CDK19 occurs when CDK19 activity, when exposed to an agent of the invention, is at least about 70% less, for example, at least about 75%, 80%, 90%, 95%, 96%, 97%, 98%, 99% less, or totally inhibited, in comparison to CDK19 activity in the presence of a control or in the absence of the agent. No significant decrease in CDK8 activity occurs when, CDK8 activity upon exposure to the agent, is at least about 90%, for example, at least 95%, 96%, 97%, 98%, 99%, or 100%, in comparison to CDK8 activity in the absence of the agent.

The term "an agent that inhibits activity of CDK19 to a greater extent than it inhibits activity of CDK8" as used herein, refers to an agent that is capable of binding and inhibiting the activity of CDK19 significantly more than the agent's effect on inhibiting the activity of CDK8 under the same conditions. For example, an agent that inhibits activity of CDK19 to a greater extent than inhibiting the activity of CDK8, occurs when CDK19 activity, when exposed to an agent of the invention, is at least about 10% less, for example, at least about 15%, 20%, 30%, 40%, or 50% less, than the activity of CDK8 under the same conditions in vitro or in vivo. In a preferred embodiment, an agent inhibits the activity of CDK19 to a greater extent than the activity of CDK8, when the activity of CDK19 observed is at least 10% less than the activity of CDK8 under the same conditions. In another embodiment, an agent inhibits the activity of CDK19 to a greater extent than CDK8 activity, when at least 2-fold, 5-fold, 10-fold, 20-fold, 50-fold, or 100-fold less CDK19 activity is observed as compared to CDK8 activity under the same conditions. The extent of inhibition (i.e., comparing CDK19 activity to CDK8 activity) can be determined using one or more methods known in the art, including but not limited to assays described herein in the Examples section of the specification and for example, "Percent Of Control (POC)" or "Normalized Percent Inhibition (NPI)". POC and NPI are methods that normalize data and are often used when comparing multiple agents (e.g., various antibodies or small molecules) against multiple targets (e.g., CDK19 and CDK8). For example, POC is a method that corrects for plate-to-plate variability (for example in high-throughput drug screening) by normalizing an agent's measurement relative to one or more controls present in the plate. Raw measurements for each agent can be divided by the "average" of within-plate controls. NPI is a control-based method in which the difference between the agent measurement and the mean of the positive controls is divided by the difference between the means of the measurements on the positive and the negative controls (Malo et al., *Nature Biotechnology*, Vol. 24, 167-175 (2006)). By normalizing the extent of inhibition observed, accurate conclusions can be made regarding which agent(s) are effective at inhibiting the activity of each target under investigation.

3.1.6. Combination Therapy

In one approach the patient is treated with a combination therapy comprising an agent that inhibits expression or activity of CDK19 and (a) radiation therapy and/or chemotherapy. In one approach radiation or chemotherapy eliminates the bulk of the tumor mass and the CDK19 inhibitor reduces the number of viable cancer stem cells (e.g., EpCAM$^{med/high}$/CD10$^{-/low}$) cells. In one approach the chemotherapy comprises administration of an anthracycline (e.g., Doxorubicin or Epirubicin), a taxane (e.g., Paclitaxel or Docetaxel), an anti-metabolite (e.g., Capecitabine or Gemcitabine), a platinum agent (e.g., Carboplatin or Cisplatin), Vinorelbine, or Eribulin.

3.2 Methods of Assessing or Predicting Therapeutic Effect

A course of therapy with the CDK19 inhibitor will have a beneficial outcome for the patient, including, for example, a reduction in tumor volume, a reduction in metastases, and a reduction in tumor cells having the phenotype EpCAM$^{med/high}$ and CD10$^{-/low}$.

Tumor volume may be measured using art-known methods. See, e.g., Wapnir et al., *Breast Cancer Res Treat* 41:15-19, 1996; Sapi et al., *PLoS One* 10:e0142190, 2015. Tumor volume may be reduced by at least 10%, optionally at least 20% and sometimes by at least 50% after a course of treatment with a CDK19 inhibiting agent as monotherapy or in combination with other agent(s) or treatments. In some embodiments, the reduction in tumor volume (e.g., at least 10%, 20%, or 30% reduction in tumor volume) may be observed as soon as within 1 month of initiating therapy. In other embodiments, the reduction in tumor volume (e.g., at least 10%, 20%, 30%, 40%, 50%, or 60% reduction in tumor volume) may be observed within 2, 3, 4, 5, or 6 months of initiating therapy. In other embodiments, the methods described herein to treat TNBC may also slow down or inhibit the further growth of a tumor. In some embodiments a patient receives combination therapy and a therapeutic benefit is observed that exceeds that of monotherapy with the second agent.

A reduction in metastases in an individual may be determined as described in Makela et al., *Sci Rep.* 7:42109, 2017 and may be observed in a population according to standard methodology.

In some embodiments, the presence or amount of cancer cells having the expression profile EpCAM$^{med/high}$ and CD10$^{-/low}$ in a TNBC tumor tissue obtained from a subject may be used to predict or assess the therapeutic responsiveness of the subject to treatments that target the CDK19 gene or its corresponding protein. As described and demonstrated herein, cells having the expression profile EpCAM$^{med/high}$/CD10$^{-/low}$ have a high tumor initiating capacity and are also enriched in CDK19. In some embodiments, subjects having a high percentage of EpCAM$^{med/high}$ and CD10$^{-/low}$ TNBC cells may be especially responsive.

In one approach the likely therapeutic responsiveness of a subject with TNBC to a CDK19 targeting agent is determined by (a) quantitating EpCAM$^{med/high}$/CD10$^{-/low}$ cells in a tumor sample obtained from the subject; (b) comparing the quantity of EpCAM$^{med/high}$/CD10$^{-low}$ cells in (a) to a reference value characteristic of tumors responsive to a CDK19 targeting therapy, and treating the patient with an inhibitor of CDK19 expression or activity if the quantity of EpCAM$^{med/high}$/CD10$^{-/low}$ cells is equal to or exceeds the reference value. The reference value can be determined by quantitating EpCAM$^{med/high}$/CD10$^{-/low}$ cells in healthy and TNBC populations and calculating statistically significant ranges characteristic of healthy and tumor tissues. In another approach tumor tissue and healthy tissue from the same subject can be tested, and subjects with elevated EpCAM$^{med/high}$/CD10$^{-low}$ cells in tumor relative to healthy tissues can be identified as likely to respond to CDK19 targeted therapy.

3.3 Delivery of Agents

The pharmaceutical compositions used in methods described herein may include an active ingredient and one or more pharmaceutically acceptable carriers or excipients, which can be formulated by methods known to those skilled in the art. In some embodiments, a pharmaceutical composition of the present invention includes, in a therapeutically effective amount, a DNA or RNA oligonucleotide that decreases the expression level of the CDK19 gene. In other embodiments, a pharmaceutical composition of the present invention includes, a pharmaceutical composition of the present invention includes a DNA or RNA oligonucleotide in a therapeutically effective amount, a small molecule that inhibits the activity of CDK19. The therapeutically effective amount of the active ingredient in a pharmaceutical composition is sufficient to prevent, alleviate, or ameliorate symptoms of a disease or to prolong the survival of the subject being treated. Determination of a therapeutically effective amount is within the capability of those skilled in the art.

In certain embodiments, a pharmaceutical composition of the present invention is formulated as a depot preparation. In general, depot preparations are typically longer acting than non-depot preparations. In some embodiments, such preparations are administered by implantation (for example subcutaneously) or by intramuscular injection. In some embodiments, depot preparations are prepared using suitable polymeric or hydrophobic materials (for example an emulsion in an acceptable oil) or ion exchange resins, or as sparingly soluble derivatives, for example, as a sparingly soluble salt.

In some embodiments, a pharmaceutical composition may include a delivery system. Examples of delivery systems include, but are not limited to, exosomes, liposomes, and emulsions. In some embodiments, an active ingredient may be loaded or packaged in exosomes that specifically target a cell type, tissue, or organ to be treated. Exosomes are small membrane-bound vesicles of endocytic origin that are released into the extracellular environment following fusion of mutivesicular bodies with the plasma membrane. Exosome production has been described for many immune cells including B cells, T cells, and dendritic cells. Techniques used to load a therapeutic compound into exosomes are known in the art and described in, e.g., U.S. Patent Publication Nos. US 20130053426 and US 20140348904, and International Patent Publication No. WO 2015002956, which are incorporated herein by reference. In some embodiments, therapeutic compounds may be loaded into exosomes by electroporation or the use of a transfection reagent (i.e., cationic liposomes). In some embodiments, an exosome-producing cell can be engineered to produce the exosome and load it with the therapeutic compound. For example, exosomes may be loaded by transforming or transfecting an exosome-producing host cell with a genetic construct that expresses the active ingredient (i.e., a DNA or RNA oligonucleotide), such that the active ingredient is taken up into the exosomes as the exosomes are produced by the host cell. Various targeting moieties may be introduced into exosomes, so that the exosomes can be targeted to a selected cell type, tissue, or organ. Targeting moieties may bind to cell-surface receptors or other cell-surface proteins or peptides that are specific to the targeted cell type, tissue, or organ. In some embodiments, exosomes have a targeting moiety expressed on their surface. In some embodiments, the targeting moiety expressed on the surface of exosomes is fused to an exosomal transmembrane protein. Techniques of introducing targeting moieties to exosomes are known in the art and described in, e.g., U.S. Patent Publication Nos. US 20130053426 and US 20140348904, and International Patent Publication No. WO 2015002956, which are incorporated herein by reference.

4. Examples

4.1 Example 1—Materials and Experimental Methods

Chemical Reagents

The following are the chemical names for the compounds used in this study. CCT152921 is 4-[(2-Phenylethyl)amino]-6-quinazolinecarbonitrile (NIH NCAT). The compound was re-suspended in vehicle (PBS+0.5% Methocel (w/v)+0.25% Tween 20 (v/v)) to a concentration of 3 mg/mL and mice were dosed at 30 mg/kg. CCT251921 or vehicle was administered via daily oral gavage.

shRNA Expression Lentiviral Plasmids

Pairs of complementary ssDNA oligonucleotides containing the sense target sequence, a 15-mer loop sequence (5'-GTTAATATTCATAGC-3' SEQ ID NO: 19), and the reverse complement of the sense sequence were synthesized (Elim Biopharmaceuticals). The oligonucleotides were annealed in 50 μM annealing buffer (10 mM Tris-HCl pH 8.0, 50 mM NaCl, 1 mM EDTA). The double-stranded DNA oligo templates were subsequently cloned into the pRSI12-U6-(sh)-HTS4-UbiC-TagRFP-2A-Puro shRNA expression vector (Cellecta) digested with Bbsl for constitutively active shRNA vector constructs and pRSITUR-U6Tet-(sh)-UbiC-TetRep-2A-TagRFP digested with Bbsl for inducible shRNA vector constructs. The sense strands in the shRNA vectors used in this study were: 5'-GCG AGA ATT GAA GTA CCT TAA-3' (shCDK19-1 (SEQ ID NO: 1)), 5'-ACC AGC AAA TAT CCT AGT AAT-3' (shCDK19-2 (SEQ ID NO:2)), and 5'-GCA GGG TAATAA CCA CATTAA-3' (shCDK8-2 (SEQ ID NO: 3)). The unmodified pRSI12-U6-(sh)-HTS4-UbiC-TagRFP-2A-Puro shRNA expression vector above was used as the 'empty' control shRNA. The pHIV-ZsGreen expression vector (Addgene) was used to produce GFP positive tumor cells. The DECIPHER 27K Pooled shRNA lentivirus library—Human Module 1 (Cellecta) used for the ANAi screen contains 27,500 unique shRNA constructs targeting 5,043 human genes (approximately five or six redundant shRNAs per gene) in the same pRSI12 shRNA expression vector.

Cell Lines

MDA-MB231, MDA-MB468, HS578T, and 293T cells were obtained from ATCC. HMEC cells were obtained from ThermoFisher Scientific. These cells were certified by the vendors to be *mycoplasma* free. None of the cell lines used are listed in the database of commonly misidentified cell lines maintained by ICLAC. All cell lines used were passaged less than 10 times from when the original cells from the vendors were thawed. All MDA-MB231, MDA-MB468, 293T, and HS578T cells were grown in DMEM (Invitrogen) supplemented with PSA (Life Technologies), 10% FBS (Hyclone), Glutamax (ThermoFisher Scientific), and sodium pyruvate (Life Technologies). HMEC cells were grown in HuMEC Ready Medium (ThermoFisher Scientific).

Mice

Nod scid gamma (NSG) mice (NOD.Cg-Prkdc$^{scid}$ IL2Rg$^{tm1Wjl}$/SzJ) were purchased from the Jackson Laboratory. Mice used for PDX experiments were adult female mice between 8 and 10 weeks old. All the mice used in this study were maintained at the Stanford Animal Facility in accordance with a protocol approved by the Stanford University APLAC committee. Mice were maintained in-house under aseptic sterile conditions. Mice were administered autoclaved food and water. For PDX experiments utilizing doxycycline inducible constructs, mice were provided rodent feed containing 625 mg Doxycycline hyclate/kg diet (Envigo) in place of their normal rodent diet.

PDX Tumors and their Pathological and Clinical Characteristics

For human samples, informed consent was obtained after the approval of protocols by the Institutional Review Boards of Stanford University and The City of Hope. See FIG. 15 for a full description of all the PDX tumors used in this study.

Single Cell Suspension of PDX Tumor Cells

Xenografts were mechanically chopped with a razor blade to approximately 1 mm pieces and then incubated at 37° C. for 3 to 4 hours with collagenase and hyaluronidase (Stem Cell Technologies) in Advanted DMEM/F12 (Invitrogen) with 120 μg/mL penicillin, 100 μg/mL streptomycin, 0.25 μg/mL amphotericin-B (PSA) (Life Technologies). Cells were then treated with ACK lysis buffer (Gibco) to lyse red blood cells, followed by 5 mins of treatment with pre-warmed dispase (Stem Cell Technologies) plus DNAseI (Sigma) and filtered through a 40 μm nylon mesh filter. Cells were finally washed with flow cytometry buffer (HBBS, 2% FCS, PSA).

Enrichment of PDX Tumor Cells

After PDX tumors were dissociated into single cells, the number of live cells were determined with Trypan blue staining and manually counted with a hemocytometer. Cells were resuspended with flow cytometry buffer to a concentration of 106 live cells/mL and incubated 1:50 (v/v) with Biotin anti-human CD326 (EpCAM) antibody (Biolegend) for 20 mins at 4° C. Cells were washed with flow cytometry buffer and then resuspended to 80 μL and incubated with 20 μL anti-biotin microbeads (Miltenyi Biotec) for 20 mins at 4° C. Cells were then washed with flow cytometry buffer and resuspended in 500 μL of buffer. Cells were applied to magnetized LS columns (Miltenyi Biotec), washed, and eluted off magnet per manufacturer's protocol.

Lentivirus Production

Lentivirus was produced with Packaging Plasmid Mix (Cellecta) and subcloned pRS112 shRNA expression plasmids using Lipofectamine 2000 (Thermofisher Scientific) in 293T cells per manufacturer's instructions. Supernatants were collected at 48 h and 72 h, filtered with a 0.45 μm filter and precipitated with Lentivirus Precipitation Solution (Alstem LLC) per manufacturer's instructions. Virus was resuspended in 1/100 original volume. Viral titers were determined by flow cytometry analyses of 293T cells infected with serial dilutions of concentrated virus.

Lentivirus Infection

For in vitro cell line experiments, concentrated lentiviral supernatant (to achieve an MOI of 3) was mixed with cells at the time of seeding. Cells were monitored by visualization of RFP under fluorescence microscopy. All flow cytometry analyses were performed after at least 72 hours of infection.

For in vivo PDX tumor growth and organoid colony formation experiments, concentrated lentiviral supernatant (to achieve an MOI of 10) was mixed with single cell suspensions of PDX tumor cells in organoid media with 4 μg/mL of Polybrene (Sigma-Aldrich). Organoid media consisted of: Advanced DMEM/F12 (Invitrogen), 10% FBS (Hyclone), 2.5% growth factor-reduced Matrigel (BD), 10 ng/mL mouse EGF (R&D), 100 ng/mL Noggin (R&D), 250 ng/mL RSPO-1 (R&D), 1× B27 (Invitrogen), 1× N2 (Invitrogen), and PSA (Life Technologies). Cells were then spinoculated by centrifuging at 15° C. for 2 hours at 1200×g. Cells were resuspended by pipetting and left overnight in 48-well ultra-low attachment cell culture plates (Corning).

For organoid colony formation assays, cells were transferred the next day to matrigel. For in vivo PDX assays, approximately 75% of the cells were injected into NSG mice as described in the PDX tumor engraftment section. The remainder 25% of cells were plated on matrigel and grown in organoid media for 72 hours until the cells became RFP positive. At that point media was removed and exchanged for dispase and incubated for 2-3 h until the matrigel dissolved. Dissociated cells were resuspended in flow cytometry buffer and analyzed by flow cytometry to determine the 'baseline' RFP percentage for cells that were injected into the mice.

Organoid Colony Formation Assay

Irradiated L1-Wnt3a feeder cells (generous gift of Dr. Roel Nusse) were mixed with growth factor reduced matrigel (BD Biosciences) and allowed to solidify at 37° C. Single cell suspensions of PDX tumor cells were transferred onto the solidified matrigel/feeder cell mix substrate and grown in organoid media. Cells were grown for approximately 2 weeks in a 37° C. incubator with 5% $CO_2$. 50% of media was exchanged with fresh media every 3-4 days. Colonies were counted under fluorescence microscopy. Only RFP positive colonies (which represent transduced cells) were counted. For experiments in which we induced expression of CDK19 shRNA, doxycycline hyclate was added to a final concentration of 100 ng/mL into the media.

Cell Viability Assay

For cell lines treated with chemical or infected with lentivirus, WST-1 Cell Proliferation Reagent (Roche) was added at 1:10 (v/v) final dilution to each well per manufacturer's instructions. Cells were subsequently incubated at 37° C. and 5% $CO_2$. Between 1 and 4 hours after addition of reagent, plates were analyzed on a SpectraMax M3 Bioanalyzer (Molecular Devices). Absorbance for each well was measured at 450 nm (signal wavelength) and 650 nm (reference wavelength). Thus, the signal for each experimental sample was $Absorbance_{experimental}$ ($A_{450nm}$-$A_{650nm}$). To correct for the effect of media, $Absorbance_{background}$ ($A_{450nm}$-$A_{650nm}$) was obtained by measuring absorbance in a blank well. Thus, the background corrected signal for each sample $A_{corrected}$=$Absorbance_{experimental}$−$Absorbance_{background}$. All $A_{corrected}$ values for the knockdowns were normalized to the $A_{corrected}$ value for the control sample to obtain a 'Relative Viability'.

Quantitative PCR RNA Expression Analyses

Cells were lysed with Trizol (Life Technologies) and RNA was extracted according to the manufacturer's instruction. RNA was then treated with DNAseI to remove contaminating genomic DNA. RNA was reverse transcribed to cDNA using SuperScript III First Strand Synthesis kit (Life Technologies) according to the manufacturer's instructions. TaqMan Gene Expression Master Mix (Applied Biosystems) and the following TaqMan Gene Expression Assays (Applied Biosystems) were used following manufacturer's instructions: ACTB, Hs00357333_g1; CDK19, Hs01039931_m1; CDK8, Hs00993274_m1. Data was collected on a 7900HT Fast Real-Time PCR System (Applied Biosystems) and data analyzed with SDS 2.4 software (Applied Biosystems). Gene expression data in each sample was normalized against the expression of beta-actin.

PDX Tumor Cell Engraftment and Limiting Dilution Assays

Single cell suspensions of PDX cells were resuspended in 50% (v/v) mixtures of normal matrigel (BD Biosciences) and flow cytometry buffer in a total volume of 50-100 μL. Using an insulin syringe, cells were injected subcutaneously into the nipple of female NSG mice at the fourth abdominal fat pad. For limiting dilution assays, the specific number of cells injected into the mice were determined by flow cytometry and secondarily by manual counting with a hemocytometer.

PDX Tumor Growth and Total Body Weights

PDX tumors were detected by palpation. Tumor volumes were determined by measuring the length (l) and width (w) and calculating volumes using the ellipsoid formula $\frac{1}{6} \times l \times w^2 \times \pi$. Tumors volumes and mice weights were determined twice per week.

Mouse PDX Tumor and Lung Dissection

Xenograft tumors and mice lungs were surgically resected after the mice were euthanized. A 3 to 4 mm section is cut from each tumor and saved in ice cold PBS for imaging. The mice lungs and tumors were imaged on a M205FA Fluorescence Stereo Microscope (Leica) and images were captured with a DFC310FX camera (Leica).

Flow Cytometry to Determine RFP Percentage

Flow cytometry was performed with a 100 μm nozzle on a Flow Cytometry Aria II (BD Biosciences) with Diva software (BD Biosciences). Data analysis was performed using Flowjo software (Flowjo). For all experiments, side scatter and forward scatter profiles (area and width) were used to eliminate debris and cell doublets. Dead cells were eliminated by excluding 4',6-diamidino-2-phenylindole (DAPI)-positive cells (Molecular Probes). For PDX tumor cells, they were gated for GFP positivity and then for RFP positivity. RFP percentage is the percentage of GFP positive cells that are also RFP positive. For each sample, we obtain the RFP fraction that is: the RFP % in the tumor divided by the baseline RFP % (see 'Lentivirus infection' section). RFP fraction for each sample is then normalized to the RFP fraction for the shRNA control sample which is set at 100% to obtain the 'Normalized % RFP'.

Flow Cytometry Using EpCAM, CD10, and CD49f Cell Surface Markers for Analysis and Cell Sorting Flow cytometry for analysis and cell sorting was performed as previously described. Human antibodies used included: EpCAM-Alexa Fluor 488 (clone 9C4, Biolegend); 1 μg $mL^{-1}$, CD49f-APC (clone GoH3, Biolegend); CD10 PeCy7/Apc-Cy7 (clone H110a, Biolegend); 1 μg $mL^{-1}$ and H-2Kd biotin/Pacific Blue (clone SF1-1.1, Biolegend); 1 μg mL-1.

RNAi Dropout Viability Screen

GFP positive PDX-T1 tumors grown in NSG mice were dissected, processed to single cells, and enriched with EpCAM as described previously. Analysis of cells at this point showed that they were approximately 98%-100% GFP positive.

For the in vitro RNAi dropout viability screen, 60 million dissociated PDX-T1 cells were transduced with the DECIPHER 27K Pooled shRNA lentivirus library-Human Module 1 (Cellecta) at an MOI of 1 in the presence of polybrene and then spinoculated for 2 hours as described previously. The next day, half the cells were spun down and frozen as the in vitro baseline reference sample. A small number of cells were plated separately in organoid colony formation conditions to determine lentiviral infection percentage after 72 hours (cells were found to be approximately 80% RFP positive). The remainder of the cells were plated into twelve 150 mm dishes prepared with 12 mL matrigel containing irradiated L1-Wnt3a feeder cells at 250,000 cells/mL of matrigel. The cells were grown for 19 days with an exchange for fresh media every 3-4 days. On the final day, all the media was exchanged with dispase in order to dissolve the matrigel and to recover the cells. The cells from all the plates were pooled, washed, and frozen as the in vitro organoid growth experimental sample.

For the in vivo RNAi dropout viability screen, 30 million dissociated PDX-T1 cells were transduced with the DECIPHER 27K Pooled shRNA lentivirus library-Human Module 1 (Cellecta) at an MOI of 1.25 in the presence of polybrene and then spinoculated for 2 hours as described previously. The next day, half the cells were spun down and frozen as the in vivo baseline reference sample. A small number of cells were plated separately in organoid colony formation conditions to determine lentiviral infection percentage after 72 hours (cells were found to be approximately 70% RFP positive). The remainder of the cells were resuspended in 50% (v/v) mixtures of normal matrigel (BD Biosciences) and flow cytometry buffer in a total volume of 1.8 mL. These cells were injected evenly into the right and left mammary fat pads of seventeen NSG mice. When tumors reached approximately 10 mm in diameter, the mice were euthanized and the tumors dissected as previously described. These tumors were then processed into single cells, pooled, washed, and frozen as the in vivo growth experimental sample.

The two pairs of samples, in vitro baseline reference sample and in vitro organoid growth experimental sample and in vivo baseline reference sample and in vivo growth experimental sample, were submitted to Cellecta, Inc. for genomic DNA extraction, bar code amplification, high-throughput sequencing and de-convolution. Twenty million barcode reads were performed for each sample.

Figure 5A:
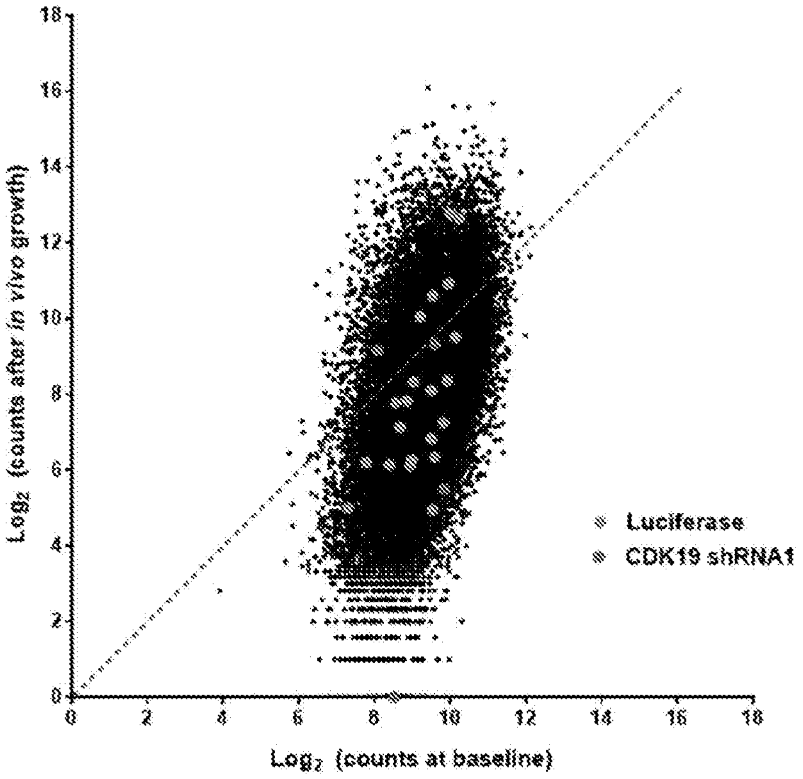
FIGS. 5A and 5B are graphs showing the shRNA counts in the in vivo growth experimental sample versus the shRNA counts in the baseline sample (FIG. 5A) and the shRNA counts in the in vitro growth experimental sample versus the shRNA counts in the baseline sample (FIG. 5B).
Figure 5B:
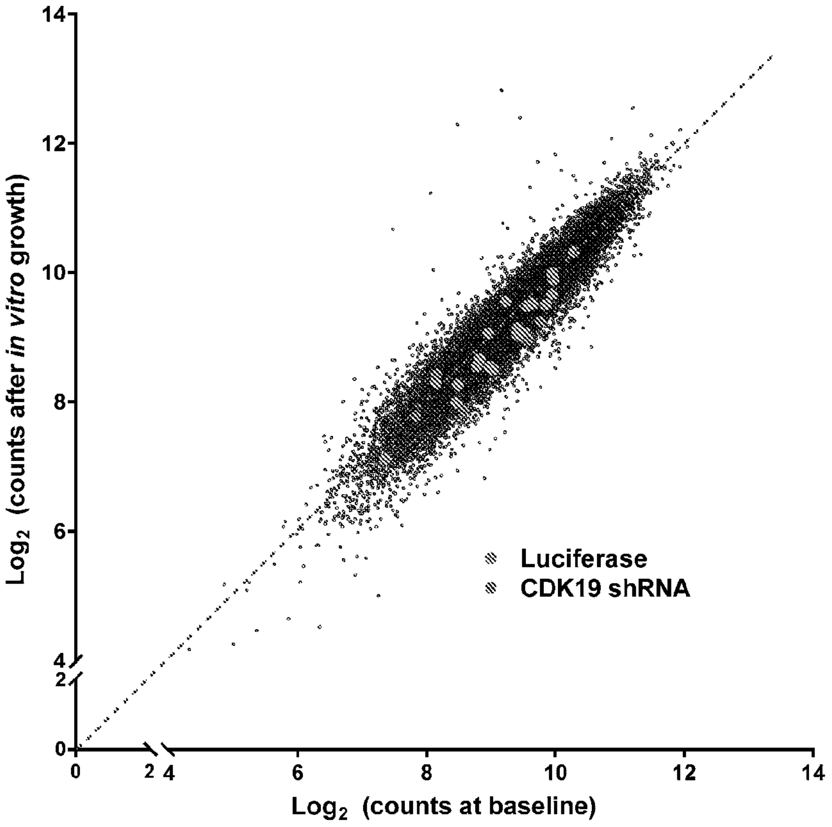
Figure 5C:
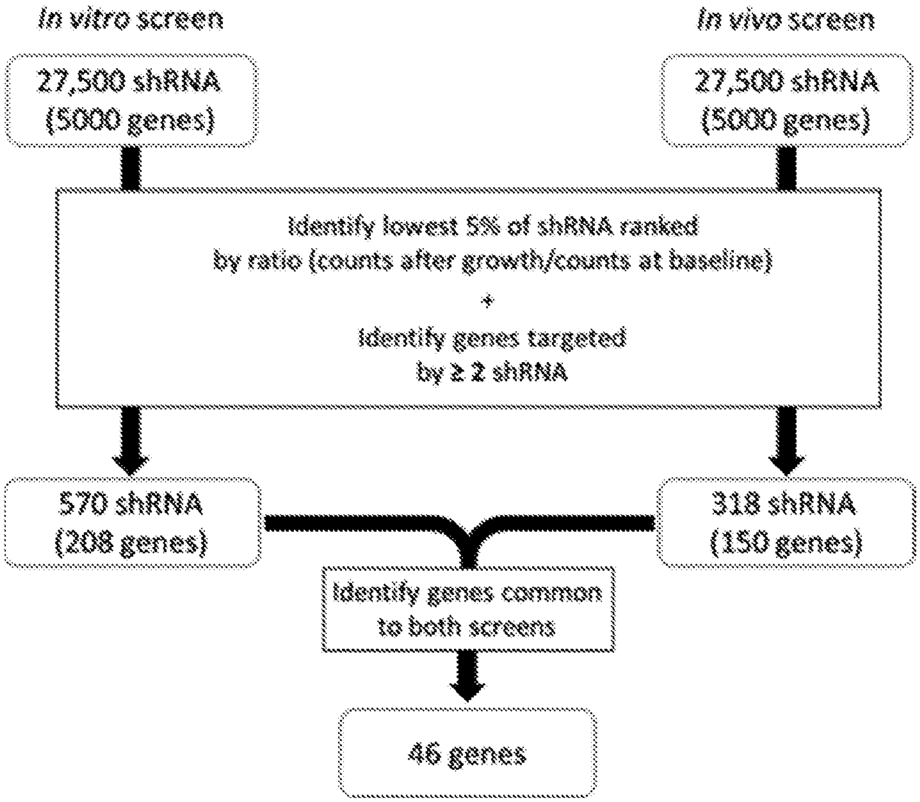
FIG. 5C is a schematic of the criteria used to narrow the initial list of hits from the in vitro and the in vivo screens down to 46 candidate genes.

'Hit' Selection Algorithm from the In Vivo and In Vitro RNAi Dropout Viability Screens Please see the schematic in FIG. 5C for an overview. We applied an algorithm to narrow our hits to a more manageable number for validation. 1) for each individual shRNA we determined a 'dropout ratio' that was shRNA barcode counts in the growth experimental sample divided by shRNA barcode counts in the baseline reference sample. In each screen, these were ranked from lowest to highest. 2) We examined the top 5% of the lowest dropout ratios in each experiment and identified genes targeted by 2 shRNA. 3) We cross-referenced the shRNA gene targets in the in vivo screen (208 genes) with those in the in vitro screen (150 genes) to identify genes that overlapped between the two experiments. These 46 overlapping 'hit' genes are shown in FIG. 5A.

Immunofluorescence of PDX Tumors

Sections of the PDX tumors were fixed in formalin overnight and then transferred to 70% ethanol. Samples were then embedded in paraffin and sectioned for histology. Formalin fixed paraffin embedded sections were de-parafinized in xylene and rehydrated in an ethanol gradient. Antigen retrieval was performed in a Tris-EDTA buffer by heating in a microwave for 20 min. The primary antibodies, polyclonal Rabbit anti-CDK19 (Sigma) and polyclonal chicken anti-CDK8 (Novus Biologicals), were diluted 1:50 and 1:100, respectively, in TBS+1% BSA before applying to samples overnight. After overnight incubation, the secondary antibodies, Cy3 Donkey anti-Rabbit (Jackson ImmunoResearch) and Alexa 488 Goat anti-Chicken (Life Technologies) were diluted 1:500 in TBS+1% BSA and incubated with the samples at room temperature. After DAPI staining, sections were mounted with ProLong® Gold antifade (Cell Signaling). A Zeiss LSM710 Confocal microscope (Carl Zeiss) was used to take the immunofluorescence images. Images for publication were processed with Fiji software.

Microarray Experiment

EpCAM enriched PDX-T1 cells were infected with shCDK19-2, shCDK8-2 or control shRNA and grown in organoid culture conditions for 72 hours. They were subsequently recovered from matrigel with dispase, resuspended in flow cytometry buffer and sorted by flow cytometry to obtain cells that were both GFP and RFP positive. RNA was extracted from these cells by RNeasy plus micro kit (Qiagen) according to manufacturer's instructions and quantified on an Agilent 2100 Bioanalyzer. 50 ng of total RNA from each sample was used. In vitro transcription, fragmentation, labeling, hybridization to the microarray and scanning was performed by the Stanford Protein and Nucleic acid facility (PAN facility). Samples were hybridized on PrimeView Human Gene Expression Arrays (Affymetrix). Gene Level Differential Expression Analysis was performed with the Transcriptome Analysis Console (Affymetrix). Downregulated genes were defined as those for which $\log_2$ (sample/control)<−1.5 and upregulated genes $\log_2$ (sample/control)>1.5.

H3K27Ac Chromatin Immunoprecipitations

ChIP assays were performed as described in, e.g., Zarnegar et al., *Nucleic Acids Research*, gkx648, *July*, 2017. Approximately 250,000 to 500,000 MDA-MB231 cells were used per ChIP. 1 μg of anti-H3K27ac (Active Motif #39133) were used per ChIP.

Library Construction

ChIP enriched DNA was quantified using a Qubit 3.0 and dsDNA HS assay. Up to 1 ng of DNA was used for library construction using transposition based NEXTERA XT (followed manufacturer's protocol with ~14 PCR cycles for indexing). Indexed samples were pooled and submitted for sequencing on a NextSeq500 to obtain 75 bp single end reads with read depths of ~60 million reads.

Sequence Analysis.

Raw sequence reads were uploaded to Galaxy (usegalaxy.org) and aligned to the human genome (hg19) using Bowtie2 (-very-fast-local). Only uniquely mapped reads were retained for further analysis. To visualize data, alignment files were used to produce signal tracks with DeepTools (100 bp bins with 200 bp read extensions and RPKM normalization) and BigWig files were loaded into Broad's integrated Genome Browser. MACS2 was used to call peaks (-nomodel, p=0.01, -broad, cuttoff 0.1, duplicates=auto, extension 200) for each replicate. A consensus peak list containing only those peaks occurring in all replicates, was generated using Bedtools. We performed differential peak analysis across consensus peaks using DiffBind. The DiffBind output peak list was annotated by fetching the nearest non-overlapping feature of the human RefSeq table from UCSC. Data for aggregation plots of ChIP signal across various peaks sets were generated using DeepTools' computeMatrix (scale-regions: 1000; 50 bp bins) and plotProfile. Data was then plotted with GraphPad Prism software.

GSEA Analysis

Gene set enrichment analysis (GSEA) was performed using the javaGSEA desktop application (GSEA 3.0) with $\log_2$ fold change values for CDK19 knockdown versus Control as the ranking metric and Hallmarks, CDK19KD-EnhancerUp and CDK19KD-EnhancerDOWN as the gene sets that were tested for enrichment.

Metascape Analysis

Metascape custom enrichment analysis of Hallmark gene sets using the CDK19KD-EnhancerUP 'core' genes and the CDK19KD-EnhancerDOWN 'core' genes (using the following parameters: H. *Sapiens* as the input species, p-value cutoffs of 0.01 and minimum enrichment 1.5) was performed online (www.metascape.org).

Statistical Analysis

Results are shown as mean±s.d. Statistical calculations were performed with GraphPad Prism software (GraphPad Software Inc). Variance was analyzed using the F-test. To determine P-values, t-test was performed on homoscedastic populations, and t-test with Welch correction was applied on samples with different variances. For animal studies, sample size was not predetermined to ensure adequate power to detect a pre-specified effect size, no animals were excluded from analyses, experiments were not randomized and investigators were not blinded to group allocation during experiments.

4.2 Example 2—Identification of Genes Essential for TNBC Growth

To identify genes essential for the growth of TNBC, two pooled RNAi dropout viability screens were performed using a 27,500 shRNA library targeting 5000 genes in PDX-T1, a TNBC PDX (FIG. 15). The screens were performed in two different formats, in vitro as organoid cultures and in vivo as PDXs in nod scid gamma (NSG) mice (FIG. 1A). The abundance of individual shRNA in each experimental sample and the baseline reference samples were determined by high throughput sequencing of the shRNA barcodes. The goal was to identify genes whose knockdown by shRNA inhibited the growth of PDX tumor cells across different experimental conditions. Consistent with screens in other tumors, the in vivo screen had a more significant shRNA dropout rate (FIG. 5A) compared to the in vitro screen (FIG. 5B). FIGS. 5A and 5B are graphs showing the shRNA counts in the in vivo growth experimental sample (FIG. 5A) and in the in vitro growth experimental sample (FIG. 5B) versus the shRNA counts in the baseline sample. Control shRNA targeting luciferase (light gray dots) and shRNA targeting CDK19 (dark gray dots) are highlighted. All other shRNA are shown as black dots (each experiment performed once). The final candidate list was restricted to genes with the lowest 5% of shRNA ratios in each screen that were targeted by more than two shRNAs and were also identified both in vitro and in vivo (FIG. 5C). This resulted in the identification of 46 candidate genes (FIG. 5D).

Figure 6A:
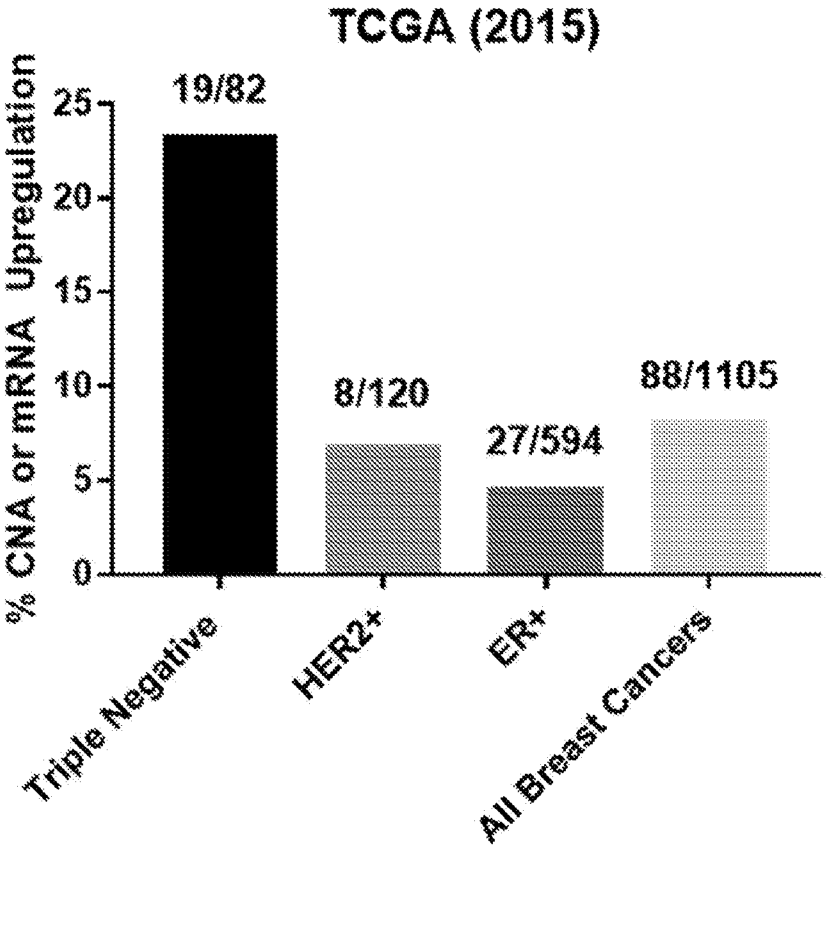
FIG. 6A is a bar graph showing that TCGA breast cancer samples from patients with the TNBC subtype are enriched in CDK19 copy number amplifications or CDK19 mRNA upregulation compared to other subtypes.
Figure 6B:
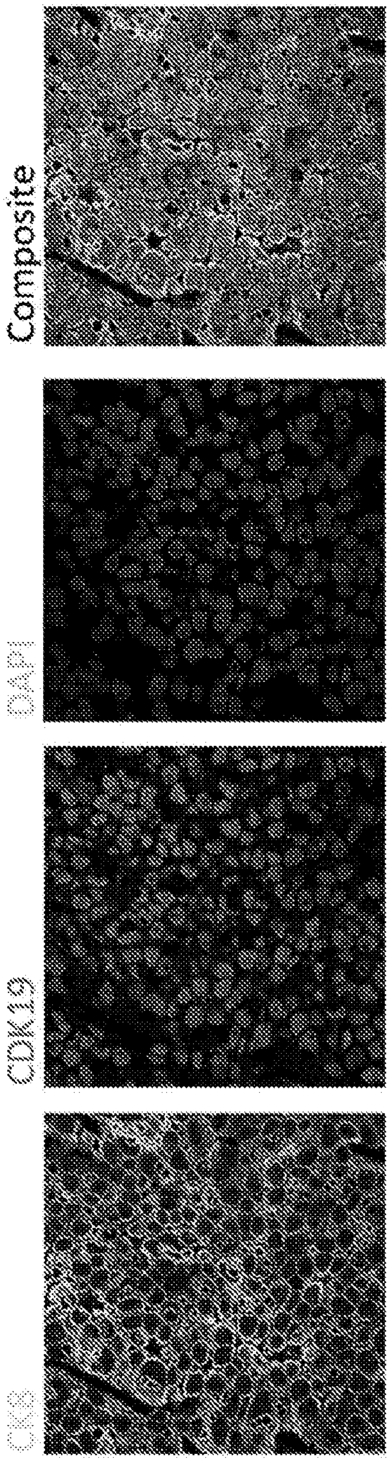
FIG. 6B includes confocal immunofluorescent images of PDX-T1 stained with cytokeratin 8 (CK8) antibodies (first image from the left), CDK19 antibodies (second image), and DAPI (third image). The composite image composed from all three aforementioned images is shown on the far right (images are representative of three independent experiments).

CDK19 was chosen because data from the Cancer Genome Atlas (TCGA) showed that CDK19 copy number amplifications and mRNA upregulation were more prevalent in TNBC patient samples (23%) compared to samples from other breast cancer subtypes (see, e.g., Cancer Genome Atlas Research, N. et al. The Cancer Genome Atlas Pan-Cancer analysis project. *Nat Genet* 45:1113-1120, 2013; FIG. 6A). Additionally, high CDK19 expression has been reported to correlate with poor relapse free survival in breast cancer patients (see, e.g., Broude et al., *Current cancer drug targets* 15, 739-749, 2015 and Porter et al., *Proc Natl Acad Sci USA* 109: 13799-13804, 2012). CDK19 belongs to a subset of the CDK family that is reportedly more associated with regulation of RNA polymerase II (RNAPII) transcription than cell cycle progression. CDK19 and its paralog, CDK8, can both form the CDK module (CKM) by binding with three other proteins: MED12, MED13, and Cyclin C. The presence and nuclear localization of CDK19 in our PDX cells were confirmed by immunofluorescence (FIG. 6B). In FIGS. 6A and 6B, the percentage shows the percentage of samples with CDK19 copy number amplifications or CDK19 mRNA upregulation in triple-negative, HER2 positive, estrogen receptor positive, and all breast cancers. The fractions show the number of positive samples and total samples in each group. Data obtained from cBioPortal (see, e.g., Gao et al., SciSignal 6, pI1, 2013).

4.3 Example 3—Growth Inhibitory Effects of CDK19 Knockdown

Figure 7A:
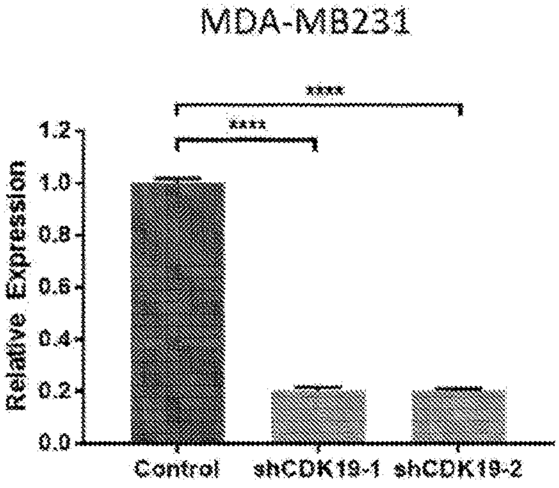
FIGS. 7A and 7B are bar graphs showing that CDK19 targeting shRNA effectively silences CDK19 in TNBC cells lines. Expression of CDK19 in MDA-MB231 (FIG. 7A) or MDA-MB468 (FIG. 7B) determined by RT-qPCR for cells transduced with control shRNA, shCDK19-1, and shCDK19-2.
Figure 7B:
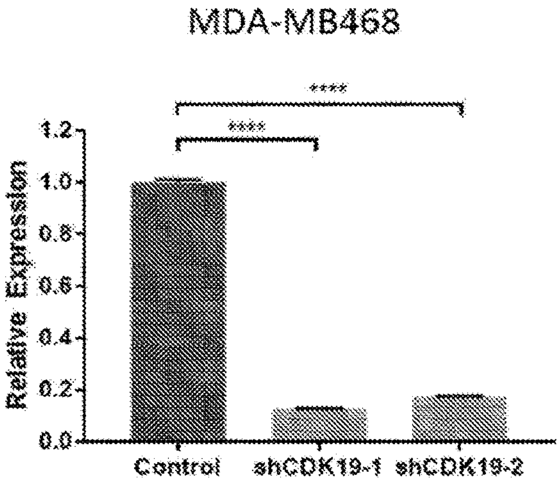
Figure 7C:
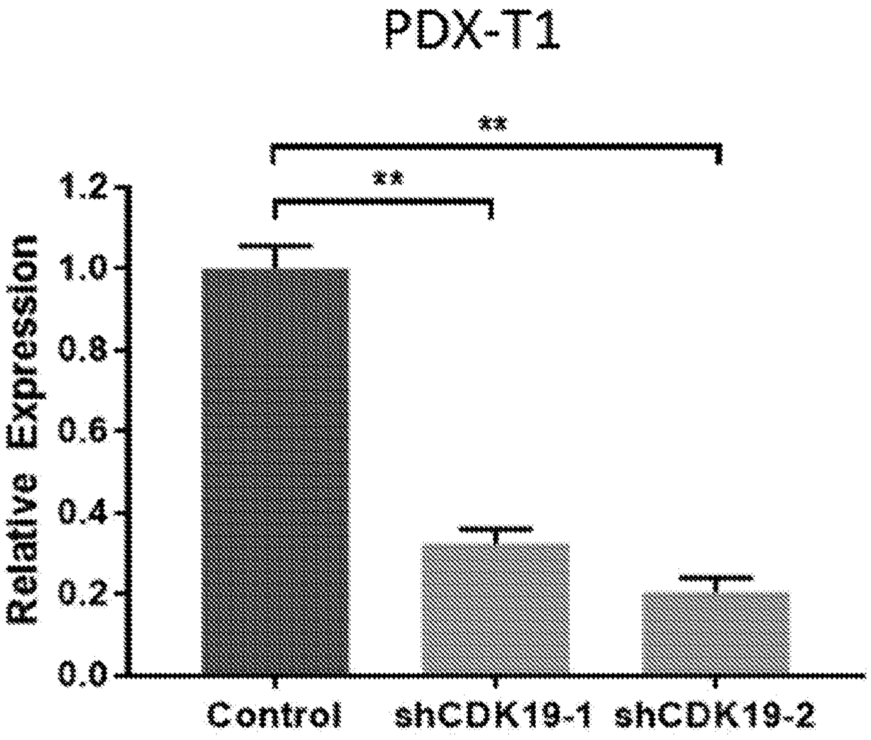
FIG. 7C is a bar graph showing that CDK19 targeting shRNA effectively silences CDK19 in a TNBC PDX. Expression of CDK19 in PDX-T1 as determined by RT-qPCR for cells transduced with control shRNA, shCDK19-1, and shCDK19-2.

To validate the growth inhibitory effect of CDK19 knockdown, three commonly used TNBC cell lines: MDA-MB231, MDA-MB468, and HS578T were used. Using two different shRNAs (shCDK19-1 (SEQ ID NO: 1) and shCDK19-2 (SEQ ID NO: 2)) that independently target CDK19, the knockdown of CDK19 (FIGS. 7A and 7B) was confirmed. For both FIGS. 7A and 7B, the relative expression of CDK19 in CDK19 knockdown cells is normalized to the mean expression of CDK19 in cells transduced with control shRNA. Gene expression in each condition is normalized to beta-actin as a housekeeping gene (P<0.01; P<0.0001, mean±s.d., (FIGS. 7A and 7B) n=3 (FIG. 7C) n=2, experiments performed twice). The knockdown of CDK19 also showed that it caused decreased proliferation in all three TNBC cell lines (FIGS. 1B-1D). FIGS. 1B-1D demonstrate that CDK19 knockdown significantly decreased the viability of TNBC cells (viability of MDA-MB231 cells, P<0.0001 (FIG. 1B), MDA-MB468 cells, *P<0.001; **P<0.0001 (FIG. 1**C), or HS578T cells, *P<0.05; **P<0.0001 (FIG. 1D) assessed 4 days after transduction with control shRNA or CDK19 targeting shRNA (shCDK19-1, shCDK19-2)). All values in FIGS. 1B-1**D were normalized to control shRNA sample (mean s.d., n=3, experiment performed twice, P values determined by unpaired t-test).

Figure 1E:
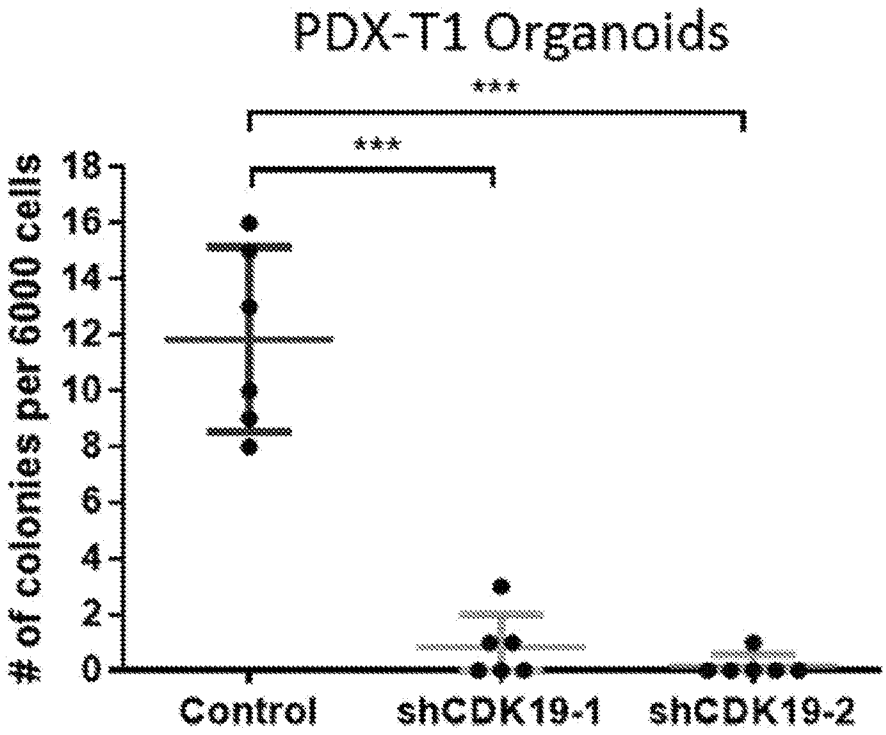
FIG. 1E is a graph showing that CDK19 knockdown significantly decreased the formation of organoid colonies in PDX-T1.
Figure 1F:
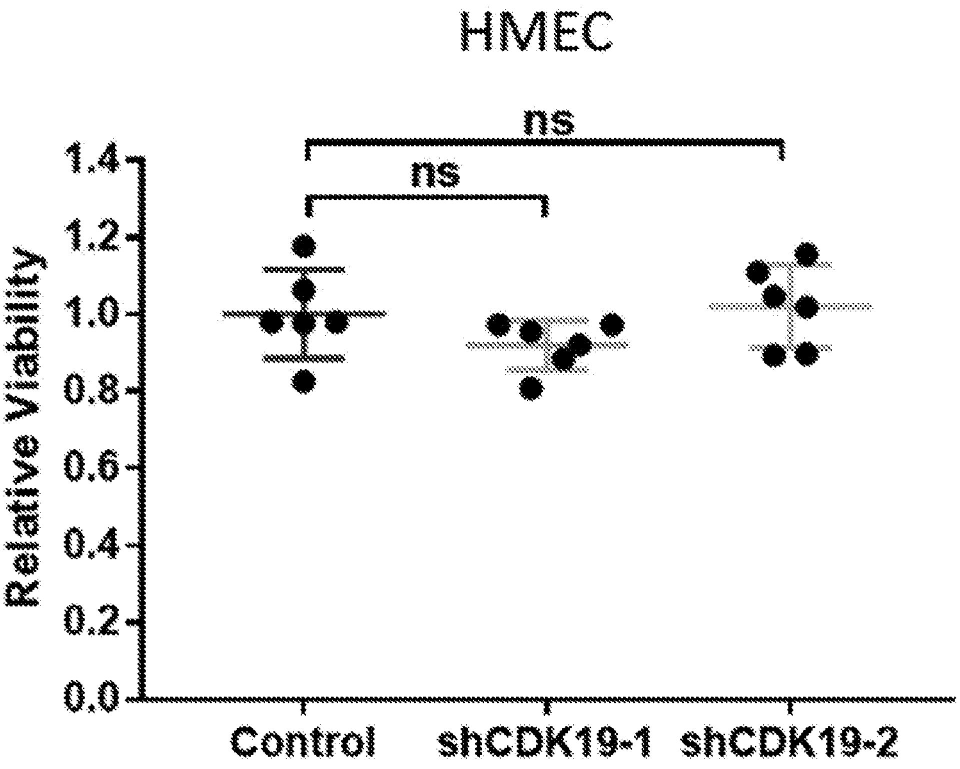
FIG. 1F is a graph showing that CDK19 knockdown does not decrease the viability of non-transformed human mammary epithelial cells (HMEC).
Figure 1G:
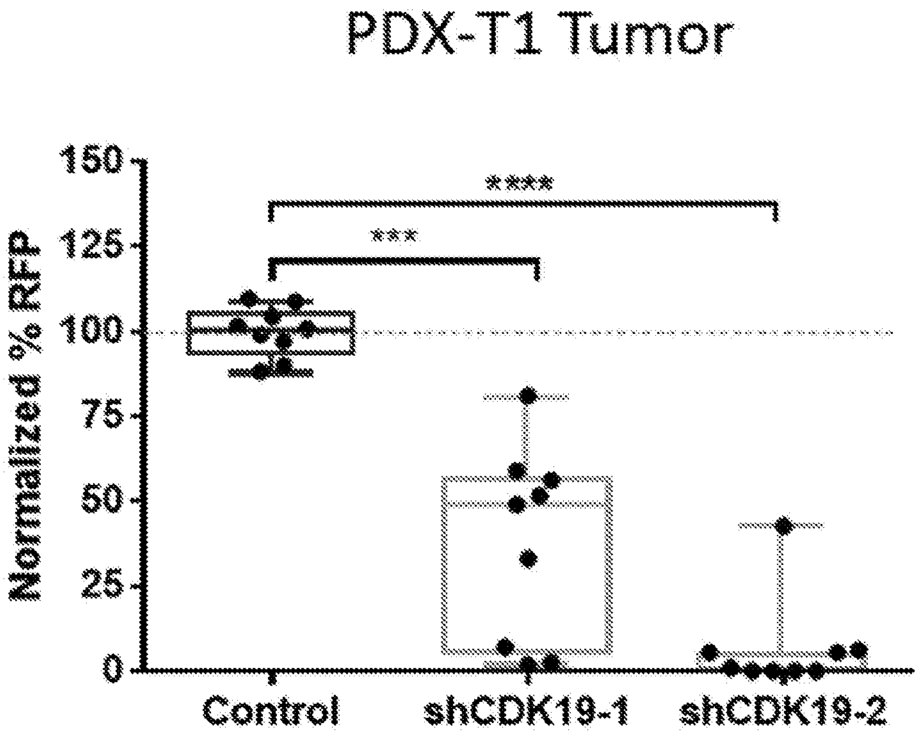
FIGS. 1G-1J are graphs showing that CDK19 knockdown significantly inhibits the proliferation of PDX tumors (FIG. 1G: PDX-T1.
Figure 1H:
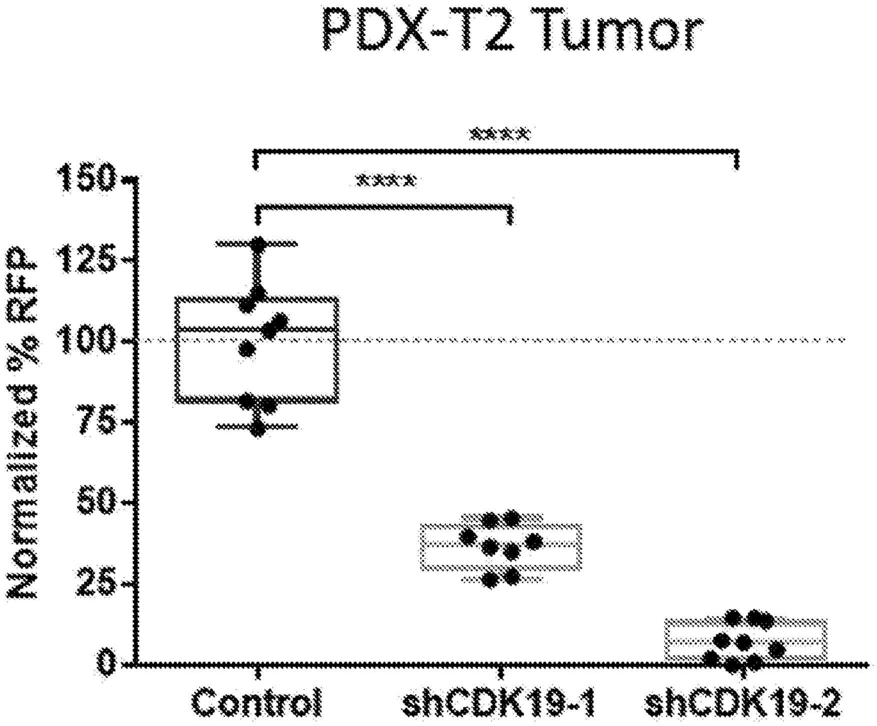
Figure 1I:
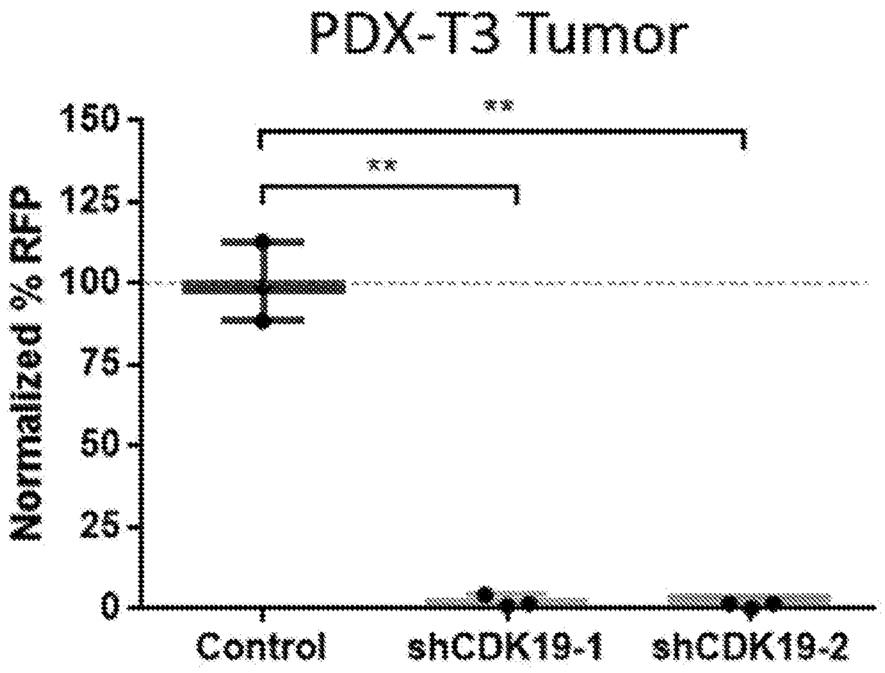
Figure 1J:
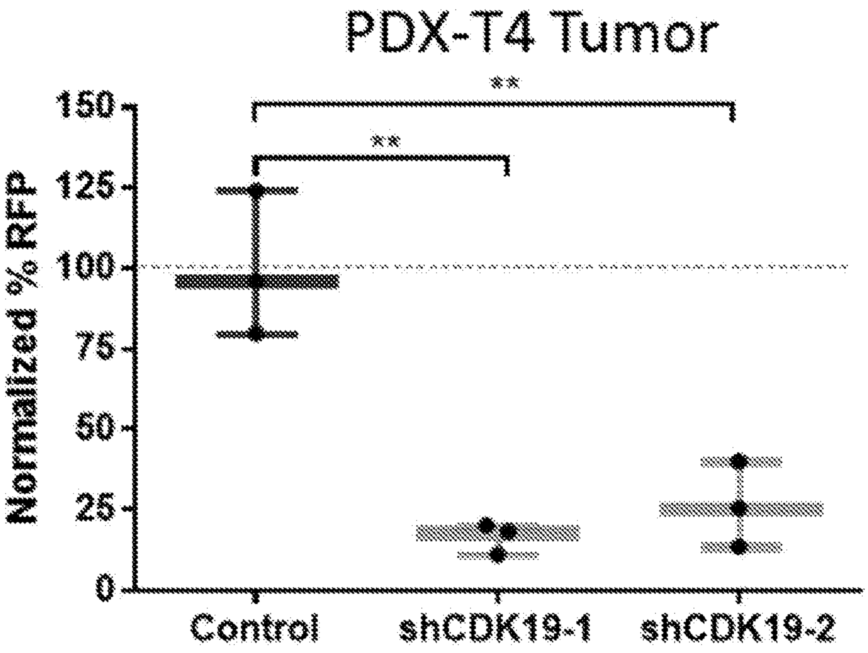

In the same TNBC PDX used in the initial dropout screen (PDX-T1), CDK19 knockdown (FIG. 7C) also inhibited the formation of organoid colonies (FIG. 1E). In FIG. 1E, colonies were counted 2 weeks after transduction with either control shRNA or CDK19 targeting shRNA (shCDK19-1, shCDK19-2), *P<0.001 (unpaired t-test) (mean s.d., n=6, experiment performed twice). To determine the effects of CDK19 knockdown in non-transformed mammary cells, human mammary epithelial cells (HMEC) were infected with shRNA targeting CDK19. In HMECs, neither of the two CDK19 knockdowns affected the viability of the cells (FIG. 1F). In FIG. 1**F, viability of HMEC cells was assessed 4 days after transduction with control shRNA or CDK19 targeting shRNA (shCDK19-1, shCDK19-2). All values are normalized to control shRNA sample, ns is P>0.05 (mean s.d., n=6, experiment performed twice, P values determined by unpaired t-test). Collectively, the studies show that in vitro, CDK19 knockdown inhibits the proliferation of multiple TNBC cell lines and the formation of PDX organoid colonies but does not adversely affect the growth of non-transformed mammary epithelial cells.

We extended our studies to more physiologically relevant in vivo systems by knocking down CDK19 in three different TNBC PDXs grown in NSG mice. These PDXs: PDX-T1, PDX-T2, and PDX-T3 were derived from chemotherapy naive patients (FIG. 15). In these studies, all PDX tumor cells were first labeled with green fluorescent protein (GFP) and cells subsequently infected with either CDK19 shRNA or control shRNA were additionally labeled with red fluorescent protein (RFP). Measuring the percentage of GFP-labeled tumor cells that were also RFP positive allowed us to determine the effect the shRNA had on the PDX tumor cells. With each of the two CDK19 shRNAs tested, CDK19 knockdown led to a significant reduction in the percentage of RFP positive cells in tumors from all three TNBC PDXs (FIGS. 1G-1I and FIG. 1M). Tumor growth was monitored and tumors were analyzed when they exceeded 17 mm. The percentage of RFP positive cells in PDX-T1, *P<0.001; P<0.0001 (FIG. 1G), PDX-T2, P<0.0001 (FIG. 1H), PDX-T3, P<0.01 (FIG. 1I), or PDX-T4, P<0.01 (FIG. 1J) were determined by flow cytometry and normalized to the mean RFP percentage of the control shRNA sample that was set to 100%. Each data point represents one mouse. For FIGS. 1H and 1H, mean±s.d., n=9, experiment performed three times. For FIGS. 11 and 1**J, mean s.d., n=3, experiment performed once. For all, P values determined by unpaired t-test).

Figure 1K:
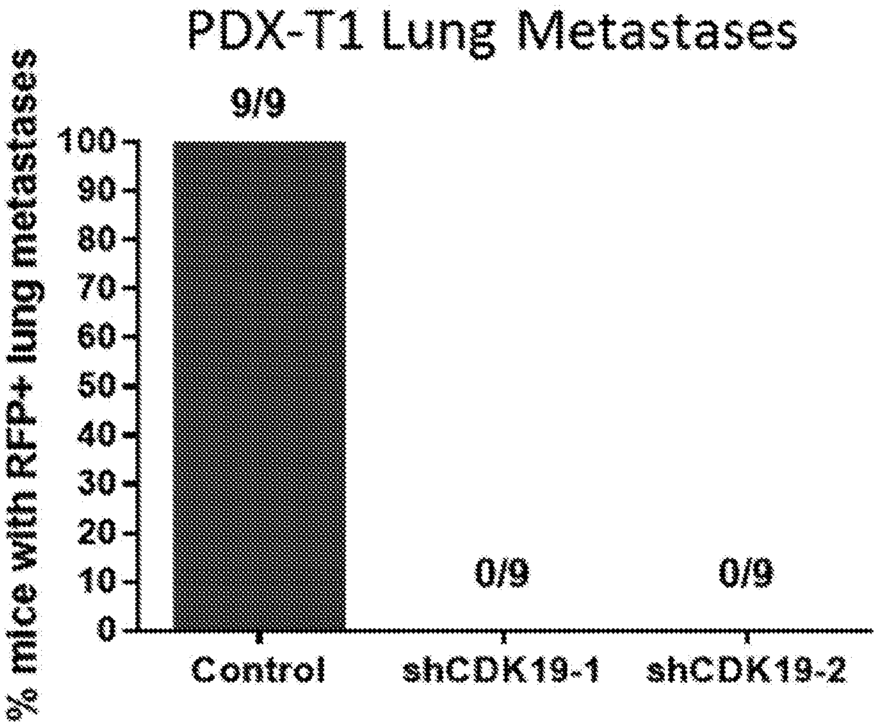
FIGS. 1K and 1L are bar graphs showing that CDK19 knockdown prevented transduced (RFP positive) TNBC cells (FIG. 1K: PDX-T1 and FIG. 1L PDX-T4) from metastasizing to the lungs in mice.
Figure 1L:
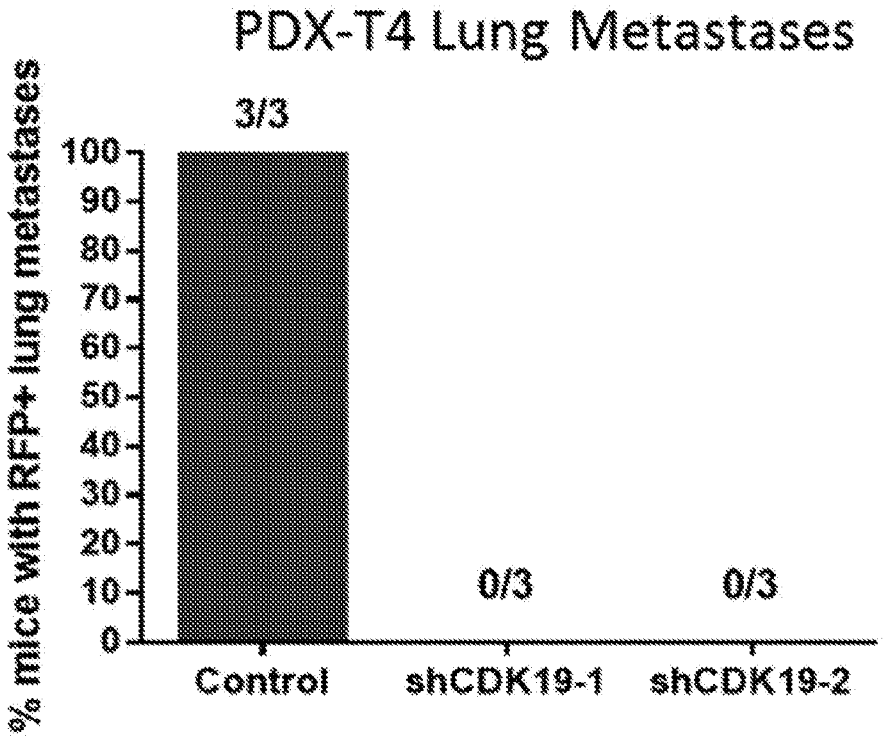
Figure 1M:
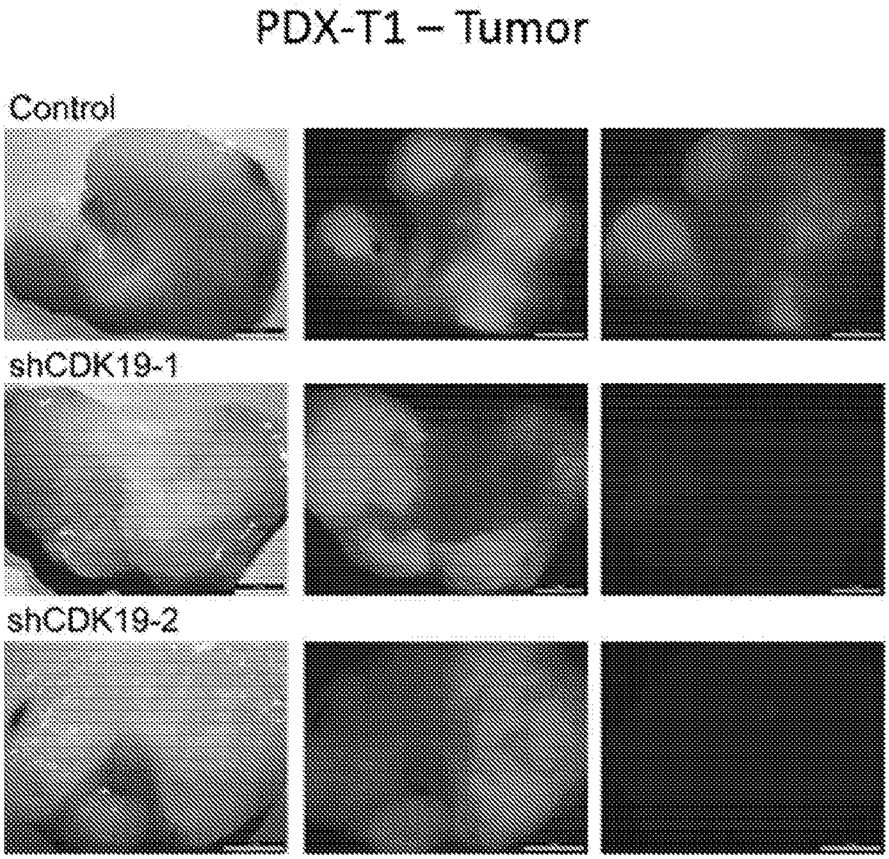
FIG. 1M shows that in PDX tumors transduced with CDK19 shRNA (images in the second and third rows), very little RFP (images in the last column) is visible. These tumors are composed primarily of un-transduced GFP positive tumor cells (images in the middle column). PDX tumor cells were first labeled with green fluorescent protein (GFP) (middle column) and cells subsequently infected with either CDK19 shRNA or control shRNA were additionally labeled with red fluorescent protein (RFP) (right column).

FIG. 1M shows representative images of PDX-T1 tumors transduced with control shRNA (top row), shCDK19-1 (middle row), or shCDK19-2 (bottom row). Bright field images (left column) show gross tumor morphology, FITC images (middle column) identify tumor cells labeled with GFP and Texas-Red images (right column) identify shRNA-transduced cells labeled with RFP.

Figure 1N:
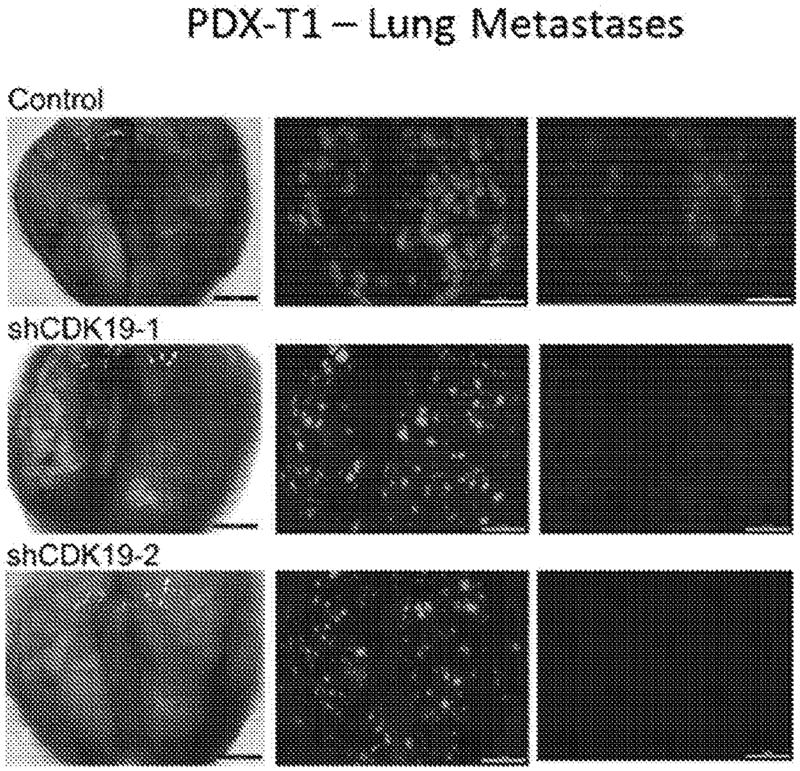
FIG. 1N shows representative images of mouse lungs with PDX-T1 metastases. Lungs from mice with PDXs transduced with control shRNA (top row), shCDK19-1 (middle row) or shCDK19-2 (bottom row) are shown. In PDX-T1, which normally metastasizes to the lung, CDK19 knockdown eliminated the detection of any lung metastases by those cells. Bright field images (left column) show gross lung morphology, FITC images (middle column) identify metastatic tumor cells labeled with GFP, and metastatic tumor cells subsequently infected with either CDK19 shRNA or control shRNA were additionally labeled with red fluorescent protein (RFP) (right column).
Figure 7D:
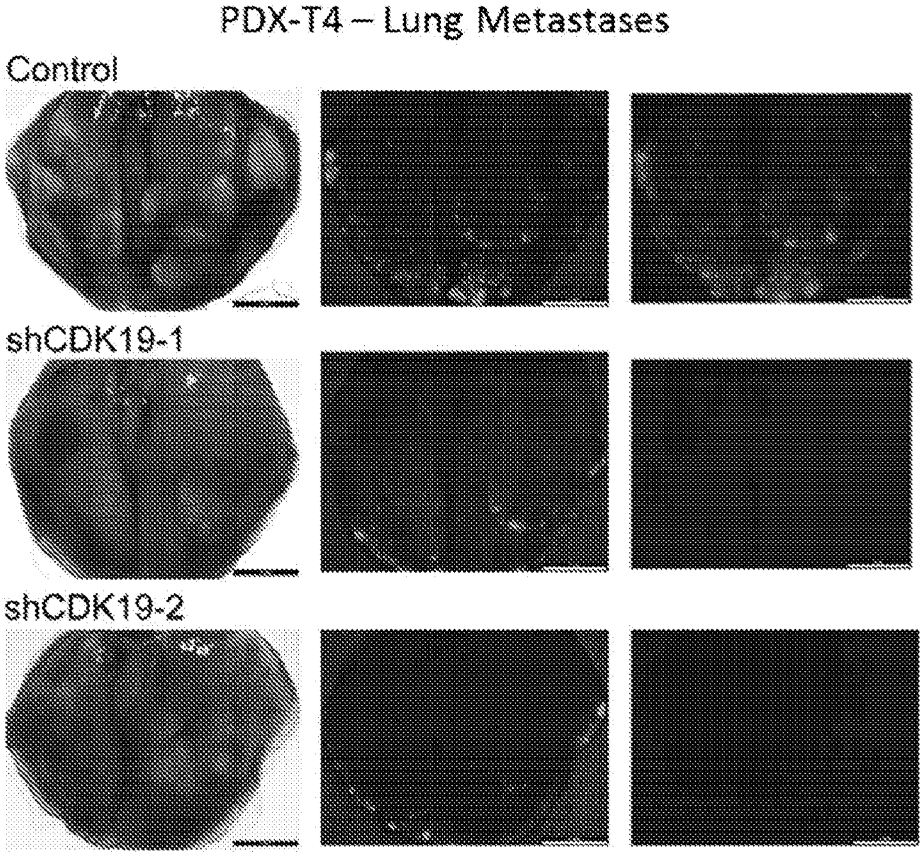
FIG. 7D includes images of tissue samples and representative images of mouse lungs bearing PDX-T4 metastases. Lungs from mice with PDXs transduced with control shRNA (top row), shCDK19-1 (middle row), or shCDK19-2 (bottom row) are shown. Bright field images (left column) show gross lung morphology, FITC images (middle column) identify metastatic tumor cells labeled with GFP, and Texas-Red images (right column) identify shRNA-transduced metastatic cells labeled with RFP.

These results confirmed that CDK19 is critical for tumor growth in vivo. CDK19 knockdown prevented transduced (RFP positive) TNBC cells from metastasizing to the lungs in mice. Percentage of mice with RFP positive lung metastases from mice bearing PDX-T1 (FIG. 1K) or PDX-T4 (FIG. 1L) tumor xenografts are shown. Number of mice with RFP positive lung metastases and total number of mice in each treatment group is shown as a fraction for each condition. PDX tumor cells were transduced with either control shRNA or CDK19 targeting shRNA (shCDK19-1, shCDK19-2) (For FIG. 1K, n=9, experiment performed three times; For FIG. 1I, n=3, experiment performed once). Furthermore, in PDX-T1, which normally metastasizes to lung, CDK19 knockdown eliminated the detection of any lung metastases by those cells (FIG. 1K and FIG. 1N). In FIG. 1N, bright field images (left column) show gross lung morphology, FITC images (middle column) identify metastatic tumor cells labeled with GFP, and Texas-Red images (right column) identify shRNA-transduced metastatic cells labeled with RFP. We also tested the effect of CDK19 knockdown on PDX-T4, an aggressive PDX obtained from the brain metastasis of a patient with a chemotherapy-resistant inflammatory breast cancer. Since inflammatory breast cancers are known to be aggressive, difficult to treat, and associated with extremely poor prognoses, it is notable that CDK19 knockdown inhibited both the growth of the PDX (FIG. 1J) and the lung metastases in these mice (FIG. 1L and FIG. 7D). These data show that in vivo, CDK19 knockdown not only affected primary tumor growth, but also inhibited tumor metastasis.

Figure 2A:
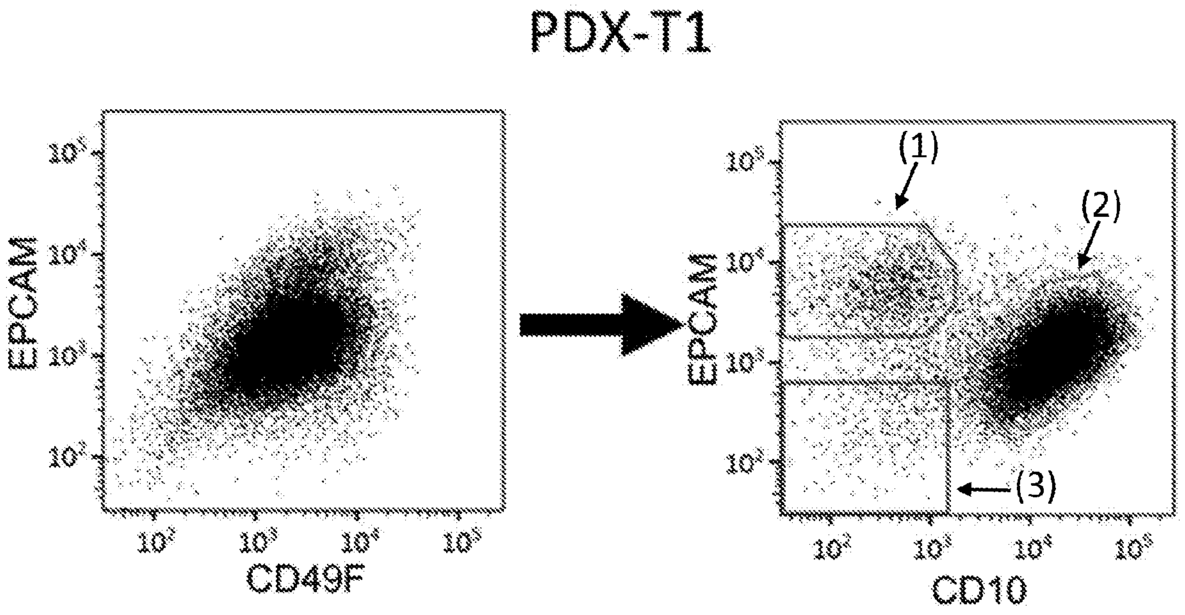
FIG. 2A shows data from representative flow cytometry analyses of a TNBC (PDX-T1) using EpCAM and CD49f (left) or EpCAM and CD10 (right) as cell surface markers.

4.4 Example 4—Identification of Tumor Initiating Cells (TICs) within the TNBC PDXs Given that CDK19 knockdown inhibited growth in two independent assays commonly used to assess tumorigenicity (PDX growth in vivo and organoid colony formation in vitro) and genes critical for tumor initiation are frequently amplified or overexpressed in a subset of cancers, it is hypothesized that the tumor initiating cells (TICs) might be sensitive to CDK19 inhibition. Thus, we sought to identify the TICs within the TNBC PDXs. Previously, EpCAM and CD49f were utilized to isolate cell sub-populations in normal breast tissue and in breast cancers. However, in many TNBC PDXs, EpCAM and CD49f often cannot clearly separate cells into distinct sub-populations (FIG. 2A, left). Thus, we utilized the basal cell marker, CD10 with EpCAM to FACS-sort breast cancer PDXs. We discovered that CD10 and EpCAM can separate PDX cells into three distinct sub-populations, $EpCAM^{med/high}/CD10^{-/low}$, $EPCAM^{low/med}/CD10^{low/+}$, and $EpCAM^{-}/CD10^{-}$ (FIG. 2A, right). In FIG. 2A, the large inseparable cell population (left) seen using EpCAM and CD49f, becomes three distinct sub-populations using EpCAM and CD10 (right): $EpCAM^{med/high}/CD10^{-/low}$ (gate (1)), $EPCAM^{low/med}/CD10^{low/+}$ (gate (2)) and $EpCAM^{-}/CD10^{-}$ (gate (3)). The overlap of these three sub-populations using EpCAM and CD49f is also shown (FIG. 8A).

Figure 2B:
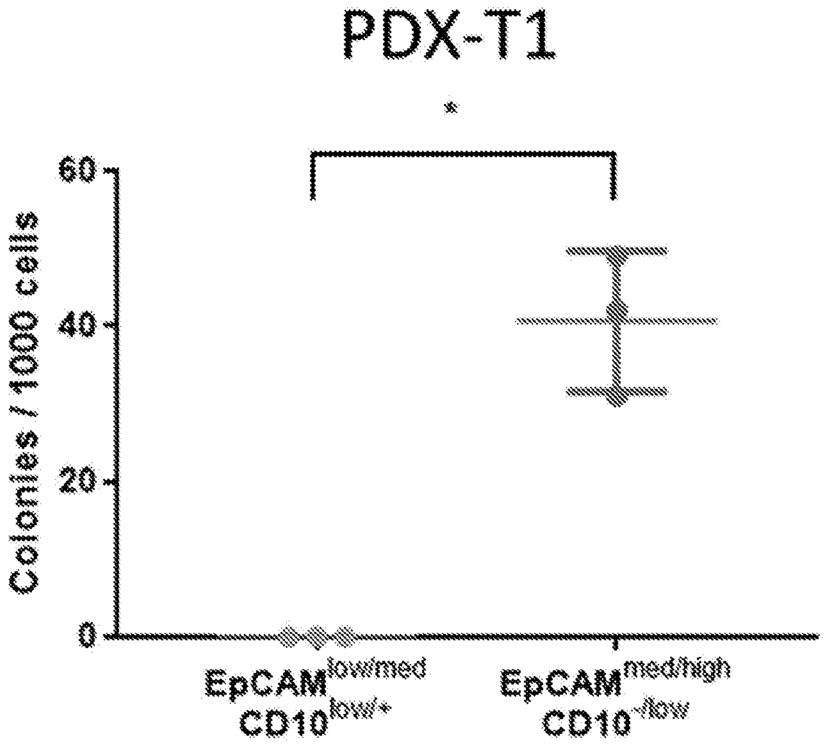
FIG. 2B is a graph that compares the organoid colony forming capabilities of the $EpCAM^{med/high}/CD10^{-/low}$ and $EPCAM^{low/med}/CD10^{low/+}$ cell sub-populations.
Figure 2D:
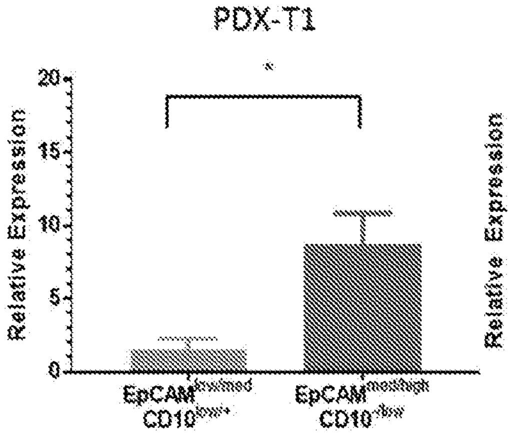
FIGS. 2D-2G are bar graphs showing that CDK19 expression is higher in the $EpCAM^{med/high}/CD10^{-/low}$ cells compared to the $EPCAM^{low/med}/CD10^{low/+}$ cells in PDX-T1, PDX-T2, and PDX-T8.
Figure 2E:
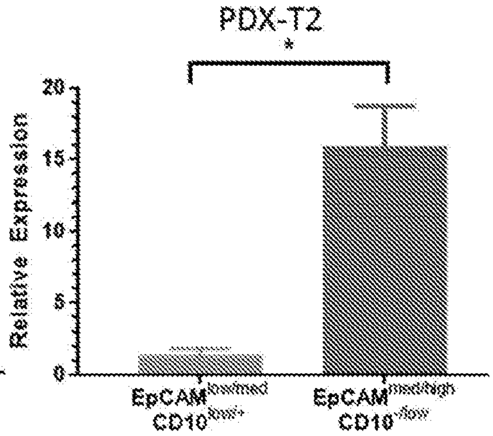
Figure 2F:
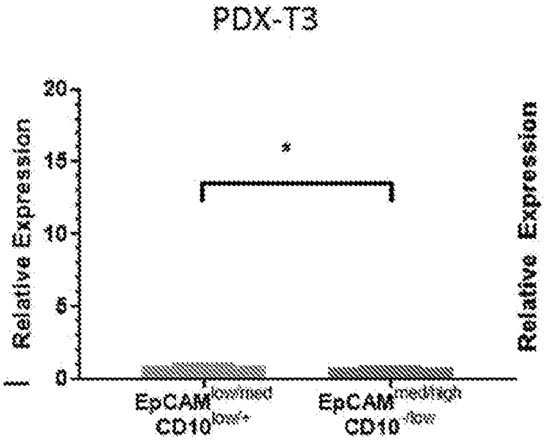
Figure 2G:
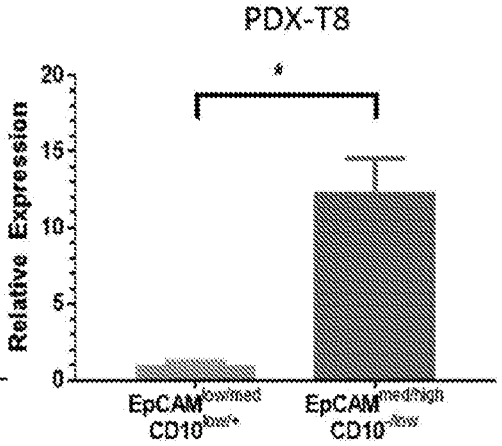

To test the tumor initiating capacity of the three EpCAM/CD10 separated sub-populations, we performed organoid colony formation assays in vitro and transplantation limiting dilution assays (LDA) in vivo. In organoid colony forming assays, the $EpCAM^{med/high}/CD10^{-/low}$ cells formed significantly more organoid colonies than the $EpCAM^{low/med}CD10^{low/+}$ cells (FIG. 2B). In FIG. 2B, the $EpCAM^{med/high}/CD10^{-/low}$ cells formed significantly more organoid colonies than the $EPCAM^{low/med}/CD10^{low/+}$ cells, *P<0.05 (unpaired t-test) (mean t s.d., n=3, experiment performed twice). In transplantation assays performed in NSG mice, injection of $EpCAM^{med/high}/CD10^{-/low}$ cells from all six PDXs consistently formed tumors (FIG. 2C), sometimes with the transplant of as little as 100 cells (PDX-T1 and PDX-T2). In contrast, transplant of $EPCAM^{low/med}/CD10^{low/+}$ cells only formed tumors in two PDXs (PDX-T1 and PDX-T2), and only when transplanting high cell numbers (i.e. 2500 cells) (FIG. 2C). Furthermore, no tumors formed from the transplant of $EpCAM^{-}$/CD10- cells from any PDX. Hence, TIC's are enriched in the $EpCAM^{med/high}/CD10^{-/low}$ sub-population of all PDX breast tumors we examined.

Having identified these distinct subpopulations, we next investigated whether CDK19 expression was enriched in the more tumorigenic $EpCAM^{med/high}/CD10^{-/low}$ cells compared to the less tumorigenic $EPCAM^{low/med}/CD10^{low/+}$ cells. In three of the four PDXs examined, CDK19 expression was higher in the more tumorigenic $EpCAM^{med/high}/CD10^{-/low}$ cells compared to the less tumorigenic $EPCAM^{low/med}/CD10^{low/+}$ cells (FIGS. 2D-2G). To generate the data in FIGS. 2D-2G, relative expression of CDK19 in the $EPCAM^{low/med}/CD10^{low/+}$ and the $EpCAM^{med/high}/CD10^{-/low}$ cells as determined by RT-qPCR. Gene expression in each condition is normalized to beta-actin as a housekeeping gene. Relative expression of CDK19 is normalized to the mean expression of CDK19 in the $EPCAM^{low/med}/CD10^{low/+}$ cells. *P<0.05 (unpaired t-test) (PDX-T1: mean+s.d., n=2; PDX-T2: mean+s.d., n=6 ($EpCAM^{low/med}/CD10^{low/+}$) and n=3 ($EpCAM^{med/high}/CD10^{-/low}$); PDX-T3: mean+s.d., n=6 ($EpCAM^{low/med}/CD10^{low/+}$) and n=3 ($EpCAM^{med/high}/CD10^{-/low}$); PDX-T8: mean+s.d., n=3. All experiments performed at least twice). Thus, while CDK19 was expressed in all the PDX tumors we examined, it was expressed at higher levels in the more tumorigenic $EpCAM^{med/high}/CD10^{-/low}$ sub-population in three of the four tumors that we investigated.

Figure 8B:
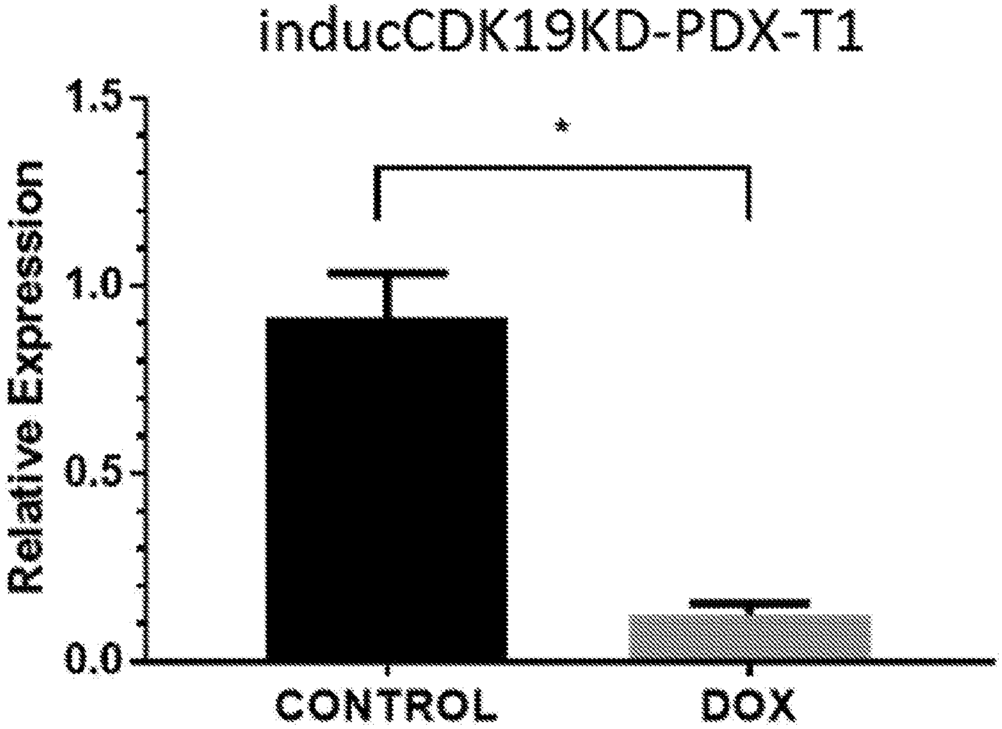
FIG. 8B is a bar graph showing that the induction of CDK19 shRNA with doxycycline effectively silences CDK19 in inducCDK19KD-PDX-T1 cells. Expression of CDK19 in control inducCDK19KD-PDX-T1 cells (black bar) and doxycycline treated inducCDK19KD-PDX-T1 cells (gray bar) as determined by RT-qPCR.
Figure 8D:
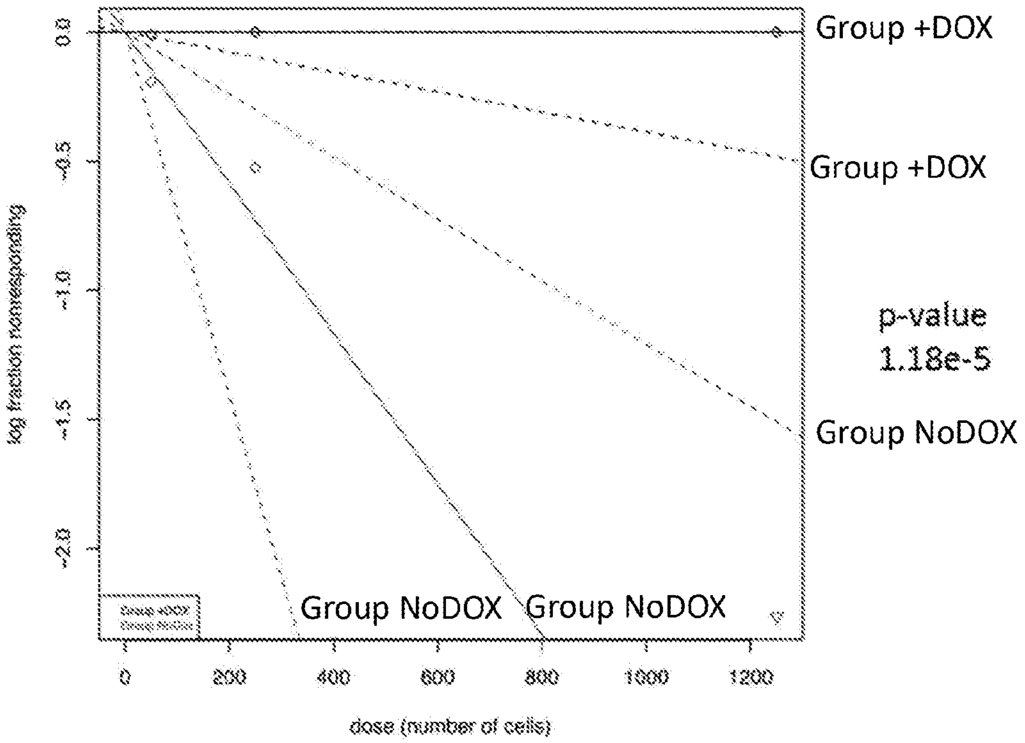
FIG. 8D is a graph showing ELDA (Hu et al., Journal of Immunol. Methods 347:70-78, 2009) analysis of the data from FIG. 8C to determine tumor initiating frequencies in the doxycycline (Group+Dox) and control groups (Group NoDox). P-values as determined by the ELDA software.

To determine tumor initiating frequencies in the setting of CDK19 knockdown, we performed LDA using PDX-T1 cells transduced with a doxycycline-inducible CDK19 knockdown construct to produce inducCDK19KD-PDX-T1 cells where we can control CDK19 expression (FIG. 8B). In FIG. 8B, the relative expression of CDK19 in doxycycline treated inducCDK19KD-PDX-T1 cells is normalized to the mean expression of CDK19 in control inducCDK19KD-PDX-T1 cells. Gene expression in each condition is normalized to beta-actin as a housekeeping gene (*P<0.05, mean s.d., n=2, experiments performed twice). By comparing the in vivo transplantation of inducCDK19KD-PDX-T1 cells in the presence of doxycycline (+Dox) with inducCDK19KD-PDX-T1 cells without doxycycline (No Dox), we find that CDK19 knockdown eliminates tumor formation in all the cell transplantation conditions examined (FIG. 8C). inducCDK19KD-PDX-T1 cells were injected into the mammary fat pads of NSG mice at 50, 250 and 1250 cells. Mice in the doxycycline group were fed a doxycycline containing rodent feed to induce CDK19 shRNA, while mice in the control group were fed a normal rodent diet. Tumors were detected by palpation of tumors. The number of tumors that formed and the number of injections that were performed are indicated for each population. Populations and injections where tumors formed are bolded (n=5 per group) in FIG. 8C. Using ELDA, we discovered that the tumor initiating frequencies significantly decreased from 1 in 342 cells (95% Cl: 1 in 828 to 1 in 142) in the control (No Dox) group to 1 in ∞ cells (95% Cl: 1 in ∞ to 1 in 2587) in the CDK19 knockdown (+Dox) group (FIG. 8D). Both the significant decrease in tumor initiating frequency caused by CDK19 knockdown and CDK19's higher expression in the TIC sub-population suggests that TIC inhibition is likely responsible for the impaired tumor growth observed with CDK19 knockdown.

4.5 Example 5—Identification of Genes and Pathways Regulated by CDK19

There is an 84% amino acid sequence homology between CDK19 and its well described paralog, CDK8 (FIG. 9). CDK8 has been shown to play a role in a variety of malignancies including colon cancer, acute myeloid leukemia, and melanoma. Higher expression of CDK8 has been associated with worse prognosis in colon cancer (Firestein et al., *Nature* 455:547-551, 2008). CDK8 knockout in embryonic stem cells was shown to prevent embryonic development (Porter et al., *Proc Natl Acad Sci USA,* 109:13799-13804, 2012) due to its essential role in the pluripotent stem cell phenotype. The known cancer-relevant activities of CDK8 may include positive regulation of Wnt/β-catenin pathway, growth factor-induced transcription, and TGFP signaling. Depending on context, CDK8 has also been shown to either negatively or positively regulate transcription. However, recent evidence has suggested that CDK19 may function differently from CDK8. In vitro studies showed that CDK19 and CDK8 participate mutually exclusively of each other in binding to other CKM components, while gene knockdown studies in cell lines of cervical cancer and colon cancer showed that CDK19 and CDK8 regulate different genes. Our goal was to investigate in TNBC whether CDK19 and CDK8 have distinct biological functions by examining global gene expression changes resulting from targeted knockdown of CDK19 or CDK8.

Figure 3A:
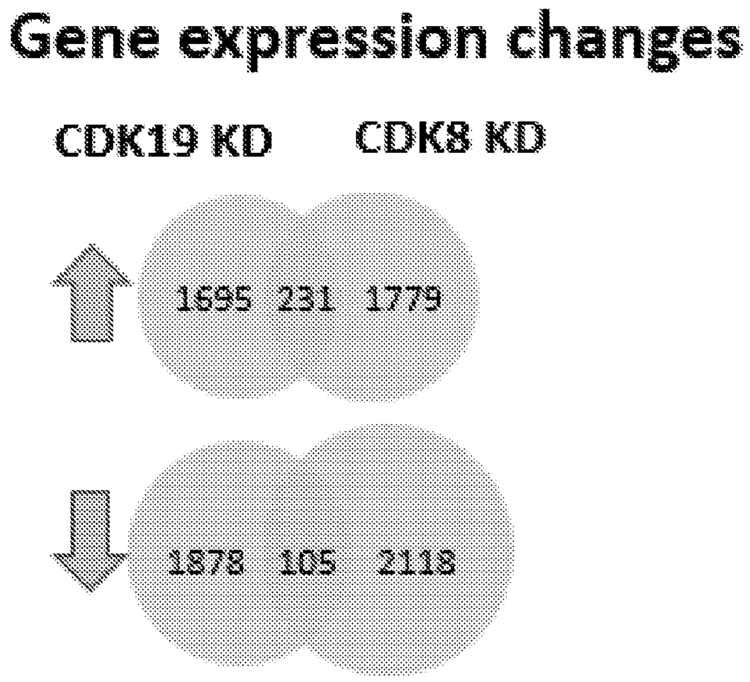
FIG. 3A includes Venn diagrams showing the number of genes upregulated (upper diagram) and downregulated (lower diagram) by CDK19 knockdown, CDK8 knockdown, or by both CDK19 and CDK8 (overlap region).

To understand whether the molecular targets of CDK19 in TNBC are unique from CDK8, we knocked down each gene in MDA-MB231 and examined the respective gene expression changes relative to control. Overall, CDK19 knockdown affected 3909 genes and CDK8 knockdown affected 4233 genes (FIG. 3A). However, only 12% of upregulated and 5% of downregulated genes in the CDK19 knockdown experiment were also affected by CDK8 knockdown. This suggested that CDK19 and CDK8 largely regulate distinct genes (FIG. 3A).

Figure 3B:
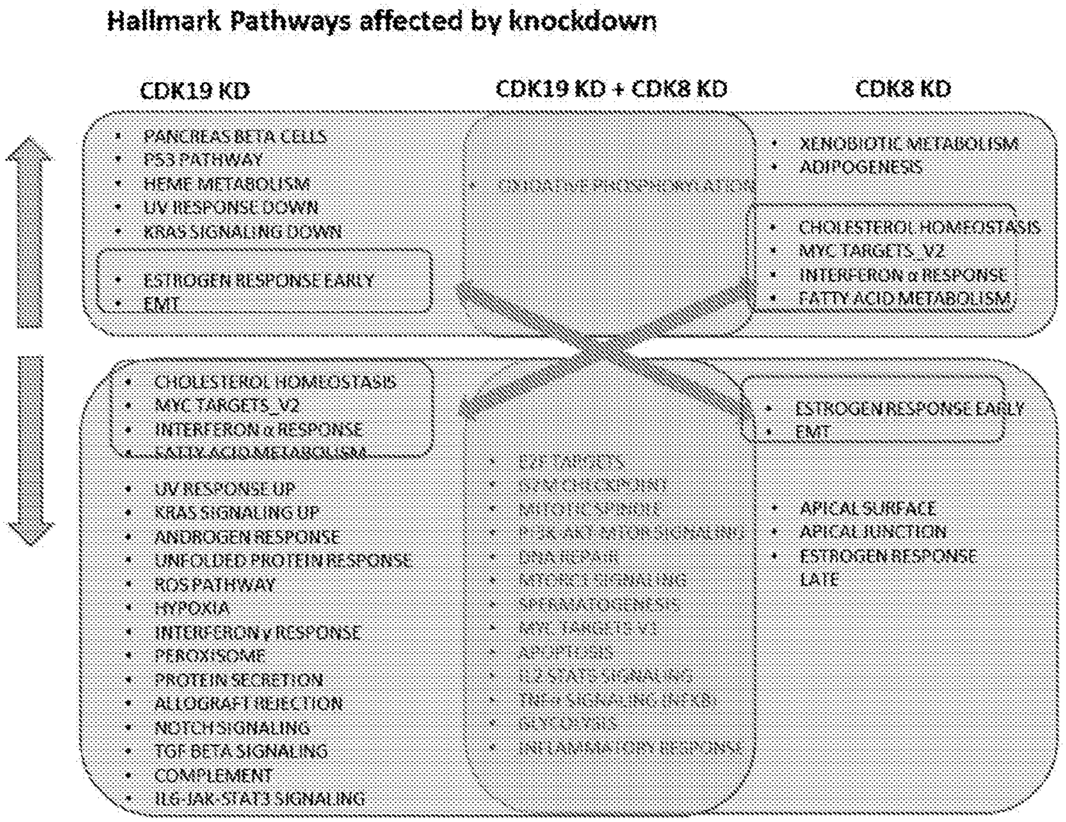
FIG. 3B is a Venn diagram of Hallmark gene sets enriched across the genes upregulated (upper diagram) or downregulated (lower diagram) by CDK19 knockdown, CDK8 knockdown, or by both CDK19 and CDK8 knockdowns (overlap region) as determined by GSEA.

Gene set enrichment analysis (GSEA) of the CDK19 and CDK8 knockdown genes allowed us to identify enriched Hallmark gene sets amongst the most upregulated or downregulated genes (FIG. 3B and FIG. 10). In FIG. 10, the Hallmark gene sets uniquely enriched in the knockdown of CDK19 or CDK8 are shown in black, enriched in both the knockdown of CDK19 and CDK8 are marked by "*" and enriched by genes expressed in opposite directions between the knockdown of CDK19 and CDK8 are marked by "*". Normalized enrichment scores and FDR q-value are determined by the GSEA software. An FDR cutoff of <0.25 was used to select significant Hallmarks. These Hallmark gene sets consist of genes that are specifically involved in certain biological states or pathways. Genes associated with known breast cancer-related Hallmarks such as mitosis (E2F targets, G2M Checkpoint, Mitotic Spindle), PI3K-AKT-MTOR signaling, MYC pathways (Myc Targets v1), glycolysis, apoptosis, and oxidative phosphorylation were changed in the same direction by CDK19 and CDK8 knockdowns (FIG. 3B, middle overlap region), demonstrating a co-regulatory relationship between CDK19 and CDK8. Further, genes associated with early estrogen response, epithelial to mesenchymal transition (EMT), cholesterol homeostasis, MYC pathways (Myc Targets v2), interferon alpha response, and fatty acid metabolism changed in the opposite direction in response to knockdown by CDK19 compared to CDK8 (FIG. 3B, boxes), which suggests a counter-regulatory relationship exists between CDK19 and CDK8. Hallmark gene sets enriched by the expression of genes in opposite directions by CDK19 knockdown compared to CDK8 knockdown are boxed. A number of the Hallmark gene sets were only enriched in the genes that uniquely changed due to CDK19 knockdown (FIG. 3B, left region). Hallmarks reflected by these gene sets included P53 signaling, KRAS signaling, androgen response, NOTCH signaling, TGF BETA signaling, and IL6-JAK-STAT3 signaling, which may be potential biological pathways for targeted therapies for TNBC. All of these biological pathways represent active areas of clinical investigation in the evaluation of targeted therapies for TNBC. Consistent with our findings, a number of the pathways found enriched in our CDK19 knockdown experiments, such as cholesterol homeostasis, P53 signaling, mitosis, and NFκB pathways have been shown previously in other cell types to also be regulated by CDK19.

In summary, these analyses showed that CDK19 and CDK8 have the potential to co-regulate certain pathways, while counter-regulating others. Furthermore, CDK19, like CDK8, is capable of positively or negatively regulating biological pathways. The multitude of clinically relevant TNBC pathways regulated by CDK19 suggests that targeting CDK19 can provide the opportunity to modulate multiple pathways simultaneously and at the same time, avoid potential toxicity because of the advantageous limited tissue distribution of CDK19. This approach could overcome the resistance to single agent therapy commonly seen in TNBC and also potentially enable the targeting of 'undruggable' processes such as those involving P53 or MYC.

4.6 Example 6—Effects of CDK19 and CDK8 on Epigenetic Modifications

Recent studies have highlighted the role of CDK19 and CDK8, as well as other transcriptional CDKs (CDK7, CDK12/CDK13), in regulating the transcription of critical oncogenic genes by acting at large clusters of enhancers (also called 'super-enhancers') that are marked by histone 3 lysine 27 acetylation (H3K27Ac). The exact mechanism for this gene regulation is unclear, but is believed to occur in part through interactions of the CKM with Mediator to regulate RNAPII-Mediator interactions and in part by phosphorylating serine residues in the C-terminal domain of RNAPII. Given the propensity of transcriptional CDKs to function at enhancers, we wanted to investigate whether CDK19 and CDK8 can also regulate the epigenetic modifications at enhancer sites as a mechanism to control gene expression. While enhancer modification through other signaling pathways have been identified, this mechanism of gene control has not yet been reported for the CDKs.

Figure 3C:
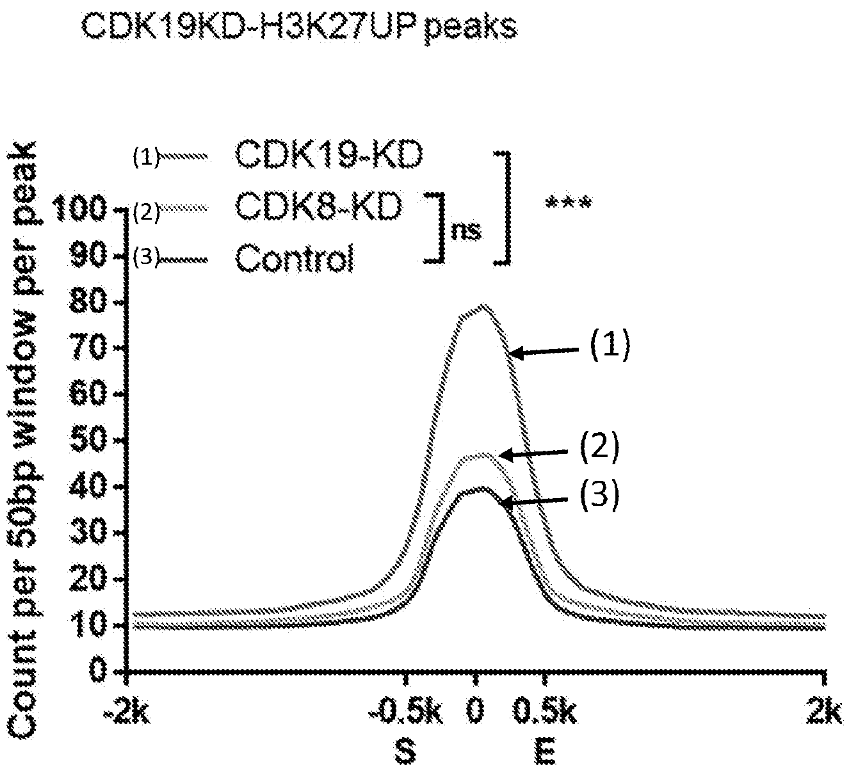
FIGS. 3C and 3D are graphs showing that CHIP-Seq signals across the CDK19KD-H3K27AcUP and CDK19KD-H3K27AcDOWN regions are significantly different in the CDK19 knockdown samples compared to control.
Figure 3D:
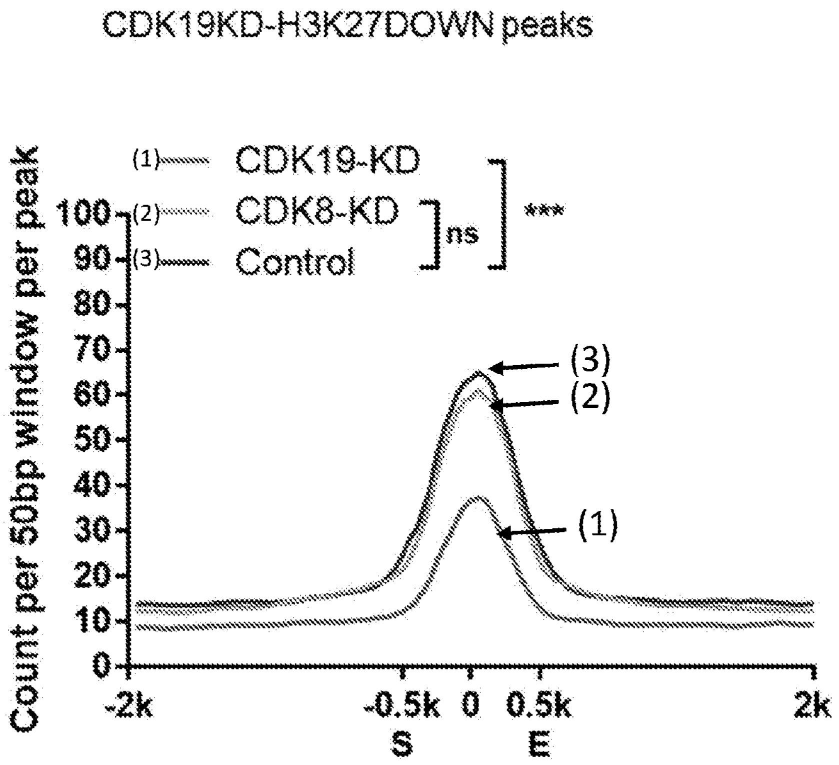
Figure 11:
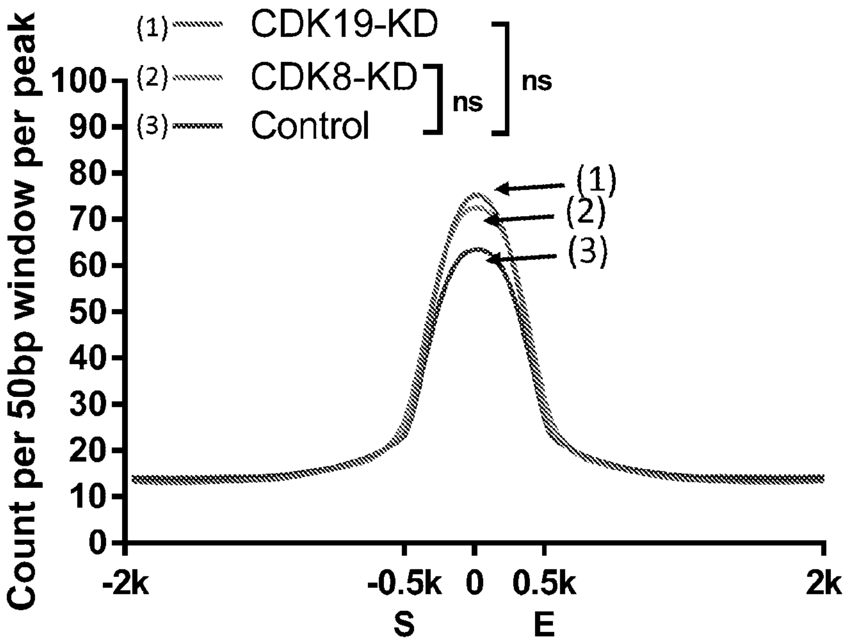
FIG. 11 is a graph showing that genome-wide H3K27Ac CHIP-Seq signals across all identified H3K27Ac peak regions are not significantly different between the CDK19 knockdown, CDK8 knockdown, and control samples. Aggregate plots of normalized H3K27Ac CHIP-Seq signals across all H3K27Ac peak regions in the CDK19 knockdown (1), CDK8 knockdown (2) and control (3) samples (ns is P>0.05, all samples n=3, experiments performed three times).

To explore the role of CDK19 in epigenetic regulation, chromatin immunoprecipitation and sequencing (CHIP-Seq) for the H3K27Ac modification was performed on MDA-MB231 cells under three different conditions: Control (empty vector transduction), CDK19 knockdown, and CDK8 knockdown. Genome-wide analysis of all H3K27Ac modified regions showed that both CDK19 knockdown and CDK8 knockdown had similar global H3K27Ac levels compared to control (FIG. 11). In FIG. 11, H3K27Ac CHIP-Seq signals across all identified H3K27Ac peak regions are normalized to 1-Kb and centered on the middle of those regions. Signals of the flanking 2-Kb regions are also shown. To compare relative signal changes, the total signal of each biological replicate was determined by summing the signals of each 50-base window 1-Kb around the center of each region. P-values between total CHIP-Seq signals of each sample were determined by unpaired t-test. Through comparative analysis of H3K27Ac levels in the CDK19 knockdown compared to the control, we identified 3034 peak regions with increased H3K27Ac signal (AII-H3K27UP) and 502 peak regions with decreased H3K27Ac signal (AII-H3K27DOWN). By excluding peak regions that were also different in CDK8 knockdown compared to control, we identified 2309 peak regions with increased H3K27Ac signal (CDK19KD-H3K27UP) and 432 regions with decreased H3K27Ac signal (CDK19KD-H3K27DOWN) that were unique to CDK19 knockdown. The specificity of these regions for CDK19 was investigated by comparing the H3K27Ac levels at these regions in CDK19 knockdown, CDK8 knockdown, and control. Compared to control, enrichment of H3K27Ac levels across the CDK19KD-H3K27UP regions (FIG. 3C) and depletion of H3K27Ac levels across the CDK19KD-H3K27DOWN regions (FIG. 3D) were significant only for CDK19 knockdown and not for CDK8 knockdown. In FIGS. 3C and 3D, ***$P<0.001$; ns is $P>0.05$ (all samples n=3, experiments performed three times). H3K27Ac CHIP-Seq signals of the CDK19KD-H3K27AcUP or CDK19KD-H3K27AcDOWN regions are normalized to 1-Kb and centered on the middle of those regions. Signals of the flanking 2-Kb regions are also shown. To compare relative signal changes, the total signal of each biological replicate was determined by summing the signals of each 50-base window 1-Kb around the center of each region. P-values between total CHIP-Seq signals of each sample were determined by unpaired t-test. Thus, CDK19KD-H3K27UP and CDK19KD-H3K27DOWN define peak regions where the H3K27Ac signal is more specific for, and most sensitive to, knockdown of CDK19 compared to knockdown of CDK8.

Figure 3E:
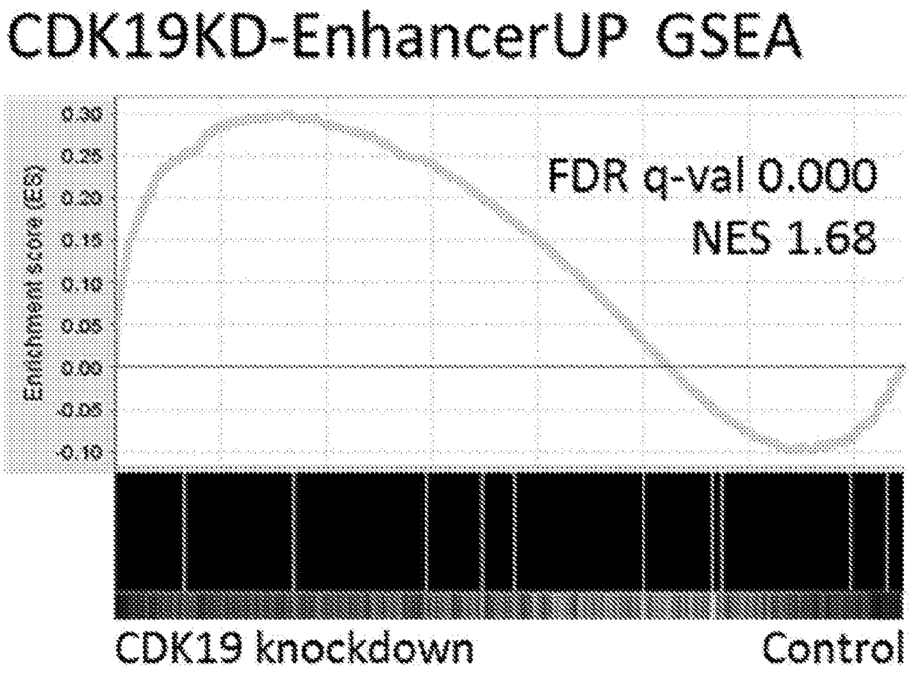
FIGS. 3E and 3F are graphs showing a gene set enrichment analysis (GSEA) of CDK19KD-EnhancerUP and CDK19KD-EnhancerDOWN genes using averaged CDK19 knockdown versus control expression data.
Figure 3F:
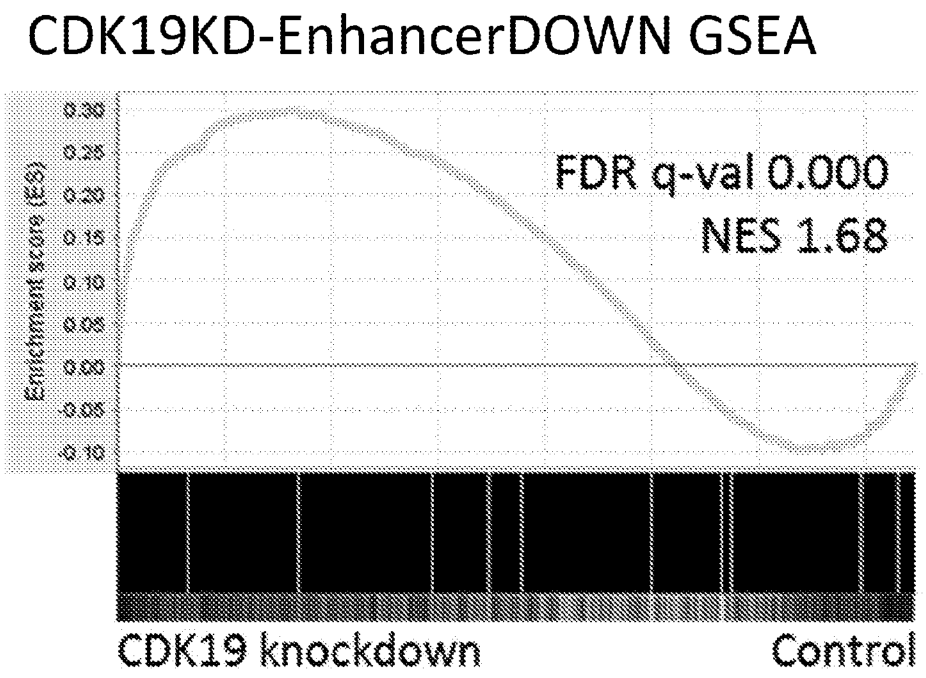

We next assessed whether increases or decreases in H3K27Ac levels as a result of CDK19 knockdown corresponded to changes in gene output. For this, the previously defined AII-H3K27UP and AII-H3K27DOWN peak regions were annotated by proximity to the nearest gene to establish two gene sets: CDK19KD-EnhancerUP (1593 genes) and CDK19KD-EnhancerDOWN (341 genes) for further analysis (Table 1 and Table 2). GSEA of these gene sets with our CDK19 knockdown gene expression data indicated that genes most upregulated by CDK19 knockdown were enriched for the CDK19KD-EnhancerUP genes (NES 1.68, FDR q-value=0.000) (FIG. 3E), while genes most down-regulated by CDK19 knockdown were enriched for the CDK19KD-EnhancerDOWN genes (NES −1.84, FDR q-value=0.000) (FIG. 3F). Thus, as a result of CDK19 knockdown, perturbations to the H3K27Ac signal at the putative enhancer elements of genes correlated well and in the expected direction with changes in gene expression.

TABLE 1

| CHIPSEQ_CDK19-KD ENHANCERDOWN | | | | | | | |
|---|---|---|---|---|---|---|---|
| NDRG3 | TTLL11 | CYB561 | KAZN | PPM1A | SLC25A32 | GRAMD4 | S100Z |
| SNRK | YWHAZ | FAM168A | KIAA1524 | CDH4 | PAQR5 | KCNK12 | NSMAF |
| RNF169 | SLC35F3 | HDAC8 | KCNAB1 | CDKAL1 | ZFYVE9 | AK7 | DDX31 |
| WDHD1 | RNF144B | DGKB | FKTN | C6orf203 | EPB41L2 | RUNX2 | CXCL8 |
| PLXNA4 | TOX2 | XPO6 | PGM2 | TRIM60 | PKP2 | TWSG1 | RGCC |
| AZU1 | NORAD | ARFIP1 | SSH2 | ALKBH8 | TMBIM4 | IPO5 | TTC39C |
| KITLG | C11orf87 | SCN5A | ZCCHC24 | FBXO11 | RAI14 | ABCA8 | PRNP |
| OC90 | STX8 | LOC341056 | MAGT1 | FOS | LPA | OPHN1 | FGF9 |
| MPP4 | IQCJ | RPL7L1 | ZFAT | ABCA13 | CSGALNACT2 | KIAA0586 | RNF114 |
| TOX | G6PC2 | BACH2 | RGMB | C1QTNF3 | MOK | MED27 | WWC1 |
| SPRED1 | C11orf63 | C12orf75 | HRH1 | NTNG1 | GGCX | ADCK2 | PDE7B |
| UBASH3B | ZNF281 | LOC100506797 | SLCO4A1-AS1 | WDR27 | RBM5 | AKR1B15 | ENKUR |
| CACNA1A | WDR89 | SLIT2 | SHTN1 | ALK | TLE1 | FAM107B | ELOVL5 |
| FZD8 | CSTF2 | XRRA1 | ARSF | STX18 | KIF3C | SLC25A12 | HIVEP1 |
| SATB2-AS1 | SNX14 | IDNK | OXCT1 | ZNF133 | TAPT1 | STK38 | STRA8 |
| TMEM18 | UTP18 | VAPA | CCR1 | SPPL3 | MBP | ASAP3 | SEMA4D |
| TBL1X | SMYD3 | ITGB1BP1 | CRTAM | MDM1 | TRHR | FAF1 | STK4 |
| SMIM19 | DNAJA3 | PDE8B | TSNARE1 | KCNV1 | AVEN | FAM20B | CDH13 |
| KIAA1109 | KHDC1 | DAP | HIPK3 | OR10V1 | VTI1A | FIP1L1 | AKAP1 |
| C20orf85 | PPP4R1L | IL10 | PIK3CB | ALG10B | ATAD1 | ZBTB10 | TNRC6A |
| COMMD2 | MLEC | NCK2 | FAM171A1 | SGPL1 | NFATC1 | GRB10 | NECAB1 |
| AMOTL1 | RHOH | HDAC9 | PDE4B | RFX8 | NR2F1-AS1 | RNF34 | TMSB10 |
| KYNU | TMEM235 | SLC26A8 | SIK3 | CHI3L2 | PPP3CA | HESX1 | CORIN |
| ARHGAP18 | SYAP1 | OLIG2 | THG1L | MAST2 | PPA2 | BTBD9 | GPR68 |
| EPB41L1 | OLFML2A | CFAP36 | KLHL5 | PRDM5 | COMMD7 | CEP112 | SVIL |
| C1orf21 | PUM2 | ST3GAL6 | MTCL1 | RPAP2 | ATG5 | PLEKHM3 | EDEM3 |
| SAP18 | PANX1 | MAB21L2 | PTPN20 | DSCR9 | SIPA1L1 | SUMF1 | CDK5RAP2 |
| UBR5 | GBF1 | UBE3A | INHBC | EPS15L1 | CD226 | TCF7 | TGFBR2 |
| HTR7 | BCAP29 | PRLR | USP43 | ATP6AP1L | RPS6KA5 | EXOSC7 | RAB10 |
| KCNG1 | CPD | KIAA1147 | RPS3A | CCDC152 | ATF7IP | CCDC88A | CASS4 |
| ADM2 | GTF2H5 | FER1L6 | DDR2 | PARD3 | PREP | RPL5 | C1GALT1C1 |
| GJD4 | WWP2 | SVIP | FZD4 | BPGM | ARMC9 | ERICH6B | MAP1B |
| TCP11 | PLS3 | NT5DC3 | CBLN1 | C5orf42 | LIN7A | FIBP | TSEN2 |
| CSNK2A1 | UBE2V2 | CMTM8 | ARHGAP25 | KAT7 | BLCAP | IFI44 | TMEM38B |
| EDNRA | LOC285696 | GOLIM4 | NEK1 | C3orf67 | PRDM8 | TBXAS1 | SND1 |
| ANAPC10 | TSPAN9 | ARC | ETV1 | CTDSPL | NDRG1 | WWTR1 | WASF2 |
| ADH7 | NNT | SLC46A3 | CTNND2 | MBD2 | HYPM | RNF217 | CHST11 |
| CLDN2 | STAG2 | INTS6 | ZMIZ2 | CHSY3 | MRPS28 | CBFA2T2 | BTD |
| CEP290 | RIN2 | COX7A2L | TMEM30B | WASF3 | APCDD1L | PARP12 | FAM46C |
| TCF12 | FKBP1A | ARFGAP2 | PUDP | LDHD | ADGRL3 | TMEM50A | TRDMT1 |
| TSEN15 | BAZ2A | TANC1 | NANS | TAOK1 | MAPK8 | PPP4R3B | FAM196A |
| OAT | AGA | DNAH6 | ARHGEF4 | PSMC4 | ANTXR2 | BASP1 | TPTE2P1 |
| OR2AT4 | MMAB | DENND2D | C7orf73 | ST18 | | | |

TABLE 2

| CHIPSEQ_CDK19-KD ENHANCERUP | | | | | | | |
|---|---|---|---|---|---|---|---|
| HLCS | EFCAB13 | FBXL20 | AGR2 | ABCC11 | MFSD7 | RIC8B | KCNT2 |
| IGF1 | SLC12A8 | AZIN1 | LYSMD4 | AVIL | ATP2B4 | ASS1 | MARCKSL1 |
| CDYL | CRABP2 | ERCC8 | OSR2 | CASQ2 | ACTL7B | TNFRSF11A | NAV2 |
| LHFPL2 | TEX35 | SLC22A16 | LUM | PRKCZ | RDH16 | ERICH2 | STPG2 |
| HGC6.3 | PTPRE | GPCPD1 | BEGAIN | BEST3 | ABCG1 | ZFPM2 | SOWAHC |
| MYL4 | TCF7L2 | HAS2 | IGSF22 | BDKRB1 | MYL12A | DNAJB11 | LOC100506797 |
| NNAT | SCAF8 | LOC100268168 | PPP1R36 | CDC42EP5 | EDN1 | SP4 | SOWAHB |
| NEURL1 | TSC1 | MIS18A | RALGPS1 | SH3BP4 | C15orf53 | GJA4 | FOPNL |
| RPIA | STOM | VEGFA | AHDC1 | DBX1 | PHACTR1 | ALDH1A3 | DACT1 |
| SLC1A2 | SRPX2 | PLXNA2 | TBC1D14 | RAD23B | MAP1A | ECHDC3 | GLI2 |
| IQSEC1 | ANKRD16 | CHAT | MAGEF1 | NOL6 | SUB1 | RFK | CHRNE |
| DENND3 | NEK6 | S1PR1 | C12orf76 | DIEXF | DHRS9 | ERICH5 | SCCPDH |
| TAF1B | XPR1 | RYBP | ANP32C | MCHR1 | DLX4 | OSBPL11 | ARHGAP12 |
| FGD2 | SNTG1 | PTGER4 | AGMO | PTRHD1 | FANCA | AES | KRBA2 |
| ZC3HC1 | TRIM24 | HMHB1 | IRF2BP2 | INPP5F | CACNG2 | HHLA3 | CFI |
| TTLL5 | ACBD3 | PLB1 | EDIL3 | IGFN1 | TROAP | HAUS8 | NOV |
| HPSE2 | YARS | PROC | LEPROTL1 | EFHD1 | GALNT12 | KANK4 | JAK3 |
| TMEM170B | DCLK1 | PTPRN | SPATA16 | CCDC97 | ZNF787 | TPRG1 | DAPK3 |
| KIF25 | LMCD1 | AADACL4 | RFXAP | ALOX5AP | BIRC7 | GBA3 | C1R |
| TMPRSS5 | TMEM100 | OR1M1 | ENO2 | PTPN3 | FAM196B | CLEC14A | TSPAN1 |
| NPC1L1 | TBL1X | PTPRR | LOC100130872 | FAM136A | HSPH1 | STK17B | GSTA3 |
| ACKR3 | OPTC | CREB5 | PHTF2 | SMIM20 | SPRED2 | SHE | AGAP1 |
| CTAGE1 | KIF16B | TRAF4 | FAM57A | KIAA1211L | CORO6 | SPNS2 | MAOB |
| SOAT1 | TRIB1 | KCTD4 | CELF2 | TWIST2 | C19orf38 | TMEM40 | THEM4 |
| GSX2 | ADAT2 | USF2 | NRP2 | NSUN7 | SEMA3E | ZNF462 | SUGCT |
| BCAT1 | CSNK1A1 | RAD51AP2 | FFAR4 | NINJ1 | SHH | SPIB | PSAT1 |
| CLDN1 | ERGIC1 | SLC15A1 | KISS1 | C11orf49 | NAT2 | HECW1 | EXOC6B |

TABLE 2-continued

| CHIPSEQ_CDK19-KD ENHANCERUP | | | | | | | |
|---|---|---|---|---|---|---|---|
| KLHL31 | YAE1D1 | PIM3 | DGKZ | MEF2A | USB1 | CAB39L | PCSK1N |
| MAST2 | STON2 | HIP1R | ELF3 | C4orf26 | ZNF429 | DISC2 | CENPB |
| MTCH1 | PALLD | GLRA3 | ZSWIM3 | NMBR | C14orf37 | GPR108 | GSTP1 |
| ATP1A2 | RBM47 | SORBS3 | RAB14 | RPS29 | ACVR2A | C11orf94 | DAW1 |
| THADA | CKAP4 | SF3B5 | ANO6 | BTBD16 | XRCC2 | OTOS | EMX1 |
| EPS8L3 | PTK2 | ZNF318 | RTN2 | CAMK2D | MRPL4 | VGLL3 | LMNTD2 |
| CAB39 | PAPSS2 | TRIML1 | ZSCAN18 | HCAR1 | RPS3A | FAM81A | FIZ1 |
| NEK2 | EHF | NEDD4L | SYT2 | LEPROT | MAP7D3 | PRTFDC1 | SEC14L5 |
| HYI | SLC44A1 | BAG1 | GFI1 | MFSD4B | GCG | PPEF1 | LAMB4 |
| NANOS1 | YWHAEP7 | ATG9B | GCNT3 | ATXN1 | LIMD1 | P2RY1 | TMEM120B |
| SLC37A1 | GRHL3 | OTUD3 | VWA2 | IGFL1 | P2RX7 | TLR10 | KIAA1324 |
| MAPK8IP1 | SLC2A8 | RHOB | CAMSAP2 | TMEM95 | FAT1 | TFAM | APIP |
| PPM1L | ETS2 | KPNA7 | HRK | ACOT11 | RGS7 | TMEM106B | CERS4 |
| NXPH2 | SLC30A6 | RREB1 | EML5 | WFIKKN2 | PAK1 | FJX1 | HMGCR |
| RCAN1 | GUCY1A2 | LAMC3 | RBFOX2 | BMP6 | DSG3 | PITPNM3 | ISL1 |
| PACSIN2 | TSN | BCOR | HES1 | NIPBL | STAT4 | CDH3 | PSG2 |
| SLC39A10 | XIRP1 | NAB1 | DYNC2H1 | TMEM51-AS1 | ARRB2 | CCL20 | MINK1 |
| MRPL15 | LY86 | PLEKHA1 | METTL6 | LRRC8D | SPR | SCRT2 | RALA |
| MAPK1IP1L | EGLN3 | CRISPLD2 | PAPLN | MOAP1 | COL24A1 | MYO5C | SLC28A3 |
| MAP3K7CL | RB1CC1 | SERPINB10 | TPD52L1 | PPARA | MZT1 | ATP8B2 | RASSF6 |
| PIGU | ADTRP | CYP1B1 | LRRFIP2 | NLN | ZC3HAV1L | NECTIN1 | CELA2A |
| SYT14 | CDCA4 | FBXO3 | ASCC3 | SH2B2 | C3orf58 | ENOX2 | PLEKHG4 |
| DAAM1 | TINAGL1 | YIPF6 | GPR135 | ZNF160 | ANXA1 | ERCC3 | SLC39A11 |
| CDKN3 | CBX4 | RALGDS | TUBA1A | PMAIP1 | MN1 | ADAMTS10 | FGFR3 |
| EPAS1 | ZCCHC10 | LRRC4C | DUSP18 | CXCR5 | CRABP1 | MAST3 | ABLIM2 |
| INO80C | TLR2 | AKAP10 | RASAL2 | NR4A1 | PNOC | SCN3A | NOCT |
| DDC | TACC2 | IFNLR1 | COL4A5 | FOXQ1 | DSG2 | PPFIBP2 | MAD2L1 |
| FILIP1L | ASH2L | TJP3 | NID2 | DAOA-AS1 | CAPZA2 | RMND5A | SLC8A2 |
| STC1 | DDX47 | RXFP3 | COL6A3 | PDE8A | RGS1 | TMEM119 | MXRA5 |
| KCTD16 | WDFY3 | EMILIN2 | PSAP | SETBP1 | GPRC5C | MAST4 | DNAH1 |
| RPUSD4 | KCNJ15 | CCDC9 | COX6B2 | MEDAG | IL6R | NUAK1 | ZP4 |
| CD276 | EVA1C | DPEP2 | ABHD5 | MRPS22 | GLDN | RPH3AL | AQP7 |
| LRRFIP1 | GHSR | NME9 | SALL4 | F5 | MCOLN3 | GPATCH1 | VSTM2L |
| PDLIM1 | KIAA0753 | STK39 | TNFRSF11B | HSPBAP1 | SLC9B2 | PEX26 | CNGB1 |
| CDKAL1 | SLC34A3 | KERA | UBAP1 | JADE1 | IQCA1 | FKBP6 | SARM1 |
| DLX1 | P3H2 | ITPR2 | BTBD10 | FBLN2 | HES2 | C1orf100 | KRT10 |
| NEDD9 | GATA6 | PLAC8 | FAM198B | FBP2 | BSN | SPINK2 | PFKP |
| C11orf88 | SIN3B | ORMDL3 | TBX21 | GPR173 | KAZN | KIAA0040 | HDAC11 |
| FAM96A | DCHS2 | UPF2 | KCNMA1 | PLA2G4E | ARL4C | HCN3 | COL14A1 |
| BEST1 | ACSBG2 | NPFFR1 | TMEM178A | CDC123 | NDUFA12 | CDNF | RBM45 |
| CBLB | PIM1 | CTSO | DUSP6 | LHFPL5 | BCL2L10 | DIXDC1 | TCF12 |
| TNFAIP8 | PPM1H | SMARCD3 | RAD54B | C4orf45 | CREB3L2 | NPVF | OR6B1 |
| HMGCS1 | SSR3 | CXCL13 | TTC8 | MAPRE3 | SLC2A6 | SERPINB7 | HTR3A |
| USP36 | VIT | C17orf99 | CYP27C1 | NFKBIZ | AHCYL2 | DHRS7C | KRT32 |
| COL19A1 | NOL10 | MUC1 | SYT17 | GRHL1 | DENND2C | CLCA1 | WNT11 |
| INTS10 | CRELD2 | LGR6 | FHL1 | ARRDC5 | PARVB | CRK | NECAP2 |
| KRTAP4-5 | CLMP | NCF2 | GGT7 | INSR | PIK3C2B | C11orf65 | CLUAP1 |
| MBL2 | ASPSCR1 | YBX3 | SLC35F2 | NEMP2 | CLDN22 | DAB2IP | MAMDC2 |
| IL37 | CDCA7 | GAREM1 | DCN | ATP12A | REPS2 | FAM216B | CTTN |
| KLHDC9 | CDKL2 | AGRN | ATP9A | OXT | OLIG2 | TSEN54 | KIRREL2 |
| HECTD1 | ME3 | INTU | PGRMC2 | RFX2 | DSPP | LSM8 | TEX9 |
| MYEOV | POLR1A | PKIG | NEBL | SOX4 | HFM1 | OSBPL5 | TANK |
| CALHM3 | TLE1 | TRIM66 | SACS | SLC10A7 | MTM1 | KLHL38 | SHCBP1L |
| SRP19 | TMC1 | TOR2A | FNDC3B | XIAP | JARID2 | ALG1L | NYX |
| BMP10 | TRAF3IP2 | WISP2 | SCN1B | C15orf56 | ARHGEF3 | EPB41L4A | AFG3L2 |
| MON1A | PSMA6 | TRIP13 | ACTR10 | GJD3 | EFCAB11 | IRF4 | SLC22A23 |
| INPP4B | HNF1B | KIAA1522 | ALPP | KRT37 | MMP24 | CMTR2 | ARHGAP29 |
| SSUH2 | NUBPL | RRAD | CDH2 | CREB1 | ZNF621 | APOBEC1 | HIPK3 |
| METAP1D | SPOCK2 | PTPN1 | INHBE | ACHE | UGP2 | PITX2 | RPS5 |
| PTAFR | P2RX4 | GJB4 | PRKCSH | C12orf71 | ZNF292 | PKP1 | MAOA |
| YPEL5 | NKAIN1 | KCNG1 | EXD1 | KRT39 | STAU2 | AFAP1L2 | MIER3 |
| ATG14 | HRH1 | CYB5B | QPCT | TRAK2 | IL12B | AP4S1 | ACSL1 |
| LAMA3 | GJA1 | OR51B6 | FOXS1 | RPTOR | VAPA | ASIP | SPIN1 |
| ZNF542P | THRB | COX11 | RPS23 | PIGC | CREBL2 | PIN1 | UNC13A |
| GPBP1 | ATOH8 | PPFIA2 | DMKN | ZBTB43 | INPP5K | STRA6 | ABR |
| DEF6 | DACH1 | LILRB3 | POLE4 | CAPZA3 | SNX13 | MMP16 | MOGAT2 |
| NRCAM | NRARP | GATA2 | TMEM65 | FBN2 | INTS7 | INPP4A | TMEM38B |
| C10orf67 | ATXN7L1 | GPM6A | GSTZ1 | GARNL3 | USP38 | AKTIP | NR2F1-AS1 |
| KMT5B | LGALS9 | ZFP36L2 | CD200R1L | GPATCH2 | DLL1 | CNGA2 | GAS7 |
| RIPPLY3 | FAM161A | C10orf113 | TRPC4 | RAB27B | CD109 | TNS3 | CDHR2 |
| TNFRSF21 | FAM50B | CAGE1 | RNF220 | ARFGEF3 | RALB | INTS1 | VWA3B |
| SLC30A1 | ITCH | UPP2 | LZTS3 | YTHDF1 | AKR1D1 | TAS2R16 | DPF3 |
| IL15 | LGMN | ST8SIA4 | PROSER2 | SHC3 | PLEKHH1 | GRIN2D | CCDC184 |
| PLEKHG6 | METTL25 | CYP26B1 | SHC4 | GSG1L | BMPER | C3orf38 | STEAP4 |
| FA2H | TMEM88B | PPARGC1A | IGFBP3 | HSD17B14 | RNF112 | CXCR4 | TESC |
| AHR | CDK14 | CD36 | CLTC | TFCP2 | PRRX2 | FOXD2 | ATP6V1H |
| GALNT15 | FSCB | YTHDC2 | C10orf35 | ZNF92 | COMMD10 | RPTN | RGS11 |
| C9orf135 | IFT81 | TTI1 | AMTN | LPIN1 | IRS2 | SLTM | MYO1G |

TABLE 2-continued

| CHIPSEQ_CDK19-KD ENHANCERUP | | | | | | | |
|---|---|---|---|---|---|---|---|
| FGFBP1 | LRRC25 | RPS6KA3 | BCR | EEPD1 | RSPH1 | LAMC1 | KLF5 |
| HRASLS2 | FOXN3 | ANO10 | GTF2E2 | TRIM9 | PAPPA | RABEP2 | PCLO |
| ATF3 | PAFAH1B2 | PRSS57 | FAM3B | CYP24A1 | CARTPT | NPEPPS | NTF3 |
| TLR3 | CABLES1 | SLN | ANGPT1 | TUFT1 | CLCNKA | ANXA4 | NCALD |
| LTBP1 | CPPED1 | DYNLT1 | MREG | C4orf19 | AIG1 | THNSL2 | RBM3 |
| SMG6 | OR2S2 | AMER3 | NAV3 | RNF13 | PPP1R2 | SLC43A3 | WIPI2 |
| PANK1 | TAMM41 | ST6GALNAC4 | TRIM54 | NAT1 | PTPRC | COX20 | CCDC65 |
| NRDE2 | SPAG9 | DCTN6 | GABBR2 | UPP1 | ARHGEF18 | C1orf226 | TTC39C |
| TGFB3 | EIF4A2 | UNC5A | TPK1 | LBH | PRKAR1A | SERBP1 | TOPBP1 |
| LARP4B | SERPINB1 | C12orf74 | GOSR2 | OSCP1 | PSTK | KNOP1 | C1orf228 |
| CD9 | ACSL5 | CT62 | DENND5A | BAIAP3 | SLIT2 | NFATC1 | DNAJC6 |
| ADAMTS6 | ADAM29 | FRMD3 | RAB8B | OR10H1 | RAB11FIP4 | TMEM45B | FABP3 |
| NNMT | WDFY1 | CEP152 | ARHGAP42 | HIC1 | SHQ1 | TARBP2 | SNX7 |
| C10orf90 | RAD51B | LRRC20 | GNLY | TIMM22 | SMARCA2 | DUSP8 | SOX8 |
| NCOA6 | CCNY | COX7A2 | TRAF3IP1 | SLC6A3 | KBTBD12 | ARHGAP39 | MDFIC |
| PPM1B | SEMA3A | PLA2G2E | DNAH11 | EGR4 | DUSP27 | TMPRSS7 | NFE2 |
| CACUL1 | TMEM86B | TRABD2A | REEP3 | NDUFB11 | CCDC186 | C7orf57 | CC2D2A |
| LEKR1 | ATP6V1G1 | MPZL2 | SLC4A1 | MGAT4C | TMPRSS9 | COL21A1 | LBP |
| TMEM247 | CCDC34 | IGF2R | CLDN4 | WNT7A | APBB1IP | CPA4 | DTWD1 |
| NSMCE4A | GDPD5 | ANKRD33 | PLEKHG3 | CYP11A1 | CDCA7L | NID1 | MAF |
| NUP155 | CAMK2B | ZEB2 | ARID5A | FRMD4B | ATXN7 | LSM3 | FGGY |
| ABI3BP | PNPLA5 | ATXN3L | ZNF396 | SOCS2 | MBTPS2 | HS1BP3 | C9orf3 |
| MUC20 | IL7R | FIGN | PPP2R2C | USP2 | ENKUR | RALBP1 | MRPS18A |
| CNIH3 | ULK1 | ADGRF1 | FLJ23867 | CRIP2 | PTHLH | FAM187B | SH2D3C |
| SH3GL3 | ODC1 | LGALSL | PRRC1 | GC | NEK10 | MAMLD1 | C4orf32 |
| SH3TC1 | LGI1 | SLC6A20 | CD180 | PLCE1 | THY1 | CTSH | SLCO4A1 |
| SLC26A9 | MPL | AACSP1 | COL26A1 | SSR2 | CMAHP | ID4 | ALCAM |
| TAGLN2 | COBL | SCNN1G | TRAF7 | MYOZ1 | AKR1C3 | CER1 | AREG |
| ABCG2 | DCK | CCDC174 | PRKCE | CBLC | SYNM | BCAS2 | BDKRB2 |
| NABP1 | TBC1D1 | DHRS3 | TES | USHBP1 | UBQLN4 | ETV7 | CCR8 |
| AGPAT2 | MLXIPL | SLC13A1 | ADAD1 | NOSTRIN | QRFPR | RHOBTB1 | SCFD2 |
| PPP4R3A | E2F6 | CDK4 | PABPC1P2 | COL5A3 | RAB31 | PPP1R14D | CASK |
| ADAMTS15 | CRTAC1 | HRC | KCNQ4 | UBE3D | MIEN1 | KIF18A | BPI |
| KIAA0895 | SIM2 | LITAF | RNF165 | CCDC77 | DIO2 | ABCA6 | ZNF473 |
| FHAD1 | BRINP1 | GRAMD1C | TAF1L | EMC7 | TRIM29 | AGXT2 | CD300LF |
| PPP1R12B | GPR37L1 | WAPL | AQP3 | LZTFL1 | YIPF5 | ENOX1 | ZC2HC1A |
| GIN1 | FHDC1 | PBOV1 | DERA | FGD4 | TYK2 | ACP6 | NLGN1 |
| ULK4 | BANK1 | PER1 | ITGA2 | LLGL2 | ALDH8A1 | FBRSL1 | TPPP3 |
| TNNI2 | TMEM167A | RGS4 | PDGFB | ZDHHC17 | APOBEC2 | THBD | HGF |
| BTN3A1 | EXOC3-AS1 | NAA20 | VAV1 | ZNF664 | TRMO | TMEM139 | PRR15 |
| PHLPP1 | GINS2 | GMDS | PCDH1 | PARD3B | MYH13 | C1orf43 | ARSB |
| TMEM217 | SLC22A2 | IL1RN | FMN1 | KCNJ12 | RASAL3 | HTR1B | PCDH8 |
| BRDT | NEK7 | MCM10 | NPSR1-AS1 | ARID5B | SEMA3C | UBB | TACR2 |
| VSX1 | LOC100132215 | MMD2 | MEF2C | SPON1 | FLVCR2 | SNX25 | GLOD5 |
| STK38L | ZNF555 | YKT6 | NR5A1 | DNAJC10 | SYNPO2L | APEH | ALDH3A1 |
| DPYSL2 | ETFB | GCM2 | FGF19 | GRN | GNAS | FCHO1 | DBN1 |
| TCEANC | SOCS6 | CEP128 | RBM24 | HEATR5A | ASAH1 | CHMP6 | RPS26 |
| MRVI1 | PLA2R1 | CDC14B | SCARB1 | SLC7A10 | SLC13A2 | WDR89 | VPS45 |
| INSIG2 | GJA3 | MCM5 | TRPS1 | CHMP4B | ZNF366 | SRMS | CNTN6 |
| MYO5B | AGTPBP1 | TMC8 | FAM173A | PITX3 | TRAFD1 | PNPLA8 | CD28 |
| YWHAQ | C9orf116 | SLC16A3 | VPS37D | ASB5 | JSRP1 | UGT8 | WBP2NL |
| TSPAN2 | EGFR | SRD5A3 | CDC16 | NDUFA10 | SPOPL | NR5A2 | ZC3H4 |
| KLF4 | C9orf153 | GADD45A | C18orf12 | EMX2 | BMF | PPP2R5A | MKL2 |
| TIMM17A | CMIP | METTL4 | FEM1C | ST6GALNAC5 | PIWIL3 | SRL | CCBE1 |
| CIT | ASB7 | C15orf54 | TMEM71 | TGIF1 | ARVCF | MEGF6 | TPPP |
| TNFRSF19 | RAB11FIP1 | MRPS36 | FTH1 | ETS1 | MAN1A1 | PELO | OXER1 |
| DYM | SLC23A3 | MMP20 | KCMF1 | TRY2P | RPS6KA5 | NPAS2 | SLC25A19 |
| CCDC112 | SOX9 | RGS9 | NUTF2 | OXSR1 | MAGEB2 | AVP | TMEM59 |
| C9orf50 | ABHD11-AS1 | GPR132 | PLCD1 | NATD1 | OTUD1 | PLA2G4D | BHLHE41 |
| AAED1 | TMIE | NDUFB6 | SPCS3 | PRRG4 | GCLC | CEACAM22P | LIN28A |
| KIF5C | PHLDB1 | E2F8 | EPHA5 | CITED2 | SLC5A1 | TBC1D23 | PLEKHG4B |
| BANF2 | GLP2R | HSD17B2 | PTPRK | SLC7A7 | SLC9A7 | SNX9 | SND1-IT1 |
| OLA1 | PEBP1 | TAPT1 | LOC401052 | CLIC5 | CPEB4 | KDM4C | SLC20A1 |
| RAPGEF2 | SGK1 | TANGO6 | SNCB | SEMA3D | FLRT2 | NTRK2 | LEPR |
| C9orf131 | IFI6 | LVRN | ZNF214 | C14orf2 | SSFA2 | PABPC4L | TMEM244 |
| C1QTNF1 | TMC5 | WDR18 | BRMS1L | CTNNB1 | PDE1A | SH3PXD2B | NTN4 |
| LIMCH1 | PSD3 | SLC38A11 | HTRA1 | DIRAS1 | EPHB6 | HTRA3 | PTGIR |
| YY1AP1 | TFAP2A | GTPBP4 | ARFGAP3 | LDHAL6A | ZNF331 | EPC1 | SNRPC |
| CREG2 | ZBTB7C | CDK20 | KIAA0825 | RXFP2 | GPR182 | CASZ1 | ZBED2 |
| ASAP2 | INPP5A | UBE2O | WNT7B | TNFRSF8 | RANBP3L | SORBS1 | GUSB |
| CFAP126 | SNHG7 | COL18A1 | CACNA1A | FKBP8 | TEKT3 | RPEL1 | GNAT2 |
| FAM107B | LCA5 | MAP1S | RHOD | ADSSL1 | SLC8A1 | PKP2 | ABHD15 |
| FAM86B3P | SNRNP35 | SLC1A4 | CLDN23 | INHBB | FAM110B | TMEM207 | HMCN1 |
| ADAM12 | PRF1 | CD38 | METRNL | OPCML | RAP1GAP2 | IQUB | TP63 |
| RECQL5 | PIK3R1 | KRT20 | CYP1A1 | DUSP14 | FTHL17 | EPYC | CCDC134 |
| B4GALNT2 | FOXE1 | ADAMTSL1 | SCIN | POPDC2 | NXNL1 | RFX7 | VTCN1 |
| CPA2 | IL21 | PPP2R2A | RAPGEF4 | ARNT2 | GSN | SIGLEC8 | LRRC29 |
| ZNF385B | NLRC5 | FUZ | CCR3 | VLDLR | MELTF | BDNF | ACSL3 |

TABLE 2-continued

| CHIPSEQ_CDK19-KD ENHANCERUP | | | | | | | |
|---|---|---|---|---|---|---|---|
| ZNF488 | FRAT2 | BATF3 | C11orf96 | SULT4A1 | ITGAV | ADGRL3 | SKIL |
| SIRT4 | MORN3 | RIPK2 | KLLN | MYO6 | MTCL1 | UBA7 | JPH2 |
| DYSF | TYROBP | CCDC83 | RHOU | NFIL3 | FKBP11 | LRPAP1 | CLDN10 |
| ERP44 | IPMK | LTBP4 | BBS10 | RNLS | SPAG17 | YOD1 | BPTF |
| FERMT2 | SYT12 | CCDC150 | S1PR2 | PRSS41 | FAM120B | TPH2 | CDKL3 |
| SFXN4 | NDRG4 | FAM171A1 | ANKRD10 | SLC29A3 | IRAK3 | KCNA10 | ZBTB16 |
| MICAL3 | C5orf51 | NAA16 | EDNRA | PRMT9 | DCST1 | PDC | VCL |
| RAD51C | OSER1 | SFRP2 | VSTM5 | BCLAF1 | CXCL16 | BFSP1 | SHISA2 |
| LGALS3BP | SCG2 | TYMP | NENF | TEX36 | C17orf107 | ST6GALNAC1 | C5orf30 |
| KCNJ6 | AGTR2 | SHANK2 | GPR156 | MICALL1 | ZNF608 | CCDC63 | AQP9 |
| MSX2 | GPC1 | GFPT1 | GPRC5B | LACC1 | NPFFR2 | FBXO7 | PARP11 |
| TIGD2 | ANKRD9 | LRRN3 | UBASH3A | CCDC68 | TDRD7 | ARHGAP24 | SH3BGRL2 |
| PNMA2 | SLC1A3 | ABCA13 | CIPC | SPIRE2 | H3F3C | EFHC2 | VILL |
| CACNA1H | KCTD12 | UBE4B | NYAP2 | DUSP23 | CCDC124 | RHOBTB2 | ERBB4 |
| RAB35 | ITPK1 | PIK3R3 | SPTSSA | MMP27 | UBASH3B | PYM1 | SPAG16 |
| TOMM5 | TLE6 | MRPL21 | JPH1 | PKD1L2 | TMEM94 | LANCL3 | IL2RG |
| FUNDC1 | | | | | | | |

Figure 3G:
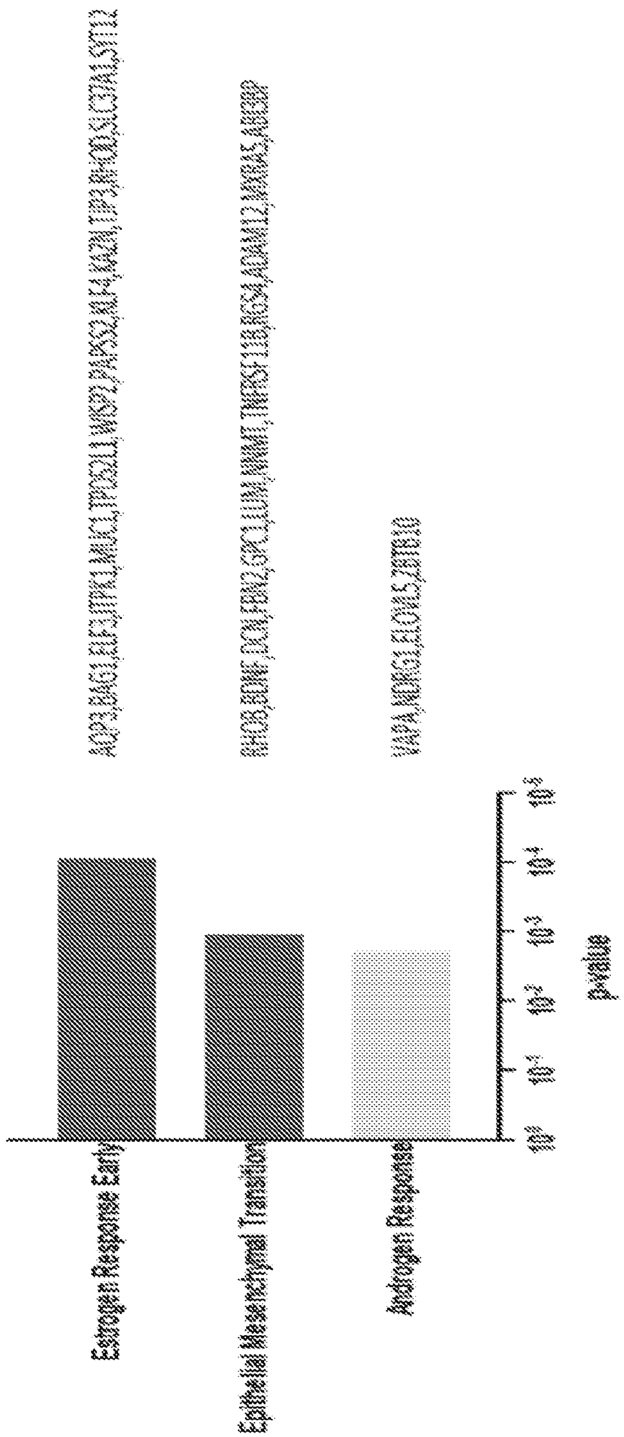
FIG. 3G is a graph showing the hallmark gene sets identified as enriched in Metascape analysis of the CDK19KD-EnhancerUP 'core' genes (top and middle bars) and CDK19KD-EnhancerDOWN 'core' (bottom bar) genes. The individual genes contributing to the enrichment of each hallmark gene set are shown to the right of each bar.
Figure 12A:
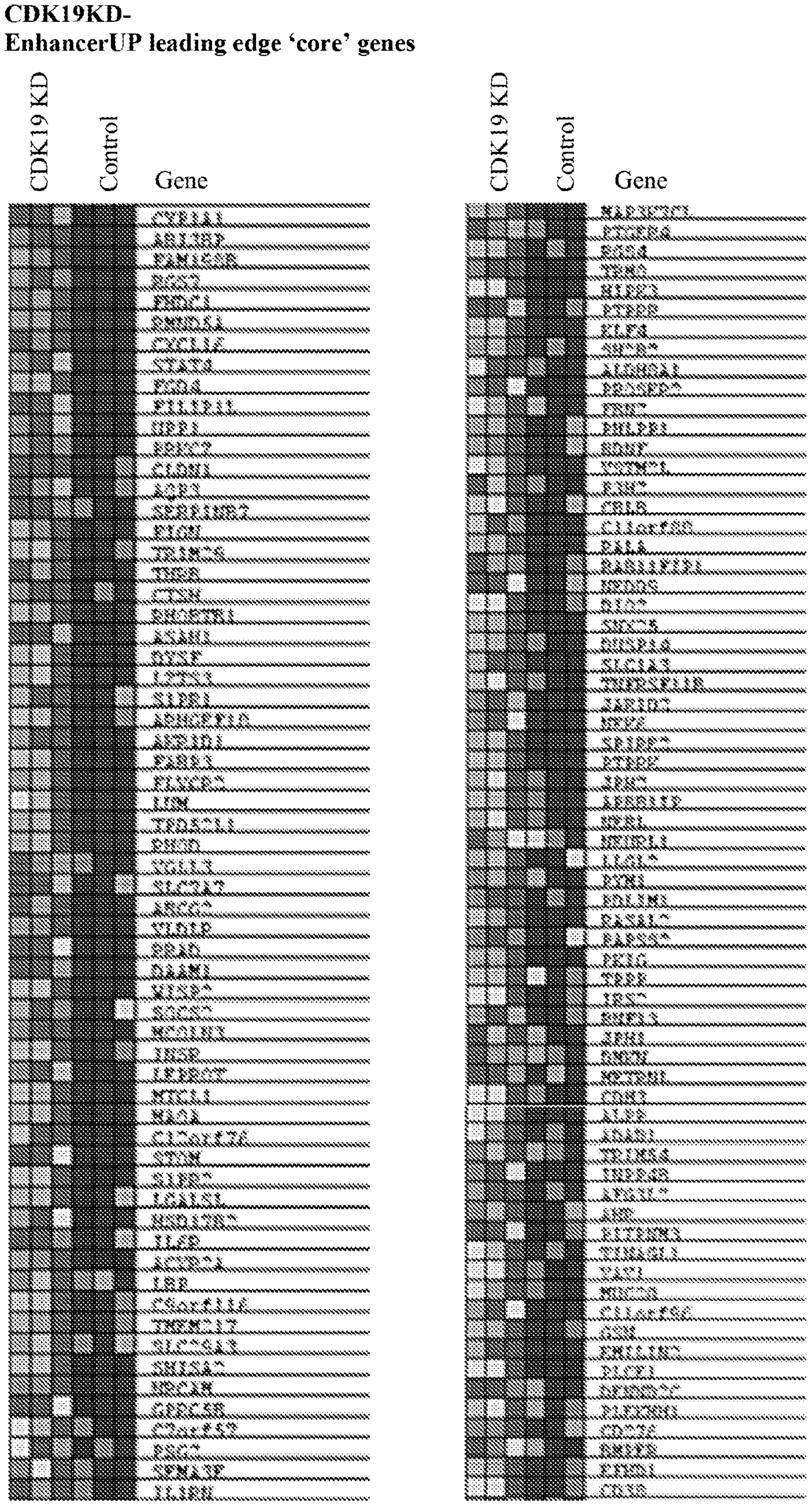
FIGS. 12A and 12B show heat map of the expression of CDK19KD-EnhancerUP 'core' genes (FIG. 12A) and CDK19KD-EnhancerDOWN 'core' genes (FIG. 12B). Normalized expression of each gene in each biological replicate of the CDK19 knockdown and Control samples are shown.
Figure 12A:
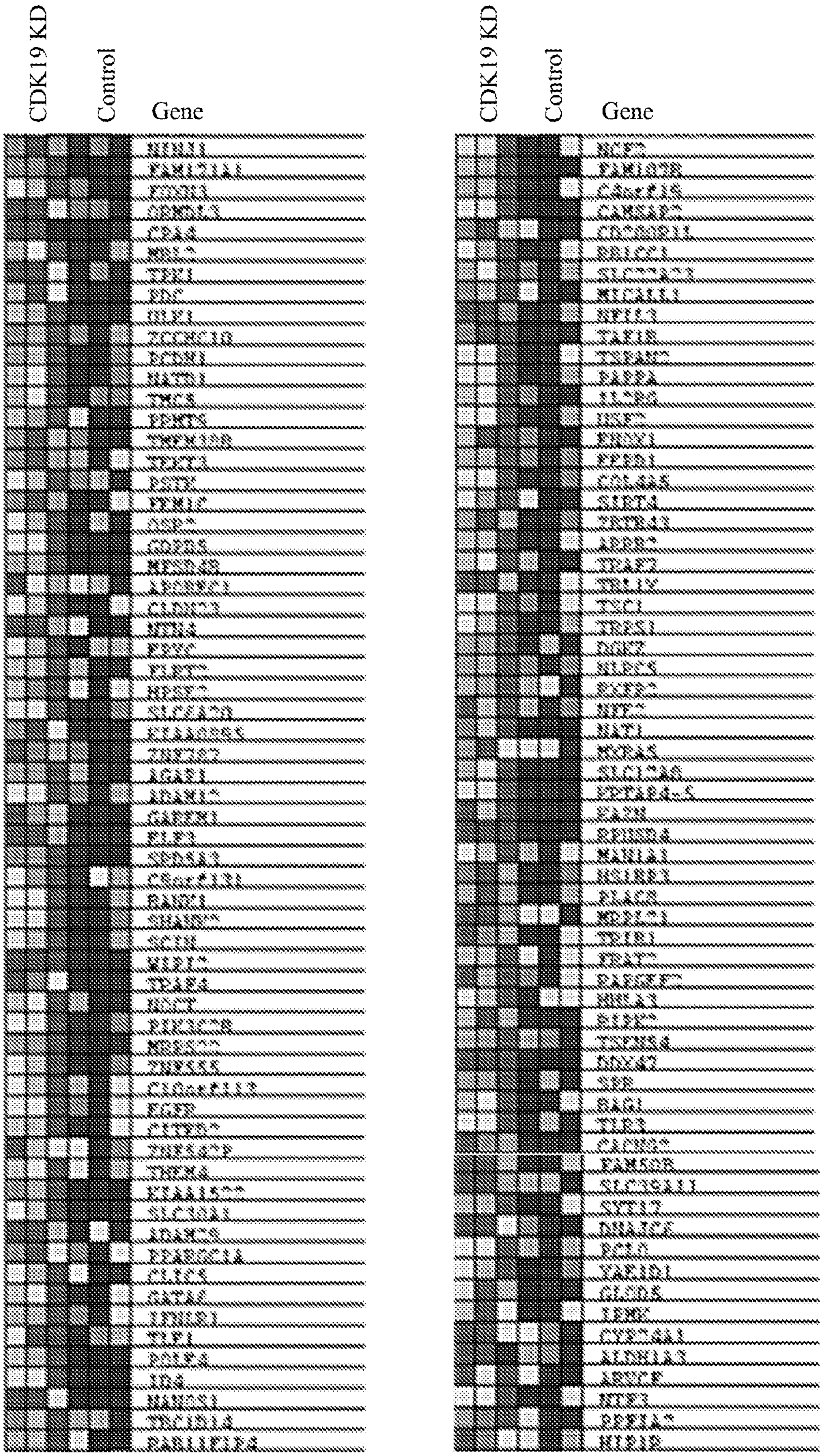
Figure 12A:
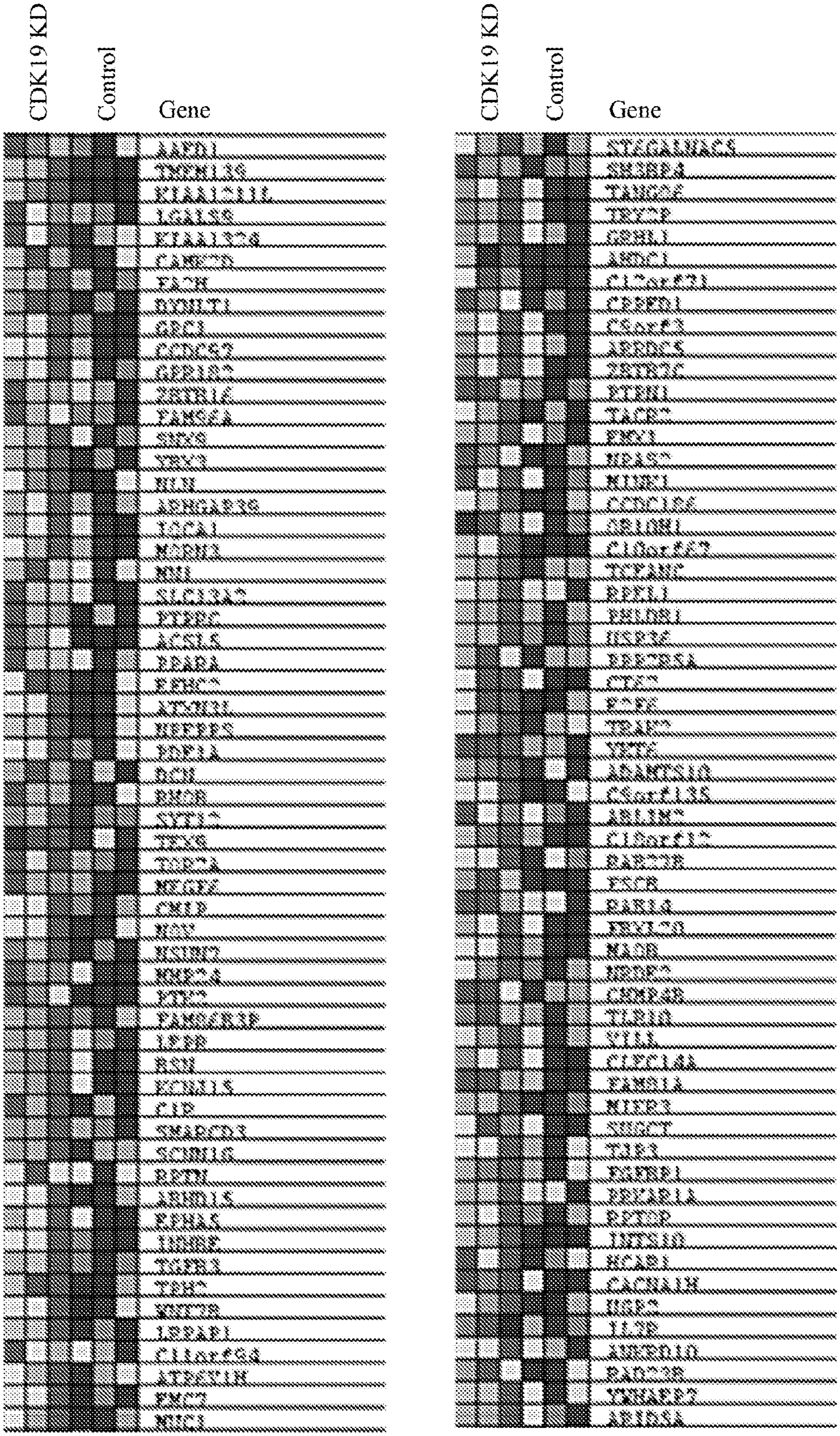
Figure 12A:
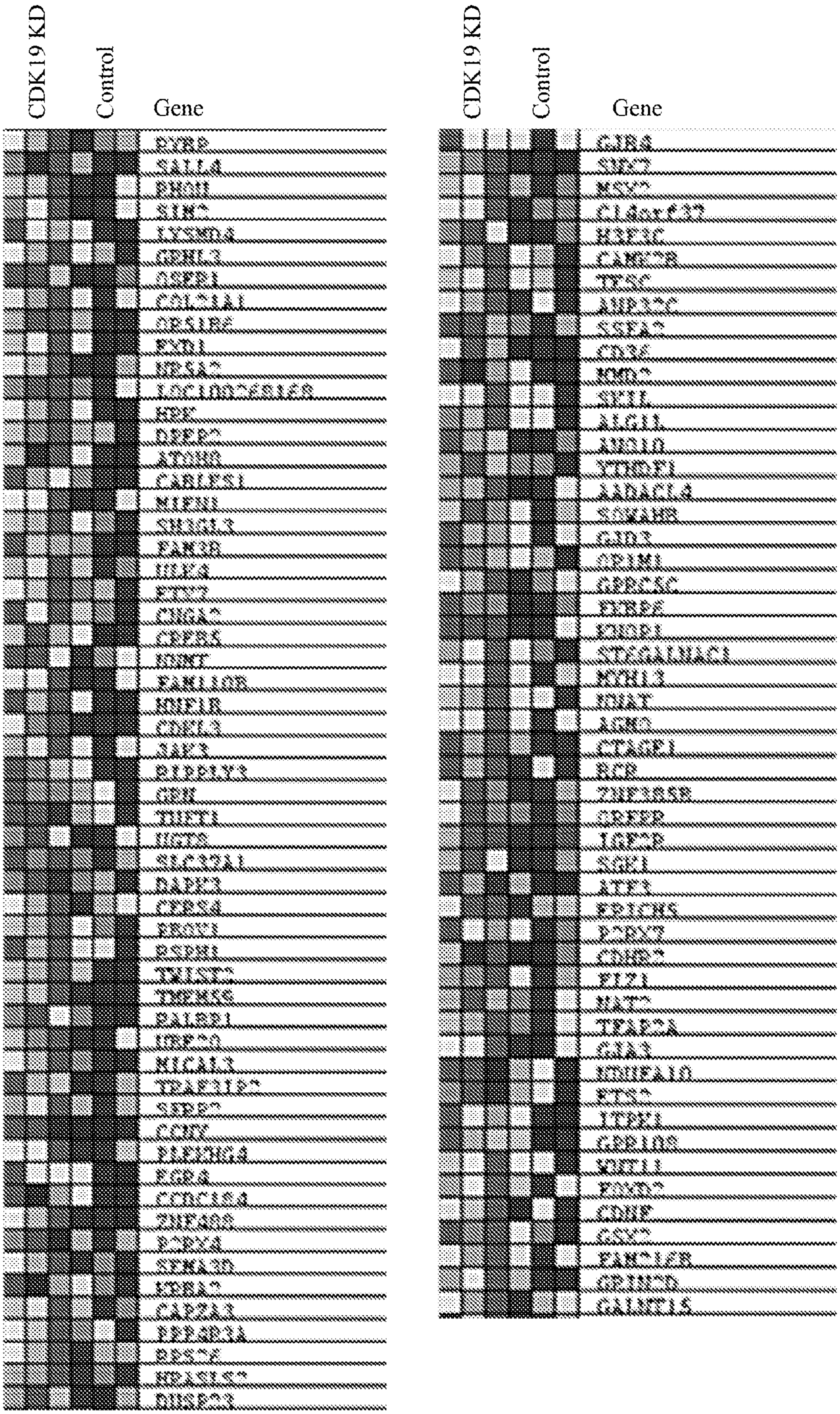
Figure 12B:
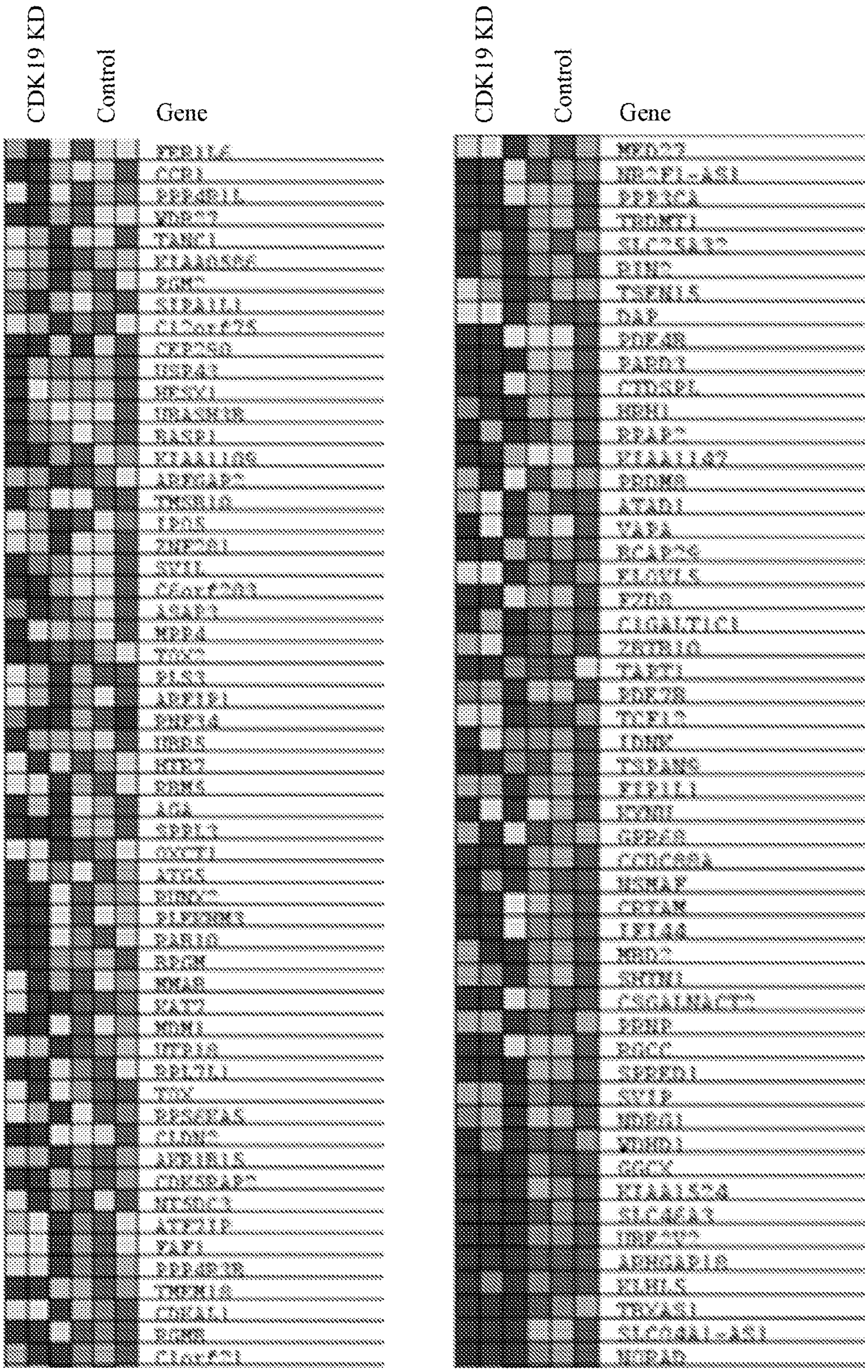
Figure 12B:
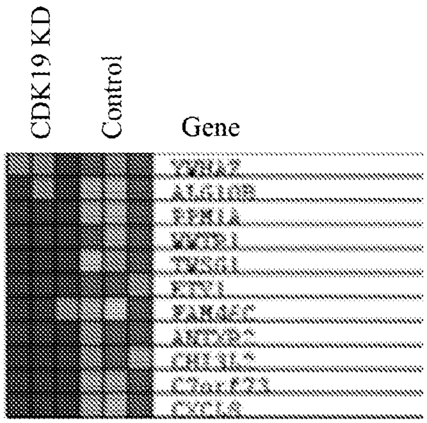
Figure 13A:
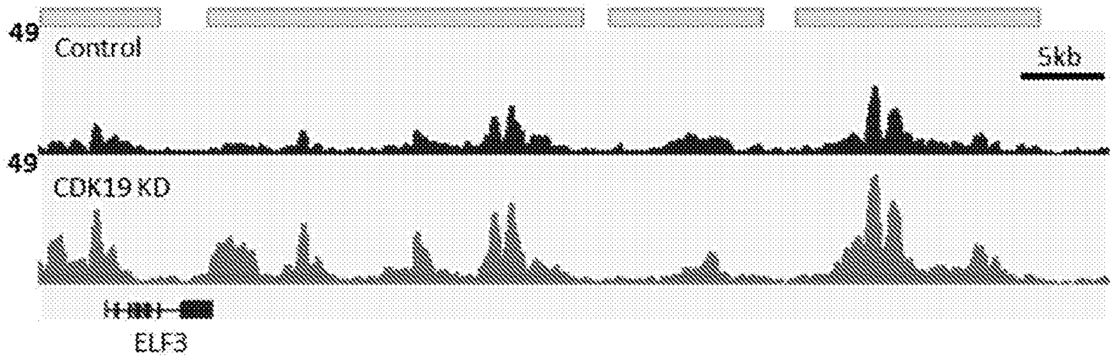
FIGS. 13A-13D are graphs showing representative genes where CDK19 knockdown leads to changes in H3K27Ac signals and corresponding changes in gene expression. Representative gene tracks depicting H3K27Ac signals at the loci of select CDK19KD-EnhancerUP 'core' (FIGS. 13A and 13B) and CDK19KD-EnhancerDOWN 'core' genes (FIGS. 13C and 13D).
Figure 13B:
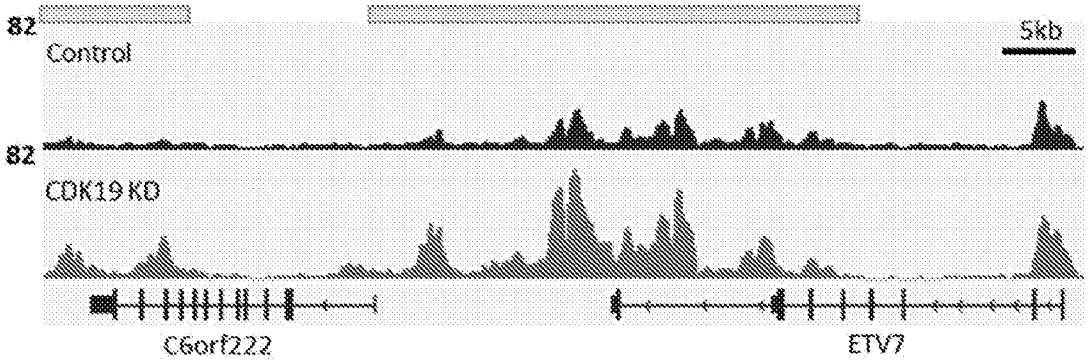
Figure 13C:
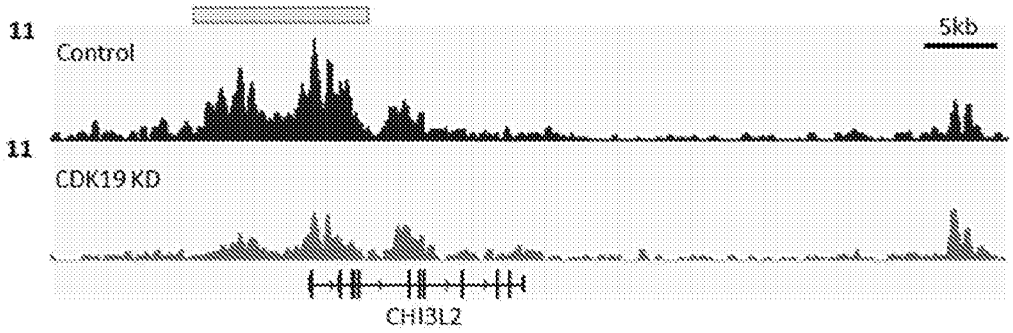
Figure 13D:
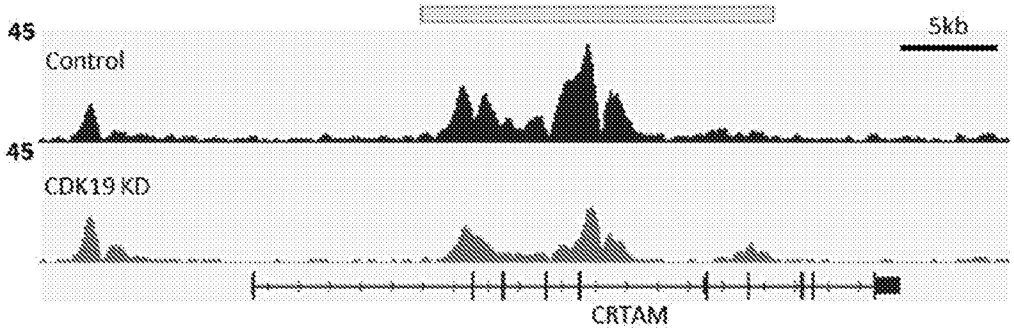
Figure 13E:
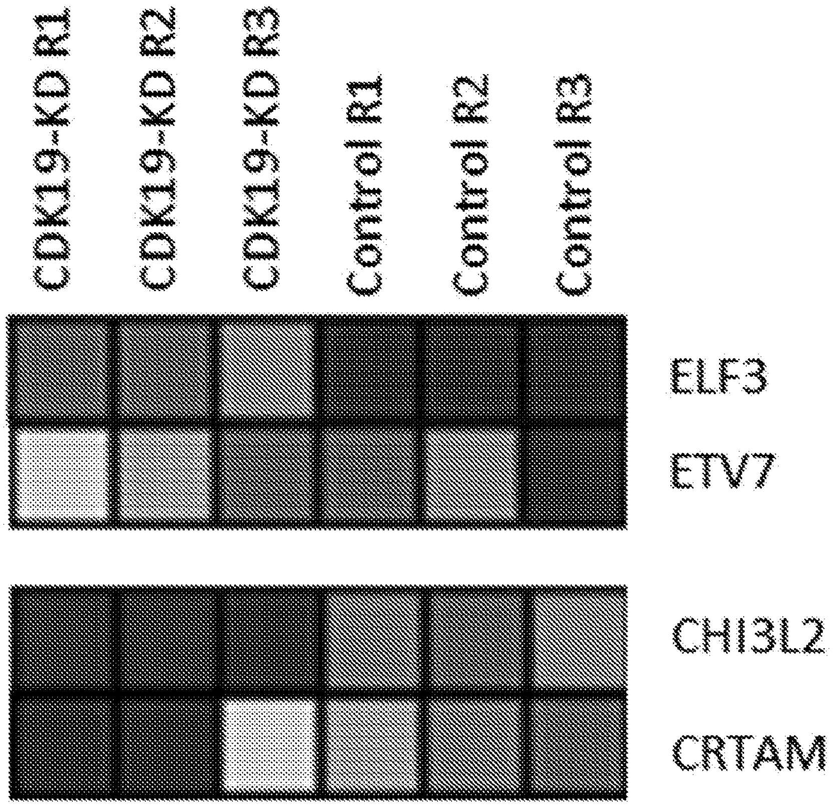
FIG. 13E is a heat map of the normalized gene expression of ELF3, ETV7, CHI3L2, and CRTAM across each of the three biological replicates in control and CDK19 knockdown samples.

The aforementioned GSEA also enabled us to identify the leading edge 'core' genes that contribute the most to each enrichment (FIGS. 12A and 12B). At these 'core' genes, differences in H3K27Ac enhancer signals due to CDK19 knockdown (FIGS. 13A-13D) result in large corresponding changes in gene expression (FIG. 13E). The gene tracks at the ELF3 (FIG. 13A) and ETV7 (FIG. 13B) loci show enrichment of H3K27Ac signals in the CDK19 knockdown samples, whereas the gene tracks at the CHI3L2 (FIG. 13C) and CRTAM (FIG. 13D) loci show enrichment of H3K27Ac signals in the Control samples. Upper tracks denote Control samples, while lower tracks denote CDK19 knockdown samples. Gray bars denote regions identified by DiffBind to be different between control and CDK19 knockdown samples (FDR<0.05). Metascape analysis was then used to evaluate Hallmark gene sets enriched within the CDK19KD-EnhancerUP 'core' and the CDK19KD-EnhancerDOWN 'core' genes. Within the CDK19KD-EnhancerUP 'core' genes, early Estrogen Response (p-value=8.72e-5) and Epithelial Mesenchymal Transition (p-value=1.08e-3) were Hallmarks identified as enriched (FIG. 3G, dark gray bars). Similarly, within the CDK19KD-EnhancerDOWN 'core' genes Androgen Response (p-value=1.89e-3) was the Hallmark found to be enriched (FIG. 3G, light gray bar). Thus, a subset of genes (FIG. 3G) within the early Estrogen Response, Epithelial to Mesenchymal Transition, and Androgen Response gene sets have changes in H3K27Ac enhancer signals and strong corresponding changes in gene expression. These genes constitute a small fraction of the total genes in each Hallmark gene set (5-10%), but highlight key genes within these biological processes where CDK19 can epigenetically regulate gene transcription.

Figure 4A:
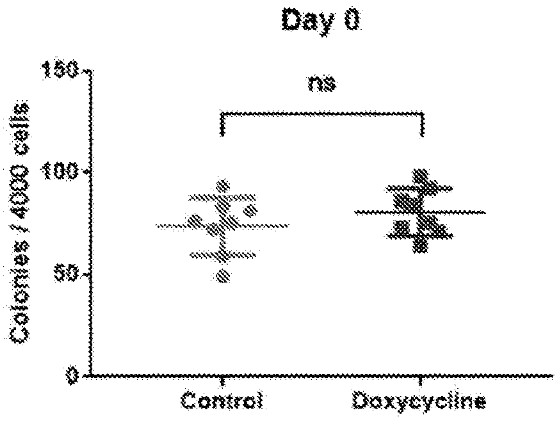
FIGS. 4A and 4B are graphs showing that in inducCDK19KD-PDX-T1 cells, induction of CDK19 shRNA by addition of doxycycline significantly decreased the number of organoid colonies in the doxycycline treatment group compared to control. Number of organoid colonies at Day 0 (FIG. 4A) and Day 16 (FIG. 4B) after initiating doxycycline treatment is shown.
Figure 4B:
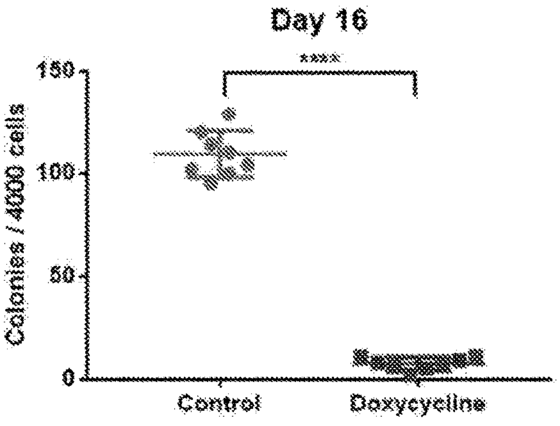
Figure 4C:
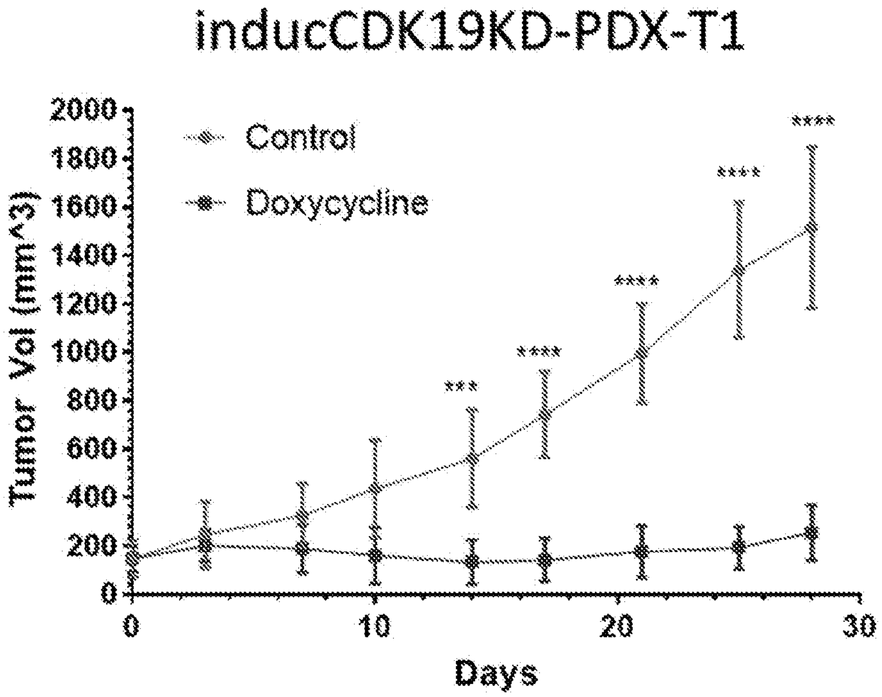
FIGS. 4C and 4D are graphs showing that the induction of CDK19 shRNA in pre-established tumors impaired tumor growth. The growth of pre-established tumors in the doxycycline fed NSG mice and control NSG mice are shown for inducCDK19KD-PDX-T1 (FIG. 4C) and inducCDK19KD-PDX-T3 (FIG. 4D).
Figure 4D:
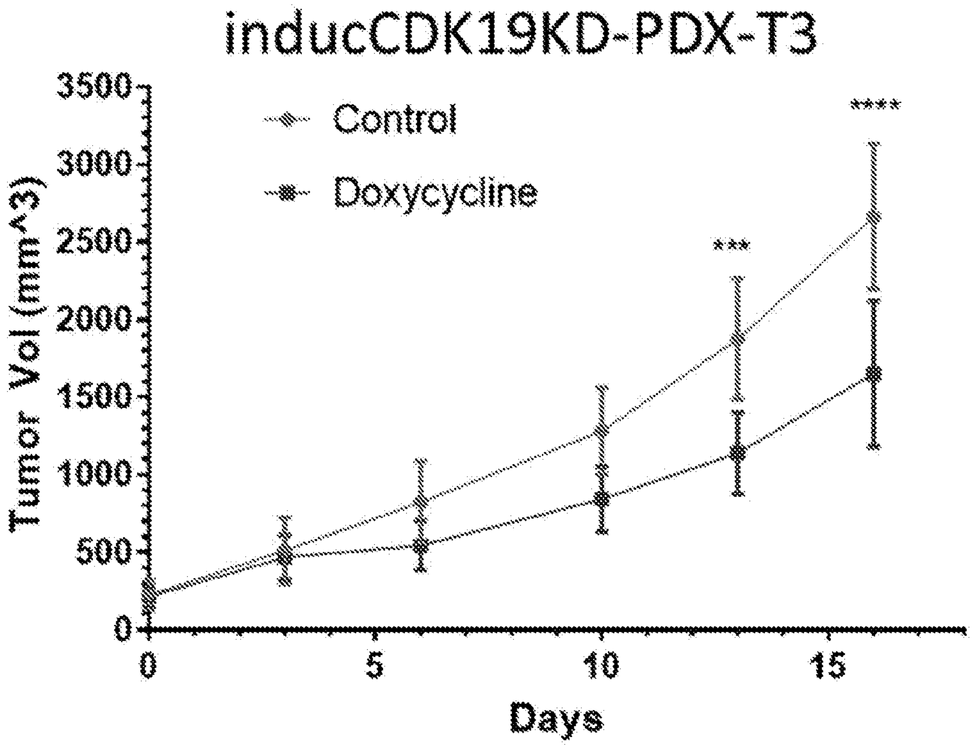
Figure 4E:
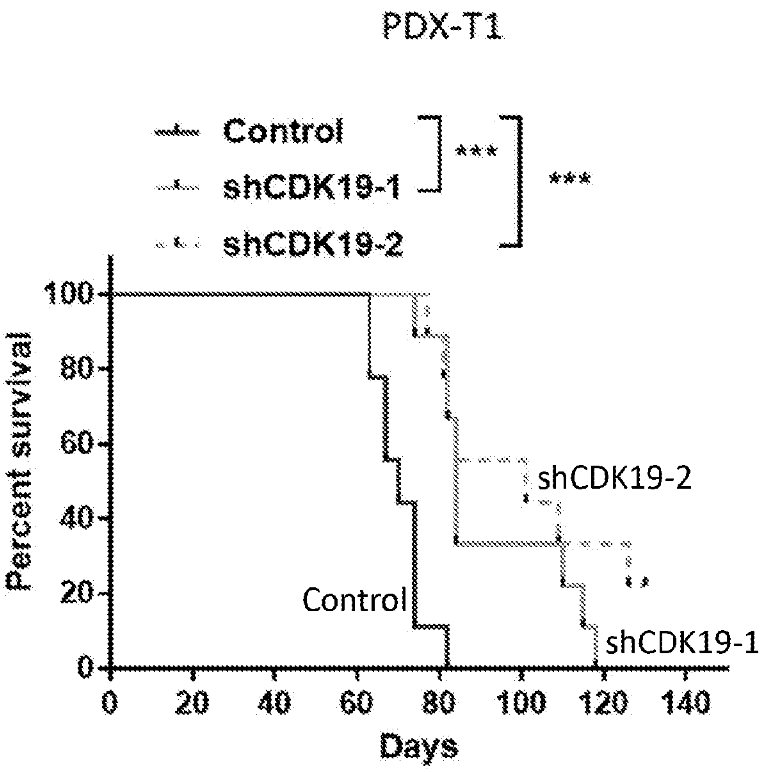
FIG. 4E is a graph showing that CDK19 knockdown extends the survival of NSG mice with PDX-T1 tumors.
Figure 14A:
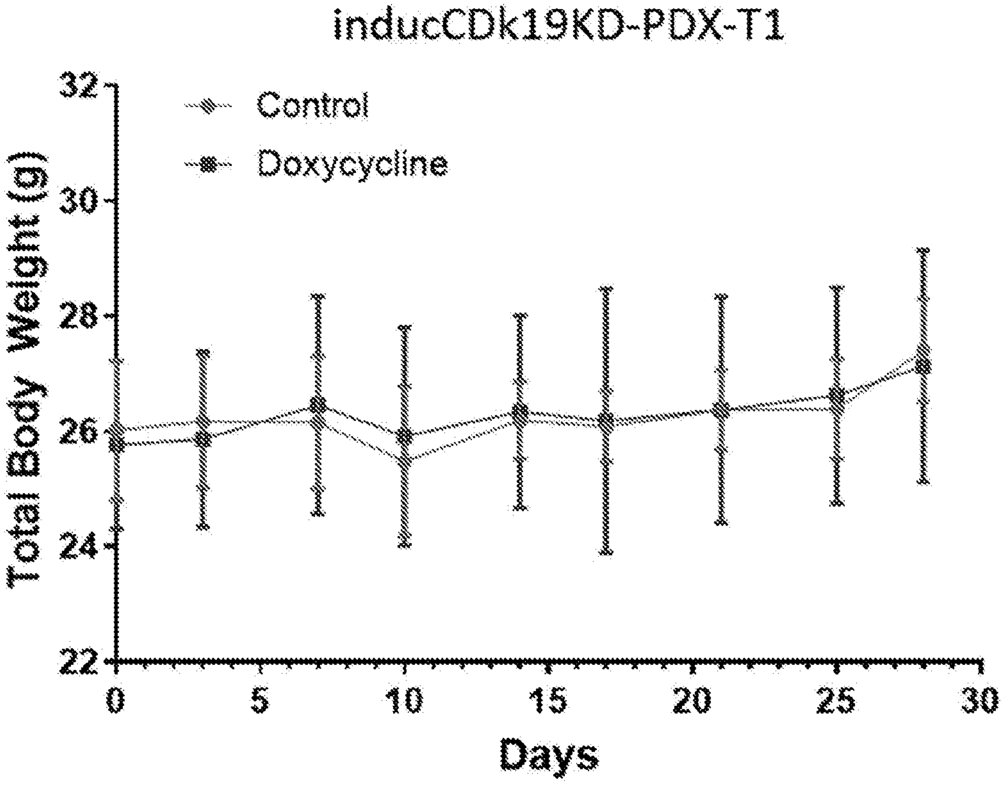
FIGS. 14A and 14B are graphs showing that total body weights of mice were not significantly different between the mice fed doxycycline rodent feed (doxycycline group) compared to the mice fed standard rodent feed (control group) in the inducCDK19KD-PDX-T1 (mean±s.d., n=5, experiments performed twice) (FIG. 14A) and inducCDK19KD-PDX-T3 (mean±s.d., n=5, experiment performed once) (FIG. 14B) tumor experiments.
Figure 14B:
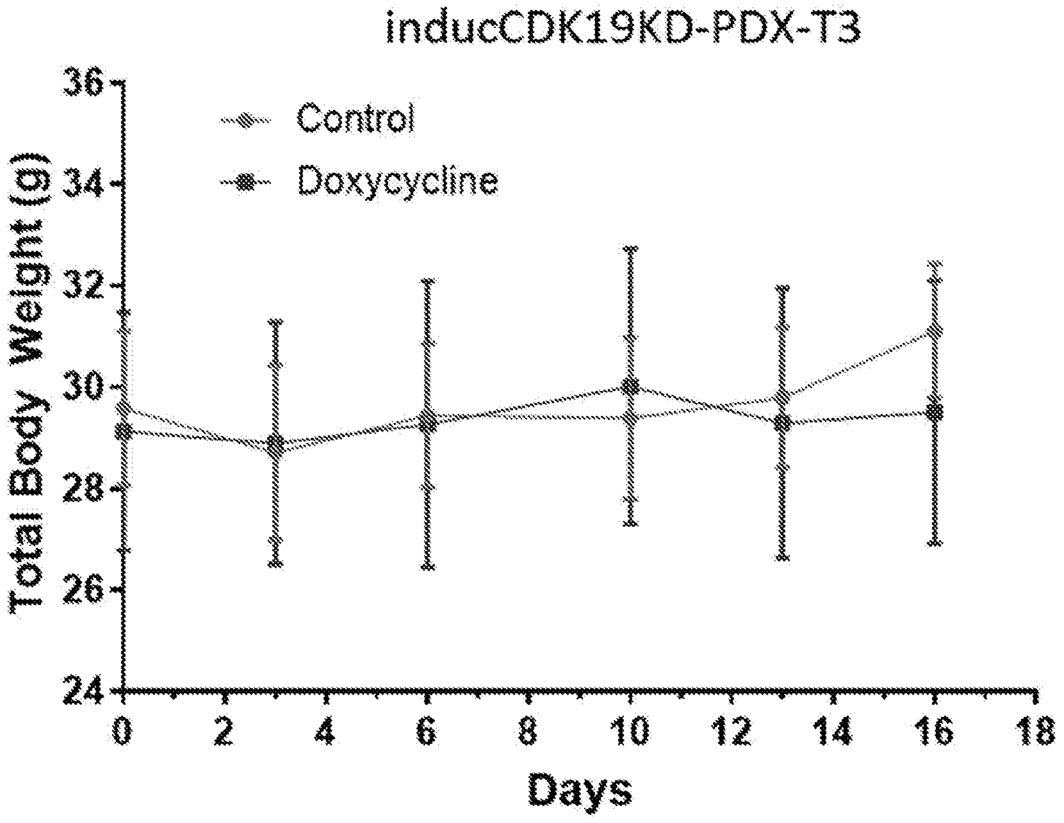

4.7 Example 7—Effects of CDK19 Knockdown on the Growth of Pre-Established Organoids We explored the effect of CDK19 knockdown on the growth of pre-established organoids in vitro and in pre-established PDX tumors in vivo. This aimed to model the treatment of patients' pre-existing tumors. In vitro, adding doxycycline to the treatment group (to induce CDK19 shRNA) significantly reduced the number of pre-established organoids compared to the control (no doxycycline) (FIGS. 4A and 4B). In FIGS. 4A and 4B, number of organoid colonies at Day 0 (FIG. 4A) and Day 16 (FIG. 4B) after initiating doxycycline treatment is shown, **P<0.0001; ns is P>0.05 (mean s.d., n=6, experiment performed twice, P values determined by unpaired t-test). In vivo, feeding doxycycline to mice with pre-established inducCDK19KD-PDX-T1 or inducCDK19KD-PDX-T3 (PDX-T3 cells transduced with a doxycycline-inducible CDK19 knockdown construct) tumors significantly impacted the growth of these tumors (FIGS. 4C and 4D). In FIGS. 4C and 4D, the growth of pre-established tumors in the doxycycline fed NSG mice and control NSG mice are shown for inducCDK19KD-PDX-T1, P<0.0001; *P<0.001 (mean±s.d., n=5, experiment performed twice, P values determined by unpaired t-test) (FIG. 4C) and inducCDK19KD-PDX-T3, **P<0.0001; *P<0.001 (mean±s.d., n=5, experiment performed once, P values determined by unpaired t-test) (FIG. 4D). CDK19 shRNA induced tumors were ultimately 82% smaller in inducCDK19KD-PDX-T1 tumors and 38% smaller in inducCDK19KD-PDX-T3 tumors when compared to control tumors (FIGS. 4C and 4D). In both inducCDK19KD-PDX-T1 and inducCDK19KD-PDX-T3 experiments, mouse total body weights were not significantly different between the treatment and control groups (FIGS. 14A and 14B). Finally, survival studies showed that overall survival was significantly longer in mice whose PDX-T1 tumors were transduced with CDK19 shRNA compared to mice transduced with control shRNA (FIG. 4E). Shown in FIG. 4E are Kaplan-Meir survival curves for mice engrafted with PDX-T1 xenografts transduced with control shRNA (black line), shCDK19-1 (solid gray line) or shCDK19-2 (dashed gray line). Mice were followed with weekly measurements of tumor diameters. Mice were sacrificed when the longest diameter of their tumor exceeded 17 mm. Two mice in the shCDK19-2 group did not develop PDX tumors and were sacrificed at the end of the experiment. These mice were censored when constructing the survival curve for the shCDK19-2 group, ***P<0.001 (n=9, experiment performed three times, log-rank (Mantel-Cox) test used to determine P values). In summary, these experiments showed that even in pre-established tumors, specifically knocking down CDK19 can significantly decrease tumor growth and that CDK19 knockdown can prolong survival in mice.

4.8 Example 8—Effects of CCT251921 on Pre-Established PDX Tumors

Figure 4F:
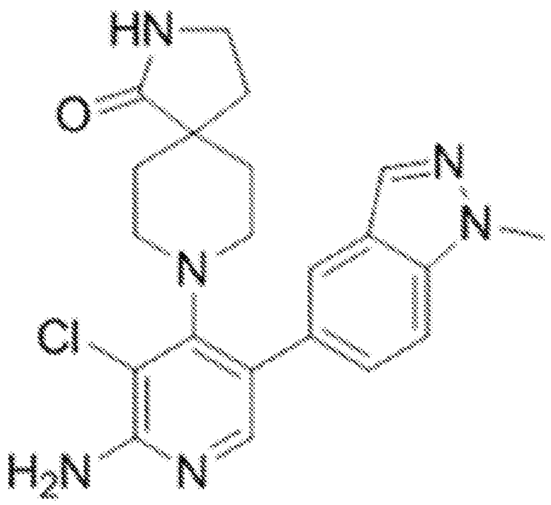
FIG. 4F shows the chemical structure of CCT251921, an orally bioavailable selective inhibitor of CDK19 and CDK8.
Figure 4G:
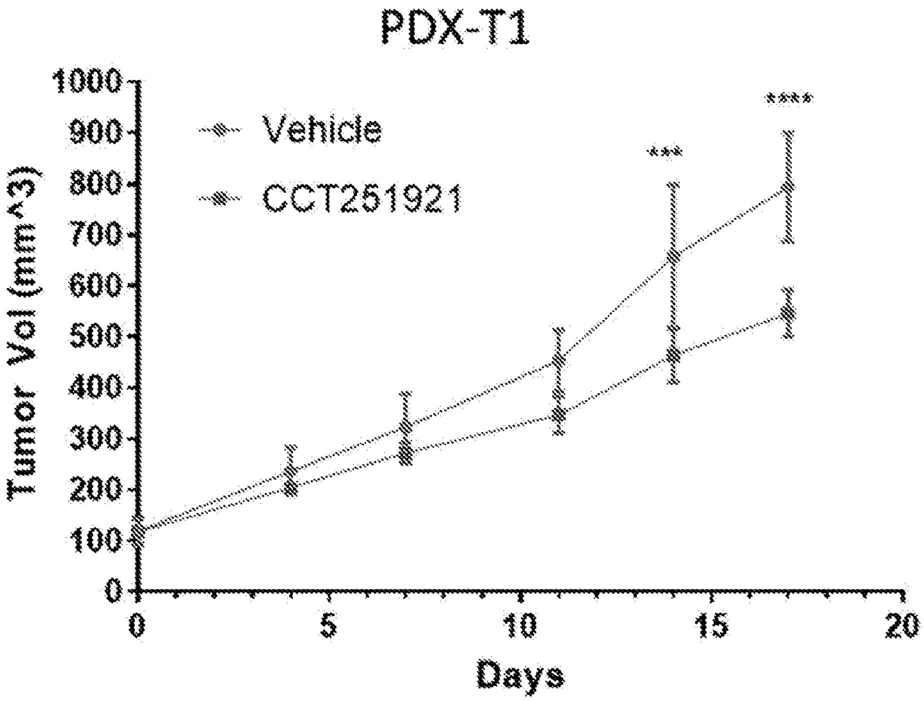
FIG. 4G is a graph showing that the treatment of mice with CCT251921 by daily oral gavage significantly impaired the growth of pre-established PDX-T1 xenograft tumors.
Figure 14C:
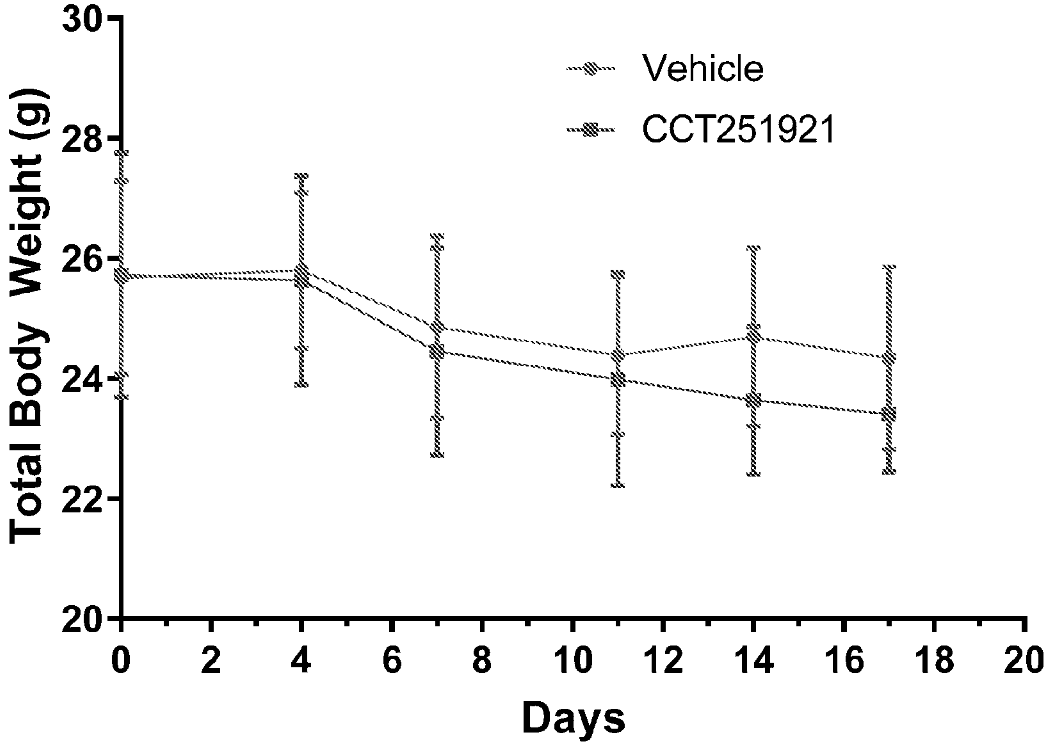
FIG. 14C is a graph showing that total body weights of mice were not significantly different between the mice receiving oral gavage with CCT251921 compared to Vehicle (mean±s.d., n=5, experiment performed once).
Figure 16A:
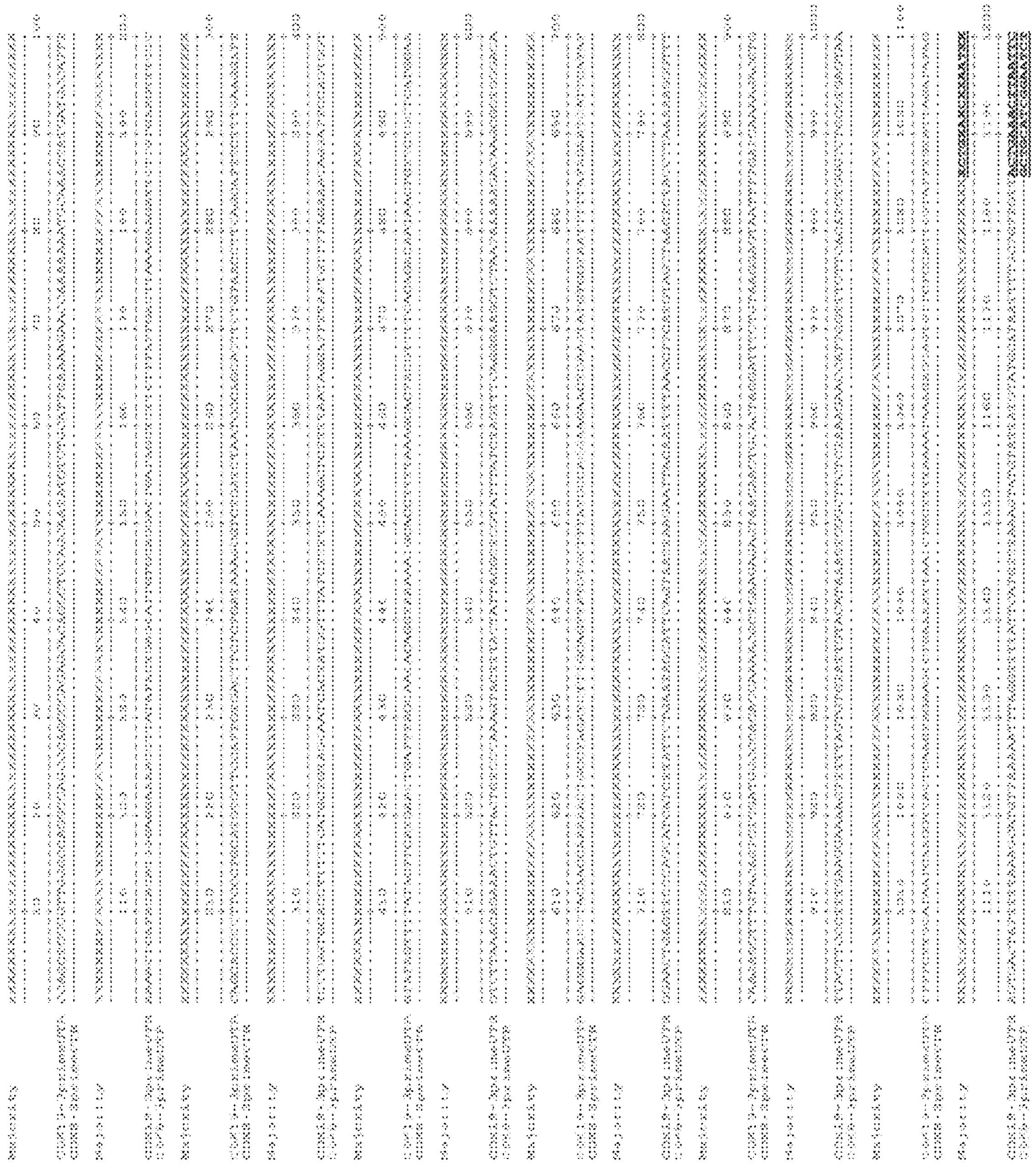
FIGS. 16A-16D show a nucleic acid alignment of the 3' UTR of CDK8 and CDK19. The underlined and bolded text indicates the overlapping regions.
Figure 16B:
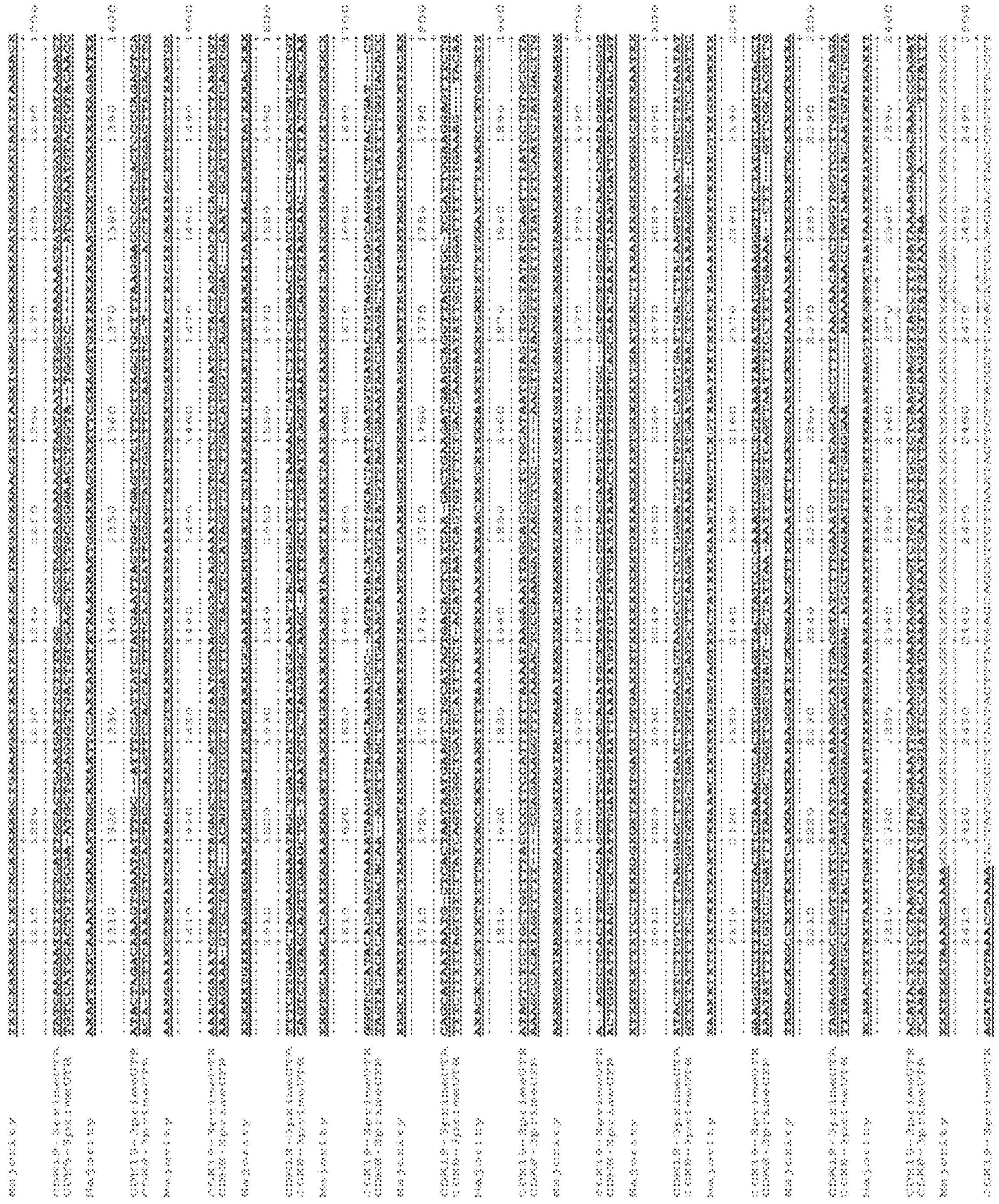
Figure 16C:
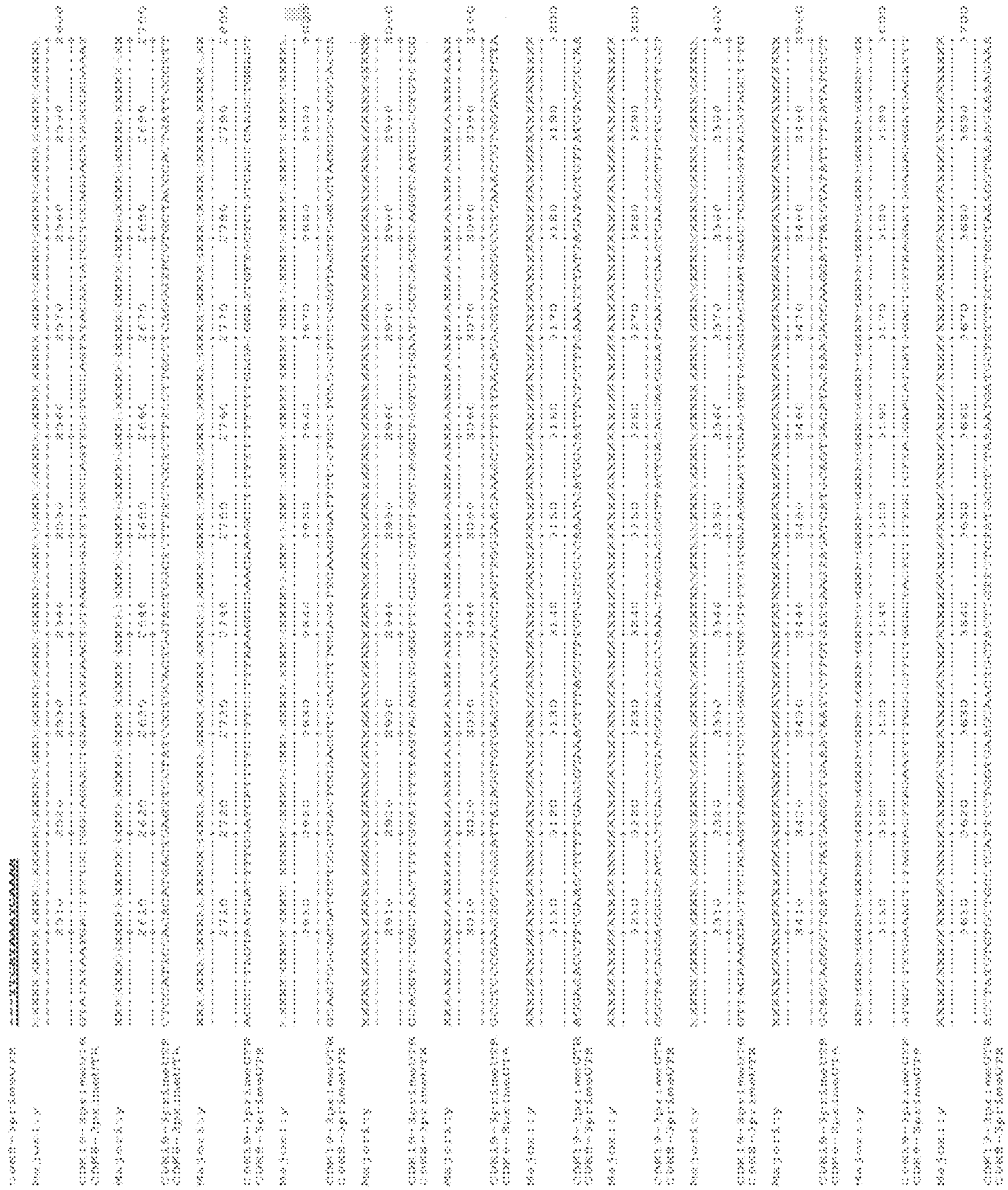
Figure 16D:
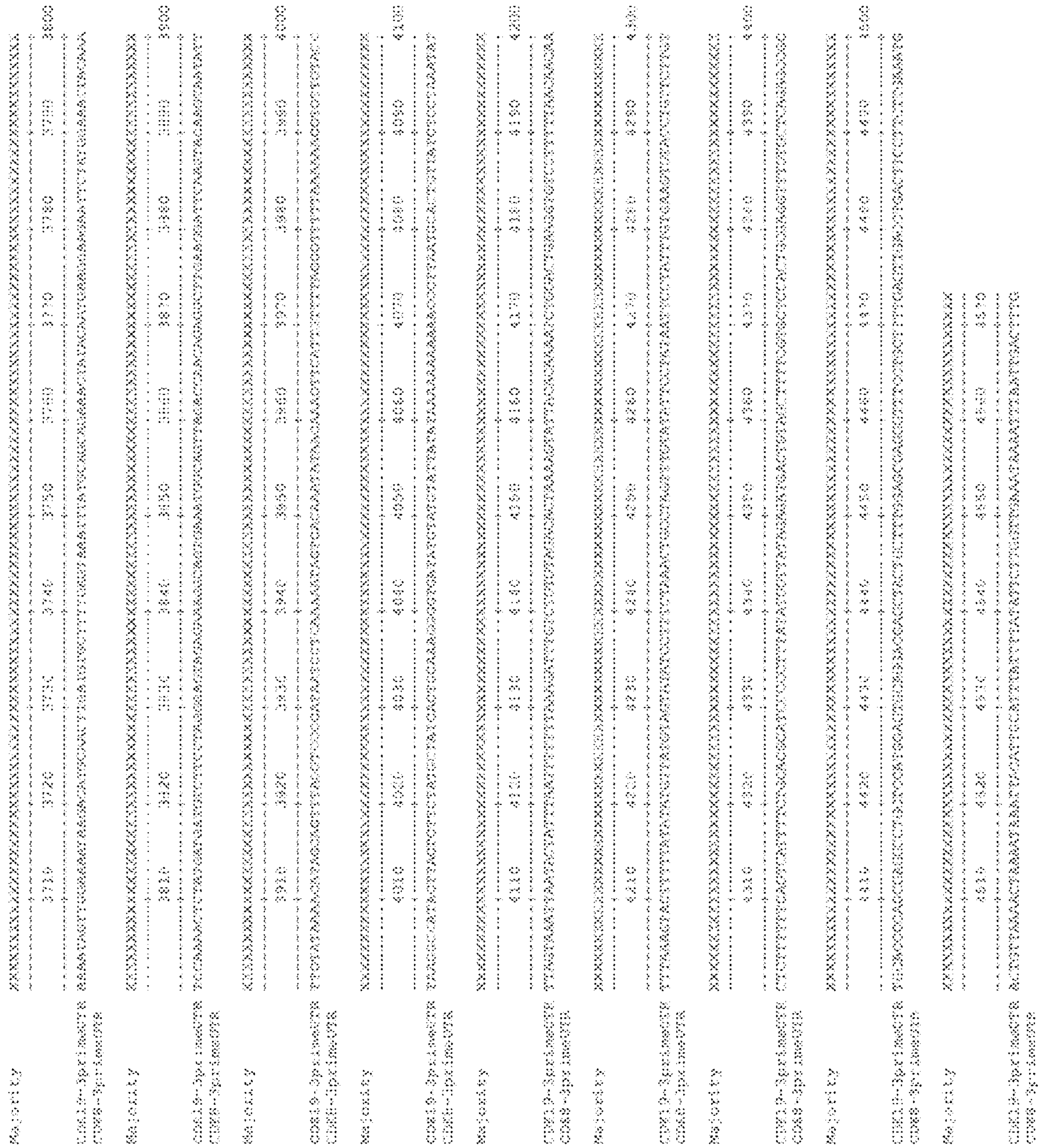

To model the use of a CDK19 targeted therapy clinically, we treated mice with pre-established PDX tumors with CCT251921 (FIG. 4F), an orally bioavailable inhibitor of both CDK19 and the closely related paralog, CDK8. PDX-T1 tumors were pre-established in mice before starting daily oral administration (30 mg/kg) of CCT251921 or vehicle. Treatment with CCT251921 resulted in a significant reduction in tumor growth by day 14 (FIG. 4G). Final volumes of the tumors in CCT251921 treated mice were over 30% smaller than the tumors of vehicle treated mice (FIG. 4G). NSG mice with pre-established PDX-T1 xenograft tumors were treated with daily oral gavage of CCT251921 or vehicle. Mice were followed with twice weekly determinations of tumor volume, **$P<0.0001$; *$P<0.001$ (mean±s.d., n=5, experiment performed once, P values determined by unpaired t-test). Mice in both the CCT251921 and vehicle cohorts suffered an overall weight loss, but this was not significantly different between the two groups and most likely due to the effect of daily oral gavage on their feeding habits (FIG. 14C). It is well known that different biological outcomes can arise from gene knockdown versus chemical inhibition. We show here in pre-established tumors that chemical inhibition of CDK19 kinase activity can recapitulate the effects of total CDK19 loss shown in our knockdown studies.

From our data, we conclude that CDK19 regulates multiple cancer relevant pathways and that it is a potential therapeutic target in TICs. Thus, CDK19 inhibition is useful both to therapeutic strategies targeting transcriptional co-factors such as CDK8, CDK9, and BRD4, and to those targeting TICs and their self-renewal pathways such as Hedgehog, Wnt/β-catenin, and Notch. However, some therapeutic approaches may be limited by toxicity caused to normal cells. This can be attributed to the ubiquitous expression of transcriptional co-factors in normal tissues and the importance of self-renewal pathways in normal stem cells. BRD4 inhibition, for example, resulted in a disruption of tissue homeostasis in multiple organs in mice. Similarly, due to the challenge of narrow therapeutic indices, Hedgehog, Notch, and Wnt pathway inhibitors have had limited clinical success thus far. The biology of CDK19 points towards potential advantages as a therapeutic target. Compared to other ubiquitous transcriptional co-factors such as its paralog CDK8, CDK9, and BRD4, CDK19 has more limited tissue distribution (see, e.g., Tsutsui et al., *Genes to cells: devoted to molecular & cellular mechanisms* 16:1208-1218, 2011), potentially limiting the toxicity from CDK19 inhibition, while CDK8, CDK9, and BRD4 knockouts are lethal (see, e.g., Brown et al., *Mamm Genome* 23:632-640, 2012; Westerling, *Molecular and Cellular Biology* 27:6177-6182, 2007; and Houzelstein et al., *Molecular and Cellular Biology* 22, 3794-3802, 2002). In addition, the limited expression of CDK19 in tissues could broaden the therapeutic window to enable the otherwise toxic inhibition of stem cell pathways such as NOTCH, or critical processes, such as G2/M checkpoint. Our studies showing that small molecule inhibition of CDK19 impaired PDX growth affirms the potential of therapeutically targeting CDK19 in TNBC.

5. REFERENCES

1 Bauer, K. R., Brown, M., Cress, R. D., Parise, C. A. & Caggiano, V. Descriptive analysis of estrogen receptor (ER)-negative, progesterone receptor (PR)-negative, and HER2-negative invasive breast cancer, the so-called triple-negative phenotype: a population-based study from the California cancer Registry. Cancer 109, 1721-1728, doi:10.1002/cncr.22618 (2007).

2 Tsutsui, T., Fukasawa, R., Tanaka, A., Hirose, Y. & Okhuma, Y. Identification of target genes for the CDK subunits of the Mediator complex. Genes to cells: devoted to molecular & cellular mechanisms 16, 1208-1218, doi:10.1111/j.1365-2443.2011.01565.x (2011).

3 Brown, S. D. & Moore, M. W. The International Mouse Phenotyping Consortium: past and future perspectives on mouse phenotyping. Mamm Genome 23, 632-640, doi:10.1007/s00335-012-9427-x (2012).

4 Diehl, P., Tedesco, D. & Chenchik, A. Use of RNAi screens to uncover resistance mechanisms in cancer cells and identify synthetic lethal interactions. Drug Discov Today Technol 11, 11-18, doi:10.1016/j.ddtec.2013.12.002 (2014).

Lee, C. Y. et al. Neuregulin autocrine signaling promotes self-renewal of breast tumor-initiating cells by triggering HER2/HER3 activation. *Cancer Res* 74, 341-352, doi:10.1158/0008-5472.CAN-13-1055 (2014).

6 Nolan-Stevaux, O. et al. Measurement of Cancer Cell Growth Heterogeneity through Lentiviral Barcoding Identifies Clonal Dominance as a Characteristic of Tumor Engraftment. PloS one 8, e67316, doi:10.1371/journal.pone.0067316 (2013).

7 Cancer Genome Atlas Research, N. et al. The Cancer Genome Atlas Pan-Cancer analysis project. Nat Genet 45, 1113-1120, doi:10.1038/ng.2764 (2013).

8 Broude, E. V. et al. Expression of CDK8 and CDK8-interacting Genes as Potential Biomarkers in Breast Cancer. Current cancer drug targets 15, 739-749 (2015).

9 Porter, D. C. et al. Cyclin-dependent kinase 8 mediates chemotherapy-induced tumor-promoting paracrine activities. Proc Natl Acad Sci USA 109, 13799-13804, doi:10.1073/pnas.1206906109 (2012).

Galbraith, M. D., Donner, A. J. & Espinosa, J. M. CDK8: a positive regulator of transcription. Transcription 1, 4-12, doi:10.4161/trns.1.1.12373 (2010).

11 Robertson, F. M. et al. Inflammatory breast cancer: the disease, the biology, the treatment. CA Cancer J Clin 60, 351-375, doi:10.3322/caac.20082 (2010).

12 Al-Hajj, M., Wicha, M. S., Benito-Hernandez, A., Morrison, S. J. & Clarke, M. F. Prospective identification of tumorigenic breast cancer cells. Proc Natl Acad Sci USA 100, 3983-3988, doi:10.1073/pnas.0530291100 (2003).

13 Lim, E. et al. Aberrant luminal progenitors as the candidate target population for basal tumor development in BRCA1 mutation carriers. Nature medicine 15, 907-913, doi:10.1038/nm.2000 (2009).

14 Prat, A. et al. Characterization of cell lines derived from breast cancers and normal mammary tissues for the study of the intrinsic molecular subtypes. Breast cancer research and treatment 142, 237-255, doi:10.1007/s10549-013-2743-3 (2013).

15 Scheeren, F. A. et al. A cell-intrinsic role for TLR2-MYD88 in intestinal and breast epithelia and oncogenesis. Nature cell biology 16, 1238-1248, doi:10.1038/ncb3058 (2014).

16 Bachelard-Cascales, E. et al. The CD10 enzyme is a key player to identify and regulate human mammary stem cells. Stem cells 28, 1081-1088, doi:10.1002/stem.435 (2010).

17 Hu, Y. & Smyth, G. K. ELDA: extreme limiting dilution analysis for comparing depleted and enriched populations in stem cell and other assays. Journal of immunological methods 347, 70-78, doi:10.1016/j.jim.2009.06.008 (2009).

18 Sato, S. et al. A set of consensus mammalian mediator subunits identified by multidimensional protein identification technology. Molecular cell 14, 685-691, doi:10.1016/j.molcel.2004.05.006 (2004).

19 Firestein, R. et al. CDK8 is a colorectal cancer oncogene that regulates beta-catenin activity. Nature 455, 547-551, doi:10.1038/nature07179 (2008).
20 Pelish, H. E. et al. Mediator kinase inhibition further activates super-enhancer-associated genes in AML. Nature 526, 273-276, doi:10.1038/nature14904 (2015).
21 Kapoor, A. et al. The histone variant macroH2A suppresses melanoma progression through regulation of CDK8. Nature 468, 1105-1109, doi:10.1038/nature09590 (2010).
22 Galbraith, M. D. et al. HIF1A employs CDK8-mediator to stimulate RNAPII elongation in response to hypoxia. Cell 153, 1327-1339, doi:10.1016/j.cell.2013.04.048 (2013).
23 Subramanian, A. et al. Gene set enrichment analysis: a knowledge-based approach for interpreting genome-wide expression profiles. Proc Natl Acad Sci USA 102, 15545-15550, doi:10.1073/pnas.0506580102 (2005).
24 Liberzon, A. et al. The Molecular Signatures Database (MSigDB) hallmark gene set collection. Cell systems 1, 417-425, doi:10.1016/j.cels.2015.12.004 (2015).
25 Kalimutho, M. et al. Targeted Therapies for Triple-Negative Breast Cancer: Combating a Stubborn Disease. Trends in pharmacological sciences 36, 822-846, doi:10.1016/j.tips.2015.08.009 (2015).
26 Chen, M. et al. CDK8/19 Mediator kinases potentiate induction of transcription by NFkappaB. Proc Natl Acad Sci USA, doi:10.1073/pnas.1710467114 (2017).
27 Audetat, K. A. et al. A Kinase-Independent Role for Cyclin-Dependent Kinase 19 in p53 Response. Molecular and cellular biology 37, doi:10.1128/MCB.00626-16 (2017).
28 Melotte, V. et al. The N-myc downstream regulated gene (NDRG) family: diverse functions, multiple applications. FASEB J 24, 4153-4166, doi:10.1096/fj.09-151464 (2010).
29 Zarnegar, M. A., Reinitz, F., Newman, A. M., Clarke, M. F. Targeted chromatin ligation, a robust epigenetic profiling technique for small cell numbers. Nucleic Acids Research, doi:10.1093/nar/gkx648 (2017).
30 Bae, D. H. et al. The role of NDRG1 in the pathology and potential treatment of human cancers. J Clin Pathol 66, 911-917, doi:10.1136/jclinpath-2013-201692 (2013).
31 Brown, J. D. et al. NF-kappaB directs dynamic super enhancer formation in inflammation and atherogenesis. Molecular cell 56, 219-231, doi:10.1016/j.molcel.2014.08.024 (2014).
32 Nabet, B. et al. Deregulation of the Ras-Erk Signaling Axis Modulates the Enhancer Landscape. Cell Rep 12, 1300-1313, doi:10.1016/j.celrep.2015.06.078 (2015).
33 Tripathi, S. et al. Meta- and Orthogonal Integration of Influenza "OMICs" Data Defines a Role for UBR4 in Virus Budding. Cell host & microbe 18, 723-735, doi:10.1016/j.chom.2015.11.002 (2015).
34 Mallinger, A. et al. Discovery of Potent, Selective, and Orally Bioavailable Small-Molecule Modulators of the Mediator Complex-Associated Kinases CDK8 and CDK19. Journal of medicinal chemistry 59, 1078-1101, doi:10.1021/acs.jmedchem.5b01685 (2016).
35 Poss, Z. C. et al. Identification of Mediator Kinase Substrates in Human Cells using Cortistatin A and Quantitative Phosphoproteomics. Cell Rep 15, 436-450, doi:10.1016/j.celrep.2016.03.030 (2016).
36 Bolden, J. E. et al. Inducible in vivo silencing of Brd4 identifies potential toxicities of sustained BET protein inhibition. Cell Rep 8, 1919-1929, doi:10.1016/j.celrep.2014.08.025 (2014).
37 Takebe, N. et al. Targeting Notch, Hedgehog, and Wnt pathways in cancer stem cells: clinical update. Nat Rev Clin Oncol 12, 445-464, doi:10.1038/nrclinonc.2015.61 (2015).
38 Westerling, T., Kuuluvainen, E. & Makela, T. P. Cdk8 is essential for preimplantation mouse development. Molecular and cellular biology 27, 6177-6182, doi:10.1128/MCB.01302-06 (2007).
39 Houzelstein, D. et al. Growth and early postimplantation defects in mice deficient for the bromodomain-containing protein Brd4. Molecular and cellular biology 22, 3794-3802 (2002).
40 Schindelin, J. et al. Fiji: an open-source platform for biological-image analysis. Nat Methods 9, 676-682, doi:10.1038/nmeth.2019 (2012).
41 Gao, J. et al. Integrative analysis of complex cancer genomics and clinical profiles using the cBioPortal. Sci Signal 6, pl1, doi:10.1126/scisignal.2004088 (2013).

While the foregoing invention has been described in some detail for purposes of clarity and understanding, it will be appreciated by those skilled in the relevant arts, once they have been made familiar with this disclosure, that various changes in form and detail can be made without departing from the true scope of the invention in the appended claims. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect, or import of the methods described.

All publications and patent documents cited herein are incorporated herein by reference as if each such publication or document was specifically and individually indicated to be incorporated herein by reference. Citation of publications and patent documents (patents, published patent applications, and unpublished patent applications) is not intended as an admission that any such document is pertinent prior art, nor does it constitute any admission as to the contents or date of the same.

```
CDK19 Transcript Variant 1 (NM_015076.4)
                                                  (SEQ ID NO: 12)
  1 tgtggccgcc gaggagtccc ttgctgaagg cggaccgcgg agcggcgggc ggcgggcggc

 61 gcgcgcgcgc gcgcgagagg cggctgttgg agaagtggag cggcggtcgc gggggggagga

121 ggaggaggga ctgagcggcg gcggcccccg cgtcccgtgc ctctatgggg gaagcagaca

181 atggattatg atttcaaggc gaagctggcg gcggagcggg agcgggtgga ggatttgttt

241 gagtacgaag ggtgcaaagt gggacgcggc acctacggtc acgtctacaa ggcgaggcgg

301 aaagatggaa aagatgaaaa ggaatatgca ttgaagcaaa ttgaaggcac aggaatatcc
```

-continued

```
 361 atgtcggctt gtagagagat tgcacttttg cgagaattga agcaccctaa tgtgattgca
 421 ttgcagaagg tgttcctttc tcacagtgac aggaaggtat ggctgctgtt tgattatgca
 481 gagcatgact tgtggcatat tattaagttt caccgtgcat caaaagcaaa taaaaagccc
 541 atgcagttgc caagatctat ggttaaatcc ttactttacc agattcttga tggtatccat
 601 tacctccatg caaattgggt gcttcacaga gacttgaaac cagcaaatat cctagtaatg
 661 ggagaaggtc ctgagagggg gagagtcaaa atagctgaca tgggttttgc cagattattc
 721 aattctcctc taaagccact agcagatttg gatccagtag ttgtgacatt ttggtatcgg
 781 gctccagaac ttttgcttgg tgcaaggcat tatacaaagg ccattgatat atgggcaata
 841 ggttgtatat ttgctgaatt gttgacttcg gaacctattt ttcactgtcg tcaggaagat
 901 ataaaaacaa gcaatccctt tcatcatgat caactggatc ggatatttag tgtcatgggg
 961 tttcctgcag ataaagactg ggaagatatt agaaagatgc cagaatatcc cacacttcaa
1021 aaagacttta gaagaacaac gtatgccaac agtagcctca taaagtacat ggagaaacac
1081 aaggtcaagc ctgacagcaa agtgttcctc ttgcttcaga aactcctgac catggatcca
1141 accaagagaa ttacctcgga gcaagctctg caggatccct attttcagga ggaccctttg
1201 ccaacattag atgtatttgc cggctgccag attccatacc ccaaacgaga attccttaat
1261 gaagatgatc ctgaagaaaa aggtgacaag aatcagcaac agcagcagaa ccagcatcag
1321 cagcccacag cccctccaca gcaggcagca gcccctccac aggcgccccc accacagcag
1381 aacagcaccc agaccaacgg gaccgcaggt ggggctgggg ccggggtcgg gggcaccgga
1441 gcagggttgc agcacagcca ggactccagc ctgaaccagg tgcctccaaa caagaagcca
1501 cggctagggc cttcaggcgc aaactcaggt ggacctgtga tgccctcgga ttatcagcac
1561 tccagttctc gcctgaatta ccaaagcagc gttcagggat cctctcagtc ccagagcaca
1621 cttggctact cttcctcgtc tcagcagagc tcacagtacc acccatctca ccaggcccac
1681 cggtactgac cagctcccgt tgggccaggc cagcccagcc cagagcacag gctccagcaa
1741 tatgtctgca ttgaaaagaa ccaaaaaaat gcaaactatg atgccattta aaactcatac
1801 acatgggagg aaaaccttat atactgagca ttgtgcagga ctgatagctc ttctttattg
1861 acttaaagaa gattcttgtg aagtttcccc agcacccctt ccctgcatgt gttccattgt
1921 gacttctctg ataaagcgtc tgatctaatc ccagcacttc tgtaaccttc agcatttctt
1981 tgaaggattt cctggtgcac ctttctcatg ctgtagcaat cactatggtt tatcttttca
2041 aagctctttt aataggattt taatgtttta gaaacaggat tccagtggtg tatagtttta
2101 tacttcatga actgatttag caacacaggt aaaaatgcac cttttaaagc actacgtttt
2161 cacagacaat aactgttctg ctcatggaag tcttaaacag aaactgttac tgtcccaaag
2221 tactttacta ttacgttcgt atttatctag tttcagggaa ggtctaataa aaagacaagc
2281 ggtgggacag agggaaccta caaccaaaaa ctgcctagat ctttgcagtt atgtgcttta
2341 tgccacgaag aactgaagta tgtggtaatt tttatagaat cattcatatg gaactgagtt
2401 cccagcatca tcttattctg aatagcattc agtaattaag aattacaatt ttaaccttca
2461 tgtagctaag tctaccttaa aaagggtttc aagagctttg tacagtctcg atggcccaca
2521 ccaaaacgct gaagagagta acaactgcac taggatttct gtaaggagta attttgatca
2581 aaagacgtgt tacttccctt tgaaggaaaa gtttttagtg tgtattgtac ataaagtcgg
2641 cttctctaaa gaaccattgg tttcttcaca tctgggtctg cgtgagtaac tttcttgcat
2701 aatcaaggtt actcaagtag aagcctgaaa attaatctgc ttttaaaata aagagcagtg
```

-continued

```
2761 ttctccattc gtatttgtat tagatataga gtgactattt ttaaagcatg ttaaaaattt
2821 aggttttatt catgtttaaa gtatgtatta tgtatgcata attttgctgt tgttactgaa
2881 acttaattct atcaagaatc tttttcattg cactgaatga tttcttttgc ccctaggaga
2941 aaacttaata attgtgccta aaaactatgg gcggatagta taagactata ctagacaaag
3001 tgaatatttg catttccatt atctatgaat tagtggctga gttctttctt agctgcttta
3061 aggagcccct cactccccag agtcaaaagg aaatgtaaaa acttagagct cccattgtaa
3121 tgtaaggggc aagaaatttg tgttcttctg aatgctacta gcagcaccag ccttgtttta
3181 aatgttttct tgagctagaa gaaatagctg attattgtat atgcaaatta catgcatttt
3241 taaaaactat tctttctgaa cttatctacc tggttatgat actgtgggtc catacacaag
3301 taaaataaga ttagacagaa gccagtatac attttgcact attgatgtga tactgtagcc
3361 agccaggacc ttactgatct cagcataata atgctcacta ataatgaagt ctgcatagtg
3421 acactcatca agactgaaga tgaagcaggt tacgtgctcc attggaagga gtttctgata
3481 gtctcctgct gttttacccc ttccattttt taaaataaga aattagcagc cctctgcata
3541 atgtagctgc ctatatgcag ttttatcctg tgccctaaag cctcactgtc cagagctgtt
3601 ggtcatcaga tgcttattgc accctcacca tgtgcctggt gccctgctgg gtagagaaca
3661 cagaggacag ggcatacttc ttgtccttaa ggagcttgtg atctgtgaca gtaagccctc
3721 ctgggatgtc tgtgccatgt gattgactta caagtgaaac tgtcttataa tatgaaggtc
3781 tttttgttta cttctaaacc cacttgggta gttactatcc ccaaatctgt tctgtaaata
3841 atattatgga agggtttcta tgtcagtcta ccttagagaa agccagtgat tcaatatcac
3901 aaaaggcatt gacgtatctt tgaaatgttc acagcagcct tttaacaaca actgggtggt
3961 ccttgtaggc agaacatact ctcctaagtg gttgtaggaa attgcaagga aaatagaagg
4021 tctgttcttg ctctcaagga ggttaccttt aataaaagaa gacaaaccca gatagatatg
4081 taaaccaaaa tactatgccc cttaatactt tataagcagc attgttaaat agttcttacg
4141 cttatacatt cacagaacta ccctgtttc cttgtatata atgacttttg ctggcagaac
4201 tgaaatataa actgtaaggg gatttcgtca gttgctccca gtatacaata tcctccagga
4261 catagccaga aatctccatt ccacacatga ctgagttcct atccctgcac tggtactggc
4321 tcttttctcc tctttccttg cctcagggtt cgtgctaccc actgattccc tttaccctta
4381 gtaataattt tggatcattt tctttccttt aaaggggaac aaagcctttt tttttttga
4441 gacggagtgt tgctctgtca cccaagctgg agtgcagtgg cacgatcttg gctcactcca
4501 acctccacct tccaggttca agtgattctc ctgcctcagc ctcccgagta gctgggacta
4561 cgggcacgca ccaccacgtc tggctaattt ttgtattttt agtagagatg ggtttcacc
4621 ctattggtca ggctggtctt gaattcctca cctcaggtca tccgcctgtc tcggcctccc
4681 gaagtgctgg gattataggt gtgagccacc gcacccagtt gggaacaaag cctttttaac
4741 acacgtaagg gccctcaaac cgtgggacct ctaaggagac ctttgaagct ttttgagggc
4801 aaactttacc tttgtggtcc ccaaatgatg gcatttctct ttgaaattta ttagatactg
4861 ttatgtcccc caagggtaca ggaggggcat ccctcagcct atgggaacac ccaaactagg
4921 aggggttatt gacaggaagg aatgaatcca agtgaaggct ttctgctctt cgtgttacaa
4981 accagtttca gagttagctt tctggggagg tgtgtgtttg tgaaaggaat tcaagtgttg
5041 caggacagat gagctcaagg taaggtagct ttggcagcag ggctgatact atgaggctga
5101 aacaatcctt gtgatgaagt agatcatgca gtgacataca aagaccaagg attatgtata
5161 tttttatatc tctgtggttt tgaaacttta gtacttagaa ttttggcctt ctgcactact
```

-continued

```
5221 cttttgctct tacgaacata atggactctt aagaatggaa agggatgaca tttacctatg
5281 tgtgctgcct cattcctggt gaagcaactg ctacttgttc tctatgcctc taaaatgatg
5341 ctgttttctc tgctaaaggt aaaagaaaag aaaaaaatag ttggaaaata agacatgcaa
5401 cttgatgtgc ttttgagtaa atttatgcag cagaaactat acaatgaagg aagaattcta
5461 tggaaattac aaatccaaaa ctctatgatg atgtcttcct agggagtaga gaaaggcagt
5521 gaaatggcag ttagaccaac agaggcttga aggattcaag tacaagtaat attttgtata
5581 aaacatagca gtttaggtcc ccataatcct caaaaatagt cacaaatata acaaagttca
5641 ttgttttagg gtttttaaaa aacgtgttgt acctaaggcc atacttactc ttctatgcta
5701 tcactgcaaa ggggtgatat gtatgtatta tataaaaaaa aaaaccctta atgcactgtt
5761 atctcctaaa tatttagtaa attaatacta tttaattttt ttaaagattt gtctgtgtag
5821 acactaaaag tattacacaa aatctggact gaaggtgtcc tttttaacaa caatttaaag
5881 tactttttat atatgttatg tagtatatcc tttctaaact gcctagtttg tatattccta
5941 taattcctat ttgtgaagtg tacctgttct tgtctctttt ttcagtcatt ttctgcacgc
6001 atccccccttt atatggttat agagatgact gtagcttttc gtgctccact gcgaggtttg
6061 tgctcagagc cgctgcaccc cagcgaggcc tgctccatgg agtgcaggac gagctactgc
6121 tttggagcga gggtttcctg cttttgagtt gacctgactt ccttcttgaa atgactgtta
6181 aaactaaaat aaattacatt gcatttattt tatattcttg gttgaaataa aatttaattg
6241 actttg
```

CDK19 Transcript Variant 2 (NM_001300960.1)

(SEQ ID NO: 13)

```
   1 tgtggccgcc gaggagtccc ttgctgaagg cggaccgcgg agcggcgggc ggcgggcggc
  61 gcgcgcgcgc gcgcgagagg cggctgttgg agaagtggag cggcggtcgc ggggggagga
 121 ggaggaggga ctgagcggcg gcggcccccg cgtcccgtgc ctctatgggg gaagcagaca
 181 atggattatg atttcaaggc gaagctggcg gcggagcggg agcgggtgga ggatttgttt
 241 gagtacgaag ggtgcaaagt gggacgcggc acctacggtc acgtctacaa ggcgaggcgg
 301 aaagatggaa aagatgaaaa ggaatatgca ttgaagcaaa ttgaaggcac aggaatatcc
 361 atgtcggctt gtagagagat tgcactttg cgagaattga agcaccctaa tgtgattgca
 421 ttgcagaagg tgttcctttc tcacagtgac aggaaggtat ggctgctgtt tgattatgca
 481 gagcatgact tgtggcatat tattaagttt caccgtgcat caaaagcaaa taaaaagccc
 541 atgcagttgc caagatctat ggttaaatcc ttactttacc agattcttga tggtatccat
 601 tacctccatg caaattgggt gcttcacaga gacttgaaac cagcaaatat cctagtaatg
 661 ggagaaggtc ctgagagggg gagagtcaaa atagatatat gggcaatagg ttgtatattt
 721 gctgaattgt tgacttcgga acctattttt cactgtcgtc aggaagatat aaaaacaagc
 781 aatccctttc atcatgatca actggatcgg atatttagtg tcatggggtt tcctgcagat
 841 aaagactggg aagatattag aaagatgcca gaatatccca cacttcaaaa agactttaga
 901 agaacaacgt atgccaacag tagcctcata aagtacatgg agaaacacaa ggtcaagcct
 961 gacagcaaag tgttcctctt gcttcagaaa ctcctgacca tggatccaac caagagaatt
1021 acctcggagc aagctctgca ggatccctat tttcaggagg acccctttgcc aacattagat
1081 gtatttgccg gctgccagat tccatacccc aaacgagaat tccttaatga agatgatcct
1141 gaagaaaaag gtgacaagaa tcagcaacag cagcagaacc agcatcagca gcccacagcc
1201 cctccacagc aggcagcagc ccctccacag gcgcccccac cacagcagaa cagcacccag
```

-continued 1261 accaacggga ccgcaggtgg ggctggggcc ggggtcgggg gcaccggagc agggttgcag
1321 cacagccagg actccagcct gaaccaggtg cctccaaaca agaagccacg gctagggcct
1381 tcaggcgcaa actcaggtgg acctgtgatg ccctcggatt atcagcactc cagttctcgc
1441 ctgaattacc aaagcagcgt tcagggatcc tctcagtccc agagcacact tggctactct
1501 tcctcgtctc agcagagctc acagtaccac ccatctcacc aggcccaccg gtactgacca
1561 gctcccgttg ggccaggcca gcccagccca gagcacaggc tccagcaata tgtctgcatt
1621 gaaaagaacc aaaaaaatgc aaactatgat gccatttaaa actcatacac atgggaggaa
1681 aaccttatat actgagcatt gtgcaggact gatagctctt ctttattgac ttaaagaaga
1741 ttcttgtgaa gtttccccag caccccttcc ctgcatgtgt tccattgtga cttctctgat
1801 aaagcgtctg atctaatccc agcacttctg taaccttcag catttctttg aaggatttcc
1861 tggtgcacct ttctcatgct gtagcaatca ctatggttta tcttttcaaa gctcttttaa
1921 taggatttta atgttttaga aacaggattc cagtggtgta tagttttata cttcatgaac
1981 tgatttagca acacaggtaa aaatgcacct tttaaagcac tacgttttca cagacaataa
2041 ctgttctgct catggaagtc ttaaacagaa actgttactg tcccaaagta ctttactatt
2101 acgttcgtat ttatctagtt tcagggaagg tctaataaaa agacaagcgg tgggacagag
2161 ggaacctaca accaaaaact gcctagatct ttgcagttat gtgctttatg ccacgaagaa
2221 ctgaagtatg tggtaatttt tatagaatca ttcatatgga actgagttcc cagcatcatc
2281 ttattctgaa tagcattcag taattaagaa ttacaatttt aaccttcatg tagctaagtc
2341 taccttaaaa agggtttcaa gagctttgta cagtctcgat ggcccacacc aaaacgctga
2401 agagagtaac aactgcacta ggatttctgt aaggagtaat tttgatcaaa agacgtgtta
2461 cttccctttg aaggaaaagt ttttagtgtg tattgtacat aaagtcggct tctctaaaga
2521 accattggtt tcttcacatc tgggtctgcg tgagtaactt tcttgcataa tcaaggttac
2581 tcaagtagaa gcctgaaaat taatctgctt ttaaaataaa gagcagtgtt ctccattcgt
2641 atttgtatta gatatagagt gactattttt aaagcatgtt aaaaatttag gttttattca
2701 tgtttaaagt atgtattatg tatgcataat tttgctgttg ttactgaaac ttaattctat
2761 caagaatctt tttcattgca ctgaatgatt tcttttgccc ctaggagaaa acttaataat
2821 tgtgcctaaa aactatgggc ggatagtata agactatact agacaaagtg aatatttgca
2881 tttccattat ctatgaatta gtggctgagt tctttcttag ctgctttaag gagcccctca
2941 ctccccagag tcaaaaggaa atgtaaaaac ttagagctcc cattgtaatg taagggggcaa
3001 gaaatttgtg ttcttctgaa tgctactagc agcaccagcc ttgttttaaa tgtttttcttg
3061 agctagaaga aatagctgat tattgtatat gcaaattaca tgcattttta aaaactattc
3121 tttctgaact tatctacctg gttatgatac tgtgggtcca tacacaagta aaataagatt
3181 agacagaagc cagtatacat tttgcactat tgatgtgata ctgtagccag ccaggacctt
3241 actgatctca gcataataat gctcactaat aatgaagtct gcatagtgac actcatcaag
3301 actgaagatg aagcaggtta cgtgctccat tggaaggagt ttctgatagt ctcctgctgt
3361 tttacccctt ccatttttta aaataagaaa ttagcagccc tctgcataat gtagctgcct
3421 atatgcagtt ttatcctgtg ccctaaagcc tcactgtcca gagctgttgg tcatcagatg
3481 cttattgcac cctcaccatg tgcctggtgc cctgctgggt agagaacaca gaggacaggg
3541 catacttctt gtccttaagg agcttgtgat ctgtgacagt aagccctcct gggatgtctg
3601 tgccatgtga ttgacttaca agtgaaactg tcttataata tgaaggtctt tttgtttact
3661 tctaaaccca cttgggtagt tactatcccc aaatctgttc tgtaaataat attatggaag -continued

```
3721 ggtttctatg tcagtctacc ttagagaaag ccagtgattc aatatcacaa aaggcattga
3781 cgtatctttg aaatgttcac agcagccttt taacaacaac tgggtggtcc ttgtaggcag
3841 aacatactct cctaagtggt tgtaggaaat tgcaaggaaa atagaaggtc tgttcttgct
3901 ctcaaggagg ttacctttaa taaaagaaga caaacccaga tagatatgta aaccaaaata
3961 ctatgcccct taatacttta taagcagcat tgttaaatag ttcttacgct tatacattca
4021 cagaactacc ctgttttcct tgtatataat gacttttgct ggcagaactg aaatataaac
4081 tgtaagggga tttcgtcagt tgctcccagt atacaatatc ctccaggaca tagccagaaa
4141 tctccattcc acacatgact gagttcctat ccctgcactg gtactggctc ttttctcctc
4201 tttccttgcc tcagggttcg tgctacccac tgattccctt tacccttagt aataattttg
4261 gatcattttc tttcctttaa aggggaacaa agcctttttt ttttttgaga cggagtgttg
4321 ctctgtcacc caagctggag tgcagtggca cgatcttggc tcactccaac ctccaccttc
4381 caggttcaag tgattctcct gcctcagcct cccgagtagc tgggactacg ggcacgcacc
4441 accacgtctg gctaattttt gtatttttag tagagatggg gtttcaccct attggtcagg
4501 ctggtcttga attcctcacc tcaggtcatc cgcctgtctc ggcctcccga agtgctggga
4561 ttataggtgt gagccaccgc acccagttgg gaacaaagcc tttttaacac acgtaagggc
4621 cctcaaaccg tgggacctct aaggagacct ttgaagcttt ttgagggcaa actttacctt
4681 tgtggtcccc aaatgatggc atttctcttt gaaatttatt agatactgtt atgtccccca
4741 agggtacagg aggggcatcc ctcagcctat gggaacaccc aaactaggag gggttattga
4801 caggaaggaa tgaatccaag tgaaggcttt ctgctcttcg tgttacaaac cagtttcaga
4861 gttagctttc tggggaggtg tgtgtttgtg aaaggaattc aagtgttgca ggacagatga
4921 gctcaaggta aggtagcttt ggcagcaggg ctgatactat gaggctgaaa caatccttgt
4981 gatgaagtag atcatgcagt gacatacaaa gaccaaggat tatgtatatt tttatatctc
5041 tgtggttttg aaactttagt acttagaatt ttggccttct gcactactct tttgctctta
5101 cgaacataat ggactcttaa gaatggaaag ggatgacatt tacctatgtg tgctgcctca
5161 ttcctggtga agcaactgct acttgttctc tatgcctcta aaatgatgct gttttctctg
5221 ctaaaggtaa aagaaaagaa aaaaatagtt ggaaaataag acatgcaact tgatgtgctt
5281 ttgagtaaat ttatgcagca gaaactatac aatgaaggaa gaattctatg gaaattacaa
5341 atccaaaact ctatgatgat gtcttcctag ggagtagaga aaggcagtga aatggcagtt
5401 agaccaacag aggcttgaag gattcaagta caagtaatat tttgtataaa acatagcagt
5461 ttaggtcccc ataatcctca aaaatagtca caaatataac aaagttcatt gttttagggt
5521 ttttaaaaaa cgtgttgtac ctaaggccat acttactctt ctatgctatc actgcaaagg
5581 ggtgatatgt atgtattata taaaaaaaaa aacccttaat gcactgttat ctcctaaata
5641 tttagtaaat taatactatt taattttttt aaagatttgt ctgtgtagac actaaaagta
5701 ttacacaaaa tctggactga aggtgtcctt tttaacaaca atttaaagta ctttttatat
5761 atgttatgta gtatatcctt tctaaactgc ctagtttgta tattcctata attcctattt
5821 gtgaagtgta cctgttcttg tctctttttt cagtcatttt ctgcacgcat ccccctttat
5881 atggttatag agatgactgt agcttttcgt gctccactgc gaggtttgtg ctcagagccg
5941 ctgcacccca gcgaggcctg ctccatggag tgcaggacga gctactgctt tggagcgagg
6001 gtttcctgct tttgagttga cctgacttcc ttcttgaaat gactgttaaa actaaaataa
6061 attacattgc atttatttta tattcttggt tgaaataaaa tttaattgac tttg
```

-continued

CDK19 Transcript Variant 3 (NM_001300963.1)

(SEQ ID NO: 14)

```
   1 gaggggcggc cctggtacgc aggcgcgcat gctttgtggg ggcgaggctg tggtggcccg
  61 agattccagg agggcttcgt gtatggacct caagcgttgg aggtagcaga cttttcagca
 121 gaagaaaaga tgaaaaggaa tatgcattga agcaaattga aggcacagga atatccatgt
 181 cggcttgtag agagattgca cttttgcgag aattgaagca ccctaatgtg attgcattgc
 241 agaaggtgtt cctttctcac agtgacagga aggtatggct gctgtttgat tatgcagagc
 301 atgacttgtg gcatattatt aagtttcacc gtgcatcaaa agcaaataaa aagcccatgc
 361 agttgccaag atctatggtt aaatccttac tttaccagat tcttgatggt atccattacc
 421 tccatgcaaa ttgggtgctt cacagagact tgaaaccagc aaatatccta gtaatgggag
 481 aaggtcctga gagggggaga gtcaaaatag ctgacatggg ttttgccaga ttattcaatt
 541 ctcctctaaa gccactagca gatttggatc cagtagttgt gacattttgg tatcgggctc
 601 cagaactttt gcttggtgca aggcattata caaaggccat tgatatatgg gcaataggtt
 661 gtatatttgc tgaattgttg acttcggaac ctatttttca ctgtcgtcag gaagatataa
 721 aaacaagcaa tccctttcat catgatcaac tggatcggat atttagtgtc atggggtttc
 781 ctgcagataa agactgggaa gatattagaa agatgccaga atatcccaca cttcaaaaag
 841 actttagaag aacaacgtat gccaacagta gcctcataaa gtacatggag aaacacaagg
 901 tcaagcctga cagcaaagtg ttcctcttgc ttcagaaact cctgaccatg gatccaacca
 961 agagaattac ctcggagcaa gctctgcagg atccctattt tcaggaggac cctttgccaa
1021 cattagatgt atttgccggc tgccagattc cataccccaa acgagaattc cttaatgaag
1081 atgatcctga agaaaaaggt gacaagaatc agcaacagca gcagaaccag catcagcagc
1141 ccacagcccc tccacagcag gcagcagccc ctccacaggc gcccccacca cagcagaaca
1201 gcacccagac caacgggacc gcaggtgggg ctggggccgg ggtcgggggc accggagcag
1261 ggttgcagca cagccaggac tccagcctga accaggtgcc tccaaacaag aagccacggc
1321 tagggccttc aggcgcaaac tcaggtggac ctgtgatgcc ctcggattat cagcactcca
1381 gttctcgcct gaattaccaa agcagcgttc agggatcctc tcagtcccag agcacacttg
1441 gctactcttc ctcgtctcag cagagctcac agtaccaccc atctcaccag gcccaccggt
1501 actgaccagc tcccgttggg ccaggccagc ccagcccaga gcacaggctc cagcaatatg
1561 tctgcattga aaagaaccaa aaaaatgcaa actatgatgc catttaaaac tcatacacat
1621 gggaggaaaa ccttatatac tgagcattgt gcaggactga tagctcttct ttattgactt
1681 aaagaagatt cttgtgaagt ttccccagca ccccttccct gcatgtgttc cattgtgact
1741 tctctgataa agcgtctgat ctaatcccag cacttctgta accttcagca tttctttgaa
1801 ggatttcctg gtgcaccttt ctcatgctgt agcaatcact atggtttatc ttttcaaagc
1861 tcttttaata ggattttaat gttttagaaa caggattcca gtggtgtata gttttatact
1921 tcatgaactg atttagcaac acaggtaaaa atgcaccttt taaagcacta cgttttcaca
1981 gacaataact gttctgctca tggaagtctt aaacagaaac tgttactgtc ccaaagtact
2041 ttactattac gttcgtattt atctagtttc agggaaggtc taataaaaag acaagcggtg
2101 ggacagaggg aacctacaac caaaaactgc ctagatcttt gcagttatgt gctttatgcc
2161 acgaagaact gaagtatgtg gtaattttta tagaatcatt catatggaac tgagttccca
2221 gcatcatctt attctgaata gcattcagta attaagaatt acaattttaa ccttcatgta
2281 gctaagtcta ccttaaaaag ggtttcaaga gctttgtaca gtctcgatgg cccacaccaa
2341 aacgctgaag agagtaacaa ctgcactagg atttctgtaa ggagtaattt tgatcaaaag
```

-continued

```
2401 acgtgttact tccctttgaa ggaaaagttt ttagtgtgta ttgtacataa agtcggcttc
2461 tctaaagaac cattggtttc ttcacatctg ggtctgcgtg agtaactttc ttgcataatc
2521 aaggttactc aagtagaagc ctgaaaatta atctgctttt aaaataaaga gcagtgttct
2581 ccattcgtat ttgtattaga tatagagtga ctatttttaa agcatgttaa aaatttaggt
2641 tttattcatg tttaaagtat gtattatgta tgcataattt tgctgttgtt actgaaactt
2701 aattctatca agaatctttt tcattgcact gaatgatttc ttttgcccct aggagaaaac
2761 ttaataattg tgcctaaaaa ctatgggcgg atagtataag actatactag acaaagtgaa
2821 tatttgcatt tccattatct atgaattagt ggctgagttc tttcttagct gctttaagga
2881 gcccctcact ccccagagtc aaaaggaaat gtaaaaactt agagctccca ttgtaatgta
2941 aggggcaaga aatttgtgtt cttctgaatg ctactagcag caccagcctt gttttaaatg
3001 ttttcttgag ctagaagaaa tagctgatta ttgtatatgc aaattacatg catttttaaa
3061 aactattctt tctgaactta tctacctggt tatgatactg tgggtccata cacaagtaaa
3121 ataagattag acagaagcca gtatacattt tgcactattg atgtgatact gtagccagcc
3181 aggaccttac tgatctcagc ataataatgc tcactaataa tgaagtctgc atagtgacac
3241 tcatcaagac tgaagatgaa gcaggttacg tgctccattg gaaggagttt ctgatagtct
3301 cctgctgttt taccccttcc atttttaaa ataagaaatt agcagccctc tgcataatgt
3361 agctgcctat atgcagtttt atcctgtgcc ctaaagcctc actgtccaga gctgttggtc
3421 atcagatgct tattgcaccc tcaccatgtg cctggtgccc tgctgggtag agaacacaga
3481 ggacagggca tacttcttgt ccttaaggag cttgtgatct gtgacagtaa gccctcctgg
3541 gatgtctgtg ccatgtgatt gacttacaag tgaaactgtc ttataatatg aaggtctttt
3601 tgtttacttc taaacccact tgggtagtta ctatccccaa atctgttctg taaataatat
3661 tatggaaggg tttctatgtc agtctacctt agagaaagcc agtgattcaa tatcacaaaa
3721 ggcattgacg tatctttgaa atgttcacag cagcctttta acaacaactg ggtggtcctt
3781 gtaggcagaa catactctcc taagtggttg taggaaattg caaggaaaat agaaggtctg
3841 ttcttgctct caaggaggtt acctttaata aaagaagaca aacccagata gatatgtaaa
3901 ccaaaatact atgcccctta atactttata agcagcattg ttaaatagtt cttacgctta
3961 tacattcaca gaactaccct gttttccttg tatataatga cttttgctgg cagaactgaa
4021 atataaactg taaggggatt tcgtcagttg ctcccagtat acaatatcct ccaggacata
4081 gccagaaatc tccattccac acatgactga gttcctatcc ctgcactggt actggctctt
4141 ttctcctctt tccttgcctc agggttcgtg ctacccactg attcccttta cccttagtaa
4201 taattttgga tcattttctt tcctttaaag gggaacaaag cctttttttt ttttgagacg
4261 gagtgttgct ctgtcaccca agctggagtg cagtggcacg atcttggctc actccaacct
4321 ccaccttcca ggttcaagtg attctcctgc ctcagcctcc cgagtagctg ggactacggg
4381 cacgcaccac cacgtctggc taatttttgt atttttagta gagatggggt ttcaccctat
4441 tggtcaggct ggtcttgaat tcctcacctc aggtcatccg cctgtctcgg cctcccgaag
4501 tgctgggatt ataggtgtga gccaccgcac ccagttggga acaaagcctt tttaacacac
4561 gtaagggccc tcaaaccgtg ggacctctaa ggagaccttt gaagcttttt gagggcaaac
4621 tttacctttg tggtccccaa atgatggcat ttctctttga aatttattag atactgttat
4681 gtcccccaag ggtacaggag gggcatccct cagcctatgg gaacacccaa actaggaggg
4741 gttattgaca ggaaggaatg aatccaagtg aaggctttct gctcttcgtg ttacaaacca
```

-continued

```
4801 gtttcagagt tagctttctg gggaggtgtg tgtttgtgaa aggaattcaa gtgttgcagg
4861 acagatgagc tcaaggtaag gtagctttgg cagcagggct gatactatga ggctgaaaca
4921 atccttgtga tgaagtagat catgcagtga catacaaaga ccaaggatta tgtatatttt
4981 tatatctctg tggttttgaa actttagtac ttagaatttt ggccttctgc actactcttt
5041 tgctcttacg aacataatgg actcttaaga atggaaaggg atgacattta cctatgtgtg
5101 ctgcctcatt cctggtgaag caactgctac ttgttctcta tgcctctaaa atgatgctgt
5161 tttctctgct aaaggtaaaa gaaaagaaaa aaatagttgg aaaataagac atgcaacttg
5221 atgtgctttt gagtaaattt atgcagcaga aactatacaa tgaaggaaga attctatgga
5281 aattacaaat ccaaaactct atgatgatgt cttcctaggg agtagagaaa ggcagtgaaa
5341 tggcagttag accaacagag gcttgaagga ttcaagtaca agtaatattt tgtataaaac
5401 atagcagttt aggtccccat aatcctcaaa aatagtcaca aatataacaa agttcattgt
5461 tttagggttt ttaaaaaacg tgttgtacct aaggccatac ttactcttct atgctatcac
5521 tgcaaagggg tgatatgtat gtattatata aaaaaaaaaa cccttaatgc actgttatct
5581 cctaaatatt tagtaaatta atactattta atttttttaa agatttgtct gtgtagacac
5641 taaaagtatt acacaaaatc tggactgaag gtgtcctttt taacaacaat ttaaagtact
5701 ttttatatat gttatgtagt atatcctttc taaactgcct agtttgtata ttcctataat
5761 tcctatttgt gaagtgtacc tgttcttgtc tcttttttca gtcattttct gcacgcatcc
5821 ccctttatat ggttatagag atgactgtag cttttcgtgc tccactgcga ggtttgtgct
5881 cagagccgct gcaccccagc gaggcctgct ccatggagtg caggacgagc tactgctttg
5941 gagcgagggt ttcctgcttt tgagttgacc tgacttcctt cttgaaatga ctgttaaaac
6001 taaaataaat tacattgcat ttattttata ttcttggttg aaataaaatt taattgactt
6061 tg
```

CDK19 Transcript Variant 4 (NM_001300964.1)

(SEQ ID NO: 15)

```
   1 agaaaagaaa caagctgcgg tacaactgtc ctcaccagcc ctcgcctccc gagtcactgc
  61 agccaaccct tcagcaagaa aagatgaaaa ggaatatgca ttgaagcaaa ttgaaggcac
 121 aggaatatcc atgtcggctt gtagagagat tgcacttttg cgagaattga agcaccctaa
 181 tgtgattgca ttgcagaagg tgttcctttc tcacagtgac aggaaggtat ggctgctgtt
 241 tgattatgca gagcatgact tgtggcatat tattaagttt caccgtgcat caaaagcaaa
 301 taaaaagccc atgcagttgc caagatctat ggttaaatcc ttactttacc agattcttga
 361 tggtatccat tacctccatg caaattgggt gcttcacaga gacttgaaac cagcaaatat
 421 cctagtaatg ggagaaggtc ctgagagggg gagagtcaaa atagctgaca tgggttttgc
 481 cagattattc aattctcctc taaagccact agcagatttg gatccagtag ttgtgacatt
 541 ttggtatcgg gctccagaac ttttgcttgg tgcaaggcat tatacaaagg ccattgatat
 601 atgggcaata ggttgtatat ttgctgaatt gttgacttcg gaacctattt ttcactgtcg
 661 tcaggaagat ataaaaacaa gcaatccctt tcatcatgat caactggatc ggatatttag
 721 tgtcatgggg tttcctgcag ataaagactg ggaagatatt agaaagatgc cagaatatcc
 781 cacacttcaa aaagacttta gaagaacaac gtatgccaac agtagcctca taaagtacat
 841 ggagaaacac aaggtcaagc ctgacagcaa agtgttcctc ttgcttcaga aactcctgac
 901 catggatcca accaagagaa ttacctcgga gcaagctctg caggatccct attttcagga
 961 ggaccctttg ccaacattag atgtatttgc cggctgccag attccatacc ccaaacgaga
1021 attccttaat gaagatgatc ctgaagaaaa aggtgacaag aatcagcaac agcagcagaa
```

-continued 1081 ccagcatcag cagcccacag cccctccaca gcaggcagca gcccctccac aggcgccccc
1141 accacagcag aacagcaccc agaccaacgg gaccgcaggt ggggctgggg ccggggtcgg
1201 gggcaccgga gcagggttgc agcacagcca ggactccagc ctgaaccagg tgcctccaaa
1261 caagaagcca cggctagggc cttcaggcgc aaactcaggt ggacctgtga tgccctcgga
1321 ttatcagcac tccagttctc gcctgaatta ccaaagcagc gttcagggat cctctcagtc
1381 ccagagcaca cttggctact cttcctcgtc tcagcagagc tcacagtacc acccatctca
1441 ccaggcccac cggtactgac cagctcccgt tgggccaggc cagcccagcc cagagcacag
1501 gctccagcaa tatgtctgca ttgaaaagaa ccaaaaaaat gcaaactatg atgccattta
1561 aaactcatac acatgggagg aaaaccttat atactgagca ttgtgcagga ctgatagctc
1621 ttctttattg acttaaagaa gattcttgtg aagtttcccc agcacccctt ccctgcatgt
1681 gttccattgt gacttctctg ataaagcgtc tgatctaatc ccagcacttc tgtaaccttc
1741 agcatttctt tgaaggattt cctggtgcac ctttctcatg ctgtagcaat cactatggtt
1801 tatcttttca aagctctttt aataggattt taatgtttta gaaacaggat tccagtggtg
1861 tatagtttta tacttcatga actgatttag caacacaggt aaaaatgcac cttttaaagc
1921 actacgtttt cacagacaat aactgttctg ctcatggaag tcttaaacag aaactgttac
1981 tgtcccaaag tactttacta ttacgttcgt atttatctag tttcagggaa ggtctaataa
2041 aaagacaagc ggtgggacag agggaaccta caaccaaaaa ctgcctagat ctttgcagtt
2101 atgtgcttta tgccacgaag aactgaagta tgtggtaatt tttatagaat cattcatatg
2161 gaactgagtt cccagcatca tcttattctg aatagcattc agtaattaag aattacaatt
2221 ttaaccttca tgtagctaag tctaccttaa aaagggtttc aagagctttg tacagtctcg
2281 atggcccaca ccaaaacgct gaagagagta acaactgcac taggatttct gtaaggagta
2341 attttgatca aaagacgtgt tacttccctt tgaaggaaaa gtttttagtg tgtattgtac
2401 ataaagtcgg cttctctaaa gaaccattgg tttcttcaca tctgggtctg cgtgagtaac
2461 tttcttgcat aatcaaggtt actcaagtag aagcctgaaa attaatctgc ttttaaaata
2521 aagagcagtg ttctccattc gtatttgtat tagatataga gtgactattt ttaaagcatg
2581 ttaaaaattt aggttttatt catgtttaaa gtatgtatta tgtatgcata attttgctgt
2641 tgttactgaa acttaattct atcaagaatc tttttcattg cactgaatga tttcttttgc
2701 ccctaggaga aaacttaata attgtgccta aaaactatgg gcggatagta taagactata
2761 ctagacaaag tgaatatttg catttccatt atctatgaat tagtggctga gttctttctt
2821 agctgcttta aggagcccct cactccccag agtcaaaagg aaatgtaaaa acttagagct
2881 cccattgtaa tgtaaggggc aagaaatttg tgttcttctg aatgctacta gcagcaccag
2941 ccttgtttta aatgttttct tgagctagaa gaaatagctg attattgtat atgcaaatta
3001 catgcatttt taaaaactat tctttctgaa cttatctacc tggttatgat actgtgggtc
3061 catacacaag taaaataaga ttagacagaa gccagtatac attttgcact attgatgtga
3121 tactgtagcc agccaggacc ttactgatct cagcataata atgctcacta ataatgaagt
3181 ctgcatagtg acactcatca agactgaaga tgaagcaggt tacgtgctcc attggaagga
3241 gtttctgata gtctcctgct gttttacccc ttccattttt taaaataaga aattagcagc
3301 cctctgcata atgtagctgc ctatatgcag ttttatcctg tgccctaaag cctcactgtc
3361 cagagctgtt ggtcatcaga tgcttattgc accctcacca tgtgcctggt gccctgctgg
3421 gtagagaaca cagaggacag ggcatacttc ttgtccttaa ggagcttgtg atctgtgaca -continued

```
3481 gtaagccctc ctgggatgtc tgtgccatgt gattgactta caagtgaaac tgtcttataa
3541 tatgaaggtc tttttgttta cttctaaacc cacttgggta gttactatcc ccaaatctgt
3601 tctgtaaata atattatgga agggtttcta tgtcagtcta ccttagagaa agccagtgat
3661 tcaatatcac aaaaggcatt gacgtatctt tgaaatgttc acagcagcct tttaacaaca
3721 actgggtggt ccttgtaggc agaacatact ctcctaagtg gttgtaggaa attgcaagga
3781 aaatagaagg tctgttcttg ctctcaagga ggttaccttt aataaaagaa gacaaaccca
3841 gatagatatg taaaccaaaa tactatgccc cttaatactt tataagcagc attgttaaat
3901 agttcttacg cttatacatt cacagaacta ccctgttttc cttgtatata atgacttttg
3961 ctggcagaac tgaaatataa actgtaaggg gatttcgtca gttgctccca gtatacaata
4021 tcctccagga catagccaga aatctccatt ccacacatga ctgagttcct atccctgcac
4081 tggtactggc tcttttctcc tctttccttg cctcagggtt cgtgctaccc actgattccc
4141 tttaccctta gtaataattt tggatcattt tctttccttt aaaggggaac aaagcctttt
4201 ttttttttga gacggagtgt tgctctgtca cccaagctgg agtgcagtgg cacgatcttg
4261 gctcactcca acctccacct tccaggttca agtgattctc ctgcctcagc ctcccgagta
4321 gctgggacta cgggcacgca ccaccacgtc tggctaattt ttgtattttt agtagagatg
4381 gggtttcacc ctattggtca ggctggtctt gaattcctca cctcaggtca tccgcctgtc
4441 tcggcctccc gaagtgctgg gattataggt gtgagccacc gcacccagtt gggaacaaag
4501 ccttttttaac acacgtaagg gccctcaaac cgtgggacct ctaaggagac ctttgaagct
4561 ttttgagggc aaactttacc tttgtggtcc ccaaatgatg gcatttctct ttgaaattta
4621 ttagatactg ttatgtcccc caagggtaca ggaggggcat ccctcagcct atgggaacac
4681 ccaaactagg aggggttatt gacaggaagg aatgaatcca agtgaaggct ttctgctctt
4741 cgtgttacaa accagtttca gagttagctt tctggggagg tgtgtgtttg tgaaaggaat
4801 tcaagtgttg caggacagat gagctcaagg taaggtagct ttggcagcag ggctgatact
4861 atgaggctga aacaatcctt gtgatgaagt agatcatgca gtgacataca aagaccaagg
4921 attatgtata tttttatatc tctgtggttt tgaaacttta gtacttagaa ttttggcctt
4981 ctgcactact cttttgctct tacgaacata atggactctt aagaatggaa agggatgaca
5041 tttacctatg tgtgctgcct cattcctggt gaagcaactg ctacttgttc tctatgcctc
5101 taaaatgatg ctgttttctc tgctaaaggt aaaagaaaag aaaaaaatag ttggaaaata
5161 agacatgcaa cttgatgtgc ttttgagtaa atttatgcag cagaaactat acaatgaagg
5221 aagaattcta tggaaattac aaatccaaaa ctctatgatg atgtcttcct agggagtaga
5281 gaaaggcagt gaaatggcag ttagaccaac agaggcttga aggattcaag tacaagtaat
5341 attttgtata aaacatagca gtttaggtcc ccataatcct caaaaatagt cacaaatata
5401 acaaagttca ttgttttagg gtttttaaaa aacgtgttgt acctaaggcc atacttactc
5461 ttctatgcta tcactgcaaa ggggtgatat gtatgtatta tataaaaaaa aaaacccttta
5521 atgcactgtt atctcctaaa tatttagtaa attaatacta tttaattttt ttaaagattt
5581 gtctgtgtag acactaaaag tattacacaa aatctggact gaaggtgtcc tttttaacaa
5641 caatttaaag tactttttat atatgttatg tagtatatcc tttctaaact gcctagtttg
5701 tatattccta taattcctat ttgtgaagtg tacctgttct tgtctctttt ttcagtcatt
5761 ttctgcacgc atcccccttt atatggttat agagatgact gtagcttttc gtgctccact
5821 gcgaggtttg tgctcagagc cgctgcaccc cagcgaggcc tgctccatgg agtgcaggac
5881 gagctactgc tttggagcga gggtttcctg cttttgagtt gacctgactt ccttcttgaa
```

-continued 5941 atgactgtta aaactaaaat aaattacatt gcatttattt tatattcttg gttgaaataa 6001 aatttaattg actttg Cyclin dependent kinase 8 (CDK8), transcript variant 1 (NM_001260.2)
(SEQ ID NO: 16)

1 gagtgccctc cctcctcctc tctttgagga ggtaccggct gttgtgcggc tctgcccttc 61 tgtttgagtg tatgggagag tgagtgagtg agtgagtgtg agcgtgtgtg tgagagcgtg 121 aggcgtgagt gcgcgtgtga gaggacgaga gcccgcctgg ccgccccgcc gctcccgccg 181 cagcaggagc agaacgcgcg gccggagaga gcggcggagc cggcgcccag ggagcccgcg 241 gggacaaggg cagagacacc gctcccacc cccagccctc gtccctcggc tctccttcgc 301 cgggggatcc tccccgttcc tccaccccg gccggcctct gccccgccgt cccccctggat 361 gtccctggcg ctttcgcggg gcctcctcct gctcttgccg catcagtcgg gctggtgctg 421 cggccggcgg gcgtagagcg ggcgggttcc cgggggctgc ggctgcccgt gcttccccgg 481 tccccacccc tgccccccgg ccccccgacc cagctctccg gcctcagagg ctgtgacaat 541 ggactatgac tttaaagtga agctgagcag cgagcgggag cgggtcgagg acctgtttga 601 atacgagggc tgcaaagttg gccgaggcac ttatggtcac gtctacaaag ccaagaggaa 661 agatgggaag gatgataaag actatgcttt aaaacaaata gaaggaactg ggatctctat 721 gtcggcatgt agagaaatag cattacttcg agagcttaag catccaaacg tcatttctct 781 tcaaaaggtg tttctgtctc atgctgatag gaaggtgtgg cttctgtttg actatgctga 841 acatgacctc tggcatataa tcaagtttca cagagcttct aaagcaaaca agaagccagt 901 tcagttacct cggggaatgg tgaagtcact attatatcag atcctagatg gtattcacta 961 cctgcatgct aactgggtgt tgcacagaga tttgaaacct gctaatattt tagttatggg 1021 tgaaggtcct gagcgaggaa gagtaaaaat tgctgacatg ggctttgccc gattatttaa 1081 ttcacctttg aagcctttag cagatttgga tccagtggtt gttacattct ggtaccgagc 1141 ccctgaacta cttcttggag caaggcatta taccaaagct attgatattt gggctatagg 1201 gtgtatattt gcagaactac taacgtcaga accaatattt cactgtcgac aagaggacat 1261 caaaactagt aatccttatc accatgacca gctggacaga atattcaatg taatgggatt 1321 tcctgcagat aaagattggg aagatataaa aaagatgcct gaacattcaa cattaatgaa 1381 agatttcaga agaaatacgt ataccaactg cagccttatc aagtatatgg aaaaacataa 1441 agttaaacca gatagtaaag cattccactt gcttcagaag ctgcttacca tggacccaat 1501 aaagcgaatt acctcagaac aggctatgca ggacccctat ttcttagaag acccacttcc 1561 tacatcagac gtttttgccg gttgtcaaat ccccttaccca aaacgagaat ttttaacgga 1621 agaagaacct gatgacaaag gagacaaaaa gaaccagcag cagcagcagg gcaataacca 1681 cactaatgga actggccacc cagggaatca agacagcagt cacacacagg gacccccgtt 1741 gaagaaagtg agagttgttc ctcctaccac tacctcaggt ggacttatca tgacctcaga 1801 ctatcagcgt tccaatccac atgctgccta tcccaaccct ggaccaagca catcacagcc 1861 gcagagcagc atgggatact cagctacctc ccagcagcct ccacagtact cacatcagac 1921 acatcggtac tgagctgcat cggaatcttg tccatgcact gttgcgaatg ctgcagggct 1981 gactgtgcag ctctctgcgg gaacctggta tgggccatga gaatgtactg tacaaccaca 2041 tcttcaaaat gtccagtagc caagttccac cacttttcac agattggggt agtggcttcc 2101 aagttgtacc tattttggag ttagacttga aaagaaagtg ctagcacagt ttgtgttgtg 2161 gatttgctac ttccatagtt tacttgacat ggttcagact gaccaatgca tttttttcag -continued

```
2221 tgacagtctg tagcagttga agctgtgaat gtgctagggg caagcatttg tctttgtatg
2281 tggtgaattt tttcagtgta acaacattat ctgaccaata gtacacacac agacacaaag
2341 tttaactggt acttgaaaca tacagtatat gttaacgaaa taaccaagac tcgaaatgag
2401 attattttgg tacacctttc tttttagtgt cttatcagtg ggctgattca ttttctacat
2461 taatcagtgt tttctgacca agaatattgc ttggattttt ttgaaagtac aaaaagccac
2521 atagtttttc cagaaaggtt tcaaaactcc caaagattaa cttccaactt ataagtttgt
2581 ttttattttc aatctatgac ttgactggta ttaaagctgc tatttgatag taattaaata
2641 tgttgtcatt gatataaacc tgtttggttc agcaaacaaa ctaaaatgat tgtcatagac
2701 agtgttttat ttttcctgtt ggtgttgctg atttgtgagc atgctttaag atgaaaaaag
2761 catgaatgat aacttcctta aaaggtgcg gcatccaatt caaatatttt cgtcctgatt
2821 ttaaagctgg ttggtgtagt gctattaaaa tttcgttcag ttaattttcc ttttgaaaac
2881 ttgttcgcac gttgtttagg gtgcccttac ttcagcaaag gagaaggagt aggagagcct
2941 tagaattttt gaggaaaaaa aaacctataa catacaatgt actgtatcaa actattttac
3001 atgaatgaca caagtattct gaataaaaaa taattgaaca ttgttaaaaa caaggtgtta
3061 tgtaataaat ttatttttca taaatcaaaa aaaaaaaaaa a
```

Cyclin dependent kinase 8 (CDK8), transcript variant 2 (NM_001318368.1)
(SEQ ID NO: 17)

```
   1 gagtgccctc cctcctcctc tctttgagga ggtaccggct gttgtgcggc tctgcccttc
  61 tgtttgagtg tatgggagag tgagtgagtg agtgagtgtg agcgtgtgtg tgagagcgtg
 121 aggcgtgagt gcgcgtgtga gaggacgaga gcccgcctgg ccgccccgcc gctcccgccg
 181 cagcaggagc agaacgcgcg gccggagaga gcggcggagc cggcgcccag ggagcccgcg
 241 gggacaaggg cagagacacc gctccccacc cccagccctc gtccctcggc tctccttcgc
 301 cgggggatcc tccccgttcc tccaccccccg gccggcctct gccccgccgt ccccctggat
 361 gtccctggcg ctttcgcggg gcctcctcct gctcttgccg catcagtcgg gctggtgctg
 421 cggccggcgg gcgtagagcg ggcgggttcc cgggggctgc ggctgcccgt gcttccccgg
 481 tccccacccc tgccccccgg ccccccgacc cagctctccg gcctcagagg ctgtgacaat
 541 ggactatgac tttaaagtga agctgagcag cgagcgggag cgggtcgagg acctgtttga
 601 atacgagggc tgcaaagttg gccgaggcac ttatggtcac gtctacaaag ccaagaggaa
 661 agatgggaag gatgataaag actatgcttt aaaacaaata gaaggaactg ggatctctat
 721 gtcggcatgt agagaaatag cattacttcg agagcttaag catccaaacg tcatttctct
 781 tcaaaaggtg tttctgtctc atgctgatag gaaggtgtgg cttctgtttg actatgctga
 841 acatgacctc tggcatataa tcaagtttca cagagcttct aaagcaaaca agaagccagt
 901 tcagttacct cggggaatgg tgaagtcact attatatcag atcctagatg gtattcacta
 961 cctgcatgct aactgggtgt tgcacagaga tttgaaacct gctaatattt tagttatggg
1021 tgaaggtcct gagcgaggaa gagtaaaaat tgctgacatg ggctttgccc gattatttaa
1081 ttcacctttg aagcctttag cagatttgga tccagtggtt gttacattct ggtaccgagc
1141 ccctgaacta cttcttggag caaggcatta taccaaagct attgatattt gggctatagg
1201 gtgtatattt gcagaactac taacgtcaga accaatattt cactgtcgac aagaggacat
1261 caaaactagt aatccttatc accatgacca gctggacaga atattcaatg taatgggatt
1321 tcctgcagat aaagattggg aagatataaa aaagatgcct gaacattcaa cattaatgaa
1381 agatttcaga agaaatacgt ataccaactg cagccttatc aagtatatgg aaaaacataa
1441 agttaaacca gatagtaaag cattccactt gcttcagaag ctgcttacca tggacccaat
```

-continued

```
1501 aaagcgaatt acctcagaac aggctatgca ggacccctat ttcttagaag acccacttcc
1561 tacatcagac gtttttgccg gttgtcaaat cccttaccca aaacgagaat ttttaacgga
1621 agaagaacct gatgacaaag gagacaaaaa ccagcagcag cagcagggca ataaccacac
1681 taatggaact ggccacccag ggaatcaaga cagcagtcac acacagggac ccccgttgaa
1741 gaaagtgaga gttgttcctc ctaccactac ctcaggtgga cttatcatga cctcagacta
1801 tcagcgttcc aatccacatg ctgcctatcc caaccctgga ccaagcacat cacagccgca
1861 gagcagcatg ggatactcag ctacctccca gcagcctcca cagtactcac atcagacaca
1921 tcggtactga gctgcatcgg aatcttgtcc atgcactgtt gcgaatgctg cagggctgac
1981 tgtgcagctc tctgcgggaa cctggtatgg gccatgagaa tgtactgtac aaccacatct
2041 tcaaaatgtc cagtagccaa gttccaccac ttttcacaga ttggggtagt ggcttccaag
2101 ttgtacctat tttggagtta gacttgaaaa gaaagtgcta gcacagtttg tgttgtggat
2161 ttgctacttc catagtttac ttgacatggt tcagactgac caatgcattt ttttcagtga
2221 cagtctgtag cagttgaagc tgtgaatgtg ctaggggcaa gcatttgtct ttgtatgtgg
2281 tgaatttttt cagtgtaaca acattatctg accaatagta cacacacaga cacaaagttt
2341 aactggtact tgaaacatac agtatatgtt aacgaaataa ccaagactcg aaatgagatt
2401 attttggtac acctttcttt ttagtgtctt atcagtgggc tgattcattt tctacattaa
2461 tcagtgtttt ctgaccaaga atattgcttg gatttttttg aaagtacaaa aagccacata
2521 gtttttccag aaaggtttca aaactcccaa agattaactt ccaacttata agtttgtttt
2581 tattttcaat ctatgacttg actggtatta aagctgctat ttgatagtaa ttaaatatgt
2641 tgtcattgat ataaacctgt ttggttcagc aaacaaacta aaatgattgt catagacagt
2701 gttttatttt tcctgttggt gttgctgatt tgtgagcatg ctttaagatg aaaaaagcat
2761 gaatgataac ttccttaaaa aggtgcggca tccaattcaa atatttcgt cctgatttta
2821 aagctggttg gtgtagtgct attaaaattt cgttcagtta attttccttt tgaaaacttg
2881 ttcgcacgtt gtttagggtg cccttacttc agcaaaggag aaggagtagg agagccttag
2941 aatttttgag gaaaaaaaaa cctataacat acaatgtact gtatcaaact attttacatg
3001 aatgacacaa gtattctgaa taaaaaataa ttgaacattg ttaaaaacaa ggtgttatgt
3061 aataaattta tttttcataa atcaaaaaaa aaaaaaaa
```

Cyclin dependent kinase 8 (CDK8), transcript variant 3 (NM_001346501.1) (SEQ ID NO: 18)

```
  1 gagtgccctc cctcctcctc tctttgagga ggtaccggct gttgtgcggc tctgcccttc
 61 tgtttgagtg tatgggagag tgagtgagtg agtgagtgtg agcgtgtgtg tgagagcgtg
121 aggcgtgagt gcgcgtgtga gaggacgaga gcccgcctgg ccgccccgcc gctcccgccg
181 cagcaggagc agaacgcgcg gccggagaga gcggcggagc cggcgcccag ggagcccgcg
241 gggacaaggg cagagacacc gctccccacc cccagccctc gtccctcggc tctccttcgc
301 cgggggatcc tccccgttcc tccacccccg gccggcctct gccccgccgt ccccctggat
361 gtccctggcg ctttcgcggg gcctcctcct gctcttgccg catcagtcgg gctggtgctg
421 cggccggcgg gcgtagagcg ggcgggttcc cgggggctgc ggctgcccgt gcttccccgg
481 tccccacccc tgccccccgg ccccccgacc cagctctccg gcctcagagg ctgtgacaat
541 ggactatgac tttaaagtga agctgagcag cgagcgggag cgggtcgagg acctgtttga
601 atacgagggc tgcaaagttg gccgaggcac ttatggtcac gtctacaaag ccaagaggaa
661 agatgggaag gatgataaag actatgcttt aaaacaaata gaaggaactg ggatctctat
```

-continued 721 gtcggcatgt agagaaatag cattacttcg agagcttaag catccaaacg tcatttctct
781 tcaaaaggtg tttctgtctc atgctgatag gaaggtgtgg cttctgtttg actatgctga
841 acatgacctc tggcatataa tcaagtttca cagagcttct aaagcaaaca agaagccagt
901 tcagttacct cggggaatgg tgaagtcact attatatcag atcctagatg gtattcacta
961 cctgcatgct aactgggtgt tgcacagaga tttgctgaca tgggctttgc ccgattattt
1021 aattcacctt tgaagccttt agcagatttg gatccagtgg ttgttacatt ctggtaccga
1081 gcccctgaac tacttcttgg agcaaggcat tataccaaag ctattgatat ttgggctata
1141 gggtgtatat ttgcagaact actaacgtca gaaccaatat ttcactgtcg acaagaggac
1201 atcaaaacta gtaatcctta tcaccatgac cagctggaca gaatattcaa tgtaatggga
1261 tttcctgcag ataaagattg ggaagatata aaaaagatgc ctgaacattc aacattaatg
1321 aaagatttca gaagaaatac gtataccaac tgcagcctta tcaagtatat ggaaaaacat
1381 aaagttaaac cagatagtaa agcattccac ttgcttcaga agctgcttac catggaccca
1441 ataaagcgaa ttacctcaga acaggctatg caggacccct atttcttaga agacccactt
1501 cctacatcag acgtttttgc cggttgtcaa atcccttacc caaaacgaga atttttaacg
1561 gaagaagaac ctgatgacaa aggagacaaa aagaaccagc agcagcagca gggcaataac
1621 cacactaatg gaactggcca cccagggaat caagacagca gtcacacaca gggacccccg
1681 ttgaagaaag tgagagttgt tcctcctacc actacctcag gtggacttat catgacctca
1741 gactatcagc gttccaatcc acatgctgcc tatcccaacc ctggaccaag cacatcacag
1801 ccgcagagca gcatgggata ctcagctacc tcccagcagc ctccacagta ctcacatcag
1861 acacatcggt actgagctgc atcggaatct tgtccatgca ctgttgcgaa tgctgcaggg
1921 ctgactgtgc agctctctgc gggaacctgg tatgggccat gagaatgtac tgtacaacca
1981 catcttcaaa atgtccagta gccaagttcc accacttttc acagattggg gtagtggctt
2041 ccaagttgta cctattttgg agttagactt gaaaagaaag tgctagcaca gtttgtgttg
2101 tggatttgct acttccatag tttacttgac atggttcaga ctgaccaatg catttttttc
2161 agtgacagtc tgtagcagtt gaagctgtga atgtgctagg ggcaagcatt tgtctttgta
2221 tgtggtgaat tttttcagtg taacaacatt atctgaccaa tagtacacac acagacacaa
2281 agtttaactg gtacttgaaa catacagtat atgttaacga aataaccaag actcgaaatg
2341 agattatttt ggtacacctt tctttttagt gtcttatcag tgggctgatt cattttctac
2401 attaatcagt gttttctgac caagaatatt gcttggattt ttttgaaagt acaaaaagcc
2461 acatagtttt tccagaaagg tttcaaaact cccaaagatt aacttccaac ttataagttt
2521 gtttttattt tcaatctatg acttgactgg tattaaagct gctatttgat agtaattaaa
2581 tatgttgtca ttgatataaa cctgtttggt tcagcaaaca aactaaaatg attgtcatag
2641 acagtgtttt atttttcctg ttggtgttgc tgatttgtga gcatgcttta agatgaaaaa
2701 agcatgaatg ataacttcct taaaaaggtg cggcatccaa ttcaaatatt ttcgtcctga
2761 ttttaaagct ggttggtgta gtgctattaa aatttcgttc agttaatttt ccttttgaaa
2821 acttgttcgc acgttgttta gggtgccctt acttcagcaa aggagaagga gtaggagagc
2881 cttagaattt ttgaggaaaa aaaaacctat aacatacaat gtactgtatc aaactatttt
2941 acatgaatga cacaagtatt ctgaataaaa aataattgaa cattgttaaa aacaaggtgt
3001 tatgtaataa atttattttt cataaatcaa aaaaaaaaaa aaa

What is claimed is:

1. A method of treating a patient diagnosed with triple-negative breast cancer (TNBC), comprising administering a therapeutically effective dose of an agent that inhibits expression of cyclin-dependent kinase 19 (CDK19), wherein the agent inhibits CDK19 gene expression to a greater extent than it inhibits cyclin-dependent kinase 8 (CDK8) gene expression, wherein the agent comprises an inhibitory nucleic acid selected from an RNA capable of hybridizing to a portion of a CDK19 RNA transcript and decreasing CDK19 gene expression, an RNAse H dependent antisense oligonucleotide capable of binding to a CDK19 transcript, and a guide RNA that directs a Cas protein to a CDK19 gene sequence, and wherein administration of the agent results in at least one of a reduction in cachexia, increase in survival time, elongation in time to tumor progression, reduction in tumor mass, reduction in tumor burden, prolongation in time to tumor metastasis, prolongation in time to tumor recurrence, and progression free survival.

2. A method of treating a patient diagnosed with triple-negative breast cancer (TNBC) characterized by a tumor comprising EpCAM$^{med/high}$ and CD10$^{-/low}$ epithelial cells, the method comprising administering a therapeutically effective dose of an agent that inhibits cyclin-dependent kinase 19 (CDK19) expression or activity, wherein the agent is an shRNA capable of hybridizing to a portion of a CDK19 RNA transcript and decreasing CDK19 gene expression, an siRNA capable of hybridizing to a portion of a CDK19 RNA transcript and decreasing CDK19 gene expression, an RNAse H dependent antisense oligonucleotide capable of binding to a CKD19 transcript, or a guide RNA that directs a Cas protein to a CDK19 polynucleotide sequence, wherein the treatment reduces the number of EpCAM$^{med/high}$ and CD10$^{-/low}$ cells in the tumor, reduces the number of EpCAM$^{med/high}$ and CD10$^{-/low}$ cells per unit volume of the tumor, or results in a reduction of the ratio of EpCAM$^{med/high}$ and CD10$^{-/low}$ epithelial cells to normal cells in the tumor.

3. A method of reducing metastasis of TNBC in a patient, the method comprising administering a therapeutically effective dose of an agent that inhibits expression or activity of CDK19, wherein the agent is a nucleic acid comprising at least one of an RNA capable of hybridizing to a portion of a CDK19 RNA transcript and decreasing CDK19 gene expression, an expression vector encoding such an RNA, an RNAse H dependent antisense oligonucleotide capable of binding to a CKD19 transcript, or a guide RNA that directs a Cas protein to a CDK19 polynucleotide sequence.

4. The method of claim 1, wherein the patient is treated with a combination therapy comprising (a) an agent that inhibits expression or activity of CDK19 and (b) radiation therapy and/or chemotherapy.

5. The method of claim 1, comprising detecting EpCAM$^{med/high}$/CD10$^{-/low}$ cells in a tissue sample from the patient prior to or after initiating therapy.

6. The method of claim 1, wherein the agent is a CRISPR/Cas9 system.

7. The method of claim 1, wherein the agent is a CDK19 targeting shRNA or a CDK19 targeting siRNA.

8. The method of claim 1, wherein the agent is a CDK19 targeting shRNA comprising a sequence selected from: SEQ ID NO: 1 and SEQ ID NO: 2 or the complement thereof.

9. The method of claim 1, wherein the agent is a CDK19 targeting shRNA or siRNA complementary or substantially complementary to the 5' UTR of CDK19, but not to the 5' UTR of CDK8.

10. The method of claim 1, wherein the agent is a CDK19 targeting shRNA or siRNA complementary or substantially complementary to the 3' UTR of CDK19, but not to the 3'UTR of CDK8.

11. The method of claim 1, wherein the agent is a CDK19 targeting shRNA or siRNA complementary or substantially complementary to the coding region of CDK19, but not to the coding region of CDK8.

12. The method of claim 1, wherein the agent binds to CDK19 in the cytoplasm of a breast epithelial cell.

13. The method of claim 1 wherein the inhibitory nucleic acid is an shRNA or siRNA that hybridizes to a portion of a CDK19 RNA transcript and decreases CDK19 gene expression.

14. The method of claim 1 wherein the RNA is an shRNA administered using an expression vector encoding the shRNA.

15. The method of claim 2 wherein the RNA is an shRNA administered using an expression vector encoding the shRNA.

16. The method of claim 1 wherein the agent is an RNAse H dependent antisense oligonucleotide.

17. The method of claim 1 wherein the agent is a guide RNA complexed to a Cas protein.

* * * * *

UNITED STATES PATENT AND TRADEMARK OFFICE

CERTIFICATE OF CORRECTION

PATENT NO. : 11,471,477 B2
APPLICATION NO. : 16/648088
DATED : October 18, 2022
INVENTOR(S) : Michael F. Clarke and Robert W. Hsieh It is certified that error appears in the above-identified patent and that said Letters Patent is hereby corrected as shown below:

On the Title Page

In Column 2, Line 24 item (56), (Other Publications):
Delete “Internation” and
Insert -- International --

In Column 2, Line 5 item (57), (Abstract):
Delete “shRNA.” and
Insert -- shRNA, --

In the Specification

In Column 23, Line 11:
Delete “anti-CKD19” and
Insert -- anti-CDK19 --

In Column 23, Line 14:
Delete “Anti-CKD19” and
Insert -- Anti-CDK19 --

In Column 23, Line 26:
Delete “CKD19” and
Insert -- CDK19 --

In the Claims

In Column 133, Line 15:
Delete “CKD19” and
Insert -- CDK19 --

Signed and Sealed this
Twenty-first Day of March, 2023

Katherine Kelly Vidal

Katherine Kelly Vidal
*Director of the United States Patent and Trademark Office*

In Column 133, Line 32:
Delete "CKD19" and
Insert -- CDK19 --

In Column 134, Line 16:
Delete "3′UTR" and
Insert -- 3' UTR --

SEQUENCE LISTING

<160> NUMBER OF SEQ ID NOS: 46

<210> SEQ ID NO 1
<211> LENGTH: 21
<212> TYPE: DNA
<213> ORGANISM: Homo sapiens

<400> SEQUENCE: 1
gcgagaattg aagtacctta a 21

<210> SEQ ID NO 2
<211> LENGTH: 21
<212> TYPE: DNA
<213> ORGANISM: Homo sapiens

<400> SEQUENCE: 2
accagcaaat atcctagtaa t 21

<210> SEQ ID NO 3
<211> LENGTH: 21
<212> TYPE: DNA
<213> ORGANISM: Homo sapiens

<400> SEQUENCE: 3
gcttgtagag agattgtact t 21

<210> SEQ ID NO 4
<211> LENGTH: 21
<212> TYPE: DNA
<213> ORGANISM: Homo sapiens

<400> SEQUENCE: 4
gaggactgat agttcttctt t 21

<210> SEQ ID NO 5
<211> LENGTH: 21
<212> TYPE: DNA
<213> ORGANISM: Homo sapiens

<400> SEQUENCE: 5
gatattagaa agatgccaga a 21

<210> SEQ ID NO 6
<211> LENGTH: 21
<212> TYPE: DNA
<213> ORGANISM: Homo sapiens

<400> SEQUENCE: 6
gccaacagta gcctcataaa g 21

<210> SEQ ID NO 7
<211> LENGTH: 21
<212> TYPE: DNA
<213> ORGANISM: Homo sapiens

<400> SEQUENCE: 7
cgttcgtatt tatctagttt c 21

<210> SEQ ID NO 8
<211> LENGTH: 21
<212> TYPE: DNA
<213> ORGANISM: Homo sapiens

<400> SEQUENCE: 8
gcatgacttg tggcatatta t 21

<210> SEQ ID NO 9
<211> LENGTH: 21
<212> TYPE: DNA
<213> ORGANISM: Homo sapiens

<400> SEQUENCE: 9
gcttgtagag agattgcact t 21

<210> SEQ ID NO 10
<211> LENGTH: 21
<212> TYPE: DNA
<213> ORGANISM: Homo sapiens

<400> SEQUENCE: 10
aggactgata gctcttcttt a 21

<210> SEQ ID NO 11
<211> LENGTH: 21
<212> TYPE: DNA
<213> ORGANISM: Homo sapiens

<400> SEQUENCE: 11
gtatggctgc tgtttgatta t 21

<210> SEQ ID NO 12
<211> LENGTH: 6246
<212> TYPE: DNA
<213> ORGANISM: Homo sapiens

<400> SEQUENCE: 12
tgtggccgcc gaggagtccc ttgctgaagg cggaccgcgg agcggcgggc ggcgggcggc 60
gcgcgcgcgc gcgcgagagg cggctgttgg agaagtggag cggcggtcgc ggggggagga 120
ggaggaggga ctgagcggcg gcggcccccg cgtcccgtgc ctctatgggg gaagcagaca 180
atggattatg atttcaaggc gaagctggcg gcggagcggg agcgggtgga ggatttgttt 240
gagtacgaag ggtgcaaagt gggacgcggc acctacggtc acgtctacaa ggcgaggcgg 300
aaagatggaa aagatgaaaa ggaatatgca ttgaagcaaa ttgaaggcac aggaatatcc 360
atgtcggctt gtagagagat tgcacttttg cgagaattga agcaccctaa tgtgattgca 420
ttgcagaagg tgttcctttc tcacagtgac aggaaggtat ggctgctgtt tgattatgca 480
gagcatgact tgtggcatat tattaagttt caccgtgcat caaaagcaaa taaaaagccc 540
atgcagttgc caagatctat ggttaaatcc ttactttacc agattcttga tggtatccat 600
tacctccatg caaattgggt gcttcacaga gacttgaaac cagcaaatat cctagtaatg 660
ggagaaggtc ctgagagggg gagagtcaaa atagctgaca tgggttttgc cagattattc 720
aattctcctc taaagccact agcagatttg gatccagtag ttgtgacatt ttggtatcgg 780
gctccagaac ttttgcttgg tgcaaggcat tatacaaagg ccattgatat atgggcaata 840
ggttgtatat ttgctgaatt gttgacttcg gaacctattt ttcactgtcg tcaggaagat 900
ataaaaacaa gcaatccctt tcatcatgat caactggatc ggatatttag tgtcatgggg 960
tttcctgcag ataaagactg ggaagatatt agaaagatgc cagaatatcc cacacttcaa 1020
aaagacttta gaagaacaac gtatgccaac agtagcctca taaagtacat ggagaaacac 1080
aaggtcaagc ctgacagcaa agtgttcctc ttgcttcaga aactcctgac catggatcca 1140

-continued

```
accaagagaa ttacctcgga gcaagctctg caggatccct attttcagga ggaccctttg   1200
ccaacattag atgtatttgc cggctgccag attccatacc ccaaacgaga attccttaat   1260
gaagatgatc ctgaagaaaa aggtgacaag aatcagcaac agcagcagaa ccagcatcag   1320
cagcccacag cccctccaca gcaggcagca gcccctccac aggcgccccc accacagcag   1380
aacagcaccc agaccaacgg gaccgcaggt ggggctgggg ccggggtcgg gggcaccgga   1440
gcagggttgc agcacagcca ggactccagc ctgaaccagg tgcctccaaa caagaagcca   1500
cggctagggc cttcaggcgc aaactcaggt ggacctgtga tgccctcgga ttatcagcac   1560
tccagttctc gcctgaatta ccaaagcagc gttcagggat cctctcagtc ccagagcaca   1620
cttggctact cttcctcgtc tcagcagagc tcacagtacc acccatctca ccaggcccac   1680
cggtactgac cagctcccgt tgggccaggc cagcccagcc cagagcacag gctccagcaa   1740
tatgtctgca ttgaaaagaa ccaaaaaaat gcaaactatg atgccattta aaactcatac   1800
acatgggagg aaaaccttat atactgagca ttgtgcagga ctgatagctc ttctttattg   1860
acttaaagaa gattcttgtg aagtttcccc agcacccctt ccctgcatgt gttccattgt   1920
gacttctctg ataaagcgtc tgatctaatc ccagcacttc tgtaaccttc agcatttctt   1980
tgaaggattt cctggtgcac ctttctcatg ctgtagcaat cactatggtt tatcttttca   2040
aagctctttt aataggattt taatgtttta gaaacaggat tccagtggtg tatagtttta   2100
tacttcatga actgatttag caacacaggt aaaaatgcac cttttaaagc actacgtttt   2160
cacagacaat aactgttctg ctcatggaag tcttaaacag aaactgttac tgtcccaaag   2220
tactttacta ttacgttcgt atttatctag tttcagggaa ggtctaataa aaagacaagc   2280
ggtgggacag agggaaccta caaccaaaaa ctgcctagat ctttgcagtt atgtgcttta   2340
tgccacgaag aactgaagta tgtggtaatt tttatagaat cattcatatg gaactgagtt   2400
cccagcatca tcttattctg aatagcattc agtaattaag aattacaatt ttaaccttca   2460
tgtagctaag tctaccttaa aaagggtttc aagagctttg tacagtctcg atggcccaca   2520
ccaaaacgct gaagagagta acaactgcac taggatttct gtaaggagta attttgatca   2580
aaagacgtgt tacttccctt tgaaggaaaa gtttttagtg tgtattgtac ataaagtcgg   2640
cttctctaaa gaaccattgg tttcttcaca tctgggtctg cgtgagtaac tttcttgcat   2700
aatcaaggtt actcaagtag aagcctgaaa attaatctgc ttttaaaata aagagcagtg   2760
ttctccattc gtatttgtat tagatataga gtgactattt ttaaagcatg ttaaaaattt   2820
aggttttatt catgtttaaa gtatgtatta tgtatgcata attttgctgt tgttactgaa   2880
acttaattct atcaagaatc tttttcattg cactgaatga tttcttttgc ccctaggaga   2940
aaacttaata attgtgccta aaaactatgg gcggatagta taagactata ctagacaaag   3000
tgaatatttg catttccatt atctatgaat tagtggctga gttctttctt agctgcttta   3060
aggagcccct cactccccag agtcaaaagg aaatgtaaaa acttagagct cccattgtaa   3120
tgtaaggggc aagaaatttg tgttcttctg aatgctacta gcagcaccag ccttgtttta   3180
aatgttttct tgagctagaa gaaatagctg attattgtat atgcaaatta catgcatttt   3240
taaaaactat tctttctgaa cttatctacc tggttatgat actgtgggtc catacacaag   3300
taaaataaga ttagacagaa gccagtatac attttgcact attgatgtga tactgtagcc   3360
agccaggacc ttactgatct cagcataata atgctcacta ataatgaagt ctgcatagtg   3420
acactcatca agactgaaga tgaagcaggt tacgtgctcc attggaagga gtttctgata   3480
gtctcctgct gttttacccc ttccattttt taaaataaga aattagcagc cctctgcata   3540
```

atgtagctgc ctatatgcag ttttatcctg tgccctaaag cctcactgtc cagagctgtt 3600
ggtcatcaga tgcttattgc accctcacca tgtgcctggt gccctgctgg gtagagaaca 3660
cagaggacag ggcatacttc ttgtccttaa ggagcttgtg atctgtgaca gtaagccctc 3720
ctgggatgtc tgtgccatgt gattgactta caagtgaaac tgtcttataa tatgaaggtc 3780
tttttgttta cttctaaacc cacttgggta gttactatcc ccaaatctgt tctgtaaata 3840
atattatgga agggtttcta tgtcagtcta ccttagagaa agccagtgat tcaatatcac 3900
aaaaggcatt gacgtatctt tgaaatgttc acagcagcct tttaacaaca actgggtggt 3960
ccttgtaggc agaacatact ctcctaagtg gttgtaggaa attgcaagga aaatagaagg 4020
tctgttcttg ctctcaagga ggttaccttt aataaaagaa gacaaaccca gatagatatg 4080
taaaccaaaa tactatgccc cttaatactt tataagcagc attgttaaat agttcttacg 4140
cttatacatt cacagaacta ccctgttttc cttgtatata atgacttttg ctggcagaac 4200
tgaaatataa actgtaaggg gatttcgtca gttgctccca gtatacaata tcctccagga 4260
catagccaga aatctccatt ccacacatga ctgagttcct atccctgcac tggtactggc 4320
tcttttctcc tctttccttg cctcagggtt cgtgctaccc actgattccc tttaccctta 4380
gtaataattt tggatcattt tctttccttt aaaggggaac aaagcctttt ttttttttga 4440
gacggagtgt tgctctgtca cccaagctgg agtgcagtgg cacgatcttg gctcactcca 4500
acctccacct tccaggttca agtgattctc ctgcctcagc ctcccgagta gctgggacta 4560
cgggcacgca ccaccacgtc tggctaattt ttgtattttt agtagagatg gggtttcacc 4620
ctattggtca ggctggtctt gaattcctca cctcaggtca tccgcctgtc tcggcctccc 4680
gaagtgctgg gattataggt gtgagccacc gcacccagtt gggaacaaag ccttttttaac 4740
acacgtaagg gccctcaaac cgtgggacct ctaaggagac ctttgaagct tttgagggc 4800
aaactttacc tttgtggtcc ccaaatgatg gcatttctct ttgaaattta ttagatactg 4860
ttatgtcccc caagggtaca ggaggggcat ccctcagcct atgggaacac ccaaactagg 4920
aggggttatt gacaggaagg aatgaatcca agtgaaggct ttctgctctt cgtgttacaa 4980
accagtttca gagttagctt tctggggagg tgtgtgtttg tgaaaggaat tcaagtgttg 5040
caggacagat gagctcaagg taaggtagct ttggcagcag ggctgatact atgaggctga 5100
aacaatcctt gtgatgaagt agatcatgca gtgacataca aagaccaagg attatgtata 5160
tttttatatc tctgtggttt tgaaacttta gtacttagaa ttttggcctt ctgcactact 5220
cttttgctct tacgaacata atggactctt aagaatggaa agggatgaca tttacctatg 5280
tgtgctgcct cattcctggt gaagcaactg ctacttgttc tctatgcctc taaaatgatg 5340
ctgttttctc tgctaaaggt aaaagaaaag aaaaaaatag ttggaaaata agacatgcaa 5400
cttgatgtgc ttttgagtaa atttatgcag cagaaactat acaatgaagg aagaattcta 5460
tggaaattac aaatccaaaa ctctatgatg atgtcttcct agggagtaga gaaaggcagt 5520
gaaatggcag ttagaccaac agaggcttga aggattcaag tacaagtaat attttgtata 5580
aaacatagca gtttaggtcc ccataatcct caaaaaatagt cacaaatata acaaagttca 5640
ttgttttagg gtttttaaaa aacgtgttgt acctaaggcc atacttactc ttctatgcta 5700
tcactgcaaa ggggtgatat gtatgtatta tataaaaaaa aaaaccctta atgcactgtt 5760
atctcctaaa tatttagtaa attaatacta tttaattttt ttaaagattt gtctgtgtag 5820
acactaaaag tattacacaa aatctggact gaaggtgtcc tttttaacaa caatttaaag 5880

-continued

```
tactttttat atatgttatg tagtatatcc tttctaaact gcctagtttg tatattccta   5940

taattcctat ttgtgaagtg tacctgttct tgtctctttt ttcagtcatt ttctgcacgc   6000

atccccctttt atatggttat agagatgact gtagcttttc gtgctccact gcgaggtttg  6060

tgctcagagc cgctgcaccc cagcgaggcc tgctccatgg agtgcaggac gagctactgc   6120

tttggagcga gggtttcctg cttttgagtt gacctgactt ccttcttgaa atgactgtta   6180

aaactaaaat aaattacatt gcatttattt tatattcttg gttgaaataa aatttaattg   6240

actttg                                                              6246
```

<210> SEQ ID NO 13
<211> LENGTH: 6114
<212> TYPE: DNA
<213> ORGANISM: Homo sapiens

<400> SEQUENCE: 13

```
tgtggccgcc gaggagtccc ttgctgaagg cggaccgcgg agcggcgggc ggcgggcggc     60

gcgcgcgcgc gcgcgagagg cggctgttgg agaagtggag cggcggtcgc gggggggagga   120

ggaggaggga ctgagcggcg gcggcccccg cgtcccgtgc ctctatgggg gaagcagaca    180

atggattatg atttcaaggc gaagctggcg gcggagcggg agcgggtgga ggatttgttt    240

gagtacgaag ggtgcaaagt gggacgcggc acctacggtc acgtctacaa ggcgaggcgg    300

aaagatggaa aagatgaaaa ggaatatgca ttgaagcaaa ttgaaggcac aggaatatcc    360

atgtcggctt gtagagagat tgcacttttg cgagaattga agcaccctaa tgtgattgca    420

ttgcagaagg tgttcctttc tcacagtgac aggaaggtat ggctgctgtt tgattatgca    480

gagcatgact tgtggcatat tattaagttt caccgtgcat caaaagcaaa taaaaagccc    540

atgcagttgc caagatctat ggttaaatcc ttactttacc agattcttga tggtatccat    600

tacctccatg caaattgggt gcttcacaga gacttgaaac cagcaaatat cctagtaatg    660

ggagaaggtc ctgagagggg gagagtcaaa atagatatat gggcaatagg ttgtatattt    720

gctgaattgt tgacttcgga acctattttt cactgtcgtc aggaagatat aaaaacaagc    780

aatccctttc atcatgatca actggatcgg atatttagtg tcatggggtt tcctgcagat    840

aaagactggg aagatattag aaagatgcca gaatatccca cacttcaaaa agactttaga    900

agaacaacgt atgccaacag tagcctcata aagtacatgg agaaacacaa ggtcaagcct    960

gacagcaaag tgttcctctt gcttcagaaa ctcctgacca tggatccaac caagagaatt   1020

acctcggagc aagctctgca ggatccctat tttcaggagg accctttgcc aacattagat   1080

gtatttgccg gctgccagat tccatacccc aaacgagaat tccttaatga agatgatcct   1140

gaagaaaaag gtgacaagaa tcagcaacag cagcagaacc agcatcagca gcccacagcc   1200

cctccacagc aggcagcagc ccctccacag gcgcccccac cacagcagaa cagcacccag   1260

accaacggga ccgcaggtgg ggctggggcc ggggtcgggg gcaccggagc agggttgcag   1320

cacagccagg actccagcct gaaccaggtg cctccaaaca agaagccacg gctagggcct   1380

tcaggcgcaa actcaggtgg acctgtgatg ccctcggatt atcagcactc cagttctcgc   1440

ctgaattacc aaagcagcgt tcagggatcc tctcagtccc agagcacact tggctactct   1500

tcctcgtctc agcagagctc acagtaccac ccatctcacc aggcccaccg gtactgacca   1560

gctcccgttg ggccaggcca gcccagccca gagcacaggc tccagcaata tgtctgcatt   1620

gaaaagaacc aaaaaaatgc aaactatgat gccatttaaa actcatacac atgggaggaa   1680

aaccttatat actgagcatt gtgcaggact gatagctctt ctttattgac ttaaagaaga   1740
```

-continued

```
ttcttgtgaa gtttccccag caccccttcc ctgcatgtgt tccattgtga cttctctgat   1800
aaagcgtctg atctaatccc agcacttctg taaccttcag catttctttg aaggatttcc   1860
tggtgcacct ttctcatgct gtagcaatca ctatggttta tcttttcaaa gctcttttaa   1920
taggatttta atgttttaga aacaggattc cagtggtgta tagttttata cttcatgaac   1980
tgatttagca acacaggtaa aaatgcacct tttaaagcac tacgttttca cagacaataa   2040
ctgttctgct catggaagtc ttaaacagaa actgttactg tcccaaagta ctttactatt   2100
acgttcgtat ttatctagtt tcagggaagg tctaataaaa agacaagcgg tgggacagag   2160
ggaacctaca accaaaaact gcctagatct ttgcagttat gtgctttatg ccacgaagaa   2220
ctgaagtatg tggtaatttt tatagaatca ttcatatgga actgagttcc cagcatcatc   2280
ttattctgaa tagcattcag taattaagaa ttacaatttt aaccttcatg tagctaagtc   2340
taccttaaaa agggtttcaa gagctttgta cagtctcgat ggcccacacc aaaacgctga   2400
agagagtaac aactgcacta ggatttctgt aaggagtaat tttgatcaaa agacgtgtta   2460
cttccctttg aaggaaaagt ttttagtgtg tattgtacat aaagtcggct tctctaaaga   2520
accattggtt tcttcacatc tgggtctgcg tgagtaactt tcttgcataa tcaaggttac   2580
tcaagtagaa gcctgaaaat taatctgctt ttaaaataaa gagcagtgtt ctccattcgt   2640
atttgtatta gatatagagt gactattttt aaagcatgtt aaaaatttag gttttattca   2700
tgtttaaagt atgtattatg tatgcataat tttgctgttg ttactgaaac ttaattctat   2760
caagaatctt tttcattgca ctgaatgatt tcttttgccc ctaggagaaa acttaataat   2820
tgtgcctaaa aactatgggc ggatagtata agactatact agacaaagtg aatatttgca   2880
tttccattat ctatgaatta gtggctgagt tctttcttag ctgctttaag gagcccctca   2940
ctccccagag tcaaaaggaa atgtaaaaac ttagagctcc cattgtaatg taaggggcaa   3000
gaaatttgtg ttcttctgaa tgctactagc agcaccagcc ttgttttaaa tgtttttcttg   3060
agctagaaga aatagctgat tattgtatat gcaaattaca tgcattttta aaaactattc   3120
tttctgaact tatctacctg gttatgatac tgtgggtcca tacacaagta aaataagatt   3180
agacagaagc cagtatacat tttgcactat tgatgtgata ctgtagccag ccaggacctt   3240
actgatctca gcataataat gctcactaat aatgaagtct gcatagtgac actcatcaag   3300
actgaagatg aagcaggtta cgtgctccat tggaaggagt ttctgatagt ctcctgctgt   3360
tttacccctt ccattttta aaataagaaa ttagcagccc tctgcataat gtagctgcct   3420
atatgcagtt ttatcctgtg ccctaaagcc tcactgtcca gagctgttgg tcatcagatg   3480
cttattgcac cctcaccatg tgcctggtgc cctgctgggt agagaacaca gaggacaggg   3540
catacttctt gtccttaagg agcttgtgat ctgtgacagt aagccctcct gggatgtctg   3600
tgccatgtga ttgacttaca agtgaaactg tcttataata tgaaggtctt tttgtttact   3660
tctaaaccca cttgggtagt tactatcccc aaatctgttc tgtaaataat attatggaag   3720
ggtttctatg tcagtctacc ttagagaaag ccagtgattc aatatcacaa aaggcattga   3780
cgtatctttg aaatgttcac agcagccttt taacaacaac tgggtggtcc ttgtaggcag   3840
aacatactct cctaagtggt tgtaggaaat tgcaaggaaa atagaaggtc tgttcttgct   3900
ctcaaggagg ttacctttaa taaaagaaga caaacccaga tagatatgta aaccaaaata   3960
ctatgcccct taatacttta taagcagcat tgttaaatag ttcttacgct tatacattca   4020
cagaactacc ctgttttcct tgtatataat gacttttgct ggcagaactg aaatataaac   4080
```

-continued

```
tgtaagggga tttcgtcagt tgctcccagt atacaatatc ctccaggaca tagccagaaa   4140
tctccattcc acacatgact gagttcctat ccctgcactg gtactggctc ttttctcctc   4200
tttccttgcc tcagggttcg tgctacccac tgattccctt tacccttagt aataattttg   4260
gatcattttc tttcctttaa aggggaacaa agcctttttt ttttttgaga cggagtgttg   4320
ctctgtcacc caagctggag tgcagtggca cgatcttggc tcactccaac ctccaccttc   4380
caggttcaag tgattctcct gcctcagcct cccgagtagc tgggactacg ggcacgcacc   4440
accacgtctg gctaattttt gtatttttag tagagatggg gtttcaccct attggtcagg   4500
ctggtcttga attcctcacc tcaggtcatc cgcctgtctc ggcctcccga agtgctggga   4560
ttataggtgt gagccaccgc acccagttgg gaacaaagcc tttttaacac acgtaagggc   4620
cctcaaaccg tgggacctct aaggagacct ttgaagcttt ttgagggcaa actttacctt   4680
tgtggtcccc aaatgatggc atttctcttt gaaatttatt agatactgtt atgtccccca   4740
agggtacagg aggggcatcc ctcagcctat gggaacaccc aaactaggag gggttattga   4800
caggaaggaa tgaatccaag tgaaggcttt ctgctcttcg tgttacaaac cagtttcaga   4860
gttagctttc tggggaggtg tgtgtttgtg aaaggaattc aagtgttgca ggacagatga   4920
gctcaaggta aggtagcttt ggcagcaggg ctgatactat gaggctgaaa caatccttgt   4980
gatgaagtag atcatgcagt gacatacaaa gaccaaggat tatgtatatt tttatatctc   5040
tgtggttttg aaactttagt acttagaatt ttggccttct gcactactct tttgctctta   5100
cgaacataat ggactcttaa gaatggaaag ggatgacatt tacctatgtg tgctgcctca   5160
ttcctggtga agcaactgct acttgttctc tatgcctcta aaatgatgct gttttctctg   5220
ctaaaggtaa aagaaaagaa aaaaatagtt ggaaaataag acatgcaact tgatgtgctt   5280
ttgagtaaat ttatgcagca gaaactatac aatgaaggaa gaattctatg gaaattacaa   5340
atccaaaact ctatgatgat gtcttcctag ggagtagaga aaggcagtga aatggcagtt   5400
agaccaacag aggcttgaag gattcaagta caagtaatat tttgtataaa acatagcagt   5460
ttaggtcccc ataatcctca aaaatagtca caaatataac aaagttcatt gttttagggt   5520
ttttaaaaaa cgtgttgtac ctaaggccat acttactctt ctatgctatc actgcaaagg   5580
ggtgatatgt atgtattata taaaaaaaaa aacccttaat gcactgttat ctcctaaata   5640
tttagtaaat taatactatt taattttttt aaagatttgt ctgtgtagac actaaaagta   5700
ttacacaaaa tctggactga aggtgtcctt tttaacaaca atttaaagta ctttttatat   5760
atgttatgta gtatatcctt tctaaactgc ctagtttgta tattcctata attcctattt   5820
gtgaagtgta cctgttcttg tctctttttt cagtcatttt ctgcacgcat ccccctttat   5880
atggttatag agatgactgt agcttttcgt gctccactgc gaggtttgtg ctcagagccg   5940
ctgcacccca gcgaggcctg ctccatggag tgcaggacga gctactgctt tggagcgagg   6000
gtttcctgct tttgagttga cctgacttcc ttcttgaaat gactgttaaa actaaaataa   6060
attacattgc atttatttta tattcttggt tgaaataaaa tttaattgac tttg         6114
```

```
<210> SEQ ID NO 14
<211> LENGTH: 6062
<212> TYPE: DNA
<213> ORGANISM: Homo sapiens

<400> SEQUENCE: 14

gaggggcggc cctggtacgc aggcgcgcat gctttgtggg ggcgaggctg tggtggcccg     60
agattccagg agggcttcgt gtatggacct caagcgttgg aggtagcaga cttttcagca    120
```

-continued

```
gaagaaaaga tgaaaaggaa tatgcattga agcaaattga aggcacagga atatccatgt    180
cggcttgtag agagattgca cttttgcgag aattgaagca ccctaatgtg attgcattgc    240
agaaggtgtt cctttctcac agtgacagga aggtatggct gctgtttgat tatgcagagc    300
atgacttgtg gcatattatt aagtttcacc gtgcatcaaa agcaaataaa aagcccatgc    360
agttgccaag atctatggtt aaatccttac tttaccagat tcttgatggt atccattacc    420
tccatgcaaa ttgggtgctt cacagagact tgaaaccagc aaatatccta gtaatgggag    480
aaggtcctga gagggggaga gtcaaaatag ctgacatggg ttttgccaga ttattcaatt    540
ctcctctaaa gccactagca gatttggatc cagtagttgt gacattttgg tatcgggctc    600
cagaactttt gcttggtgca aggcattata caaaggccat tgatatatgg gcaataggtt    660
gtatatttgc tgaattgttg acttcggaac ctatttttca ctgtcgtcag gaagatataa    720
aaacaagcaa tccctttcat catgatcaac tggatcggat atttagtgtc atggggtttc    780
ctgcagataa agactgggaa gatattagaa agatgccaga atatcccaca cttcaaaaag    840
actttagaag aacaacgtat gccaacagta gcctcataaa gtacatggag aaacacaagg    900
tcaagcctga cagcaaagtg ttcctcttgc ttcagaaact cctgaccatg gatccaacca    960
agagaattac ctcggagcaa gctctgcagg atccctattt tcaggaggac cctttgccaa   1020
cattagatgt atttgccggc tgccagattc cataccccaa acgagaattc cttaatgaag   1080
atgatcctga agaaaaaggt gacaagaatc agcaacagca gcagaaccag catcagcagc   1140
ccacagcccc tccacagcag gcagcagccc ctccacaggc gcccccacca cagcagaaca   1200
gcacccagac caacgggacc gcaggtgggg ctggggccgg ggtcgggggc accggagcag   1260
ggttgcagca cagccaggac tccagcctga accaggtgcc tccaaacaag aagccacggc   1320
tagggccttc aggcgcaaac tcaggtggac ctgtgatgcc ctcggattat cagcactcca   1380
gttctcgcct gaattaccaa agcagcgttc agggatcctc tcagtcccag agcacacttg   1440
gctactcttc ctcgtctcag cagagctcac agtaccaccc atctcaccag gcccaccggt   1500
actgaccagc tcccgttggg ccaggccagc ccagcccaga gcacaggctc cagcaatatg   1560
tctgcattga aaagaaccaa aaaaatgcaa actatgatgc catttaaaac tcatacacat   1620
gggaggaaaa ccttatatac tgagcattgt gcaggactga tagctcttct ttattgactt   1680
aaagaagatt cttgtgaagt ttccccagca ccccttccct gcatgtgttc cattgtgact   1740
tctctgataa agcgtctgat ctaatcccag cacttctgta accttcagca tttctttgaa   1800
ggatttcctg gtgcaccttt ctcatgctgt agcaatcact atggtttatc ttttcaaagc   1860
tcttttaata ggattttaat gttttagaaa caggattcca gtggtgtata gttttatact   1920
tcatgaactg atttagcaac acaggtaaaa atgcaccttt taaagcacta cgttttcaca   1980
gacaataact gttctgctca tggaagtctt aaacagaaac tgttactgtc ccaaagtact   2040
ttactattac gttcgtattt atctagtttc agggaaggtc taataaaaag acaagcggtg   2100
ggacagaggg aacctacaac caaaaactgc ctagatcttt gcagttatgt gctttatgcc   2160
acgaagaact gaagtatgtg gtaattttta tagaatcatt catatggaac tgagttccca   2220
gcatcatctt attctgaata gcattcagta attaagaatt acaattttaa ccttcatgta   2280
gctaagtcta ccttaaaaag ggtttcaaga gctttgtaca gtctcgatgg cccacaccaa   2340
aacgctgaag agagtaacaa ctgcactagg atttctgtaa ggagtaattt tgatcaaaag   2400
acgtgttact tccctttgaa ggaaaagttt ttagtgtgta ttgtacataa agtcggcttc   2460
```

-continued

```
tctaaagaac cattggtttc ttcacatctg ggtctgcgtg agtaactttc ttgcataatc   2520
aaggttactc aagtagaagc ctgaaaatta atctgctttt aaaataaaga gcagtgttct   2580
ccattcgtat ttgtattaga tatagagtga ctatttttaa agcatgttaa aaatttaggt   2640
tttattcatg tttaaagtat gtattatgta tgcataattt tgctgttgtt actgaaactt   2700
aattctatca agaatctttt tcattgcact gaatgatttc ttttgcccct aggagaaaac   2760
ttaataattg tgcctaaaaa ctatgggcgg atagtataag actatactag acaaagtgaa   2820
tatttgcatt tccattatct atgaattagt ggctgagttc tttcttagct gctttaagga   2880
gcccctcact ccccagagtc aaaaggaaat gtaaaaactt agagctccca ttgtaatgta   2940
aggggcaaga aatttgtgtt cttctgaatg ctactagcag caccagcctt gttttaaatg   3000
ttttcttgag ctagaagaaa tagctgatta ttgtatatgc aaattacatg catttttaaa   3060
aactattctt tctgaactta tctacctggt tatgatactg tgggtccata cacaagtaaa   3120
ataagattag acagaagcca gtatacattt tgcactattg atgtgatact gtagccagcc   3180
aggaccttac tgatctcagc ataataatgc tcactaataa tgaagtctgc atagtgacac   3240
tcatcaagac tgaagatgaa gcaggttacg tgctccattg gaaggagttt ctgatagtct   3300
cctgctgttt taccccttcc attttttaaa ataagaaatt agcagccctc tgcataatgt   3360
agctgcctat atgcagtttt atcctgtgcc ctaaagcctc actgtccaga gctgttggtc   3420
atcagatgct tattgcaccc tcaccatgtg cctggtgccc tgctgggtag agaacacaga   3480
ggacagggca tacttcttgt ccttaaggag cttgtgatct gtgacagtaa gccctcctgg   3540
gatgtctgtg ccatgtgatt gacttacaag tgaaactgtc ttataatatg aaggtctttt   3600
tgtttacttc taaacccact tggtagtta ctatccccaa atctgttctg taaataatat   3660
tatggaaggg tttctatgtc agtctacctt agagaaagcc agtgattcaa tatcacaaaa   3720
ggcattgacg tatctttgaa atgttcacag cagcctttta acaacaactg ggtggtcctt   3780
gtaggcagaa catactctcc taagtggttg taggaaattg caaggaaaat agaaggtctg   3840
ttcttgctct caaggaggtt acctttaata aaagaagaca aacccagata gatatgtaaa   3900
ccaaaatact atgcccctta atactttata agcagcattg ttaaatagtt cttacgctta   3960
tacattcaca gaactaccct gttttccttg tatataatga cttttgctgg cagaactgaa   4020
atataaactg taaggggatt tcgtcagttg ctcccagtat acaatatcct ccaggacata   4080
gccagaaatc tccattccac acatgactga gttcctatcc ctgcactggt actggctctt   4140
ttctcctctt tccttgcctc agggttcgtg ctacccactg attcccttta cccttagtaa   4200
taattttgga tcattttctt tcctttaaag gggaacaaag ccttttttt ttttgagacg   4260
gagtgttgct ctgtcaccca agctggagtg cagtggcacg atcttggctc actccaacct   4320
ccaccttcca ggttcaagtg attctcctgc ctcagcctcc cgagtagctg ggactacggg   4380
cacgcaccac cacgtctggc taatttttgt atttttagta gagatggggt ttcaccctat   4440
tggtcaggct ggtcttgaat tcctcacctc aggtcatccg cctgtctcgg cctcccgaag   4500
tgctgggatt ataggtgtga gccaccgcac ccagttggga acaaagcctt tttaacacac   4560
gtaagggccc tcaaaccgtg ggacctctaa ggagaccttt gaagcttttt gagggcaaac   4620
tttacctttg tggtccccaa atgatggcat ttctctttga aatttattag atactgttat   4680
gtcccccaag ggtacaggag gggcatccct cagcctatgg gaacacccaa actaggaggg   4740
gttattgaca ggaaggaatg aatccaagtg aaggctttct gctcttcgtg ttacaaacca   4800
gtttcagagt tagctttctg gggaggtgtg tgtttgtgaa aggaattcaa gtgttgcagg   4860
```

acagatgagc tcaaggtaag gtagctttgg cagcagggct gatactatga ggctgaaaca 4920
atccttgtga tgaagtagat catgcagtga catacaaaga ccaaggatta tgtatatttt 4980
tatatctctg tggttttgaa actttagtac ttagaatttt ggccttctgc actactcttt 5040
tgctcttacg aacataatgg actcttaaga atggaaaggg atgacattta cctatgtgtg 5100
ctgcctcatt cctggtgaag caactgctac ttgttctcta tgcctctaaa atgatgctgt 5160
tttctctgct aaaggtaaaa gaaaagaaaa aaatagttgg aaaataagac atgcaacttg 5220
atgtgctttt gagtaaattt atgcagcaga aactatacaa tgaaggaaga attctatgga 5280
aattacaaat ccaaaactct atgatgatgt cttcctaggg agtagagaaa ggcagtgaaa 5340
tggcagttag accaacagag gcttgaagga ttcaagtaca agtaatattt tgtataaaac 5400
atagcagttt aggtccccat aatcctcaaa aatagtcaca aatataacaa agttcattgt 5460
tttagggttt ttaaaaaacg tgttgtacct aaggccatac ttactcttct atgctatcac 5520
tgcaaagggg tgatatgtat gtattatata aaaaaaaaaa cccttaatgc actgttatct 5580
cctaaatatt tagtaaatta atactattta atttttttaa agatttgtct gtgtagacac 5640
taaaagtatt acacaaaatc tggactgaag gtgtcctttt taacaacaat ttaaagtact 5700
ttttatatat gttatgtagt atatcctttc taaactgcct agtttgtata ttcctataat 5760
tcctatttgt gaagtgtacc tgttcttgtc tctttttttca gtcattttct gcacgcatcc 5820
ccctttatat ggttatagag atgactgtag cttttcgtgc tccactgcga ggtttgtgct 5880
cagagccgct gcaccccagc gaggcctgct ccatggagtg caggacgagc tactgctttg 5940
gagcgagggt ttcctgcttt tgagttgacc tgacttcctt cttgaaatga ctgttaaaac 6000
taaaataaat tacattgcat ttattttata ttcttggttg aaataaaatt taattgactt 6060
tg 6062

<210> SEQ ID NO 15
<211> LENGTH: 6016
<212> TYPE: DNA
<213> ORGANISM: Homo sapiens

<400> SEQUENCE: 15
agaaaagaaa caagctgcgg tacaactgtc ctcaccagcc ctcgcctccc gagtcactgc 60
agccaaccct tcagcaagaa aagatgaaaa ggaatatgca ttgaagcaaa ttgaaggcac 120
aggaatatcc atgtcggctt gtagagagat tgcacttttg cgagaattga agcaccctaa 180
tgtgattgca ttgcagaagg tgttcctttc tcacagtgac aggaaggtat ggctgctgtt 240
tgattatgca gagcatgact tgtggcatat tattaagttt caccgtgcat caaaagcaaa 300
taaaaagccc atgcagttgc caagatctat ggttaaatcc ttactttacc agattcttga 360
tggtatccat tacctccatg caaattgggt gcttcacaga gacttgaaac cagcaaatat 420
cctagtaatg ggagaaggtc ctgagagggg gagagtcaaa atagctgaca tgggttttgc 480
cagattattc aattctcctc taaagccact agcagatttg gatccagtag ttgtgacatt 540
ttggtatcgg gctccagaac ttttgcttgg tgcaaggcat tatacaaagg ccattgatat 600
atgggcaata ggttgtatat ttgctgaatt gttgacttcg gaacctattt ttcactgtcg 660
tcaggaagat ataaaaacaa gcaatccctt tcatcatgat caactggatc ggatatttag 720
tgtcatgggg tttcctgcag ataaagactg ggaagatatt agaaagatgc cagaatatcc 780
cacacttcaa aaagacttta gaagaacaac gtatgccaac agtagcctca taaagtacat 840

-continued

```
ggagaaacac aaggtcaagc ctgacagcaa agtgttcctc ttgcttcaga aactcctgac    900
catggatcca accaagagaa ttacctcgga gcaagctctg caggatccct attttcagga    960
ggaccctttg ccaacattag atgtatttgc cggctgccag attccatacc ccaaacgaga   1020
attccttaat gaagatgatc ctgaagaaaa aggtgacaag aatcagcaac agcagcagaa   1080
ccagcatcag cagcccacag cccctccaca gcaggcagca gcccctccac aggcgccccc   1140
accacagcag aacagcaccc agaccaacgg gaccgcaggt ggggctgggg ccggggtcgg   1200
gggcaccgga gcagggttgc agcacagcca ggactccagc ctgaaccagg tgcctccaaa   1260
caagaagcca cggctagggc cttcaggcgc aaactcaggt ggacctgtga tgccctcgga   1320
ttatcagcac tccagttctc gcctgaatta ccaaagcagc gttcagggat cctctcagtc   1380
ccagagcaca cttggctact cttcctcgtc tcagcagagc tcacagtacc acccatctca   1440
ccaggcccac cggtactgac cagctcccgt tgggccaggc cagcccagcc cagagcacag   1500
gctccagcaa tatgtctgca ttgaaaagaa ccaaaaaaat gcaaactatg atgccattta   1560
aaactcatac acatgggagg aaaaccttat atactgagca ttgtgcagga ctgatagctc   1620
ttctttattg acttaaagaa gattcttgtg aagtttcccc agcacccctt ccctgcatgt   1680
gttccattgt gacttctctg ataaagcgtc tgatctaatc ccagcacttc tgtaaccttc   1740
agcatttctt tgaaggattt cctggtgcac ctttctcatg ctgtagcaat cactatggtt   1800
tatcttttca aagctctttt aataggattt taatgtttta gaaacaggat tccagtggtg   1860
tatagtttta tacttcatga actgatttag caacacaggt aaaaatgcac cttttaaagc   1920
actacgtttt cacagacaat aactgttctg ctcatggaag tcttaaacag aaactgttac   1980
tgtcccaaag tactttacta ttacgttcgt atttatctag tttcagggaa ggtctaataa   2040
aaagacaagc ggtgggacag agggaaccta caaccaaaaa ctgcctagat ctttgcagtt   2100
atgtgcttta tgccacgaag aactgaagta tgtggtaatt tttatagaat cattcatatg   2160
gaactgagtt cccagcatca tcttattctg aatagcattc agtaattaag aattacaatt   2220
ttaaccttca tgtagctaag tctaccttaa aaagggtttc aagagctttg tacagtctcg   2280
atggcccaca ccaaaacgct gaagagagta acaactgcac taggatttct gtaaggagta   2340
attttgatca aaagacgtgt tacttccctt tgaaggaaaa gtttttagtg tgtattgtac   2400
ataaagtcgg cttctctaaa gaaccattgg tttcttcaca tctgggtctg cgtgagtaac   2460
tttcttgcat aatcaaggtt actcaagtag aagcctgaaa attaatctgc ttttaaaata   2520
aagagcagtg ttctccattc gtatttgtat tagatataga gtgactattt ttaaagcatg   2580
ttaaaaattt aggttttatt catgtttaaa gtatgtatta tgtatgcata attttgctgt   2640
tgttactgaa acttaattct atcaagaatc tttttcattg cactgaatga tttcttttgc   2700
ccctaggaga aaacttaata attgtgccta aaaactatgg gcggatagta taagactata   2760
ctagacaaag tgaatatttg catttccatt atctatgaat tagtggctga gttctttctt   2820
agctgcttta aggagcccct cactccccag agtcaaaagg aaatgtaaaa acttagagct   2880
cccattgtaa tgtaaggggc aagaaatttg tgttcttctg aatgctacta gcagcaccag   2940
ccttgtttta aatgttttct tgagctagaa gaaatagctg attattgtat atgcaaatta   3000
catgcatttt taaaaactat tctttctgaa cttatctacc tggttatgat actgtgggtc   3060
catacacaag taaaataaga ttagacagaa gccagtatac attttgcact attgatgtga   3120
tactgtagcc agccaggacc ttactgatct cagcataata atgctcacta ataatgaagt   3180
ctgcatagtg acactcatca agactgaaga tgaagcaggt tacgtgctcc attggaagga   3240
```

gtttctgata gtctcctgct gttttacccc ttccattttt taaaataaga aattagcagc 3300
cctctgcata atgtagctgc ctatatgcag ttttatcctg tgccctaaag cctcactgtc 3360
cagagctgtt ggtcatcaga tgcttattgc accctcacca tgtgcctggt gccctgctgg 3420
gtagagaaca cagaggacag ggcatacttc ttgtccttaa ggagcttgtg atctgtgaca 3480
gtaagccctc ctgggatgtc tgtgccatgt gattgactta caagtgaaac tgtcttataa 3540
tatgaaggtc tttttgttta cttctaaacc cacttgggta gttactatcc ccaaatctgt 3600
tctgtaaata atattatgga agggtttcta tgtcagtcta ccttagagaa agccagtgat 3660
tcaatatcac aaaaggcatt gacgtatctt tgaaatgttc acagcagcct tttaacaaca 3720
actgggtggt ccttgtaggc agaacatact ctcctaagtg gttgtaggaa attgcaagga 3780
aaatagaagg tctgttcttg ctctcaagga ggttaccttt aataaaagaa gacaaaccca 3840
gatagatatg taaaccaaaa tactatgccc cttaatactt tataagcagc attgttaaat 3900
agttcttacg cttatacatt cacagaacta ccctgttttc cttgtatata atgacttttg 3960
ctggcagaac tgaaatataa actgtaaggg gatttcgtca gttgctccca gtatacaata 4020
tcctccagga catagccaga aatctccatt ccacacatga ctgagttcct atccctgcac 4080
tggtactggc tcttttctcc tctttccttg cctcagggtt cgtgctaccc actgattccc 4140
tttaccctta gtaataattt tggatcattt tctttccttt aaaggggaac aaagcctttt 4200
tttttttgga gacggagtgt tgctctgtca cccaagctgg agtgcagtgg cacgatcttg 4260
gctcactcca acctccacct tccaggttca agtgattctc ctgcctcagc ctcccgagta 4320
gctgggacta cgggcacgca ccaccacgtc tggctaattt ttgtattttt agtagagatg 4380
gggtttcacc ctattggtca ggctggtctt gaattcctca cctcaggtca tccgcctgtc 4440
tcggcctccc gaagtgctgg gattataggt gtgagccacc gcacccagtt gggaacaaag 4500
cctttttaac acacgtaagg gccctcaaac cgtgggacct ctaaggagac ctttgaagct 4560
ttttgagggc aaactttacc tttgtggtcc ccaaatgatg gcatttctct ttgaaattta 4620
ttagatactg ttatgtcccc caagggtaca ggaggggcat ccctcagcct atgggaacac 4680
ccaaactagg aggggttatt gacaggaagg aatgaatcca agtgaaggct ttctgctctt 4740
cgtgttacaa accagtttca gagttagctt tctggggagg tgtgtgtttg tgaaaggaat 4800
tcaagtgttg caggacagat gagctcaagg taaggtagct ttggcagcag ggctgatact 4860
atgaggctga aacaatcctt gtgatgaagt agatcatgca gtgacataca aagaccaagg 4920
attatgtata tttttatatc tctgtggttt tgaaacttta gtacttagaa ttttggcctt 4980
ctgcactact cttttgctct tacgaacata atggactctt aagaatggaa agggatgaca 5040
tttacctatg tgtgctgcct cattcctggt gaagcaactg ctacttgttc tctatgcctc 5100
taaaatgatg ctgttttctc tgctaaaggt aaaagaaaag aaaaaaatag ttggaaaata 5160
agacatgcaa cttgatgtgc ttttgagtaa atttatgcag cagaaactat acaatgaagg 5220
aagaattcta tggaaattac aaatccaaaa ctctatgatg atgtcttcct agggagtaga 5280
gaaaggcagt gaaatggcag ttagaccaac agaggcttga aggattcaag tacaagtaat 5340
attttgtata aaacatagca gtttaggtcc ccataatcct caaaaatagt cacaaatata 5400
acaaagttca ttgttttagg gtttttaaaa aacgtgttgt acctaaggcc atacttactc 5460
ttctatgcta tcactgcaaa ggggtgatat gtatgtatta tataaaaaaa aaaacccctta 5520
atgcactgtt atctcctaaa tatttagtaa attaatacta tttaattttt ttaaagattt 5580

-continued

```
gtctgtgtag acactaaaag tattacacaa aatctggact gaaggtgtcc tttttaacaa   5640
caatttaaag tactttttat atatgttatg tagtatatcc tttctaaact gcctagtttg   5700
tatattccta taattcctat ttgtgaagtg tacctgttct tgtctctttt ttcagtcatt   5760
ttctgcacgc atccccccttt atatggttat agagatgact gtagcttttc gtgctccact   5820
gcgaggtttg tgctcagagc cgctgcaccc cagcgaggcc tgctccatgg agtgcaggac   5880
gagctactgc tttggagcga gggtttcctg cttttgagtt gacctgactt ccttcttgaa   5940
atgactgtta aaactaaaat aaattacatt gcatttattt tatattcttg gttgaaataa   6000
aatttaattg actttg                                                   6016
```

```
<210> SEQ ID NO 16
<211> LENGTH: 3101
<212> TYPE: DNA
<213> ORGANISM: Homo sapiens

<400> SEQUENCE: 16

gagtgccctc cctcctcctc tctttgagga ggtaccggct gttgtgcggc tctgcccttc     60
tgtttgagtg tatgggagag tgagtgagtg agtgagtgtg agcgtgtgtg tgagagcgtg    120
aggcgtgagt gcgcgtgtga gaggacgaga gcccgcctgg ccgccccgcc gctcccgccg    180
cagcaggagc agaacgcgcg gccggagaga gcggcggagc cggcgcccag ggagcccgcg    240
gggacaaggg cagagacacc gctccccacc cccagccctc gtccctcggc tctccttcgc    300
cgggggatcc tccccgttcc tccacccccg gccggcctct gccccgccgt ccccctggat    360
gtccctggcg ctttcgcggg gcctcctcct gctcttgccg catcagtcgg gctggtgctg    420
cggccggcgg gcgtagagcg ggcgggttcc cgggggctgc ggctgcccgt gcttccccgg    480
tccccacccc tgccccccgg ccccccgacc cagctctccg gcctcagagg ctgtgacaat    540
ggactatgac tttaaagtga agctgagcag cgagcgggag cgggtcgagg acctgtttga    600
atacgagggc tgcaaagttg gccgaggcac ttatggtcac gtctacaaag ccaagaggaa    660
agatgggaag gatgataaag actatgcttt aaaacaaata gaaggaactg ggatctctat    720
gtcggcatgt agagaaatag cattacttcg agagcttaag catccaaacg tcatttctct    780
tcaaaaggtg tttctgtctc atgctgatag gaaggtgtgg cttctgtttg actatgctga    840
acatgacctc tggcatataa tcaagtttca cagagcttct aaagcaaaca agaagccagt    900
tcagttacct cggggaatgg tgaagtcact attatatcag atcctagatg gtattcacta    960
cctgcatgct aactgggtgt tgcacagaga tttgaaacct gctaatattt tagttatggg   1020
tgaaggtcct gagcgaggaa gagtaaaaat tgctgacatg ggctttgccc gattatttaa   1080
ttcacctttg aagcctttag cagatttgga tccagtggtt gttacattct ggtaccgagc   1140
ccctgaacta cttcttggag caaggcatta taccaaagct attgatattt gggctatagg   1200
gtgtatattt gcagaactac taacgtcaga accaatattt cactgtcgac aagaggacat   1260
caaaactagt aatccttatc accatgacca gctggacaga atattcaatg taatgggatt   1320
tcctgcagat aaagattggg aagatataaa aaagatgcct gaacattcaa cattaatgaa   1380
agatttcaga agaaatacgt ataccaactg cagccttatc aagtatatgg aaaaacataa   1440
agttaaacca gatagtaaag cattccactt gcttcagaag ctgcttacca tggacccaat   1500
aaagcgaatt acctcagaac aggctatgca ggacccctat ttcttagaag acccacttcc   1560
tacatcagac gtttttgccg gttgtcaaat ccccttaccca aaacgagaat tttaacgga   1620
agaagaacct gatgacaaag gagacaaaaa gaaccagcag cagcagcagg gcaataacca   1680
```

-continued

```
cactaatgga actggccacc cagggaatca agacagcagt cacacacagg gacccccgtt   1740
gaagaaagtg agagttgttc ctcctaccac tacctcaggt ggacttatca tgacctcaga   1800
ctatcagcgt tccaatccac atgctgccta tcccaaccct ggaccaagca catcacagcc   1860
gcagagcagc atgggatact cagctacctc ccagcagcct ccacagtact cacatcagac   1920
acatcggtac tgagctgcat cggaatcttg tccatgcact gttgcgaatg ctgcagggct   1980
gactgtgcag ctctctgcgg gaacctggta tgggccatga gaatgtactg tacaaccaca   2040
tcttcaaaat gtccagtagc caagttccac cacttttcac agattggggt agtggcttcc   2100
aagttgtacc tattttggag ttagacttga aaagaaagtg ctagcacagt ttgtgttgtg   2160
gatttgctac ttccatagtt tacttgacat ggttcagact gaccaatgca tttttttcag   2220
tgacagtctg tagcagttga agctgtgaat gtgctagggg caagcatttg tctttgtatg   2280
tggtgaattt tttcagtgta acaacattat ctgaccaata gtacacacac agacacaaag   2340
tttaactggt acttgaaaca tacagtatat gttaacgaaa taaccaagac tcgaaatgag   2400
attattttgg tacacctttc tttttagtgt cttatcagtg ggctgattca ttttctacat   2460
taatcagtgt tttctgacca agaatattgc ttggattttt ttgaaagtac aaaaagccac   2520
atagtttttc cagaaaggtt tcaaaactcc caaagattaa cttccaactt ataagtttgt   2580
ttttattttc aatctatgac ttgactggta ttaaagctgc tatttgatag taattaaata   2640
tgttgtcatt gatataaacc tgtttggttc agcaaacaaa ctaaaatgat tgtcatagac   2700
agtgttttat ttttcctgtt ggtgttgctg atttgtgagc atgctttaag atgaaaaaag   2760
catgaatgat aacttcctta aaaaggtgcg gcatccaatt caaatatttt cgtcctgatt   2820
ttaaagctgg ttggtgtagt gctattaaaa tttcgttcag ttaattttcc ttttgaaaac   2880
ttgttcgcac gttgtttagg gtgcccttac ttcagcaaag gagaaggagt aggagagcct   2940
tagaattttt gaggaaaaaa aaacctataa catacaatgt actgtatcaa actattttac   3000
atgaatgaca caagtattct gaataaaaaa taattgaaca ttgttaaaaa caaggtgtta   3060
tgtaataaat ttatttttca taaatcaaaa aaaaaaaaaa a                       3101
```

<210> SEQ ID NO 17
<211> LENGTH: 3098
<212> TYPE: DNA
<213> ORGANISM: Homo sapiens

<400> SEQUENCE: 17

```
gagtgccctc cctcctcctc tctttgagga ggtaccggct gttgtgcggc tctgcccttc     60
tgtttgagtg tatgggagag tgagtgagtg agtgagtgtg agcgtgtgtg tgagagcgtg    120
aggcgtgagt gcgcgtgtga gaggacgaga gcccgcctgg ccgccccgcc gctcccgccg    180
cagcaggagc agaacgcgcg gccggagaga gcggcggagc cggcgcccag ggagcccgcg    240
gggacaaggg cagagacacc gctccccacc cccagccctc gtccctcggc tctccttcgc    300
cgggggatcc tccccgttcc tccacccccg gccggcctct gccccgccgt ccccctggat    360
gtccctggcg ctttcgcggg gcctcctcct gctcttgccg catcagtcgg gctggtgctg    420
cggccggcgg gcgtagagcg ggcgggttcc cgggggctgc ggctgcccgt gcttccccgg    480
tccccacccc tgcccccccgg ccccccgacc cagctctccg gcctcagagg ctgtgacaat    540
ggactatgac tttaaagtga agctgagcag cgagcgggag cgggtcgagg acctgtttga    600
atacgagggc tgcaaagttg gccgaggcac ttatggtcac gtctacaaag ccaagaggaa    660
```

-continued

```
agatgggaag gatgataaag actatgcttt aaaacaaata gaaggaactg ggatctctat    720
gtcggcatgt agagaaatag cattacttcg agagcttaag catccaaacg tcatttctct    780
tcaaaaggtg tttctgtctc atgctgatag gaaggtgtgg cttctgtttg actatgctga    840
acatgacctc tggcatataa tcaagtttca cagagcttct aaagcaaaca agaagccagt    900
tcagttacct cggggaatgg tgaagtcact attatatcag atcctagatg gtattcacta    960
cctgcatgct aactgggtgt tgcacagaga tttgaaacct gctaatattt tagttatggg   1020
tgaaggtcct gagcgaggaa gagtaaaaat tgctgacatg ggctttgccc gattatttaa   1080
ttcacctttg aagcctttag cagatttgga tccagtggtt gttacattct ggtaccgagc   1140
ccctgaacta cttcttggag caaggcatta taccaaagct attgatattt gggctatagg   1200
gtgtatattt gcagaactac taacgtcaga accaatattt cactgtcgac aagaggacat   1260
caaaactagt aatccttatc accatgacca gctggacaga atattcaatg taatgggatt   1320
tcctgcagat aaagattggg aagatataaa aaagatgcct gaacattcaa cattaatgaa   1380
agatttcaga agaaatacgt ataccaactg cagccttatc aagtatatgg aaaaacataa   1440
agttaaacca gatagtaaag cattccactt gcttcagaag ctgcttacca tggacccaat   1500
aaagcgaatt acctcagaac aggctatgca ggacccctat ttcttagaag acccacttcc   1560
tacatcagac gtttttgccg gttgtcaaat cccttaccca aaacgagaat ttttaacgga   1620
agaagaacct gatgacaaag gagacaaaaa ccagcagcag cagcagggca ataaccacac   1680
taatggaact ggccacccag ggaatcaaga cagcagtcac acacagggac ccccgttgaa   1740
gaaagtgaga gttgttcctc ctaccactac ctcaggtgga cttatcatga cctcagacta   1800
tcagcgttcc aatccacatg ctgcctatcc caaccctgga ccaagcacat cacagccgca   1860
gagcagcatg ggatactcag ctacctccca gcagcctcca cagtactcac atcagacaca   1920
tcggtactga gctgcatcgg aatcttgtcc atgcactgtt gcgaatgctg cagggctgac   1980
tgtgcagctc tctgcgggaa cctggtatgg gccatgagaa tgtactgtac aaccacatct   2040
tcaaaatgtc cagtagccaa gttccaccac ttttcacaga ttggggtagt ggcttccaag   2100
ttgtacctat tttggagtta gacttgaaaa gaaagtgcta gcacagtttg tgttgtggat   2160
ttgctacttc catagtttac ttgacatggt tcagactgac caatgcattt ttttcagtga   2220
cagtctgtag cagttgaagc tgtgaatgtg ctaggggcaa gcatttgtct ttgtatgtgg   2280
tgaatttttt cagtgtaaca acattatctg accaatagta cacacacaga cacaaagttt   2340
aactggtact tgaaacatac agtatatgtt aacgaaataa ccaagactcg aaatgagatt   2400
attttggtac acctttcttt ttagtgtctt atcagtgggc tgattcattt tctacattaa   2460
tcagtgtttt ctgaccaaga atattgcttg gatttttttg aaagtacaaa aagccacata   2520
gtttttccag aaaggtttca aaactcccaa agattaactt ccaacttata agtttgtttt   2580
tattttcaat ctatgacttg actggtatta aagctgctat ttgatagtaa ttaaatatgt   2640
tgtcattgat ataaacctgt ttggttcagc aaacaaacta aaatgattgt catagacagt   2700
gttttatttt tcctgttggt gttgctgatt tgtgagcatg ctttaagatg aaaaaagcat   2760
gaatgataac ttccttaaaa aggtgcggca tccaattcaa atattttcgt cctgatttta   2820
aagctggttg gtgtagtgct attaaaattt cgttcagtta attttccttt tgaaaacttg   2880
ttcgcacgtt gtttagggtg cccttacttc agcaaaggag aaggagtagg agagccttag   2940
aatttttgag gaaaaaaaaa cctataacat acaatgtact gtatcaaact attttacatg   3000
aatgacacaa gtattctgaa taaaaaataa ttgaacattg ttaaaaacaa ggtgttatgt   3060
```

aataaattta tttttcataa atcaaaaaaa aaaaaaaa 3098

<210> SEQ ID NO 18
<211> LENGTH: 3043
<212> TYPE: DNA
<213> ORGANISM: Homo sapiens

<400> SEQUENCE: 18
gagtgccctc cctcctcctc tctttgagga ggtaccggct gttgtgcggc tctgcccttc 60
tgtttgagtg tatgggagag tgagtgagtg agtgagtgtg agcgtgtgtg tgagagcgtg 120
aggcgtgagt gcgcgtgtga gaggacgaga gcccgcctgg ccgcccccgcc gctcccgccg 180 cagcaggagc agaacgcgcg gccggagaga gcggcggagc cggcgcccag ggagcccgcg 240
gggacaaggg cagagacacc gctccccacc cccagccctc gtccctcggc tctccttcgc 300
cgggggatcc tccccgttcc tccacccccg gccggcctct gccccgccgt ccccctggat 360
gtccctggcg ctttcgcggg gcctcctcct gctcttgccg catcagtcgg gctggtgctg 420
cggccggcgg gcgtagagcg ggcgggttcc cgggggctgc ggctgcccgt gcttccccgg 480
tccccacccc tgccccccgg ccccccgacc cagctctccg gcctcagagg ctgtgacaat 540
ggactatgac tttaaagtga agctgagcag cgagcgggag cgggtcgagg acctgtttga 600
atacgagggc tgcaaagttg gccgaggcac ttatggtcac gtctacaaag ccaagaggaa 660
agatgggaag gatgataaag actatgcttt aaaacaaata gaaggaactg ggatctctat 720
gtcggcatgt agagaaatag cattacttcg agagcttaag catccaaacg tcatttctct 780
tcaaaaggtg tttctgtctc atgctgatag gaaggtgtgg cttctgtttg actatgctga 840
acatgacctc tggcatataa tcaagtttca cagagcttct aaagcaaaca agaagccagt 900
tcagttacct cggggaatgg tgaagtcact attatatcag atcctagatg gtattcacta 960
cctgcatgct aactgggtgt tgcacagaga tttgctgaca tgggctttgc ccgattattt 1020
aattcacctt tgaagccttt agcagatttg gatccagtgg ttgttacatt ctggtaccga 1080
gcccctgaac tacttcttgg agcaaggcat tataccaaag ctattgatat ttgggctata 1140
gggtgtatat ttgcagaact actaacgtca gaaccaatat ttcactgtcg acaagaggac 1200
atcaaaacta gtaatcctta tcaccatgac cagctggaca gaatattcaa tgtaatggga 1260
tttcctgcag ataaagattg ggaagatata aaaaagatgc ctgaacattc aacattaatg 1320
aaagatttca gaagaaatac gtataccaac tgcagcctta tcaagtatat ggaaaaacat 1380
aaagttaaac cagatagtaa agcattccac ttgcttcaga agctgcttac catggaccca 1440
ataaagcgaa ttacctcaga acaggctatg caggacccct atttcttaga agacccactt 1500
cctacatcag acgtttttgc cggttgtcaa atcccttacc caaaacgaga atttttaacg 1560
gaagaagaac ctgatgacaa aggagacaaa aagaaccagc agcagcagca gggcaataac 1620
cacactaatg gaactggcca cccagggaat caagacagca gtcacacaca gggacccccg 1680
ttgaagaaag tgagagttgt tcctcctacc actacctcag gtggacttat catgacctca 1740
gactatcagc gttccaatcc acatgctgcc tatcccaacc ctggaccaag cacatcacag 1800
ccgcagagca gcatgggata ctcagctacc tcccagcagc ctccacagta ctcacatcag 1860
acacatcggt actgagctgc atcggaatct tgtccatgca ctgttgcgaa tgctgcaggg 1920
ctgactgtgc agctctctgc gggaacctgg tatgggccat gagaatgtac tgtacaacca 1980
catcttcaaa atgtccagta gccaagttcc accacttttc acagattggg gtagtggctt 2040

-continued

```
ccaagttgta cctattttgg agttagactt gaaaagaaag tgctagcaca gtttgtgttg   2100

tggatttgct acttccatag tttacttgac atggttcaga ctgaccaatg catttttttc   2160

agtgacagtc tgtagcagtt gaagctgtga atgtgctagg ggcaagcatt tgtctttgta   2220

tgtggtgaat tttttcagtg taacaacatt atctgaccaa tagtacacac acagacacaa   2280

agtttaactg gtacttgaaa catacagtat atgttaacga aataaccaag actcgaaatg   2340

agattatttt ggtacacctt tctttttagt gtcttatcag tgggctgatt cattttctac   2400

attaatcagt gttttctgac caagaatatt gcttggattt ttttgaaagt acaaaaaagcc   2460

acatagtttt tccagaaagg tttcaaaact cccaaagatt aacttccaac ttataagttt   2520

gtttttattt tcaatctatg acttgactgg tattaaagct gctatttgat agtaattaaa   2580

tatgttgtca ttgatataaa cctgtttggt tcagcaaaca aactaaaatg attgtcatag   2640

acagtgtttt atttttcctg ttggtgttgc tgatttgtga gcatgcttta agatgaaaaa   2700

agcatgaatg ataacttcct taaaaaggtg cggcatccaa ttcaaatatt ttcgtcctga   2760

ttttaaagct ggttggtgta gtgctattaa aatttcgttc agttaatttt cctttttgaaa   2820

acttgttcgc acgttgttta gggtgccctt acttcagcaa aggagaagga gtaggagagc   2880

cttagaattt ttgaggaaaa aaaaaacctat aacatacaat gtactgtatc aaactatttt   2940

acatgaatga cacaagtatt ctgaataaaa aataattgaa cattgttaaa aacaaggtgt   3000

tatgtaataa atttattttt cataaatcaa aaaaaaaaaa aaa                    3043
```

<210> SEQ ID NO 19
<211> LENGTH: 15
<212> TYPE: DNA
<213> ORGANISM: Homo sapiens

<400> SEQUENCE: 19
gttaatattc atagc 15

<210> SEQ ID NO 20
<211> LENGTH: 29
<212> TYPE: DNA
<213> ORGANISM: Homo sapiens

<400> SEQUENCE: 20
ctccagctcc cgttgggcca ggccagccc 29

<210> SEQ ID NO 21
<211> LENGTH: 29
<212> TYPE: DNA
<213> ORGANISM: Homo sapiens

<400> SEQUENCE: 21
agcccagagc acaggctcca gcaatatgt 29

<210> SEQ ID NO 22
<211> LENGTH: 29
<212> TYPE: DNA
<213> ORGANISM: Homo sapiens

<400> SEQUENCE: 22
ctgcattgaa aagaaccaaa aaaatgcaa 29

<210> SEQ ID NO 23
<211> LENGTH: 29
<212> TYPE: DNA
<213> ORGANISM: Homo sapiens

<400> SEQUENCE: 23
actatgatgc catttctatc taaaactca 29

<210> SEQ ID NO 24
<211> LENGTH: 29
<212> TYPE: DNA
<213> ORGANISM: Homo sapiens

<400> SEQUENCE: 24
tacacatggg aggaaaacct tatatactg 29

<210> SEQ ID NO 25
<211> LENGTH: 29
<212> TYPE: DNA
<213> ORGANISM: Homo sapiens

<400> SEQUENCE: 25
agcattgtgc aggactgata gctcttctt 29

<210> SEQ ID NO 26
<211> LENGTH: 29
<212> TYPE: DNA
<213> ORGANISM: Homo sapiens

<400> SEQUENCE: 26
tattgactta aagaagattc ttgtgaagt 29

<210> SEQ ID NO 27
<211> LENGTH: 29
<212> TYPE: DNA
<213> ORGANISM: Homo sapiens

<400> SEQUENCE: 27
ttcccctatc tcagcacccc ttccctgca 29

<210> SEQ ID NO 28
<211> LENGTH: 29
<212> TYPE: DNA
<213> ORGANISM: Homo sapiens

<400> SEQUENCE: 28
tgtgttccat tgtgacttct ctgataaag 29

<210> SEQ ID NO 29
<211> LENGTH: 29
<212> TYPE: DNA
<213> ORGANISM: Homo sapiens

<400> SEQUENCE: 29
cgtctgatct aatcccagca cttctgtaa 29

<210> SEQ ID NO 30
<211> LENGTH: 29
<212> TYPE: DNA
<213> ORGANISM: Homo sapiens

<400> SEQUENCE: 30
ccttcagcat ttctttgaag gattctatc 29

<210> SEQ ID NO 31
<211> LENGTH: 29
<212> TYPE: DNA

<213> ORGANISM: Homo sapiens

<400> SEQUENCE: 31
tggccgcccc gccgctcccg ccgcagcag 29

<210> SEQ ID NO 32
<211> LENGTH: 29
<212> TYPE: DNA
<213> ORGANISM: Homo sapiens

<400> SEQUENCE: 32
gagcagaacg cgcggccgga gagagcggc 29

<210> SEQ ID NO 33
<211> LENGTH: 29
<212> TYPE: DNA
<213> ORGANISM: Homo sapiens

<400> SEQUENCE: 33
ggagccggcg cccagggagc ccgcgggga 29

<210> SEQ ID NO 34
<211> LENGTH: 29
<212> TYPE: DNA
<213> ORGANISM: Homo sapiens

<400> SEQUENCE: 34
caagggcaga gacaccgctc cccaccccc 29

<210> SEQ ID NO 35
<211> LENGTH: 29
<212> TYPE: DNA
<213> ORGANISM: Homo sapiens

<400> SEQUENCE: 35
agccctcgtc cctcggctct ccttcgccg 29

<210> SEQ ID NO 36
<211> LENGTH: 29
<212> TYPE: DNA
<213> ORGANISM: Homo sapiens

<400> SEQUENCE: 36
ggggatcctc cccgttcctc cacccccgg 29

<210> SEQ ID NO 37
<211> LENGTH: 29
<212> TYPE: DNA
<213> ORGANISM: Homo sapiens

<400> SEQUENCE: 37
ccggcctctg ccccgccgtc cccctggat 29

<210> SEQ ID NO 38
<211> LENGTH: 29
<212> TYPE: DNA
<213> ORGANISM: Homo sapiens

<400> SEQUENCE: 38
gtccctggcg ctttcgcggg gcctcctcc 29

<210> SEQ ID NO 39
<211> LENGTH: 29

<212> TYPE: DNA
<213> ORGANISM: Homo sapiens

<400> SEQUENCE: 39
tgctcttgcc gcatcagtcg ggctggtgc 29

<210> SEQ ID NO 40
<211> LENGTH: 29
<212> TYPE: DNA
<213> ORGANISM: Homo sapiens

<400> SEQUENCE: 40
tgcggccggc gggcgtagag cgggcgggt 29

<210> SEQ ID NO 41
<211> LENGTH: 180
<212> TYPE: DNA
<213> ORGANISM: Homo sapiens

<400> SEQUENCE: 41
tgtggccgcc gaggagtccc ttgctgaagg cggaccgcgg agcggcgggc ggcgggcggc 60
gcgcgcgcgc gcgcgagagg cggctgttgg agaagtggag cggcggtcgc ggggggagga 120
ggaggaggga ctgagcggcg gcggcccccg cgtcccgtgc ctctatgggg gaagcagaca 180

<210> SEQ ID NO 42
<211> LENGTH: 4557
<212> TYPE: DNA
<213> ORGANISM: Homo sapiens

<400> SEQUENCE: 42
ccagctcccg ttgggccagg ccagcccagc ccagagcaca ggctccagca atatgtctgc 60
attgaaaaga accaaaaaaa tgcaaactat gatgccattt aaaactcata cacatgggag 120
gaaaacctta tatactgagc attgtgcagg actgatagct cttctttatt gacttaaaga 180
agattcttgt gaagtttccc cagcacccct tccctgcatg tgttccattg tgacttctct 240
gataaagcgt ctgatctaat cccagcactt ctgtaacctt cagcatttct ttgaaggatt 300
tcctggtgca cctttctcat gctgtagcaa tcactatggt ttatcttttc aaagctcttt 360
taataggatt ttaatgtttt agaaacagga ttccagtggt gtatagtttt atacttcatg 420
aactgattta gcaacacagg taaaaatgca ccttttaaag cactacgttt tcacagacaa 480
taactgttct gctcatggaa gtcttaaaca gaaactgtta ctgtcccaaa gtactttact 540
attacgttcg tatttatcta gtttcaggga aggtctaata aaaagacaag cggtgggaca 600
gagggaacct acaaccaaaa actgcctaga tctttgcagt tatgtgcttt atgccacgaa 660
gaactgaagt atgtggtaat ttttatagaa tcattcatat ggaactgagt tcccagcatc 720
atcttattct gaatagcatt cagtaattaa gaattacaat tttaaccttc atgtagctaa 780
gtctacctta aaaagggttt caagagcttt gtacagtctc gatggcccac accaaaacgc 840
tgaagagagt aacaactgca ctaggatttc tgtaaggagt aattttgatc aaaagacgtg 900
ttacttccct ttgaaggaaa agtttttagt gtgtattgta cataaagtcg gcttctctaa 960
agaaccattg gtttcttcac atctgggtct gcgtgagtaa ctttcttgca taatcaaggt 1020
tactcaagta gaagcctgaa aattaatctg cttttaaaat aaagagcagt gttctccatt 1080
cgtatttgta ttagatatag agtgactatt tttaaagcat gttaaaaatt taggttttat 1140
tcatgtttaa agtatgtatt atgtatgcat aattttgctg ttgttactga aacttaattc 1200

-continued

```
tatcaagaat cttttcatt gcactgaatg atttcttttg cccctaggag aaaacttaat   1260
aattgtgcct aaaaactatg ggcggatagt ataagactat actagacaaa gtgaatattt   1320
gcatttccat tatctatgaa ttagtggctg agttctttct tagctgcttt aaggagcccc   1380
tcactcccca gagtcaaaag gaaatgtaaa aacttagagc tcccattgta atgtaagggg   1440
caagaaattt gtgttcttct gaatgctact agcagcacca gccttgtttt aaatgttttc   1500
ttgagctaga agaaatagct gattattgta tatgcaaatt acatgcattt ttaaaaacta   1560
ttctttctga acttatctac ctggttatga tactgtgggt ccatacacaa gtaaaataag   1620
attagacaga agccagtata cattttgcac tattgatgtg atactgtagc cagccaggac   1680
cttactgatc tcagcataat aatgctcact aataatgaag tctgcatagt gacactcatc   1740
aagactgaag atgaagcagg ttacgtgctc cattggaagg agtttctgat agtctcctgc   1800
tgttttaccc cttccatttt ttaaaataag aaattagcag ccctctgcat aatgtagctg   1860
cctatatgca gttttatcct gtgccctaaa gcctcactgt ccagagctgt tggtcatcag   1920
atgcttattg caccctcacc atgtgcctgg tgccctgctg ggtagagaac acagaggaca   1980
gggcatactt cttgtcctta aggagcttgt gatctgtgac agtaagccct cctgggatgt   2040
ctgtgccatg tgattgactt acaagtgaaa ctgtcttata atatgaaggt ctttttgttt   2100
acttctaaac ccacttgggt agttactatc cccaaatctg ttctgtaaat aatattatgg   2160
aagggtttct atgtcagtct accttagaga aagccagtga ttcaatatca caaaaggcat   2220
tgacgtatct ttgaaatgtt cacagcagcc ttttaacaac aactgggtgg tccttgtagg   2280
cagaacatac tctcctaagt ggttgtagga aattgcaagg aaaatagaag gtctgttctt   2340
gctctcaagg aggttacctt taataaaaga agacaaaccc agatagatat gtaaaccaaa   2400
atactatgcc ccttaatact ttataagcag cattgttaaa tagttcttac gcttatacat   2460
tcacagaact accctgtttt ccttgtatat aatgactttt gctggcagaa ctgaaatata   2520
aactgtaagg ggatttcgtc agttgctccc agtatacaat atcctccagg acatagccag   2580
aaatctccat tccacacatg actgagttcc tatccctgca ctggtactgg ctcttttctc   2640
ctctttcctt gcctcagggt tcgtgctacc cactgattcc ctttaccctt agtaataatt   2700
ttggatcatt ttctttcctt taaaggggaa caaagccttt tttttttttg agacggagtg   2760
ttgctctgtc acccaagctg gagtgcagtg gcacgatctt ggctcactcc aacctccacc   2820
ttccaggttc aagtgattct cctgcctcag cctcccgagt agctgggact acgggcacgc   2880
accaccacgt ctggctaatt tttgtatttt tagtagagat ggggtttcac cctattggtc   2940
aggctggtct tgaattcctc acctcaggtc atccgcctgt ctcggcctcc cgaagtgctg   3000
ggattatagg tgtgagccac cgcacccagt tgggaacaaa gcctttttaa cacacgtaag   3060
ggccctcaaa ccgtgggacc tctaaggaga cctttgaagc tttttgaggg caaactttac   3120
ctttgtggtc cccaaatgat ggcatttctc tttgaaattt attagatact gttatgtccc   3180
ccaagggtac aggaggggca tccctcagcc tatgggaaca cccaaactag gaggggttat   3240
tgacaggaag gaatgaatcc aagtgaaggc tttctgctct tcgtgttaca aaccagtttc   3300
agagttagct ttctggggag gtgtgtgttt gtgaaaggaa ttcaagtgtt gcaggacaga   3360
tgagctcaag gtaaggtagc tttggcagca gggctgatac tatgaggctg aaacaatcct   3420
tgtgatgaag tagatcatgc agtgacatac aaagaccaag gattatgtat atttttatat   3480
ctctgtggtt ttgaaacttt agtacttaga attttggcct tctgcactac tcttttgctc   3540
ttacgaacat aatggactct taagaatgga aagggatgac atttacctat gtgtgctgcc   3600
```

-continued tcattcctgg tgaagcaact gctacttgtt ctctatgcct ctaaaatgat gctgttttct 3660
ctgctaaagg taaaagaaaa gaaaaaaata gttggaaaat aagacatgca acttgatgtg 3720
cttttgagta aatttatgca gcagaaacta tacaatgaag gaagaattct atggaaatta 3780
caaatccaaa actctatgat gatgtcttcc tagggagtag agaaaggcag tgaaatggca 3840
gttagaccaa cagaggcttg aaggattcaa gtacaagtaa tattttgtat aaaacatagc 3900
agtttaggtc cccataatcc tcaaaaatag tcacaaatat aacaaagttc attgttttag 3960
ggtttttaaa aaacgtgttg tacctaaggc catacttact cttctatgct atcactgcaa 4020
aggggtgata tgtatgtatt atataaaaaa aaaaaccctt aatgcactgt tatctcctaa 4080
atatttagta aattaatact atttaatttt tttaaagatt tgtctgtgta gacactaaaa 4140
gtattacaca aaatctggac tgaaggtgtc ctttttaaca acaatttaaa gtacttttta 4200
tatatgttat gtagtatatc ctttctaaac tgcctagttt gtatattcct ataattccta 4260
tttgtgaagt gtacctgttc ttgtctcttt tttcagtcat tttctgcacg catcccccctt 4320 tatatggtta tagagatgac tgtagctttt cgtgctccac tgcgaggttt gtgctcagag 4380
ccgctgcacc ccagcgaggc ctgctccatg gagtgcagga cgagctactg ctttggagcg 4440
agggtttcct gcttttgagt tgacctgact tccttcttga aatgactgtt aaaactaaaa 4500
taaattacat tgcatttatt ttatattctt ggttgaaata aaatttaatt gactttg 4557

<210> SEQ ID NO 43
<211> LENGTH: 503
<212> TYPE: DNA
<213> ORGANISM: Homo sapiens

<400> SEQUENCE: 43
cggctgttgt gcggctctgc ccttctgttt gagtgtatgg gagagtgagt gagtgagtga 60
gtgtgagcgt gtgtgtgaga gcgtgaggcg tgagtgcgcg tgtgagagga cgagagcccg 120
cctggccgcc ccgccgctcc cgccgcagca ggagcagaac gcgcggccgg agagagcggc 180
ggagccggcg cccagggagc ccgcggggac aagggcagag acaccgctcc ccaccccccag 240 ccctcgtccc tcggctctcc ttcgccgggg gatcctcccc gttcctccac ccccggccgg 300
cctctgcccc gccgtccccc tggatgtccc tggcgctttc gcggggcctc ctcctgctct 360
tgccgcatca gtcgggctgg tgctgcggcc ggcgggcgta gagcgggcgg gttcccgggg 420
gctgcggctg cccgtgcttc cccggtcccc acccctgccc cccggccccc cgacccagct 480
ctccggcctc agaggctgtg aca 503

<210> SEQ ID NO 44
<211> LENGTH: 1157
<212> TYPE: DNA
<213> ORGANISM: Homo sapiens

<400> SEQUENCE: 44
gctgcatcgg aatcttgtcc atgcactgtt gcgaatgctg cagggctgac tgtgcagctc 60
tctgcgggaa cctggtatgg gccatgagaa tgtactgtac aaccacatct tcaaaatgtc 120
cagtagccaa gttccaccac ttttcacaga ttggggtagt ggcttccaag ttgtacctat 180
tttggagtta gacttgaaaa gaaagtgcta gcacagtttg tgttgtggat ttgctacttc 240
catagtttac ttgacatggt tcagactgac caatgcattt ttttcagtga cagtctgtag 300
cagttgaagc tgtgaatgtg ctaggggcaa gcatttgtct ttgtatgtgg tgaatttttt 360

-continued

```
cagtgtaaca acattatctg accaatagta cacacacaga cacaaagttt aactggtact    420

tgaaacatac agtatatgtt aacgaaataa ccaagactcg aaatgagatt attttggtac    480

acctttcttt ttagtgtctt atcagtgggc tgattcattt tctacattaa tcagtgtttt    540

ctgaccaaga atattgcttg gatttttttg aaagtacaaa aagccacata gtttttccag    600

aaaggtttca aaactcccaa agattaactt ccaacttata agtttgtttt tattttcaat    660

ctatgacttg actggtatta aagctgctat ttgatagtaa ttaaatatgt tgtcattgat    720

ataaacctgt ttggttcagc aaacaaacta aaatgattgt catagacagt gttttatttt    780

tcctgttggt gttgctgatt tgtgagcatg ctttaagatg aaaaaagcat gaatgataac    840

ttccttaaaa aggtgcggca tccaattcaa atattttcgt cctgatttta aagctggttg    900

gtgtagtgct attaaaattt cgttcagtta attttccttt tgaaaacttg ttcgcacgtt    960

gtttagggtg cccttacttc agcaaaggag aaggagtagg agagccttag aatttttgag   1020

gaaaaaaaaa cctataacat acaatgtact gtatcaaact attttacatg aatgacacaa   1080

gtattctgaa taaaaaataa ttgaacattg ttaaaaacaa ggtgttatgt aataaattta   1140

tttttcataa atcaaaa                                                  1157


<210> SEQ ID NO 45
<211> LENGTH: 502
<212> TYPE: PRT
<213> ORGANISM: Homo sapiens

<400> SEQUENCE: 45

Met Asp Tyr Asp Phe Lys Ala Lys Leu Ala Ala Glu Arg Glu Arg Val
1               5                   10                  15

Glu Asp Leu Phe Glu Tyr Glu Gly Cys Lys Val Gly Arg Gly Thr Tyr
            20                  25                  30

Gly His Val Tyr Lys Ala Arg Arg Lys Asp Gly Lys Asp Glu Lys Glu
        35                  40                  45

Tyr Ala Leu Lys Gln Ile Glu Gly Thr Gly Ile Ser Met Ser Ala Cys
    50                  55                  60

Arg Glu Ile Ala Leu Leu Arg Glu Leu Lys His Pro Asn Val Ile Ala
65                  70                  75                  80

Leu Gln Lys Val Phe Leu Ser His Ser Asp Arg Lys Val Trp Leu Leu
                85                  90                  95

Phe Asp Tyr Ala Glu His Asp Leu Trp His Ile Ile Lys Phe His Arg
            100                 105                 110

Ala Ser Lys Ala Asn Lys Lys Pro Met Gln Leu Pro Arg Ser Met Val
        115                 120                 125

Lys Ser Leu Leu Tyr Gln Ile Leu Asp Gly Ile His Tyr Leu His Ala
    130                 135                 140

Asn Trp Val Leu His Arg Asp Leu Lys Pro Ala Asn Ile Leu Val Met
145                 150                 155                 160

Gly Glu Gly Pro Glu Arg Gly Arg Val Lys Ile Ala Asp Met Gly Phe
                165                 170                 175

Ala Arg Leu Phe Asn Ser Pro Leu Lys Pro Leu Ala Asp Leu Asp Pro
            180                 185                 190

Val Val Val Thr Phe Trp Tyr Arg Ala Pro Glu Leu Leu Leu Gly Ala
        195                 200                 205

Arg His Tyr Thr Lys Ala Ile Asp Ile Trp Ala Ile Gly Cys Ile Phe
    210                 215                 220

Ala Glu Leu Leu Thr Ser Glu Pro Ile Phe His Cys Arg Gln Glu Asp
```

-continued

```
225                 230                 235                 240

Ile Lys Thr Ser Asn Pro Phe His His Asp Gln Leu Asp Arg Ile Phe
                245                 250                 255

Ser Val Met Gly Phe Pro Ala Asp Lys Asp Trp Glu Asp Ile Arg Lys
            260                 265                 270

Met Pro Glu Tyr Pro Thr Leu Gln Lys Asp Phe Arg Arg Thr Thr Tyr
        275                 280                 285

Ala Asn Ser Ser Leu Ile Lys Tyr Met Glu Lys His Lys Val Lys Pro
    290                 295                 300

Asp Ser Lys Val Phe Leu Leu Leu Gln Lys Leu Leu Thr Met Asp Pro
305                 310                 315                 320

Thr Lys Arg Ile Thr Ser Glu Gln Ala Leu Gln Asp Pro Tyr Phe Gln
                325                 330                 335

Glu Asp Pro Leu Pro Thr Leu Asp Val Phe Ala Gly Cys Gln Ile Pro
            340                 345                 350

Tyr Pro Lys Arg Glu Phe Leu Asn Glu Asp Asp Pro Glu Glu Lys Gly
        355                 360                 365

Asp Lys Asn Gln Gln Gln Gln Gln Asn Gln His Gln Gln Pro Thr Ala
    370                 375                 380

Pro Pro Gln Gln Ala Ala Ala Pro Pro Gln Ala Pro Pro Pro Gln Gln
385                 390                 395                 400

Asn Ser Thr Gln Thr Asn Gly Thr Ala Gly Gly Ala Gly Ala Gly Val
                405                 410                 415

Gly Gly Thr Gly Ala Gly Leu Gln His Ser Gln Asp Ser Ser Leu Asn
            420                 425                 430

Gln Val Pro Pro Asn Lys Lys Pro Arg Leu Gly Pro Ser Gly Ala Asn
        435                 440                 445

Ser Gly Gly Pro Val Met Pro Ser Asp Tyr Gln His Ser Ser Ser Arg
    450                 455                 460

Leu Asn Tyr Gln Ser Ser Val Gln Gly Ser Ser Gln Ser Gln Ser Thr
465                 470                 475                 480

Leu Gly Tyr Ser Ser Ser Ser Gln Gln Ser Ser Gln Tyr His Pro Ser
                485                 490                 495

His Gln Ala His Arg Tyr
            500


<210> SEQ ID NO 46
<211> LENGTH: 464
<212> TYPE: PRT
<213> ORGANISM: Homo sapiens

<400> SEQUENCE: 46

Met Asp Tyr Asp Phe Lys Val Lys Leu Ser Ser Glu Arg Glu Arg Val
1               5                   10                  15

Glu Asp Leu Phe Glu Tyr Glu Gly Cys Lys Val Gly Arg Gly Thr Tyr
            20                  25                  30

Gly His Val Tyr Lys Ala Lys Arg Lys Asp Gly Lys Asp Asp Lys Asp
        35                  40                  45

Tyr Ala Leu Lys Gln Ile Glu Gly Thr Gly Ile Ser Met Ser Ala Cys
    50                  55                  60

Arg Glu Ile Ala Leu Leu Arg Glu Leu Lys His Pro Asn Val Ile Ser
65                  70                  75                  80

Leu Gln Lys Val Phe Leu Ser His Ala Asp Arg Lys Val Trp Leu Leu
                85                  90                  95
```

-continued

```
Phe Asp Tyr Ala Glu His Asp Leu Trp His Ile Ile Lys Phe His Arg
            100                 105                 110

Ala Ser Lys Ala Asn Lys Lys Pro Val Gln Leu Pro Arg Gly Met Val
        115                 120                 125

Lys Ser Leu Leu Tyr Gln Ile Leu Asp Gly Ile His Tyr Leu His Ala
    130                 135                 140

Asn Trp Val Leu His Arg Asp Leu Lys Pro Ala Asn Ile Leu Val Met
145                 150                 155                 160

Gly Glu Gly Pro Glu Arg Gly Arg Val Lys Ile Ala Asp Met Gly Phe
                165                 170                 175

Ala Arg Leu Phe Asn Ser Pro Leu Lys Pro Leu Ala Asp Leu Asp Pro
            180                 185                 190

Val Val Val Thr Phe Trp Tyr Arg Ala Pro Glu Leu Leu Leu Gly Ala
        195                 200                 205

Arg His Tyr Thr Lys Ala Ile Asp Ile Trp Ala Ile Gly Cys Ile Phe
    210                 215                 220

Ala Glu Leu Leu Thr Ser Glu Pro Ile Phe His Cys Arg Gln Glu Asp
225                 230                 235                 240

Ile Lys Thr Ser Asn Pro Tyr His His Asp Gln Leu Asp Arg Ile Phe
                245                 250                 255

Asn Val Met Gly Phe Pro Ala Asp Lys Asp Trp Glu Asp Ile Lys Lys
            260                 265                 270

Met Pro Glu His Ser Thr Leu Met Lys Asp Phe Arg Arg Asn Thr Tyr
        275                 280                 285

Thr Asn Cys Ser Leu Ile Lys Tyr Met Glu Lys His Lys Val Lys Pro
    290                 295                 300

Asp Ser Lys Ala Phe His Leu Leu Gln Lys Leu Leu Thr Met Asp Pro
305                 310                 315                 320

Ile Lys Arg Ile Thr Ser Glu Gln Ala Met Gln Asp Pro Tyr Phe Leu
                325                 330                 335

Glu Asp Pro Leu Pro Thr Ser Asp Val Phe Ala Gly Cys Gln Ile Pro
            340                 345                 350

Tyr Pro Lys Arg Glu Phe Leu Thr Glu Glu Glu Pro Asp Asp Lys Gly
        355                 360                 365

Asp Lys Lys Asn Gln Gln Gln Gln Gln Gly Asn Asn His Thr Asn Gly
    370                 375                 380

Thr Gly His Pro Gly Asn Gln Asp Ser Ser His Thr Gln Gly Pro Pro
385                 390                 395                 400

Leu Lys Lys Val Arg Val Val Pro Pro Thr Thr Thr Ser Gly Gly Leu
                405                 410                 415

Ile Met Thr Ser Asp Tyr Gln Arg Ser Asn Pro His Ala Ala Tyr Pro
            420                 425                 430

Asn Pro Gly Pro Ser Thr Ser Gln Pro Gln Ser Ser Met Gly Tyr Ser
        435                 440                 445

Ala Thr Ser Gln Gln Pro Pro Gln Tyr Ser His Gln Thr His Arg Tyr
    450                 455                 460
```